(12) United States Patent
Shen et al.

(10) Patent No.: US 10,676,788 B2
(45) Date of Patent: Jun. 9, 2020

(54) MODIFIED NUCLEOTIDE REAGENTS

(71) Applicant: Pacific Biosciences of California, Inc., Menlo Park, CA (US)

(72) Inventors: Gene Shen, Santa Clara, CA (US); Stephen Yue, Eugene, OR (US); Lubomir Sebo, Hayward, CA (US); Louis Brogley, Santa Cruz, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 349 days.

(21) Appl. No.: 15/600,665

(22) Filed: May 19, 2017

(65) Prior Publication Data

US 2017/0321268 A1 Nov. 9, 2017

Related U.S. Application Data

(63) Continuation-in-part of application No. 15/357,958, filed on Nov. 21, 2016, now abandoned.

(60) Provisional application No. 62/258,414, filed on Nov. 20, 2015.

(51) Int. Cl.

| *C12Q 1/6869* | (2018.01) |
| *C07H 21/04* | (2006.01) |
| *C07H 19/207* | (2006.01) |
| *C07H 19/052* | (2006.01) |
| *C12Q 1/6876* | (2018.01) |
| *C09B 23/08* | (2006.01) |
| *C09B 23/06* | (2006.01) |
| *C09B 69/00* | (2006.01) |

(52) U.S. Cl.
CPC ......... *C12Q 1/6869* (2013.01); *C07H 19/052* (2013.01); *C07H 19/207* (2013.01); *C07H 21/04* (2013.01); *C09B 23/06* (2013.01); *C09B 23/083* (2013.01); *C09B 69/00* (2013.01); *C12Q 1/6876* (2013.01)

(58) Field of Classification Search
CPC .............................. C12Q 1/6869; C07H 21/04
USPC ....................................................... 536/26.6
See application file for complete search history.

(56) References Cited

U.S. PATENT DOCUMENTS

| 4,711,955 | A | 12/1987 | Ward et al. |
| 5,223,384 | A | 6/1993 | Ohbayashi et al. |
| 5,688,648 | A | 11/1997 | Mathies et al. |
| 6,153,442 | A | 11/2000 | Pirio et al. |
| 6,255,083 | B1 | 7/2001 | Williams |
| 6,399,335 | B1 | 6/2002 | Kao et al. |
| 6,787,308 | B2 | 9/2004 | Balasubramanian et al. |
| 6,917,726 | B2 | 7/2005 | Levene et al. |
| 7,013,054 | B2 | 3/2006 | Levene et al. |
| 7,041,812 | B2 | 5/2006 | Kumar et al. |
| 7,056,661 | B2 | 6/2006 | Korlach et al. |
| 7,405,281 | B2 | 7/2008 | Xu et al. |
| 7,476,503 | B2 | 1/2009 | Turner et al. |
| 7,767,805 | B2 | 8/2010 | Buzby |
| 7,777,013 | B2 | 8/2010 | Xu et al. |
| 7,842,475 | B2 | 11/2010 | Zheng et al. |
| 7,906,284 | B2 | 3/2011 | Turner et al. |
| 7,968,702 | B2 | 6/2011 | Wegener et al. |
| 7,973,146 | B2 | 7/2011 | Shen et al. |
| 8,058,031 | B2 | 11/2011 | Xu et al. |
| 8,133,672 | B2 | 3/2012 | Bjornson et al. |
| 8,133,702 | B2 | 3/2012 | Shen et al. |
| 8,182,993 | B2 | 5/2012 | Tomaney et al. |
| 8,236,499 | B2 | 8/2012 | Patel et al. |
| 8,257,954 | B2 | 9/2012 | Clark et al. |
| 9,062,091 | B2 | 6/2015 | Bjornson et al. |
| 2003/0077610 | A1 | 4/2003 | Nelson et al. |
| 2003/0162213 | A1 | 8/2003 | Fuller et al. |
| 2003/0162216 | A1 | 8/2003 | Gold et al. |
| 2004/0241716 | A1 | 12/2004 | Kumar et al. |
| 2006/0281911 | A1 | 12/2006 | Beaucage et al. |
| 2007/0249652 | A1 | 10/2007 | Parenty et al. |

(Continued)

FOREIGN PATENT DOCUMENTS

| WO | 9106678 A1 | 5/1991 |
| WO | 9627025 A1 | 9/1996 |

(Continued)

OTHER PUBLICATIONS

Kolb et al. (2001) Angew. Chem. Int. Ed. Engl. 40:2004-20212.
Levene et al. (2003) Science 299:682-686.
Baskin et al. (2007) PNAS 104:16793-16797.
Evans (2007) Aus. J. Chem. 60:384-395.
Eid et al. (2009) Science 323:133-158.

(Continued)

*Primary Examiner* — Jezia Riley
(74) *Attorney, Agent, or Firm* — VLP Law Group LLP

(57) ABSTRACT

Labeled nucleotide analogs comprising at least one avidin protein, at least one dye-labeled compound, and at least one nucleotide compound are provided. The analogs are useful in various fluorescence-based analytical methods, including the analysis of highly multiplexed optical reactions in large numbers at high densities, such as single molecule real time nucleic acid sequencing reactions. The analogs are detectable with high sensitivity at desirable wavelengths. They contain structural components that modulate the interactions of the analogs with DNA polymerase, thus decreasing photodamage and improving the kinetic and other properties of the analogs in sequencing reactions. Also provided are nucleotide and dye-labeled compounds of the subject analogs, as well as intermediates useful in the preparation of the compounds and analogs. Compositions comprising the compounds, methods of synthesis of the intermediates, compounds, and analogs, and mutant DNA polymerases are also provided.

27 Claims, 76 Drawing Sheets

Specification includes a Sequence Listing.

(56) References Cited

U.S. PATENT DOCUMENTS

| | | |
|---|---|---|
| 2008/0076189 A1 | 3/2008 | Belosludtsev et al. |
| 2009/0024331 A1 | 1/2009 | Tomaney et al. |
| 2009/0118129 A1 | 5/2009 | Turner |
| 2009/0142316 A1 | 6/2009 | Majoral et al. |
| 2009/0186343 A1 | 7/2009 | Wang et al. |
| 2009/0208957 A1 | 8/2009 | Korlach et al. |
| 2009/0325260 A1 | 12/2009 | Otto et al. |
| 2010/0075328 A1 | 3/2010 | Bjornson et al. |
| 2010/0136592 A1 | 6/2010 | Kong et al. |
| 2010/0152424 A1 | 6/2010 | Korlach et al. |
| 2010/0167299 A1 | 7/2010 | Korlach |
| 2010/0221716 A1 | 9/2010 | Flusberg et al. |
| 2010/0255488 A1 | 10/2010 | Kong et al. |
| 2010/0261185 A1 | 10/2010 | Nikiforov |
| 2011/0183320 A1 | 7/2011 | Flusberg et al. |
| 2011/0244447 A1 | 10/2011 | Korlach |
| 2011/0256618 A1 | 10/2011 | Eid et al. |
| 2012/0052506 A1* | 3/2012 | Yue .................. C07D 401/14 435/6.12 |
| 2012/0052507 A1 | 3/2012 | Shen |
| 2012/0058469 A1 | 3/2012 | Shen |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0115736 A1 | 5/2012 | Bjornson et al. |
| 2012/0122779 A1 | 5/2012 | Kirshenbaum et al. |
| 2013/0289253 A1 | 10/2013 | Luescher et al. |
| 2013/0316912 A1 | 11/2013 | Bjornson et al. |
| 2014/0005404 A1 | 1/2014 | Yue et al. |
| 2014/0080127 A1 | 3/2014 | Yue et al. |
| 2014/0094374 A1 | 4/2014 | Kamtekar et al. |
| 2014/0094375 A1 | 4/2014 | Kamtekar et al. |
| 2017/0145495 A1 | 5/2017 | Sebo et al. |

FOREIGN PATENT DOCUMENTS

| | | | |
|---|---|---|---|
| WO | 2009145828 A2 | 12/2009 | |
| WO | 2010057185 A1 | 5/2010 | |
| WO | 2012027618 A2 | 3/2012 | |
| WO | 2012027625 A2 | 3/2012 | |
| WO | WO-2012027625 A2 * | 3/2012 | ........... C07D 401/14 |
| WO | 2013123258 A1 | 8/2013 | |
| WO | 2013173844 A1 | 11/2013 | |
| WO | 2017087973 A1 | 5/2017 | |
| WO | 2017087974 A1 | 5/2017 | |
| WO | 2017087975 A1 | 5/2017 | |

OTHER PUBLICATIONS

Siripom et al. (ChemComm 2009, p. 806-808).
Astruc et al. (2010) Chem. Rev. 110:1857-1959.
Genisphere POC Tech. Note (2012).
Kim et al. (2013) Biophys. J. 104:1566-1575.
International Search Report and Written Opinion dated Apr. 5, 2017 for Related PCT/US2016/063176.

* cited by examiner

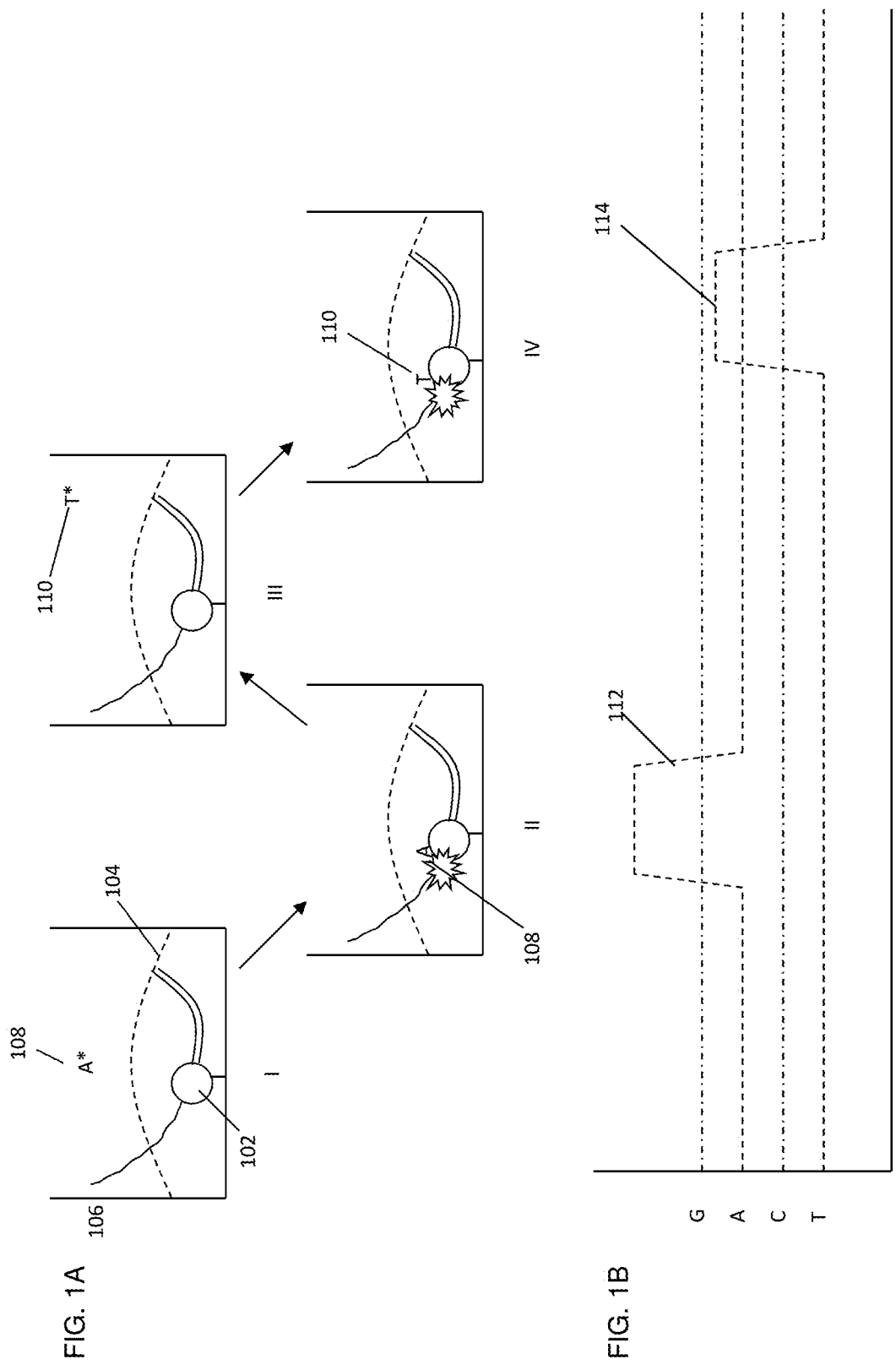

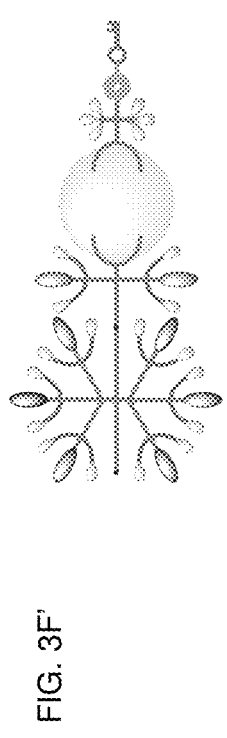
FIG. 3B'
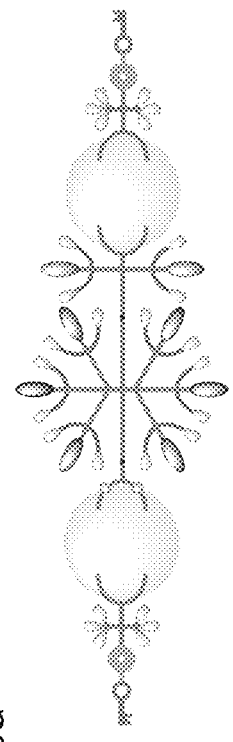
FIG. 3C'
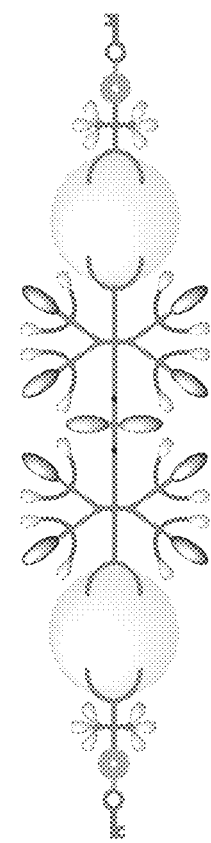
FIG. 3D'
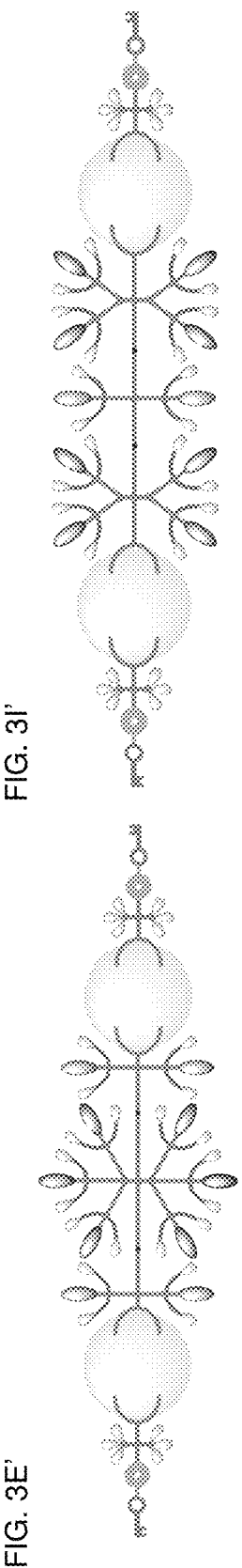
FIG. 3E'
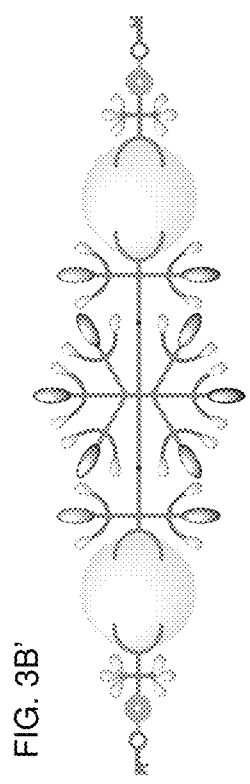
FIG. 3F'
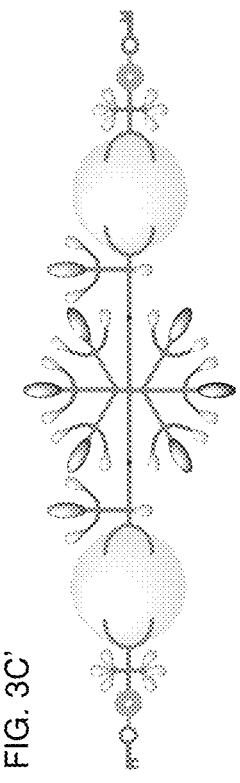
FIG. 3G'
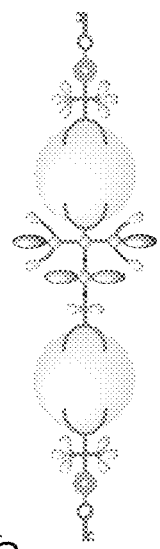
FIG. 3H'
FIG. 3I'

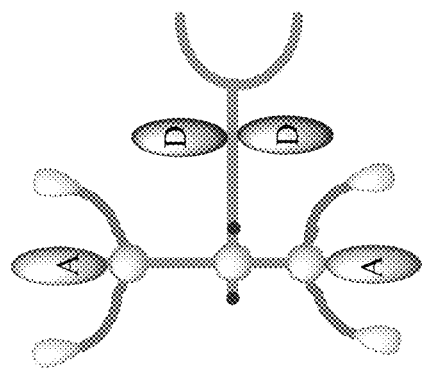
FIG. 5A
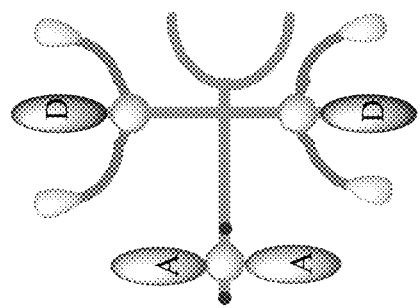
FIG. 5B
FIG. 5C
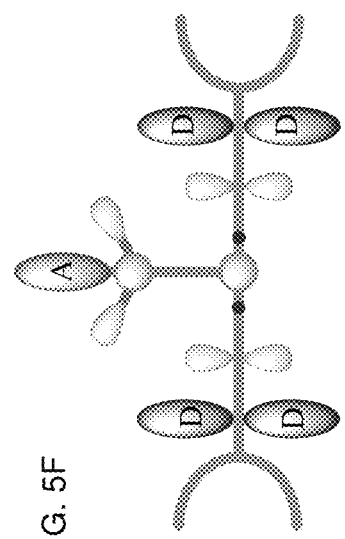
FIG. 5D
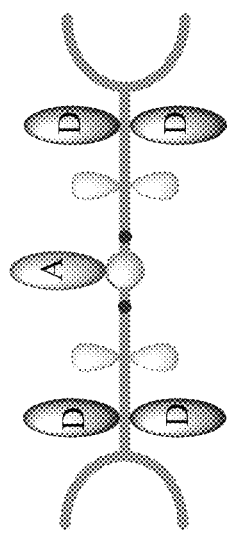
FIG. 5E
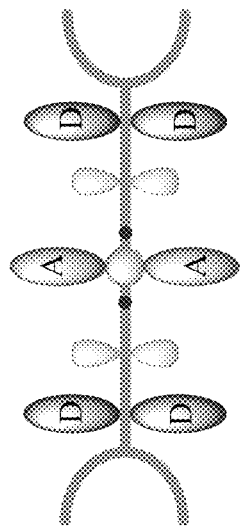
FIG. 5F

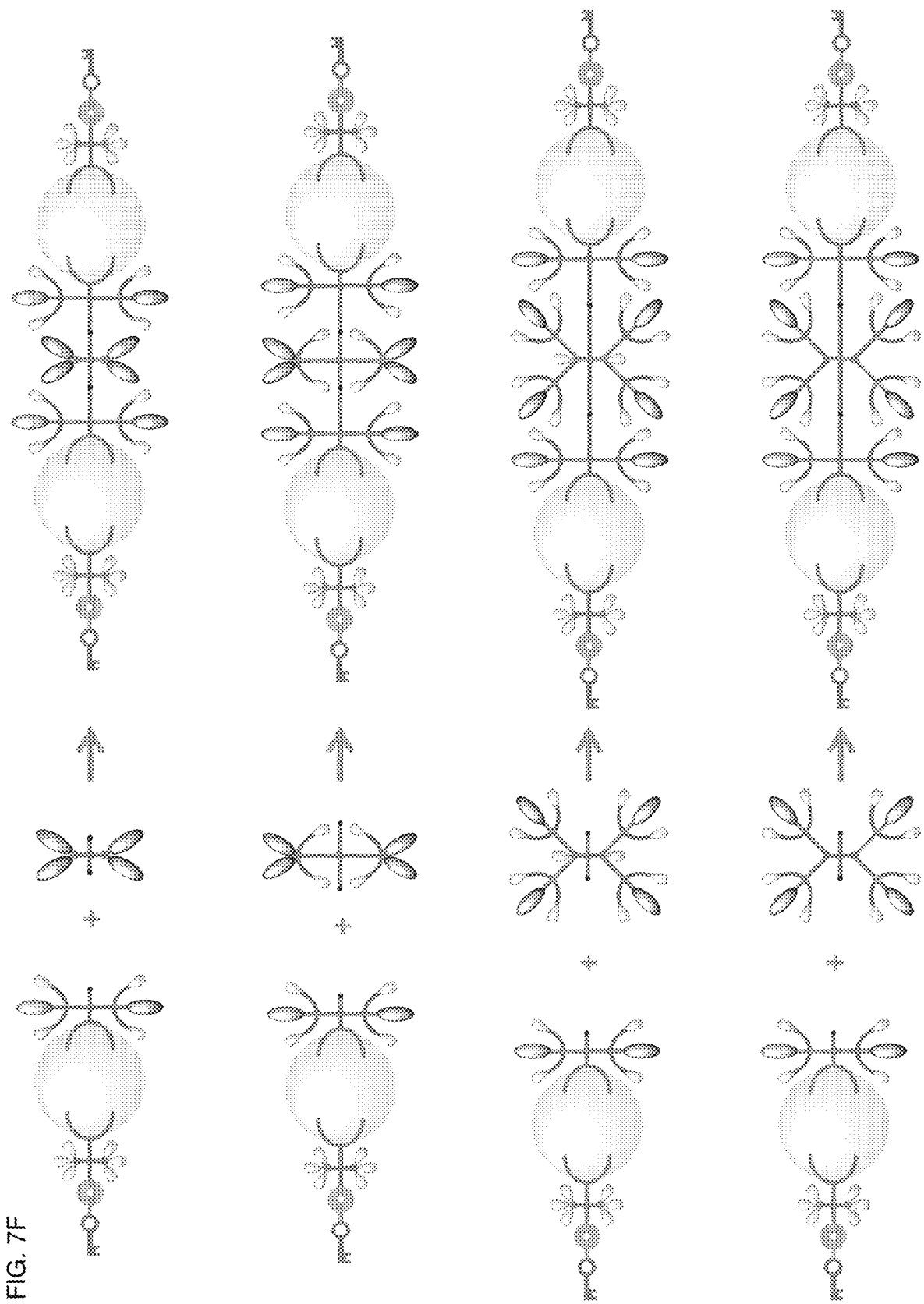

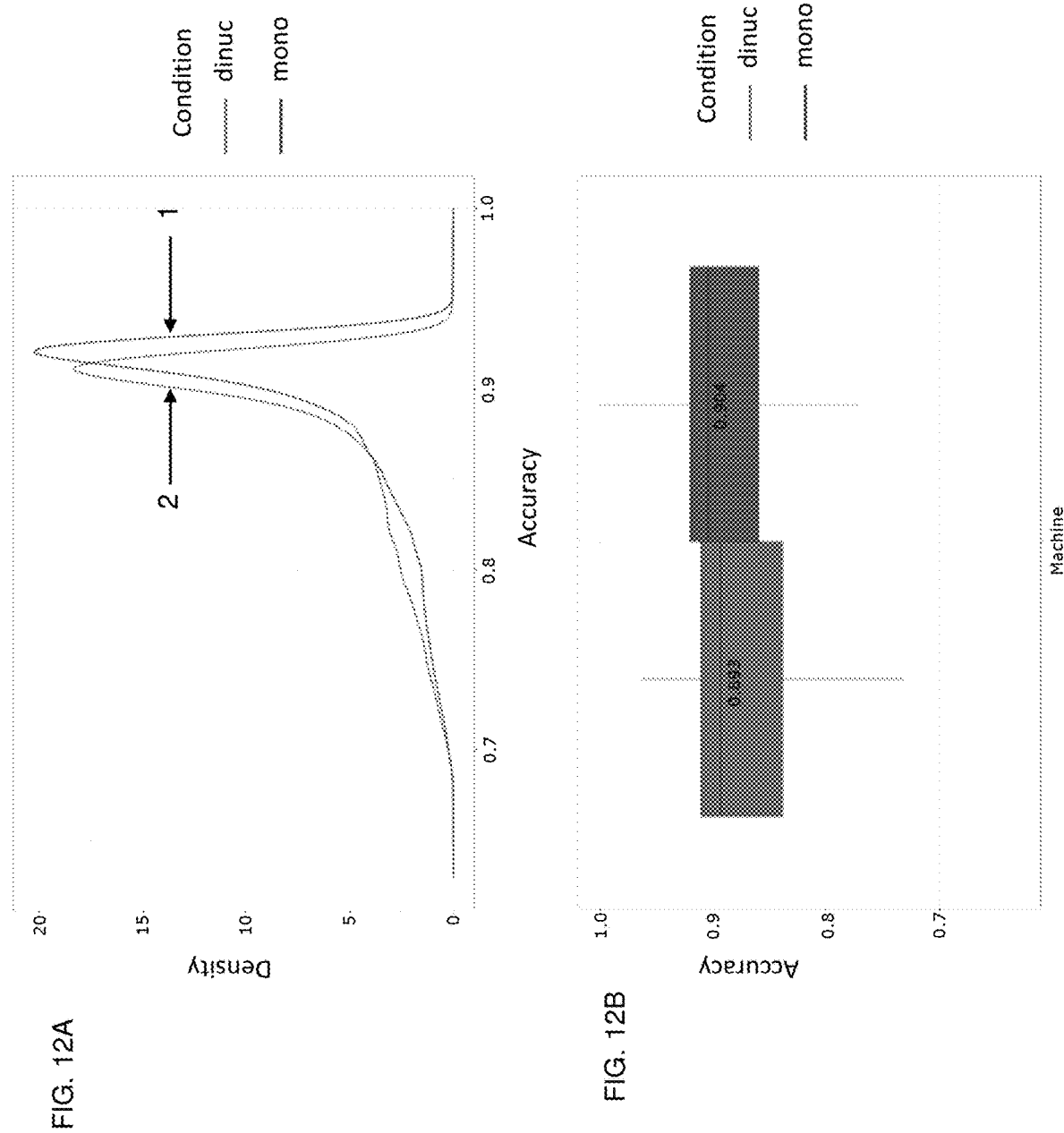

FIG. 30 Control-SG1x4-dG2

FIG. 31 Control-SG1x2-dG

FIG. 32
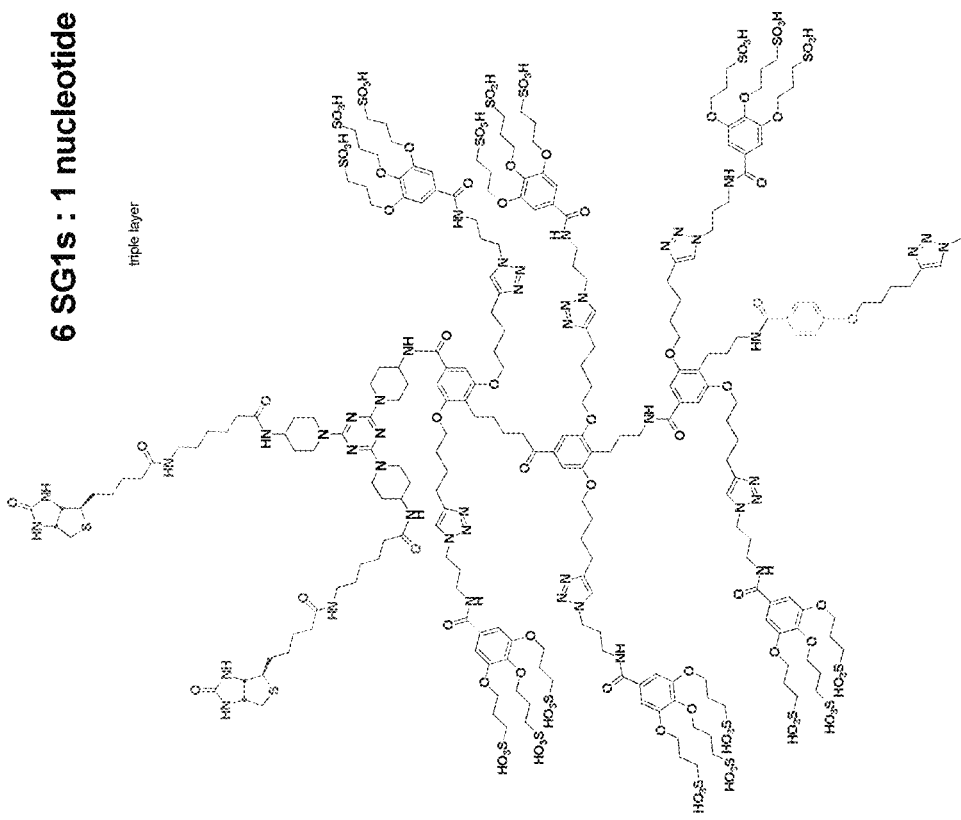
4 SG1s : 1 nucleotide
double layer
Layered-SG1x4-dG
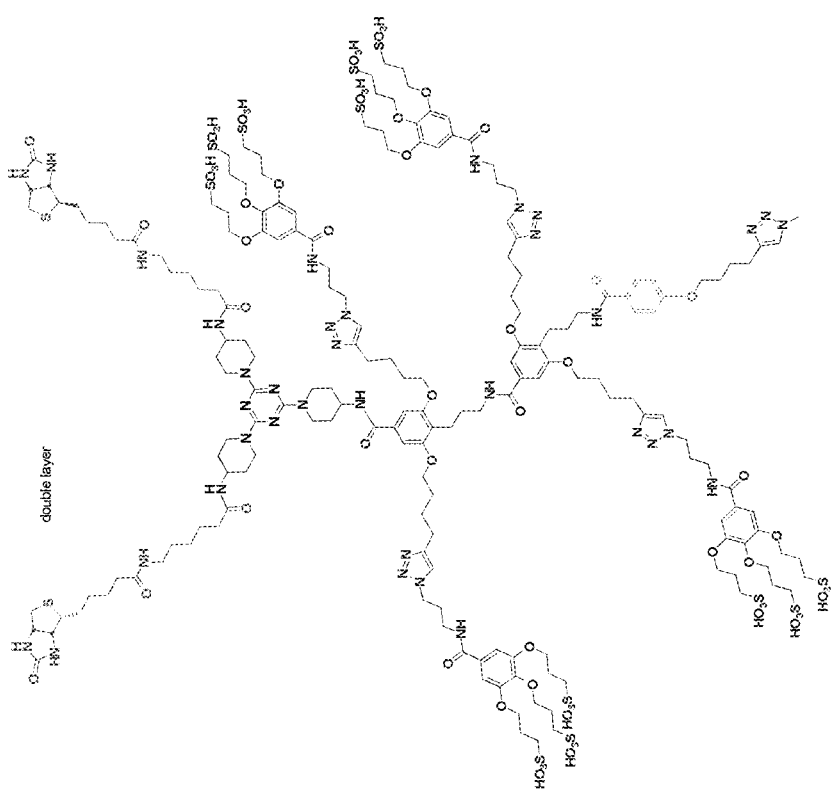
6 SG1s : 1 nucleotide
triple layer
Layered-SG1x6-dG DISC-Split-SG1x4-dA DISC-Split-SG1x6-dG DISC2-Split-SG1x12(amide)-dG2

FIG. 39　DISC2-Split-SG1x12(click)-dG2

FIG. 40  DISC-Split-SG1x6-dG

DISC-Split-SG1x6-dG(click)

MODIFIED NUCLEOTIDE REAGENTS

CROSS-REFERENCE TO RELATED APPLICATIONS

This application is a continuation-in-part of U.S. patent application Ser. No. 15/357,958, filed on Nov. 21, 2016, which claims the benefit of U.S. Provisional Application No. 62/258,414, filed on Nov. 20, 2015, the disclosures of which are incorporated herein by reference in their entireties.

SEQUENCE LISTING

This application includes a Sequence Listing, as set forth in an ASCII-compliant text file named "1407-00-012U02_2017-05-16_Seq_list_ST25.txt", created on May 16, 2017, and containing 136,087 bytes, which is incorporated herein by reference in its entirety.

BACKGROUND OF THE INVENTION

The development of novel modified nucleotide reagents, in particular the generation of nucleotide reagents containing fluorescent labels, has increased the power of nucleotide sequencing reactions, for example nucleotide sequencing reactions that provide for the identification of all four bases in a single reaction solution. Such methods have been employed in the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added. See, e.g., Eid, J. et al. (2009) *Science* 323:133-138.

At the same time, however, the demands of next-generation sequencing, including whole-genome sequencing and resequencing, transcriptome profiling, epigenomic characterization, analysis of DNA-protein interactions, and the like, require increased throughput at lower cost per base sequenced. Higher throughput can impact the quality of the sequencing data obtained, however. For example, in any enzyme-mediated, template-dependent sequencing process, the overall fidelity, processivity, and/or accuracy of the incorporation process can have direct impacts on sequence identification. In turn, lower accuracy may require multiple fold coverage to identify a particular sequence with a high level of confidence.

There is therefore a continuing need to increase the performance of nucleotide sequencing reactions in analytical systems. In particular, there is a continuing need to develop modified nucleotide reagents that have improved kinetic properties in single-molecule real time sequencing reactions and that display other desirable characteristics.

SUMMARY OF THE INVENTION

The present disclosure addresses these and other needs by providing in one aspect a nucleotide compound represented by structural formula (I):

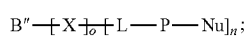

$$B''\text{---}[X\text{-}_o\text{-}L\text{---}P\text{---}Nu]_n;\quad (I)$$

wherein

L is a nucleotide linker element comprising at least one affinity modulating element;
P is a polyphosphate element;
Nu is a nucleoside element;
X is a multivalent central core element;
B" is a terminal coupling element;
n is an integer from 1 to 4; and
o is 0 or 1.

In some embodiments, the at least one affinity modulating element decreases the $K_m$ of a nucleotide-dependent enzyme for the nucleotide compound or increases the enzymatic rate of the nucleotide-dependent enzyme.

In some embodiments, the at least one affinity modulating element is an aromatic spacer element or a shield element. More specifically, the aromatic spacer element can be a substituted or unsubstituted monocyclic, bicyclic, tricyclic, or tetracyclic aromatic moiety, including an anionic aromatic moiety.

In other embodiments, the at least one affinity modulating element is a shield element, including embodiments wherein the shield element comprises a plurality of side chains, including side chains comprising a negatively-charged component.

In some embodiments, the terminal coupling element comprises a biotin moiety, such as a bis-biotin moiety.

Also provided are nucleotide reagent compositions comprising an avidin protein and a nucleotide compound of the disclosure.

The disclosure still further provides labeled nucleotide analogs comprising at least a first avidin protein, at least a first nucleotide compound, wherein the nucleotide compound comprises at least one affinity modulating element, and at least a first dye-labeled compound. Still further provided are polymerase enzymes, reaction mixtures and methods for sequencing a nucleic acid template, and systems for sequencing nucleic acids.

While primarily described in terms of nucleic acid polymerases, and particularly DNA polymerases, it will be appreciated that the approach of providing improved nucleotide compounds, dye-labeled compounds, and labeled nucleotide analogs comprising those compounds can be usefully applied to other enzyme systems where one may wish to directly observe the enzyme reaction, in real time. Such enzyme systems include, for example, other synthesizing enzymes, e.g., RNA polymerases, reverse transcriptases, ribosomal polymerases, as well as other enzyme systems, such as kinases, phosphatases, proteases, nucleases, ligases, and the like.

Related compounds, analogs, enzymes, reaction mixtures, methods, and systems have been disclosed in PCT International Application Nos. PCT/US2016/063176, PCT/US2016/063177, and PCT/US2016/063178, filed on Nov. 21, 2016, the disclosures of which are incorporated herein by reference in their entireties.

BRIEF DESCRIPTION OF THE DRAWINGS

FIGS. 1A and 1B schematically illustrate an exemplary nucleic acid sequencing process that can be carried out using aspects of the invention.

FIGS. 5A-5M illustrate exemplary dye-labeled compounds of the disclosure comprising shield elements.

FIG. 7F illustrates additional labeled nucleotide analog structures and their assembly from nucleotide and dye-labeled intermediate components and avidin proteins.

FIGS. 12A and 12B illustrate a comparison of the accuracy of sequencing with mononucleotide and dinucleotide analogs.

FIGS. 30-41 illustrate exemplary nucleotide reagent compounds of the disclosure.

DETAILED DESCRIPTION OF THE INVENTION

Figure 2A:
FIG. 2A illustrates a bis-biotin-labeled dye component and two biotin-labeled nucleotide components associated with an avidin protein shield.

Labeled nucleotide analogs are used in a wide variety of different applications. Such applications include, for example, the observation of single molecules, such as single biomolecules, in real time as they carry out reactions. For ease of discussion, such labeled nucleotide analogs, and particularly the exemplary nucleotide analogs of the instant disclosure, are discussed herein in terms of a preferred application: the analysis of nucleic acid sequence information, and particularly, single molecule nucleic acid sequence analysis.

In the preferred application, single molecule primer extension reactions are monitored in real-time, to identify the ongoing incorporation of nucleotides into the extension product to elucidate the underlying template sequence. In such single molecule real time (or SMRT™) sequencing, the process of incorporation of nucleotides in a polymerase-mediated template dependent primer extension reaction is monitored as it occurs. In preferred aspects, the template/polymerase primer complex is provided, typically immobilized, within an optically confined region, such as a zero mode waveguide (ZMW), or proximal to the surface of a transparent substrate, optical waveguide, or the like (see e.g., U.S. Pat. Nos. 6,917,726, and 7,170,050 and U.S. Patent Application Publication No. 2007/0134128, the disclosures of which are hereby incorporated by reference herein in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

A schematic illustration of this sequencing process is shown in FIGS. 1A-1B. As shown in FIG. 1A, an immobilized complex 102 of a polymerase enzyme, a template nucleic acid, and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time, corresponding to the retention time of the labeled nucleotide analog within the observation volume during incorporation, which produces a signal associated with that retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

As described in PCT International Publication No. WO 2009/145828A2, which is incorporated by reference herein in its entirety for all purposes, the incorporation of specific nucleotides can be determined by observing bright phases and dark phases which correspond, for example, to reaction steps in which a fluorescent label is associated with the polymerase enzyme, and steps in which the fluorescent label is not associated with the enzyme. Under some conditions, the polymerase reaction system will exhibit two slow (kinetically observable) reaction steps, wherein each of the steps is in a bright phase. Under other conditions, the system will exhibit two kinetically observable reaction steps, wherein each of the steps is in a dark phase. Under still other conditions, the system will exhibit four kinetically observable (slow) reaction steps, two slow steps in a bright phase and two slow steps in a dark phase. Factors influencing the observed kinetics include the type of polymerase enzyme, the polymerase reaction conditions, including the type and levels of cofactors, and the reaction substrates.

The labeled nucleotide analogs disclosed herein, including their nucleotide and dye-labeled components, comprise structural features that modulate the kinetics of the polymerase reaction to improve the performance of the system. The improved performance of the instant nucleotide analogs thus provides advantages for the use of these analogs in various analytical techniques. In particular, the instant disclosure provides labeled nucleotide analogs that in some cases, among other advantageous properties, display shortened IPDs (inter-pulse distances) during SMRT™ DNA sequencing. The polymerase rates with these analogs is accordingly increased. By modulating the IPD, which is related to the concentration of the analogs added for the DNA sequencing reaction, the concentration of the analog can be reduced. Reduction of analog concentration correspondingly reduces background noise derived from diffusion of the analog in the ZMW and thus improves the signal to noise ratio. Improvement in these, and other, parameters is particularly important where sequencing instruments would otherwise require higher powers of laser illumination. Reduction of laser power in turn reduces photo-bleaching of the fluorophores and other related photo damage.

While the usefulness of the labeled nucleotide analogs of the invention is illustrated with the description above of SMRT™ sequencing, it is to be understood that these analogs, and their nucleotide compound components and dye-labeled compound components, can be used with any appropriate enzymatic or binding reaction and will thus have broader application in other analytical techniques. For example, the labeled nucleotide analogs of the instant disclosure are also useful in the measurement of any type of binding interaction, not just binding interactions that result in the reaction of the reagent. While in preferred embodiments, such as single-molecule, real-time nucleic acid sequencing reactions and other nucleotide-dependent enzymatic reactions, the analogs serve as an enzyme substrate and are chemically altered as a result of the interaction, in other embodiments, such as, for example, the binding of a labeled nucleotide analog to an antibody, a receptor, or other affinity agent, the analog remains unaltered as a result of the interaction. Measurement of an enzymatic reaction, a binding interaction, or any other type of reaction or interaction, can be performed using well-known fluorescence techniques and biochemical processes. Examples of such techniques and processes include fluorescence resonance energy transfer (FRET), fluorescence cross-correlation spectroscopy, fluorescence quenching, fluorescence polarization, flow cytometry, and the like.

The instant disclosure provides chemical formulae and specific chemical structures for the inventive nucleotide and dye-labeled compounds. Where chemical moieties are specified by their conventional chemical formulae, written from left to right, they optionally equally encompass the moiety which would result from writing the structure from right to left, e.g., —$CH_2O$— is intended to also recite —$OCH_2$—; —$NHS(O)_2$— is also intended to optionally represent —$S(O)_2NH$—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of ordinary skill in the art. Similarly, where the salt is disclosed, this structure also discloses the compound in a free acid or free base form. Methods of making salts and free acids and free bases are well-known in the art.

The labeled nucleotide analogs of the instant disclosure are generally meant to be used as substrates for polymerase enzymes, particularly in the context of nucleic acid sequencing. Therefore, generally, any non-natural base, sugar, or phosphate of the nucleotide or nucleoside phosphate can be included as a nucleotide or nucleoside phosphate of the invention if the nucleoside phosphate is capable of acting as a substrate for any natural or modified polymerase enzyme.

"Activated derivatives of carboxyl moieties", and equivalent species, refers to a moiety on a component of the instant compounds or their precursors or derivatives or on another reagent component in which an oxygen-containing, or other, leaving group is formally accessed through a carboxyl moiety, e.g., an active ester, acyl halide, acyl imidazolide, etc. Such activated moieties can be useful in coupling the various components of the instant nucleotide and dye-labeled compounds and analogs as they are assembled.

The term "alkyl", by itself or as part of another substituent, means, unless otherwise stated, a straight or branched chain, or cyclic hydrocarbon radical, or combination thereof, which can be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl", unless otherwise noted, includes "alkylene", "alkynyl", and optionally, those derivatives of alkyl defined in more detail below, such as "heteroalkyl".

The term "heteroalkyl", by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P, and S, and wherein the nitrogen and sulfur atoms can optionally be oxidized and the nitrogen heteroatom can optionally be quaternized. The heteroatom(s) O, N, S, P, and Si can be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms can be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like).

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen", by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl", "heteroalkyl", "aryl", and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', SO$_3$R', —NR'—C(O)NR"R''', —NR"C(O)$_2$R', —NR—C(NR'R"R''')=NR''', —NR—C(NR'R")=NR''', —S(O)R', —S(O)$_2$R', —S(O)$_2$NR'R", —NRSO$_2$R', —CN, and —NO$_2$ in a number ranging from zero to (2m"+1), where m" is the total number of carbon atoms in such radical. R', R", R'', and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound or reagent of the invention includes more than one R group, for example, each of the R groups is independently selected as are each R', R", R'", and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of ordinary skill in the art will understand that the terms "substituted alkyl" and "heteroalkyl" are meant to include groups that have carbon atoms bound to groups other than hydrogen atoms, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

The substituents set forth in the paragraph above are referred to herein as "alkyl group substituents".

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —$CO_2$R', —CONR'R", .OC(O)NR'R", —NR"C(O)R', —NR'—C(O)NR"R'", —NR"C(O)$_2$R', —NR—C(NR'R")=NR'", —S(O)R', —S(O)$_2$R', $SO_3$R', —S(O)$_2$NR'R", —NRSO$_2$R', —CN, and —$NO_2$, —R', —$N_3$, —CH(Ph)$_2$, fluoro($C_1$-$C_4$)alkoxy, and fluoro($C_1$-$C_4$) alkyl, in a number ranging from zero to the total number of open valences on the aromatic ring system; and where R', R", R'", and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound or reagent of the invention includes more than one R group, for example, each of the R groups is independently selected as are each R', R", R'", and R"" groups when more than one of these groups is present.

Two of the substituents on adjacent atoms of the aryl or heteroaryl ring can optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring can optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$-J-(CR"R'")$_d$—, where s and d are independently integers of from 0 to 3, and J is —O—, —NR'—, —S—, —S(O)—, —S(O)$_2$—, or —S(O)$_2$NR'—. The substituents R, R', R", and R'" are preferably independently selected from hydrogen or substituted or unsubstituted ($C_1$-$C_6$)-alkyl.

The substituents set forth in the two paragraphs above are referred to herein as "aryl group substituents".

When referring to components of the compounds and analogs of the disclosure, the term "residue derived from," refers to a residue formed by the reaction of a first reactive functional group on a first component (e.g., a multivalent central core element, a dye element, a shield element, a linker element, a terminal coupling element, and the like) and a second reactive functional group on a second component (e.g., a multivalent central core element, a dye element, a shield element, a linker element, a terminal coupling element, and the like) to form a covalent bond. In exemplary embodiments, an amine group on the first component is reacted with an activated carboxyl group on the second component to form a residue including one or more amide moieties. Other permutations of first and second reactive functional groups are encompassed by the invention. For example, the copper-catalyzed reaction of an azide-substituted first component with an alkyne-substituted second component results in a triazole-containing residue through the well-known "click" reaction, as would be understood by those of ordinary skill in the art. See Kolb et al. (2001) *Angew. Chem. Int. Ed. Engl.* 40:2004; Evans (2007) *Aus. J. Chem.* 60:384.

In some embodiments, a copper-free variant of the click reaction can be used to couple the first and second reactive groups. See, e.g., Baskin et al. (2007) *Proc. Natl Acad. Sci. U.S.A.* 104:16793-97. For example, an azide-substituted first component can be reacted with a cycloalkyne, ideally a cyclooctyne, attached to the second component, in the absence of a copper catalyst. Such so-called copper-free click reagents are available commercially. Examples of such cycloalkynes include, without limitation, dibenzocyclooctyne-amine, bicyclo[6.1.0]non-4-yn-9-yl, or monofluorinated cyclooctynes. Other coupling chemistries can also be usefully employed in the synthesis of the compounds of the instant disclosure, as would be understood by those of ordinary skill in the art.

Copper-catalyzed and copper-free click reactions result in the following exemplary linkages, including triazole and cycloalkyl-containing residues. Such residues should therefore be considered within the scope of any linker or other substructure of the compounds disclosed herein, wherever they occur.

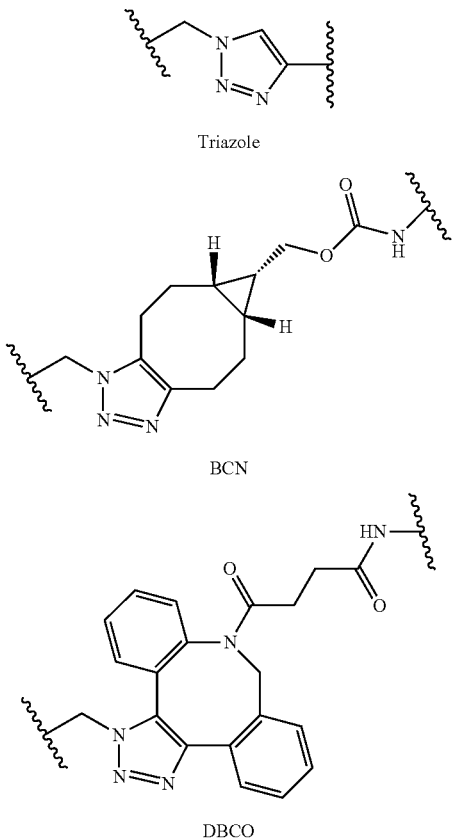

Triazole

BCN

DBCO

-continued

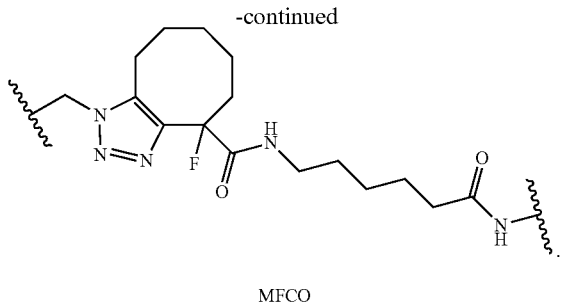

MFCO

In addition, variation in the above linkages, for example where the lengths of the alkyl linker groups are altered, or where heteroatoms or other intervening chemical moieties are substituted for the structures shown, are envisioned where such substitution does not interfere with the function of the linker group, as would be understood by those of ordinary skill in the art.

It should also be understood that the attachment sites for the first and second reactive functional groups in the just-described reactions can generally be reversed if so desired, depending on the situation. For example, in the case of a "click" reaction, the first component can be azide-substituted and the second component can be alkyne-substituted, as described above, or the first component can be alkyne-substituted and the second component can be azide-substituted. Such variation in the reactions is well within the skill of those in the art.

As used herein, a listed range of integers includes each of the integers within the range. For example, an integer from 2 to 6 includes the integers 2, 3, 4, 5, and 6.

Labeled Nucleotide Analogs

Figure 2C:
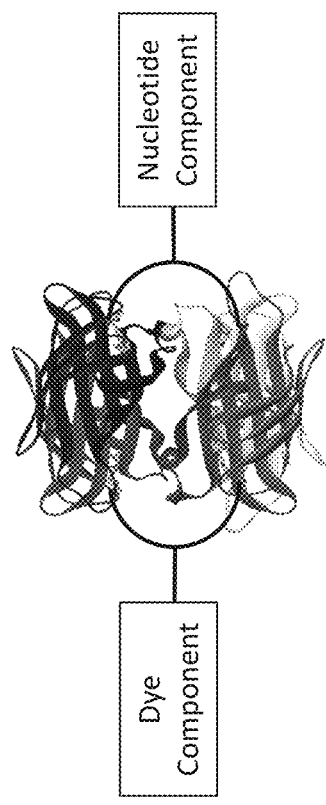
FIG. 2C illustrates a bis-biotin-labeled dye component and a bis-biotin-labeled nucleotide component associated with an avidin protein shield.
Figure 2B:
FIG. 2B illustrates a bis-biotin-labeled nucleotide component and two biotin-labeled dye components associated with an avidin protein shield.
Figure 2D:
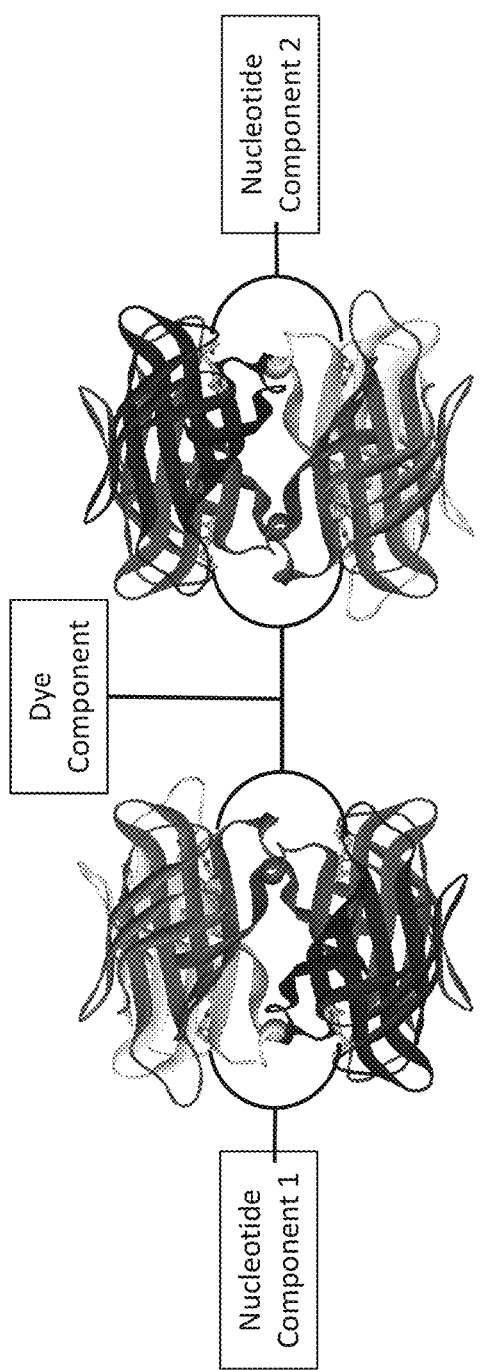
FIG. 2D illustrates a dye component labeled with two bis-biotin moieties associating with two avidin protein shields, each of which is associated with a nucleotide component comprising a bis-biotin.

The instant disclosure provides novel labeled nucleotide analogs for use in the measurement and analysis of enzymatic reactions and other molecular recognition events, such as, for example, single-molecule real-time sequencing of nucleic acids. The analogs comprise at least one protein shield, preferably an avidin protein shield, that is associated with at least one nucleotide compound and at least one dye-labeled compound. As is well known in the art, avidin proteins, including avidin, streptavidin, tamavidin, traptavidin, xenavidin, bradavidin, AVR2, AVR4, and homologs thereof, typically comprise four subunits, each subunit comprising one biotin binding site. An avidin protein can, therefore, tightly associate with one or more biotin-labeled nucleotide compounds and with one or more biotin-labeled dye-containing compounds, thus creating a dye-labeled, protein-shielded, nucleotide analog, examples of which are described in U.S. Patent Application Publication No. 2013/0316912 A1, issued as U.S. Pat. No. 9,062,091, which is incorporated by reference herein in its entirety for all purposes. As shown in FIGS. 2A-2C, the previously-described protein-shielded nucleotide analogs can include one or two dye components and one or two nucleotide components, depending on whether the dye component and nucleotide component has two or one biotin labels, respectively. As shown in FIG. 2D, these analogs can also contain more than one avidin protein shield, if either the nucleotide or dye component is designed to bridge multiple avidin tetramers. In the illustrations of FIGS. 2A-2D, a straight line between the dye or nucleotide component and an avidin subunit represents the association of a single biotin label on the component with one avidin subunit, whereas a semicircle contacting two avidin subunits represents the association of a bis-biotin label on the component with both avidin subunits.

Other examples of protected fluorescent reagent compounds, including nucleotide analog compounds and multimeric protected fluorescent reagent compounds, are described in U.S. Patent Application Publication Nos. 2015/0050659 A1 and 2016/0237279 A1, the disclosures of which are incorporated by reference herein in their entireties for all purposes.

Figure 3E:
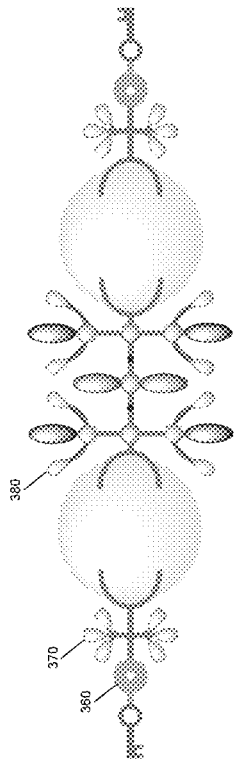
FIGS. 3A-3O' illustrate exemplary labeled nucleotide analogs of the disclosure.
Figure 3F:
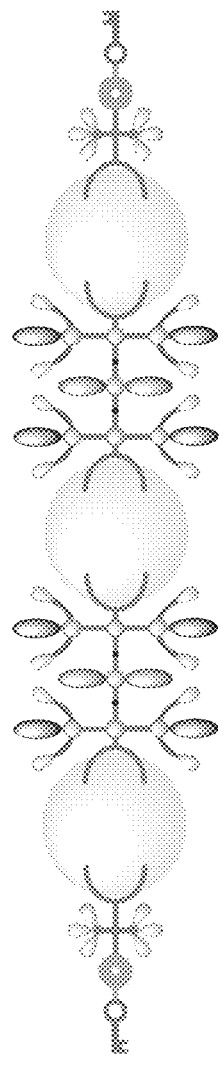
Figure 3G:
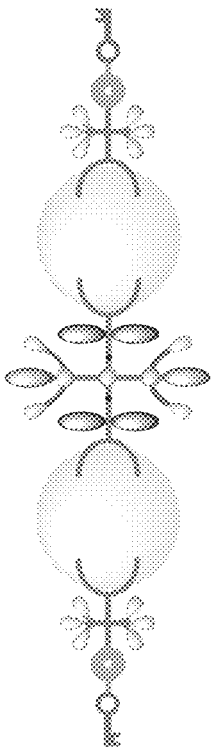
Figure 3A:
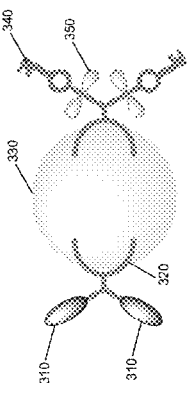
Figure 3B:
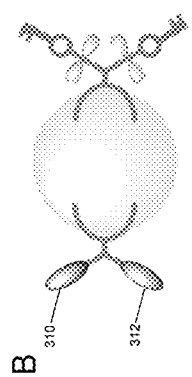
Figure 3C:
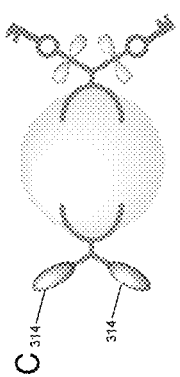
Figure 3D:
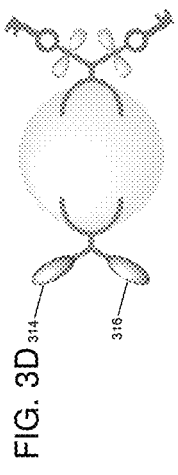
Figure 3H:
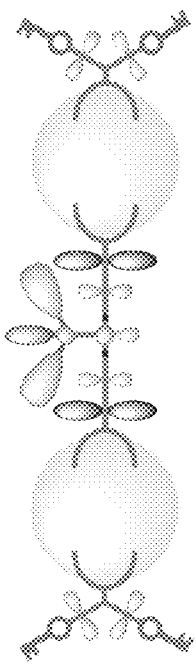
Figure 3K:
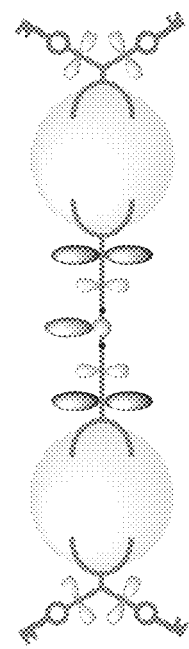
Figure 3I:
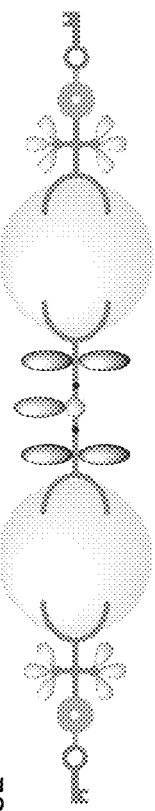
Figure 3L:
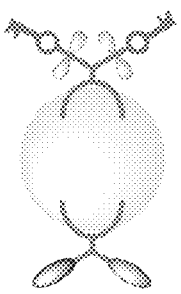
Figure 3M:
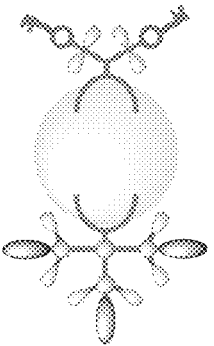
Figure 3J:
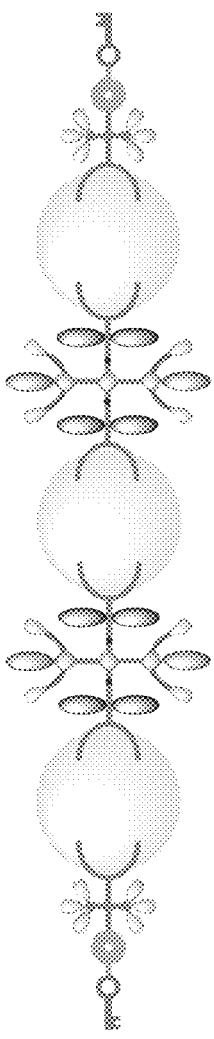
Figure 3P:
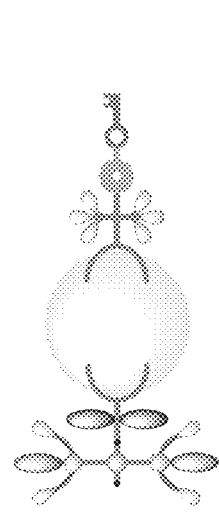
Figure 3Q:
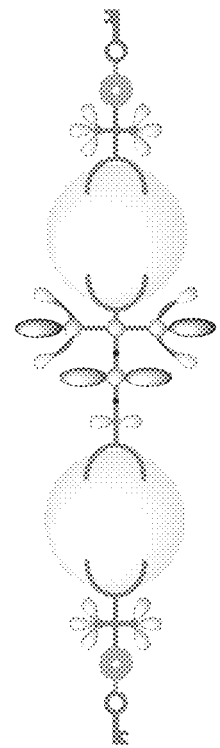
Figure 3N:
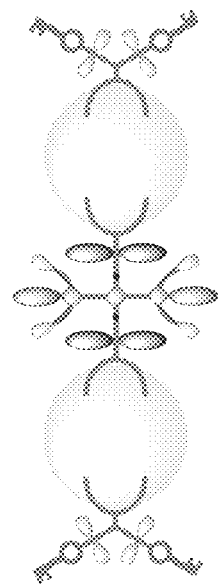
Figure 3O:
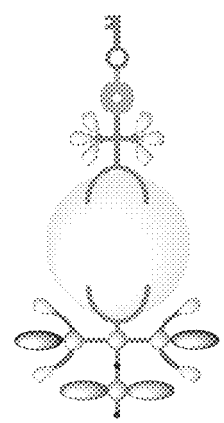
Figure 3W:
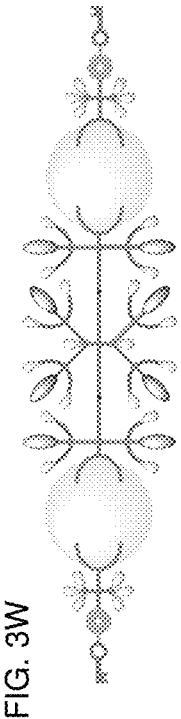
Figure 3X:
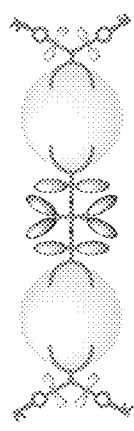
Figure 3Y:
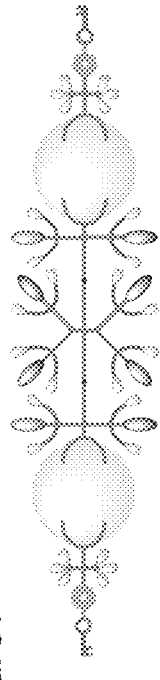
Figure 3Z:
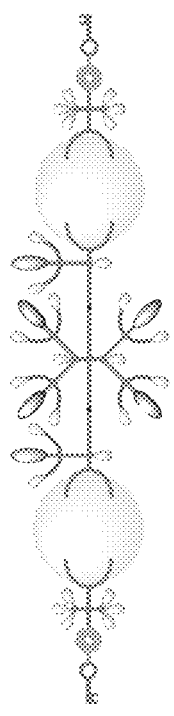
Figure 3A:
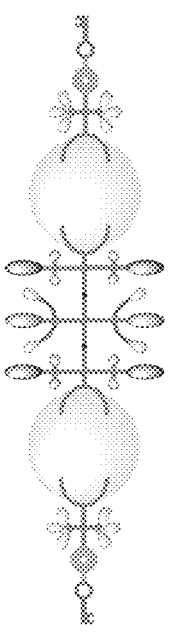
Figure 3R:
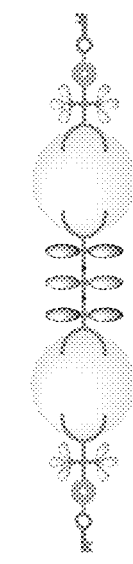
Figure 3S:
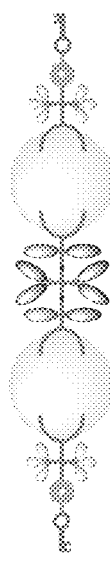
Figure 3T:
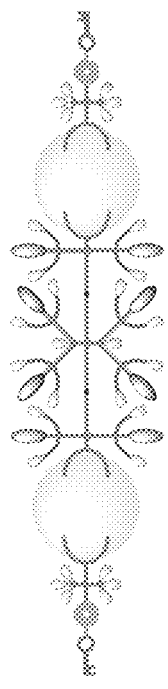

FIGS. 3A-3O' illustrate the higher-order structure of exemplary dye-labeled nucleotide analogs of the disclosure. For example, in FIG. 3A, the spherical component (330) represents a tetrameric avidin protein shield, containing four binding sites for biotin. The semicircles (320) on the associated nucleotide and dye-labeled compound components represent bis-biotin moieties. The large, symmetric oblong globules (310) represent dye elements, whereas the smaller, asymmetric globules associated with the two-lobed structure (350) represent the side chains of a shield element, in this context serving as an affinity modulating element within the nucleotide linker. The key-shaped groups (340) correspond to nucleotides (i.e., a nucleoside element plus a polyphosphate element).

FIG. 3E illustrates three other elements of the instant nucleotide and dye-labeled compounds. Specifically, the circular structure (360) represents an aromatic spacer element, and the six-lobed structure (370) represents a shield element. Each of these components can serve as an affinity modulating element within the nucleotide linker of the nucleotide compound. The two-lobed structure (380) represents a photo-protective shield element within the dye-labeled compound of the analog. All of these components will be described in detail below. Exemplary chemical structures corresponding to each of the above components, and others, are also illustrated in FIGS. 7E and 7G.

The superstructures shown in FIGS. 3A-3O' illustrate the wide structural diversity available through the assembly of various dye-labeled components and nucleotide-labeled components with one or more avidin proteins. For example, the analogs can contain one (e.g., FIGS. 3A, 3B, 3C, 3D, 3I, 3M, 3O, 3P, and 3F'), two (e.g., FIGS. 3E, 3G, 3H, 3K, 3L, 3N, 3Q, 3R-3E', and 3G'-3O'), or three (e.g., FIGS. 3F and 3J) avidin proteins, and even larger superstructures can be assembled, if desired. The analogs can contain nucleotide compounds with one (e.g., FIGS. 3E, 3F, 3G, 3J, 3L, 3O-3W, and 3Y-3O'), two (e.g., FIGS. 3A, 3B, 3C, 3D, 3H, 3I, 3K, 3M, 3N, and 3X), or more nucleoside elements. Other features, such as the use of a shield element and/or an aromatic spacer element, for example an anionic aromatic spacer element, within the linker element of a nucleotide compound to modulate the affinity and/or kinetics of an associated binding protein or enzyme, as well as the shielding of the dye-labeled compound, either by direct coupling of the shield element and the dye or by including a shield element and/or side chain in the dye linker, can be included as desired in a variety of combinations. Although the exemplary analogs of FIGS. 3A-3O' all include nucleotide and dye-labeled compounds that are attached through bis-biotin moieties, it should be understood that analogs can also be usefully assembled from compounds having single biotin moieties, such as in the structures of FIGS. 2A-2C.

Accordingly, the instant labeled nucleotide analogs can comprise any desired number of avidin tetramers, nucleotide compounds, and dye-labeled compounds. For example, the analogs can comprise 1, 2, 3, 4, 6, 10, or even more of each of these components, in any combination. In specific embodiments, the labeled nucleotide analogs comprise from 1 to 4 of each of the components. In even more specific embodiments, the labeled nucleotide analogs comprise 1, 2, or 3 avidin proteins, 1 or 2 dye-labeled compounds, and 1 or 2 nucleotide compounds.

It is particularly advantageous to vary the number and type of dye elements within a labeled nucleotide analog in order to provide the desired colors and intensities of absorption and emission. Furthermore, as will be described in more detail below, the inclusion of dyes with overlapping spectra within the dye-labeled compound of an analog complex enables the use of more advanced fluorescence techniques, such as, for example, fluorescence resonance energy transfer, where an input optical signal is transferred from a "donor" dye within the structure to a neighboring "acceptor" dye, which then emits an optical signal at a longer wavelength than would occur from the donor fluorophore alone. Changing the number of fluorescent dyes within a single labeled nucleotide analog additionally allows the intensity of the output optical signal to be modulated in useful ways if desired.

For example, when the labeled nucleotide analogs are used in DNA sequencing reactions, it can be useful to vary the color or other optical property of analog as a function of the nucleotide component associated with the analog. In particular, the nucleotide components of the analogs represented in FIGS. 3A-3D may differ only in the nature of the base group, e.g., dA, dG, dC, and dT. In combination with that variation, the dye components of the analogs can also be varied, for example as shown by the different dye structures, 310, 312, 314, and 316. Each of the nucleotide analogs is thus uniquely identifiable by the color and/or intensity of its optical output.

Figure 4C:
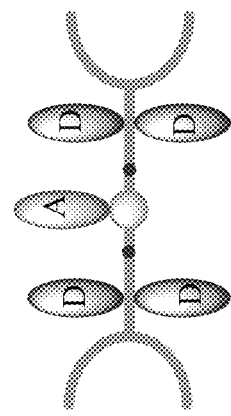
FIGS. 4A-4C illustrate exemplary dye-labeled compounds lacking shield elements.
Figure 4B:
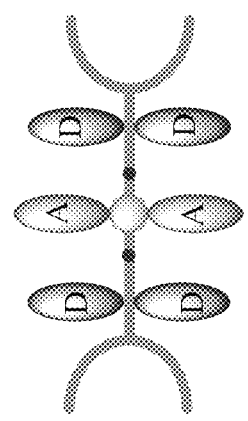
Figure 4A:
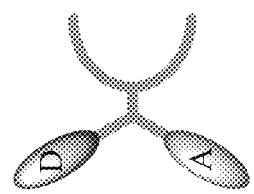
Figure 5G:
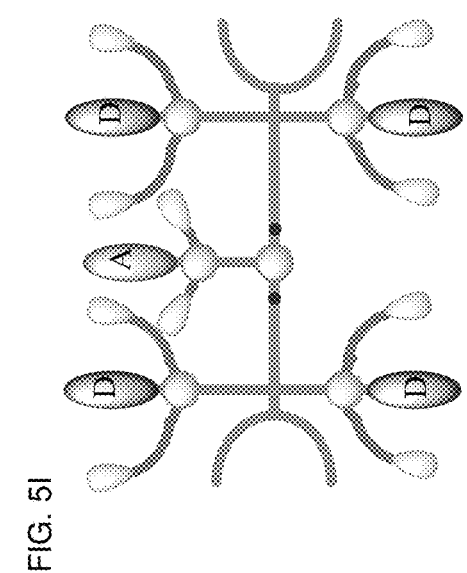
Figure 5H:
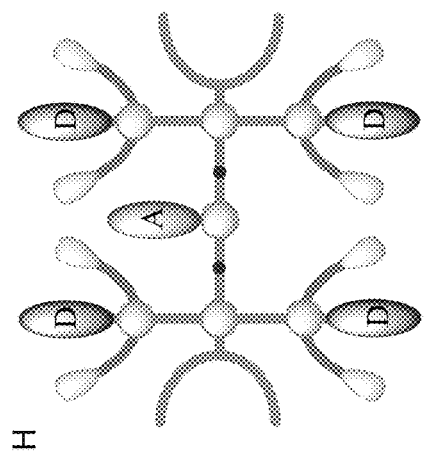
Figure 5I:
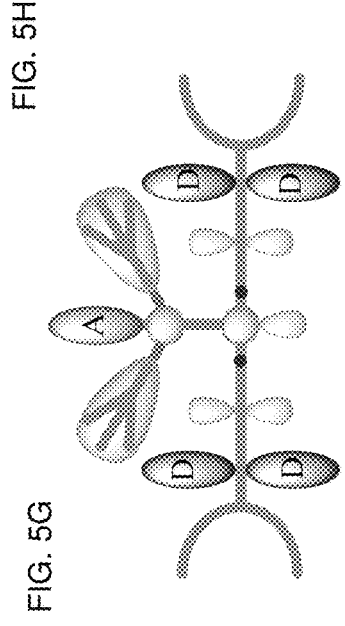
Figure 5J:
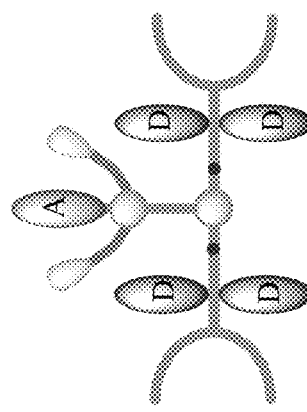
Figure 5K:
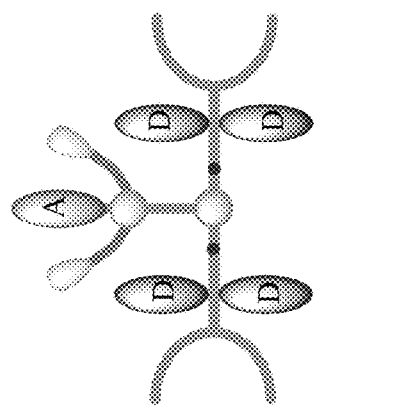
Figure 5L:
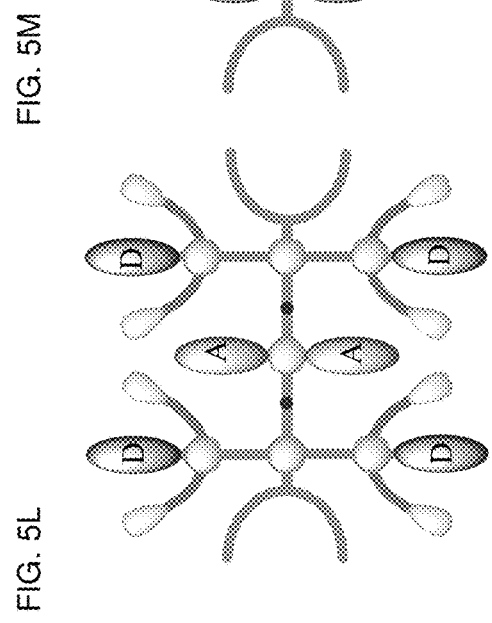
Figure 5M:
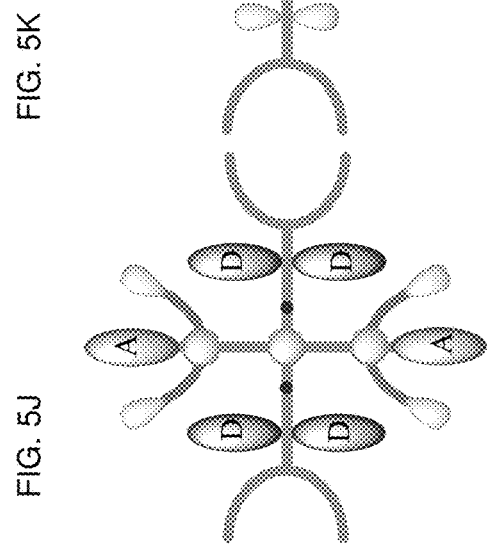

The dye-labeled compounds used to assemble the labeled nucleotide analogs disclosed herein advantageously further include shield elements. As mentioned above and in FIGS. 2A-2D, protein-shielded dye-labeled polymerase substrates have been described in U.S. Patent Application Publication No. 2013/0316912 A1. Some of the dye-labeled components utilized in those analogs contained multiple acceptor dyes and donor dyes, but the dye-labeled compounds themselves do not contain shield elements. Examples of unshielded dye-labeled compounds are shown in FIGS. 4A-4C, where the acceptor dyes are designated "A", the donor dyes are designated "D", the terminal coupling element, in these examples a bis-biotin, is designated by a semi-circle, and the dye compound linker element is designated by the line linking the different components of the structure. The small dots within the dye compound linker elements of the compounds illustrated in FIGS. 4B and 4C represent a triazole structure or other residue resulting from a copper-catalyzed click reaction, a copper-free click reaction, or other suitable coupling reaction.

The compounds of FIGS. 4A-4C can be compared to those illustrated in FIGS. 5A-5M, which represent dye-labeled compounds comprising one or more shield elements. As was also shown in the structures of FIGS. 3A-3O', the side chains of shield elements within the compounds are designated as asymmetric globule structures in FIGS. 5A-5M.

The compounds of FIGS. 5A-5M illustrate the wide diversity of structural variation possible within the scope of the instant dye-labeled compounds. Specifically, the compounds can include, without limitation, a single bis-biotin moiety (e.g., FIGS. 5A, 5B, and 5C) or a double bis-biotin moiety (e.g., FIGS. 5D-5M); they can include unshielded acceptors and directly shielded donors (e.g., FIGS. 5B, 5H, 5K, and 5L); they can include directly shielded acceptors and unshielded donors (e.g., FIGS. 5C, 5F, 5G, 5J, and 5M); they can include both directly shielded acceptors and directly shielded donors (e.g., FIGS. 5A and 5I); or they can include compounds with shield elements and/or side chains in their dye compound linker elements (e.g., FIGS. 5D, 5E, 5F, 5G, and 5K). It should be understood that some compounds can include both shield elements associated with an acceptor and/or a donor and shield elements and/or side chains included within the dye compound linker element. It should also be understood that while the drawings of FIGS. 5A-5M can indicate different sizes, shapes, and/or locations of the dyes, shields, and linkers (e.g., in FIG. 5G where the side chains of the acceptor shield element are shown as being larger than the side chains of the shield elements within the dye linker), the size, shape, and/or location of any component shown in the drawings should not be considered limiting of the actual structures, except as described explicitly herein.

Figure 3U:
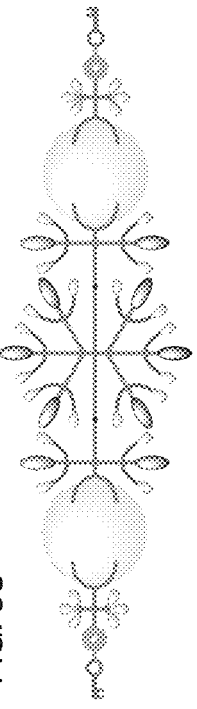
Figure 3V:
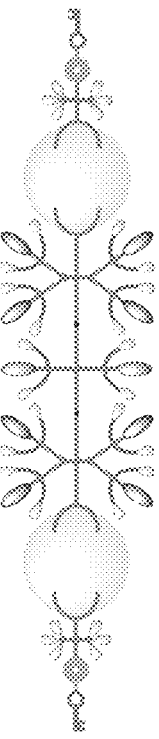
Figure 3N:
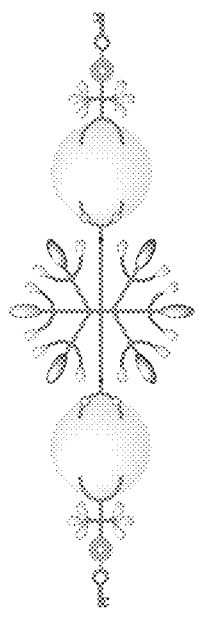
Figure 3O:
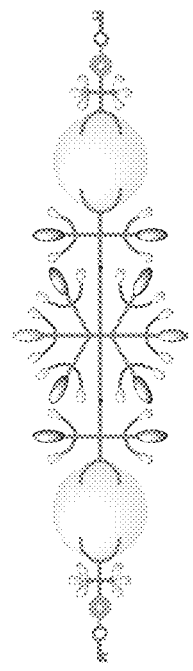
Figure 3J:
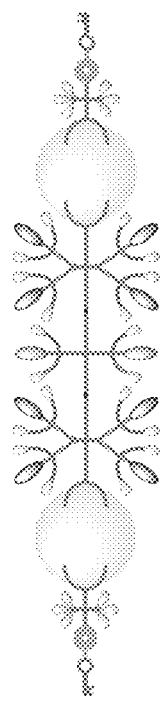
Figure 3K:
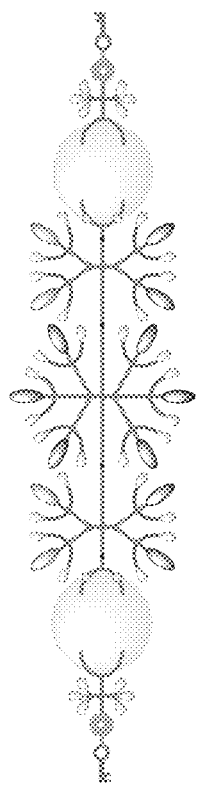
Figure 3L:
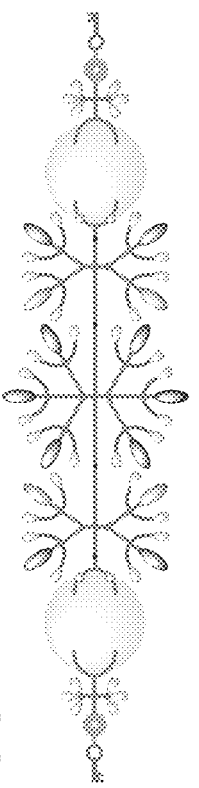
Figure 3M:
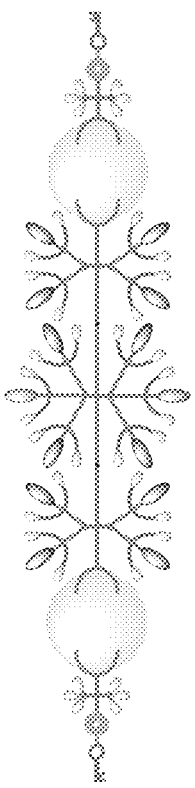

Further diversity of dye-labeled compounds is illustrated in the nucleotide analogs shown in FIGS. 3E-3O', where the dye-labeled components include one-donor, one-acceptor compounds ("D1A1") (FIG. 3I), two-donor, one-acceptor compounds ("D2A1") (FIG. 3M), two-donor, two-acceptor ("D2A2") (FIGS. 3O-3Q and 3D'), four-donor, one-acceptor compounds ("D4A1") (FIGS. 3H, 3K, and 3L), four-donor, two-acceptor compounds ("D4A2") (FIGS. 3E-3G, 3J, 3N, 3R, 3Z, 3A', and 3N'), four-donor, four-acceptor compounds ("D4A4") (FIGS. 3T, 3W, and 3X), six-donor, two-acceptor compounds ("D6A2") (FIGS. 3S, 3Y, 3C', 3F', and 3G'), six-donor, four-acceptor compounds ("D6A4") (FIG. 3E'), eight-donor, two-acceptor compounds ("D8A2") (FIGS. 3U, 3V, 3B', 3H', 3I', 3J' (where the difference between the nucleotide compound of FIG. 3I' and FIG. 3J' is the structure of the acceptor dye), and 3O'), ten-donor, four-acceptor compounds ("D10A4") (FIGS. 3K' and 3L'), and twelve-donor, two-acceptor compounds ("D12A2") (FIG. 3M'). As is apparent from the dye-labeled compound structures of these figures, the location and number of donor dyes, acceptor dyes, and shield elements can advantageously be varied to obtain desired properties, including brightness, excitation and emission wavelength, photostability, and reaction kinetics in automated DNA sequencing reactions involving DNA polymerase, as will be described in further detail below.

In order to provide a more specific description of each of these components, the structural and functional properties of the different novel nucleotide and dye-labeled compounds, the assembly of those compounds into novel labeled nucleotide analogs, and the interactions of those novel analogs with wild-type and mutated DNA polymerases will be described in detail in the following sections.

Nucleotide Compounds

As just described, the instant disclosure provides novel nucleotide compounds useful in the assembly of labeled nucleotide analogs having utility in the measurement and analysis of enzymatic reactions and other molecular recognition events, such as, for example, the single-molecule real-time sequencing of nucleic acids.

Accordingly, in one aspect, the disclosure thus provides compounds of structural formula (I):

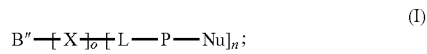

(I)

wherein
L is a nucleotide linker element comprising at least one affinity modulating element;
P is a polyphosphate element;
Nu is a nucleoside element;
X is a multivalent central core element;
B" is a terminal coupling element;
n is an integer from 1 to 4; and
o is 0 or 1.

In general, a "linker" of the instant disclosure should be considered broadly to include any chemical moiety that provides a suitable covalent connection between two or more components within a given compound. A linker can be hydrophilic (e.g., tetraethylene glycol, hexaethylene glycol, polyethylene glycol) or it can be hydrophobic (e.g., hexane, decane, etc.). Exemplary linkers include substituted or unsubstituted C6-C30 alkyl groups, polyols (e.g., glycerol), polyethers (e.g., poly(ethyleneglycol)), polyamines, amino acids (e.g., polyaminoacids), peptides, saccharides (e.g., polysaccharides) and combinations thereof. Such linkers typically comprise linear or branched chains, wherein the chain can be substituted at any suitable position, as desired, and wherein any carbon atom can be replaced by any suitable heteroatom. A linker can comprise one or more alkyl, heteroalkyl, cycloalkyl, cycloheteroalkyl, aryl, or heteroaryl groups, if so desired.

The nucleotide linker element, L, of structural formula (I) more specifically attaches the polyphosphate element of this structure to the multivalent central core element, if present, or directly to the terminal coupling element. In specific embodiments, the nucleotide linker element comprises a C6-C20 alkyl group, optionally comprising, e.g., an amide bond, an ether bond, a phenylene group, a triazole group, another coupling residue, or the like, in any combination. In addition, in the instant nucleotide compounds of structural formula (I), the nucleotide linker element comprises at least one affinity modulating element, which can be an aromatic spacer element, a shield element, or both an aromatic spacer element and a shield element.

As will be described in more detail below, the affinity modulating element of the instant nucleotide compounds can serve to enhance the interaction between a labeled nucleotide analog of the invention and a biomolecule, such as an enzyme or binding protein. The affinity modulating element can enhance the interaction through electrostatic, hydrophobic, steric, or other means. In an exemplary embodiment in which a labeled nucleotide analog, comprising a nucleotide compound with an affinity modulating element within the nucleotide linker element, is utilized in a single molecule nucleic acid sequencing technique, the affinity modulating element can, in particular, enhance the interaction between the nucleotide analog and the DNA polymerase, thereby lowering the $K_m$ or otherwise influencing the kinetics of the sequencing reaction to achieve optimized residence time of the analog on the polymerase or other desired behavior. In particular, and without intending to be bound by theory, it is believed that the affinity modulating element, preferably an aromatic spacer element, such as an anionic aromatic spacer element, and/or a shield element, interacts favorably with specific amino acid residues near the active site of the polymerase enzyme and that these interactions are responsible for the improved kinetic properties.

Accordingly, in some embodiments of the compounds of structural formula (I), the nucleotide linker element comprises an affinity modulating element, and in some of these compounds, the affinity modulating element is an aromatic spacer element or a shield element. In some embodiments, the aromatic spacer element is a substituted or unsubstituted monocyclic, bicyclic, tricyclic, or tetracyclic aromatic moiety.

In more specific embodiments, the aromatic spacer element is represented by structural formula (II):

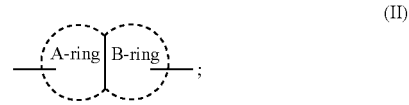

(II)

wherein
the A-ring and the B-ring is each independently an optionally substituted 5-7 atom cyclic structure, wherein at least one of the A-ring or the B-ring is aromatic; and
the A-ring or the B-ring optionally comprises at least one anionic substituent.

Even more specifically, the optional at least one anionic substituent is —SO₃H.

In other specific embodiments, the aromatic spacer element is represented by structural formula (IIA) or (IIB):

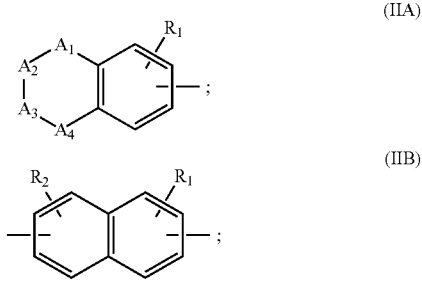

wherein
one of the $A_1$, $A_2$, $A_3$, and $A_4$ groups is

and the other groups are —CH₂— or a bond; and
$R_1$ is H or an anionic substituent and $R_2$ is H or an anionic substituent.

More specifically, the aromatic spacer element can be represented by structural formula (IIC) or (IIC'):

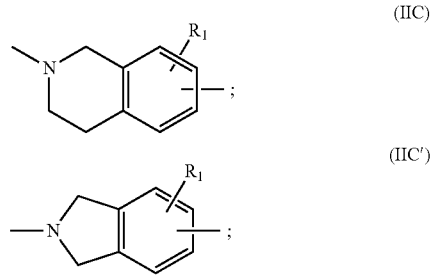

wherein
$R_1$ is H or an anionic substituent.

In some alternative embodiments, the aromatic spacer element can be represented by structural formula (IV):

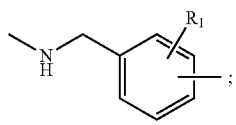
(IV)

wherein $R_1$ is H or an anionic substituent.

According to some more specific nucleotide compound embodiments, the at least one affinity modulating element is an anionic aromatic spacer element. Still more specifically, the anionic aromatic spacer element is a substituted bicyclic or tricyclic anionic aromatic moiety. Even more specifically, the anionic aromatic spacer element is represented by structural formula (II):

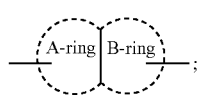
(II)

wherein the A-ring and the B-ring is each independently a 5-7 atom cyclic structure, wherein at least one of the A-ring or the B-ring is aromatic; and the A-ring or the B-ring comprises at least one anionic substituent. In some of these embodiments, the at least one anionic substituent is —SO$_3$H. In some of these embodiments, the anionic aromatic spacer element is represented by structural formula (IIA) or (IIB):

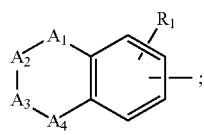
(IIA)

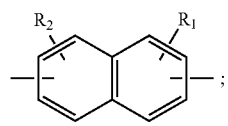
(IIB)

wherein one of the $A_1$, $A_2$, $A_3$, and $A_4$ groups is

and the other groups are —CH$_2$—; and $R_1$ is the at least one anionic substituent and $R_2$ is H or the at least one anionic substituent, including embodiments wherein the anionic substituent is —SO$_3$H. In some of these embodiments, the anionic aromatic spacer element is represented by structural formula (IIC):

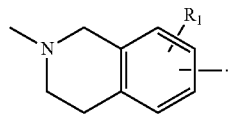
(IIC)

In some embodiments, the aromatic spacer element optionally comprises at least one anionic substituent or at least two anionic substituents. More specifically, the optional anionic substituent can be —SO$_3$H.

In some embodiments, the aromatic spacer element can be represented by one of the following structural formulae:

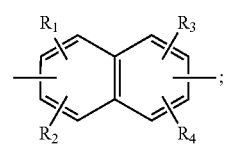
(IID)

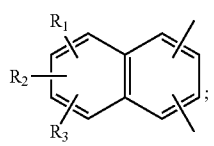
(IIE)

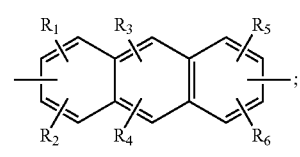
(IIF)

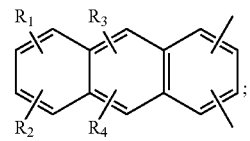
(IIG)

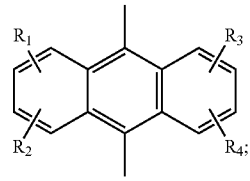
(IIH)

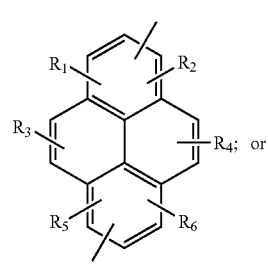
(IIJ) or

-continued
(IIK)
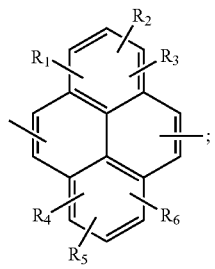
wherein
R₁, R₂, R₃, R₄, R₅, and R₆ are independently H or an anionic substituent.
In more specific embodiments, the aromatic spacer element can be represented by one of the following structural formulae:
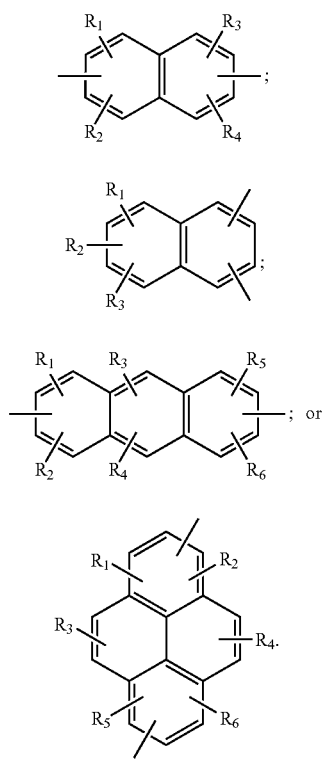
(IID)
(IIE)
(IIF) ; or
(IIJ)
Even more specifically, the aromatic spacer element can be represented by one of the following structural formulae:
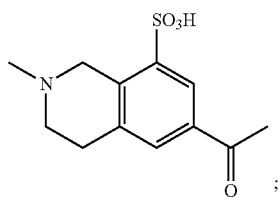
-continued
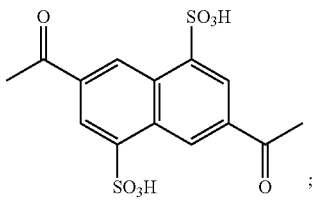
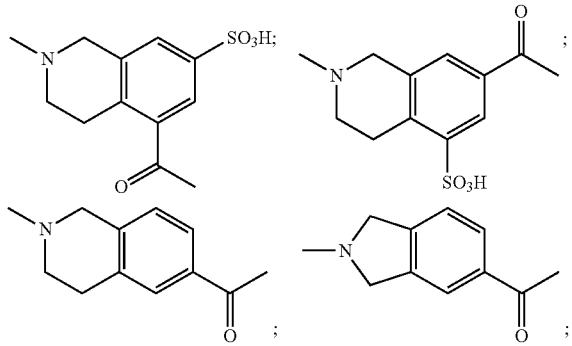
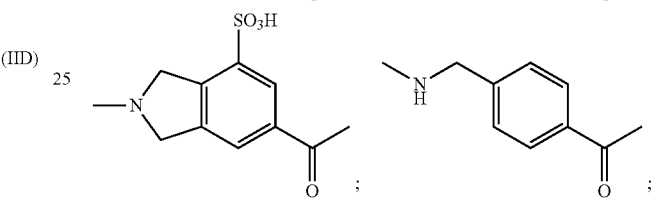
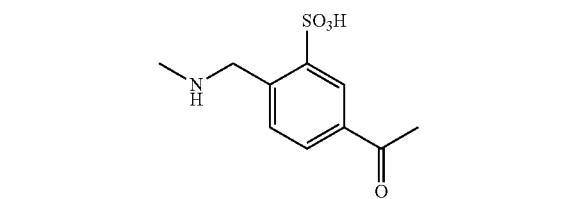
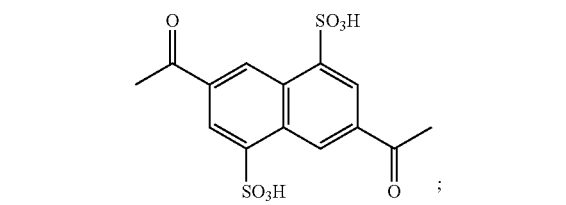
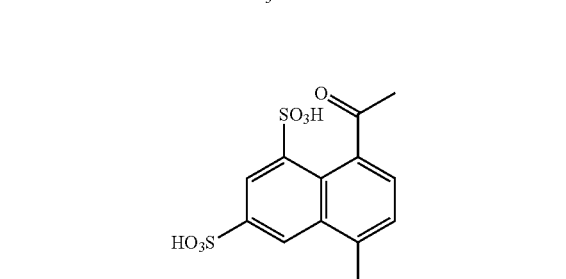
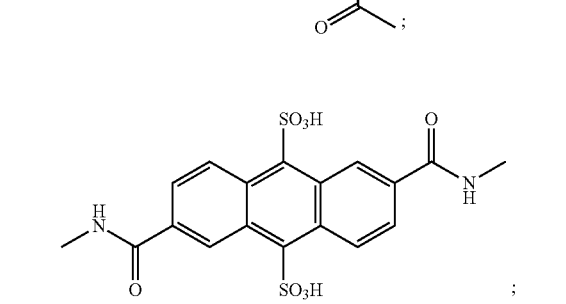

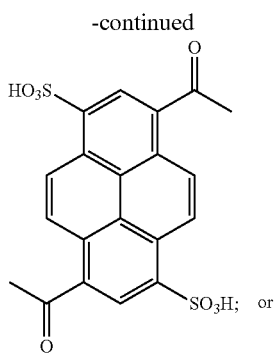

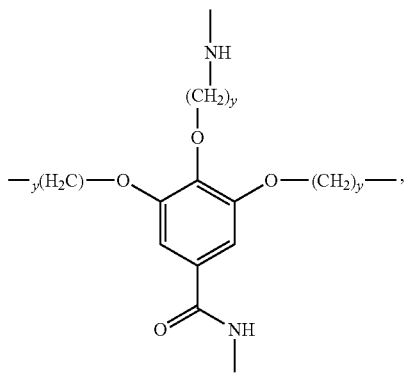

wherein each y is independently an integer from 1 to 6.

In some embodiments, the shield core elements provide a "layered" structure, where each linker element includes more than one shield element core. The side chains attached to the different shield element cores can optionally be different types of side chain, if desired. The use of different side chains in the different layers can provide for different microenvironments within the shield element. The different layers can, for example, comprise pairs of neutral or negatively charged groups, depending on the desired behavior and the intended use of the shielded compound.

Figure 20:
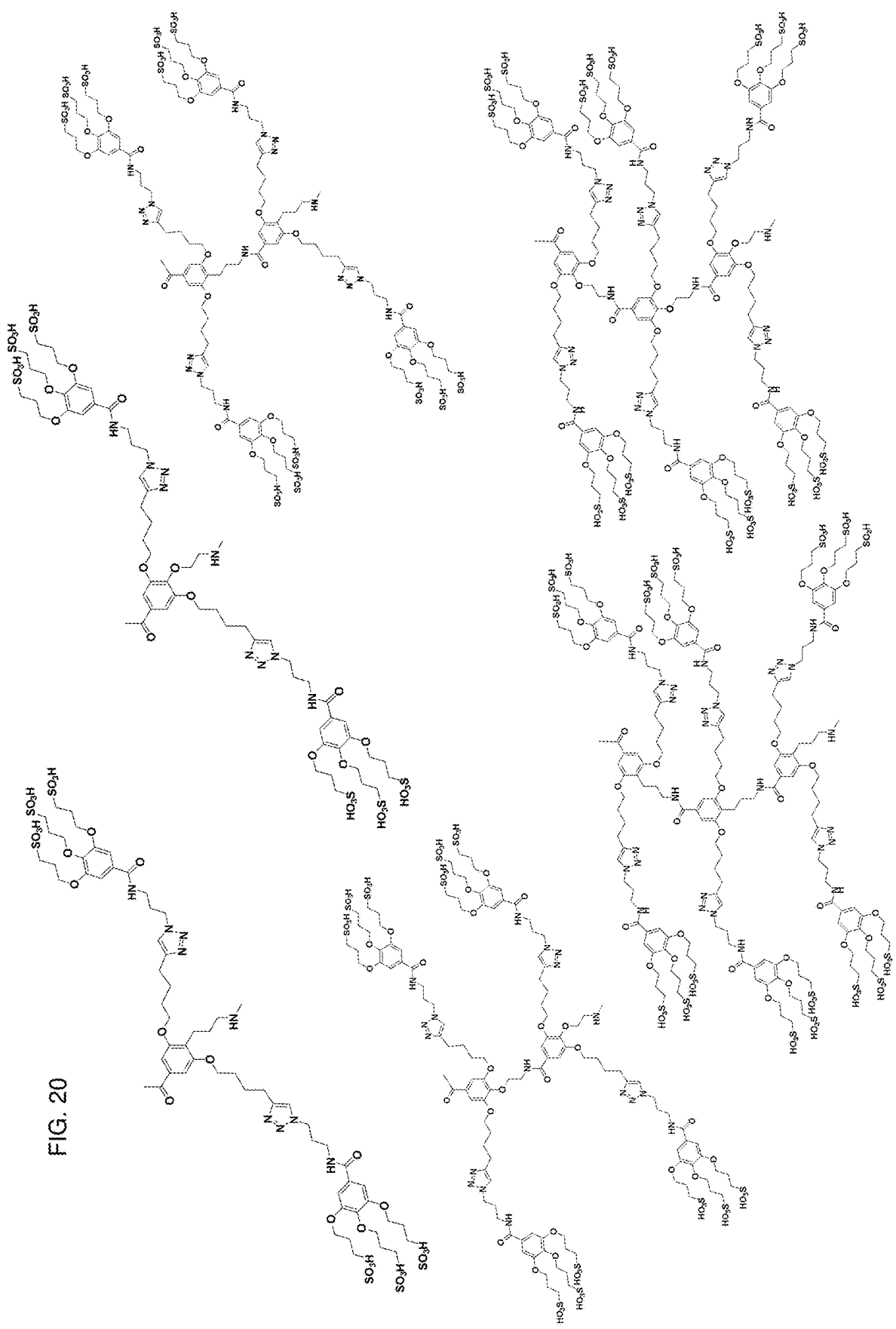
FIG. 20 illustrates shield element embodiments of the disclosure.

Exemplary shield elements usefully incorporated into the nucleotide compounds of the instant disclosure include the non-limiting structures illustrated in FIG. 20. It should be understood that these groups can be inserted within a nucleotide linker element, or other component of the nucleotide compound, in any orientation, as would be understood by those of ordinary skill in the art. The nucleotide linker element preferably further comprises a short alkyl or cycloalkyl group, such as, for example, a hexyl or cyclohexyl group, to link the shield element or elements to the rest of the structure, but other moieties can be suitably employed for this purpose. For example, the linker element can be chosen from any of the linkers described herein. The linker element can, in more specific embodiments, comprise a triazole.

In this regard, it should be understood that the shield elements are, in some embodiments, synthetically assembled into a nucleotide linker element using "click" reactions, or "copper-free click" reactions, as is described, for example in U.S. Patent Application Publication No. 2015/0050659 A1. The intermediate components are therefore preferably labeled with azide groups and acetylene groups that react with one another to form a triazole structure. It should also be understood, however, that other methods of attachment can be used to generate the instant analogs within the scope of the instant invention, as would be understood by those of ordinary skill in the art.

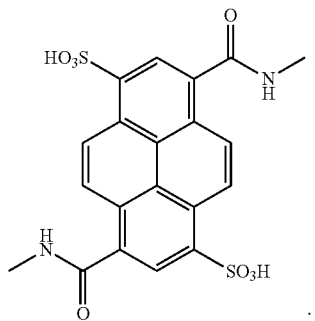

In some embodiments of compounds of structural formula (I), the nucleotide linker element comprises a shield element. As described above, a shield element can serve as an affinity modulating element in the instant nucleotide compounds, thus modulating the interactions between the nucleotide compound and an associated enzyme or binding protein. The exact structure of the shield element is not believed to be critical, so long as the structure is large enough to modulate contacts between the labeled analog and a protein, or other molecule of interest that binds to the analog. As disclosed herein, shield elements can lead to improved kinetic and/or other properties in nucleotide analogs containing these structures, in particular through their interactions with an enzyme, such DNA polymerase, or a binding protein. In the nucleotide compounds of structural formula (I) disclosed herein, the shield element does not comprise a protein.

In some embodiments, the shield element of the instant nucleotide compounds preferably comprises a shield core element that provides multivalent attachment sites for shield element side chains, where the shield element side chains provide the primary bulkiness or charge density of the shield element moiety and are thus believed to be responsible for the advantageous interactions with nucleotide-binding proteins.

Accordingly, the shield elements can in some embodiments comprise a suitable core structure that provides for the attachment of a plurality of side chains to the shield element core. In specific embodiments, the shield element comprises the structure:

Some shield element structures can include three, four, or even more "layers" of side chains, for example as shown in the following formulae:

-Sh($R_1$)$_2$-Sh($R_2$)$_2$-Sh($R_3$)$_2$—; and

-Sh($R_1$)$_2$-Sh($R_2$)$_2$-Sh($R_3$)$_2$-Sh($R_4$)$_2$;

where "Sh" is a shield core element, such as, for example,

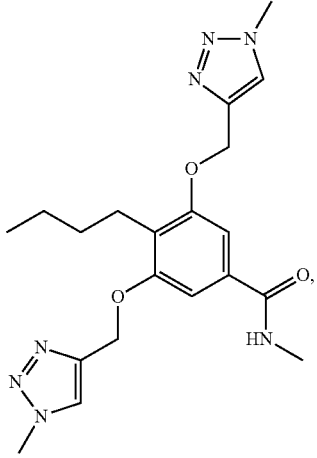

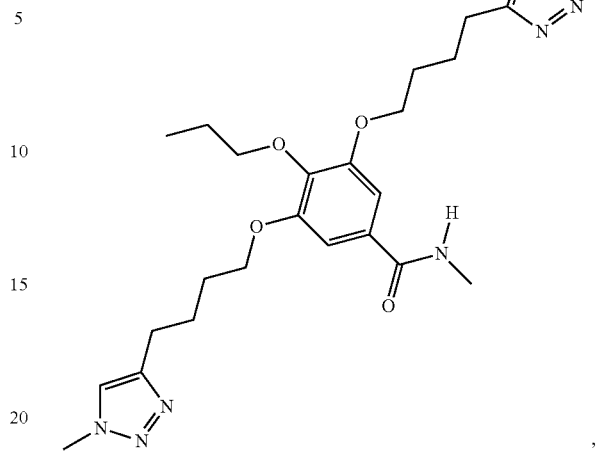

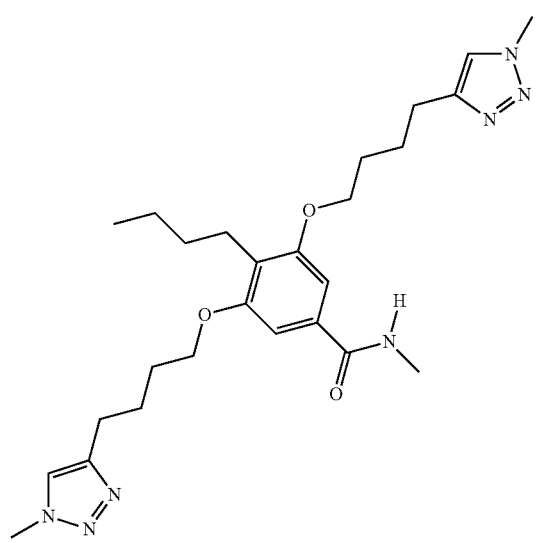

,

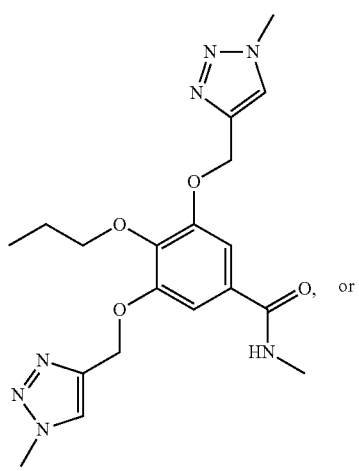

, or and "R$_1$", "R$_2$", "R$_3$", and "R$_4$" are side chains. It should be understood that the "R$_1$", "R$_2$", "R$_3$", and "R$_4$" side chain groups can be the same or different side chains, in any combination, as desired to achieve improved kinetic or other properties of the instant labeled nucleotide analogs. The shield element is attached to the linker element through the Sh group from either end of the shield element structure in these examples.

As is true of the shield elements generally, the exact structures of the side chain components of the shield elements are not believed to be critical, so long as they are large enough to provide the desired effects. In some embodiments, the side chains comprise polyethylene glycol (PEG). In specific embodiments, the polyethylene glycol side chains comprise polyethylene glycol with from 3 to 20 repeating ethylene oxide units. In more specific embodiments, the polyethylene glycol side chains comprise polyethylene glycol with from 4 to 10 repeating ethylene oxide units. In some embodiments, the side chains comprise a negatively-charged component, such as, for example, a component comprising a sulfonic acid. In some embodiments, the side chains comprise a combination of polyethylene glycol and another component, such as, for example a negatively-charged component.

The side chains can additionally comprise a core structure that provides for branching within the side chains. In some embodiments, the side chain comprises a substituted phenyl group. In specific embodiments, the side chain comprises the structure:

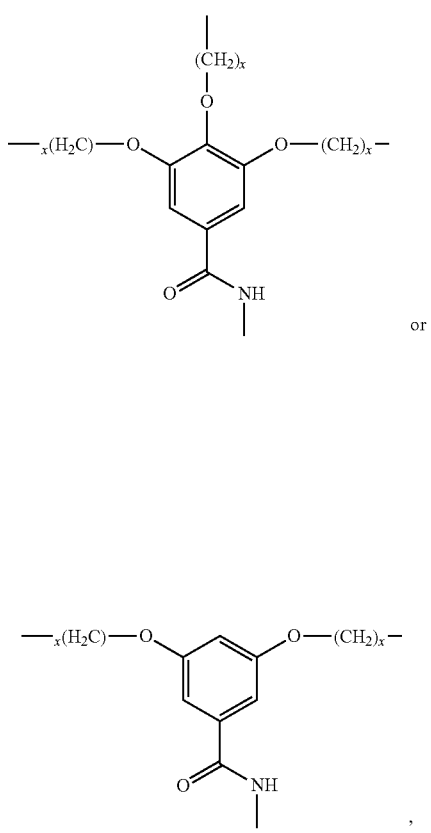

wherein each x is independently an integer from 1 to 6. In more specific embodiments, each x is independently an integer from 1 to 4.

The side chain can, in some embodiments, comprise a dendrimer. A dendrimer (or "dendron") is a repetitively branched molecule that is typically symmetric around the core and that can adopt a spherical three-dimensional morphology. See, e.g., Astruc et al. (2010) *Chem. Rev.* 110:1857. Incorporation of such structures into the shield elements of the instant compounds provides for advantageous properties through the modulation of contacts between the labeled nucleotide analog and one or more biomolecules associated with the nucleotide analog. Refinement of the chemical and physical properties of the dendrimer through variation in primary structure of the molecule, including potential functionalization of the dendrimer surface, allows the functional properties of the nucleotide analog to be adjusted as desired. Dendrimers can be synthesized by a variety of techniques using a wide range of materials and branching reactions, including those described below, as is well-known in the art.

Figure 21:
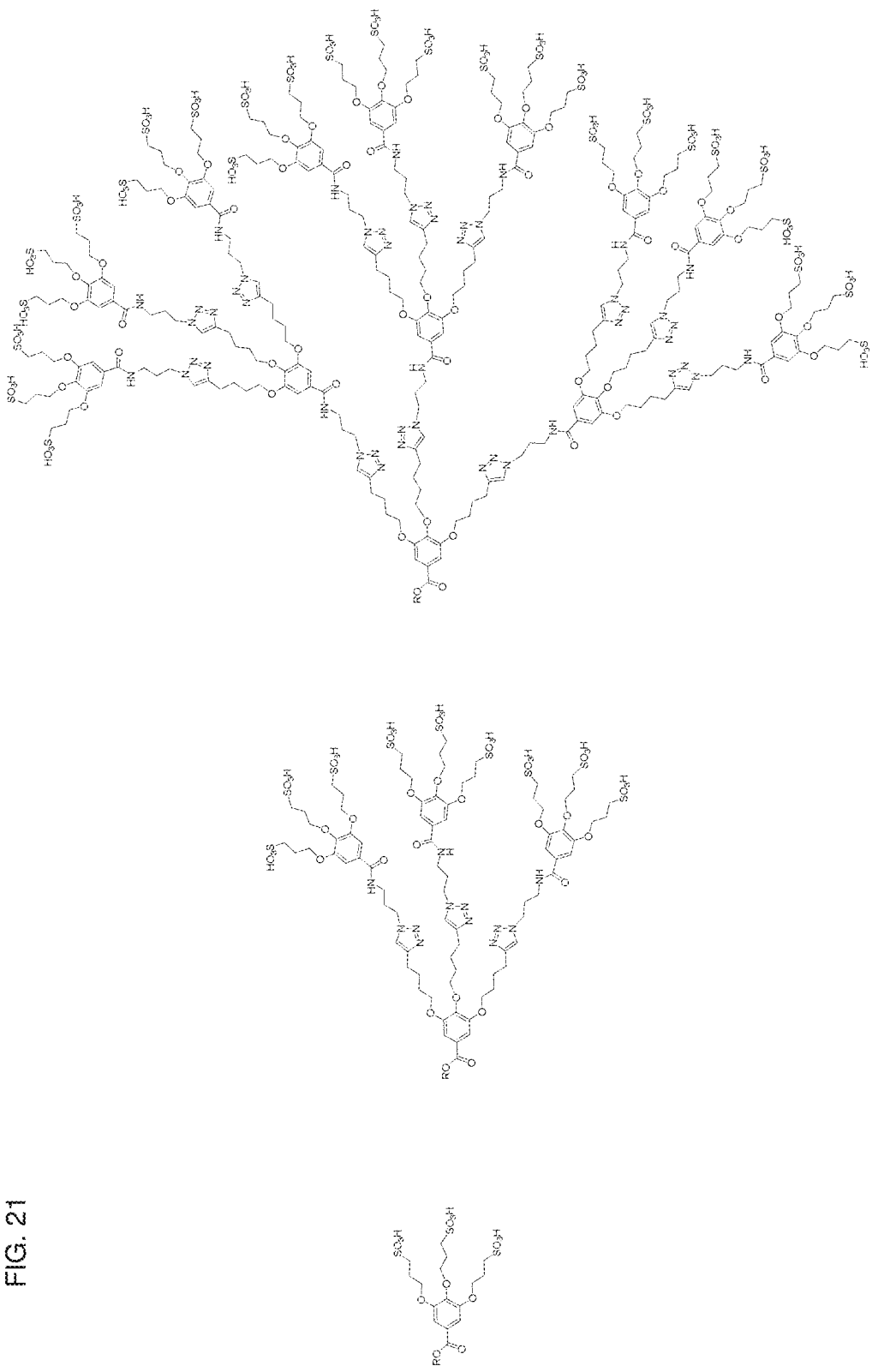
FIG. 21 illustrates exemplary dendrimer structures of the disclosure.

Exemplary dendrimer structures usefully incorporated into the side chains of the instant molecules include the structures illustrated in FIG. 21. The structural and functional properties of the dendrimer sidechains used in the instant compounds can be tuned by, for example, variation in (a) chain lengths and types, (b) position and degree of branching, and (c) end group presentations (neutral or charged, hydrophobic or hydrophilic groups, etc.).

In some embodiments, at least one side chain comprises a peptide chain.

In some embodiments, at least one side chain comprises a polysaccharide.

Non-limiting side chain examples include the following structures:

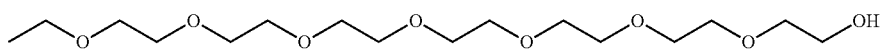 [SMILES: CCOCCOCCOCCOCCOCCOCCOCCO]

Figure 22:
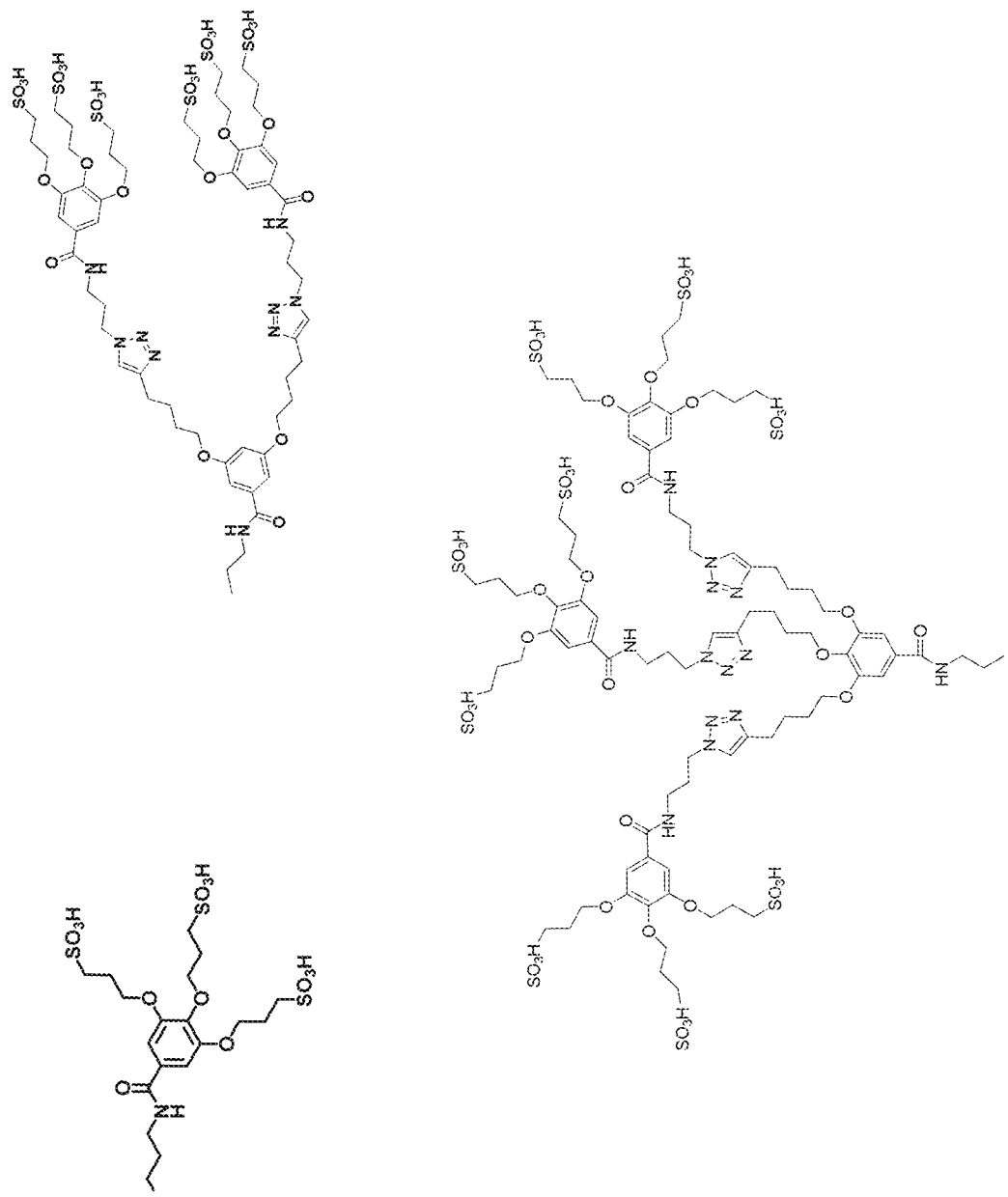
FIG. 22 illustrates exemplary side chains of the disclosure.

(corresponding to PEG7) and polyethylene glycols with other numbers of repeating unit; and the structures illustrated in FIG. 22. Some side chain embodiments can include combinations of any of the above components, such as, for example, the following combination of a polyethylene and a negatively-charged side chain:

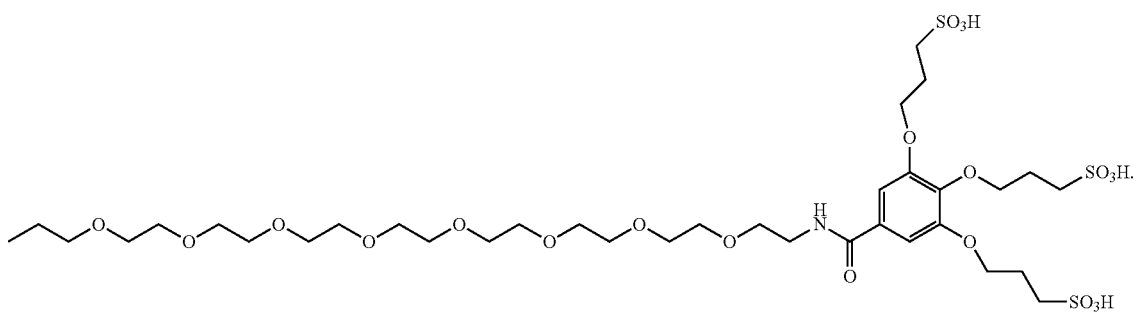

In some embodiments, the molecular weight of the side chain is at least 300, 350, 400, 450, or even higher. In preferred embodiments, the molecular weight of the side chain is at least 300.

In preferred embodiments of the compounds of structural formula (I), the nucleotide linker element comprises both an anionic aromatic spacer element and a shield element, where these elements have the definitions provided herein.

The polyphosphate element of structural formula (I) comprises a pyrophosphate or a higher homologue of phosphate, such as a 3-mer, 4-mer, 5-mer, 6-mer, 7-mer, 8-mer, or the like. The polyphosphate element thus generally comprises from 2 to 10 phosphates. In preferred embodiments, the polyphosphate element comprises 4, 5, 6, 7, or 8 phosphates. In some embodiments, a methylene moiety, NH moiety, or S moiety can bridge two or more of the phosphorus atoms, replacing the POP link with a PCH$_2$P link, a PNHP link, a PSP link, or the like. The polyphosphate element can be further modified if desired, for example by substitution of any of the other oxygen atoms with carbon or another heteroatom or by alkylation or other similar modification of any of the non-bridging oxygens.

The nucleotide compounds of the instant disclosure further comprise one or more nucleoside elements. As previously described, the nucleoside element is responsible for recognition of the analog by an enzyme, such as DNA polymerase, during an enzymatic reaction, such as a sequencing reaction. As is known in the art, nucleosides contain nucleobases. In addition to the naturally occurring nucleobases of ribonucleic acids and deoxyribonucleic acids, i.e., adenine, cytosine, guanine, thymine, and uracil, the nucleotide compounds and analogs of the invention can optionally include modified bases. For example, the nucleoside elements described herein can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-d-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

Typically, the nucleoside elements described herein can comprise either ribose or deoxyribose. In some embodiments, the nucleoside elements can comprise a modified sugar moiety selected from the group including, but not limited to, arabinose, 2-fluoroarabinose, xylulose, and hexose.

The nucleoside elements of the instant nucleotide compounds and analogs preferably comprise adenosine, guanosine, thymidine, uridine, or cytidine, and are preferably deoxyribose nucleosides, e.g., dA, dG, dT, or dC.

The multivalent central core element of structural formula (I) is an optional component of the structure that enables a plurality of polyphosphate elements and nucleoside elements to be attached to the nucleotide compound. As is clear from the structure of formula (I), the multivalent central core element, when present, also serves as an attachment site for the terminal coupling element.

In some embodiments, the multivalent central core element comprises a polyamine moiety. Polyamines can be readily reacted with appropriate electrophilic reagents, such as electrophilic nucleotide linker elements, and the like, to generate nucleotide compounds or their intermediates. It should be understood that the order of such reactions can be varied, depending on the desired outcome, as would be understood by those of ordinary skill in the art. Non-limiting examples of polyamines usefully employed in the multivalent central core elements of the instant disclosure include the following:

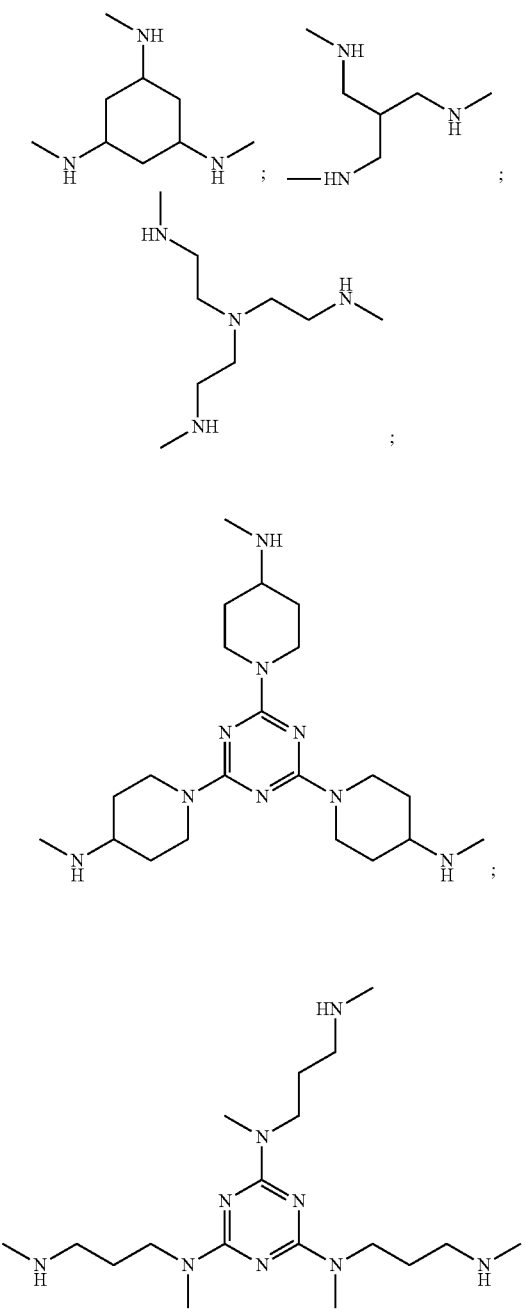

-continued

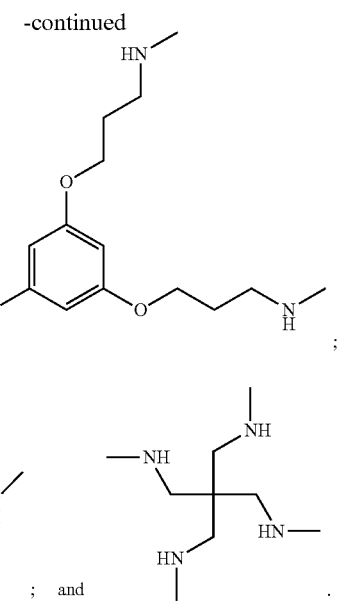
; and

The skilled artisan would understand, however, that other polyamines can be readily utilized in the nucleotide compounds of the instant disclosure.

In specific embodiments, the multivalent central core element comprises a substituted cyclohexane, more specifically a 1,3,5-triamino-cyclohexane.

In other specific embodiments, the multivalent central core element comprises a substituted 1,3,5-triazine.

In still other specific embodiments, the multivalent central core element comprises a substituted benzene.

In some embodiments the multivalent central core element comprises an ether linkage. In some embodiments, the multivalent central core element comprises an acyl linkage. Examples of such ether and acyl-linked central core elements include the following structures:

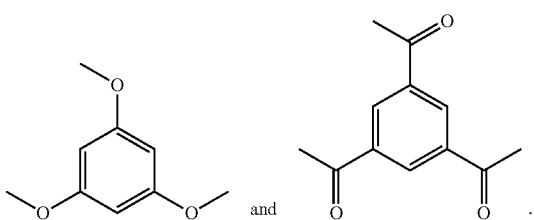

These structures can be incorporated into the instant nucleotide compounds as described in detail below and in U.S. Patent Application Publication No. 2015/0050659 A1. In particular, ether-linked central core elements can be modified with acetylene-containing groups, including cycloalkyne-containing groups, and the acetylene groups can then be coupled to azide-containing reagents using "click" chemistry or "copper-free click" chemistry. Likewise, carboxylate-containing central core elements can be activated using suitable reagents, and the activated acyl groups can then be coupled to appropriate nucleophilic reagents as desired. Alternatively, or in addition, the central core elements can be activated using azide-containing groups, and those groups can be coupled to acetylene-containing reagents, including cycloalkyne-containing reagents, using "click" chemistry or "copper-free click" chemistry. Such reactions are well understood by those of ordinary skill in the art.

The nucleotide compounds of structural formula (I) still further comprise a terminal coupling element. In some embodiments, the terminal coupling element comprises biotin. As is well known in the art, biotin is bound with high affinity by avidin proteins such as avidin, streptavidin, and the like. In preferred embodiments, the terminal coupling element comprises bis-biotin. The linker coupling the two biotin moieties in a bis-biotin terminal coupling element can be any suitable linker, including the linkers described above. The linker preferably includes a multivalent central core element, such as the structures described above, both to couple the two biotin moieties to one another and to serve as an attachment point for the terminal coupling element to the rest of the nucleotide compound.

Figure 23:
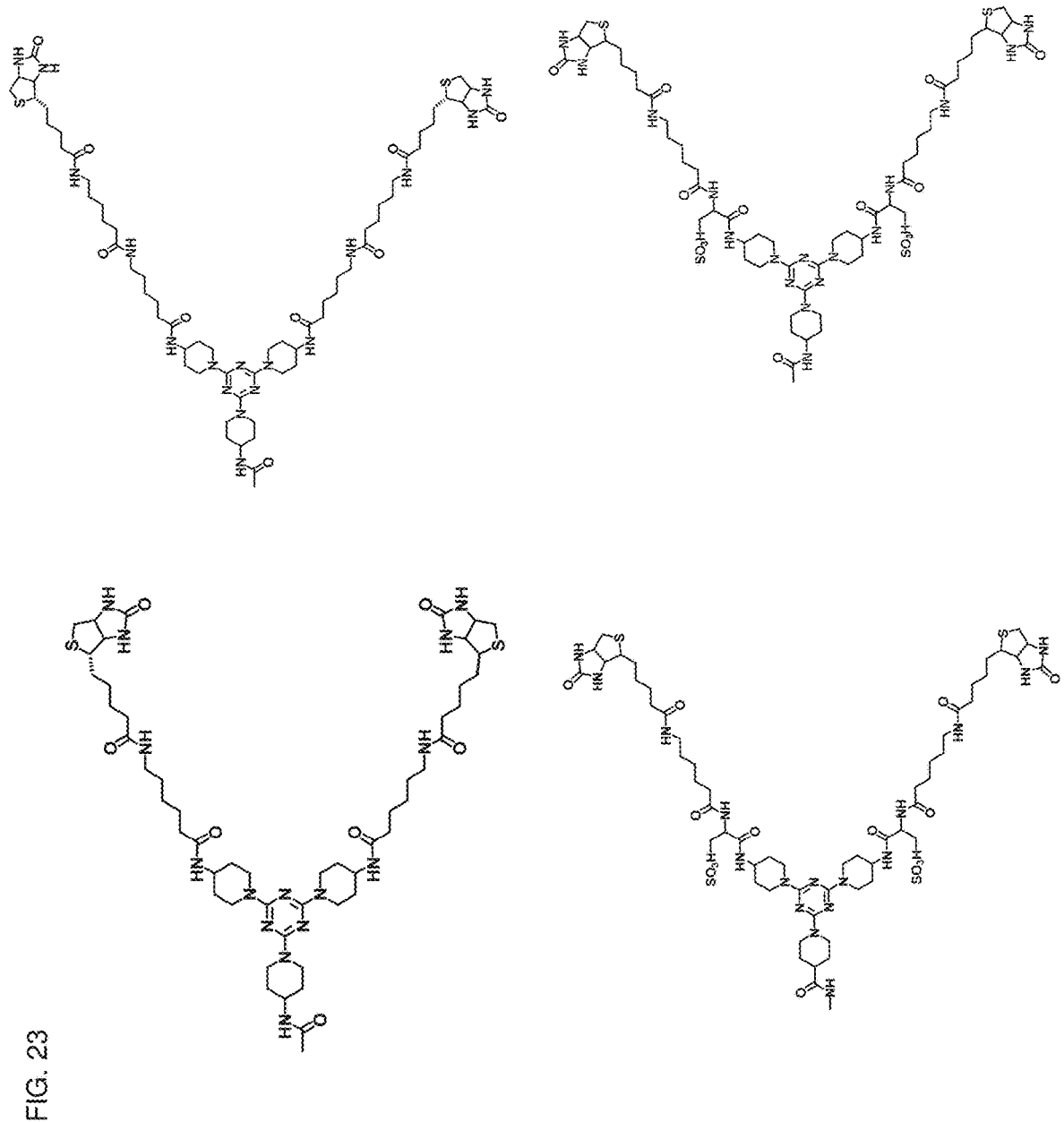
FIG. 23 illustrates exemplary terminal coupling elements comprising bis-biotin.

Exemplary terminal coupling elements comprising bis-biotin include the structures illustrated in FIG. 23.

In embodiments of the nucleotide compounds of structural formula (I), n is an integer from 1 to 4, and o is 0 or 1. As should be clear from the structure, when n is 1, a multivalent central core element need not be included, so o is preferably 0. In addition, it should be understood that when n is 2 to 4, a multivalent central core element is preferably included in the compound, so o should be 1. In specific embodiments, n is 2 and o is 1. In other specific embodiments, n is 1 and o is 0.

In preferred embodiments, the nucleotide compounds of the instant disclosure, whether comprising an aromatic spacer element, a shield element, or both an aromatic spacer element and a shield element as the affinity modulating element, do not contain a fluorescent dye or any other directly detectable label.

As should be understood from the instant disclosure, the terminal coupling element of the nucleotide compounds of structural formula (I) typically mediates association of the nucleotide compound with other components of the instant labeled nucleotide analogs. For example, and as will be described in detail below, where the terminal coupling element is a biotin or bis-biotin, the nucleotide compound can associate non-covalently with an avidin protein with high affinity. In some aspects, the disclosure thus further provides compositions comprising a nucleotide compound of structural formula (I) and an avidin protein. In these compositions, it should be understood that the terminal coupling element is not covalently modified by the association of the nucleotide compound with the avidin protein shield, and the composition thus distinctly comprises the original nucleotide compound and the avidin protein shield as separate molecular entities.

In another aspect of the disclosure, however, it should be contemplated that the terminal coupling element of a nucleotide compound may comprise a reactive functional group that can be covalently bound to a complementary reactive group on a second component, for example on an appropriately modified linker element, shield element, or dye-labeled compound. Unlike the just-described non-covalent compositions, such reactions generate a new molecular entity connected by a residue derived from the reactive group of each component. As described elsewhere in the specification, such residues can comprise, for example, an amide moiety derived from an amine group and an appropriately activated carboxyl group or a residue resulting from a click reaction.

In yet another aspect of the disclosure are provided methods of synthesis of the instant nucleotide compounds, including nucleotide compounds of structural formula (I), and their intermediates. Such methods can comprise the step of reacting any of the intermediate compounds illustrated throughout the specification with a second intermediate compound to generate a nucleotide compound or intermediate of the invention. Exemplary synthetic pathways are illustrated in the reaction schemes below, in the Examples, and in the accompanying drawings.

Dye-Labeled Compounds

In yet another aspect, the disclosure provides dye-labeled compounds for use in generating the instant labeled nucleotide analogs.

In embodiments according to this aspect of the disclosure, the dye-labeled compound comprises:
 a donor dye;
 an acceptor dye;
 a shield element;
 a terminal coupling element; and
 a dye compound linker element;
wherein the dye compound linker element covalently connects the terminal coupling element to the donor dye, the acceptor dye, or the shield element.

In specific embodiments, the acceptor dye or the donor dye is directly coupled to the shield element.

In other embodiments, the dye-labeled compound is a compound of structural formula (IIIA), (IIIB), (IIIC), (IIID), or (IIIE):

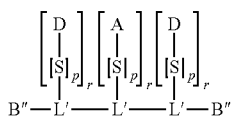

(IIIA)

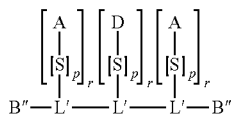

(IIIB)

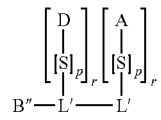

(IIIC)

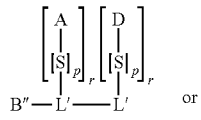

(IIID)

or

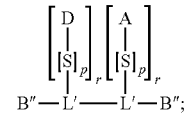

(IIIE)

wherein
 each L' is independently a dye compound linker element;
 each S is independently a shield element;
 each A is independently an acceptor dye;
 each D is independently a donor dye;
 each B" is independently a terminal coupling element;
 each p is independently 0 or 1; and
 each r is independently an integer from 0 to 8;
wherein the compound comprises at least one shield element, at least one acceptor dye, and at least one donor dye.

In specific embodiments, the at least one acceptor dye or the at least one donor dye is directly coupled to the at least one shield element.

In other specific embodiments, each r is independently an integer from 0 to 4.

In even more specific embodiments of the compounds of structural formula (IIIA), (IIIB), (IIIC), (IIID), and (IIIE), each r is independently 1 or 2.

In any of the dye-labeled compound embodiments it should be understood that the compounds can comprise more than one donor dye, more than one acceptor dye, and/or more than one shield element. In specific embodiments, the compound comprises at least two donor dyes, and in some of those embodiments each donor dye is directly coupled to a donor shield element. More specifically, the compound can comprise at least four donor dyes, and in some of those embodiments each donor dye is directly coupled to a donor shield element. Even more specifically, the compound can comprise at least six donor dyes, at least eight donor dyes, at least ten donor dyes, or even at least twelve donor dyes. In some of these embodiments, each donor dye can be directly coupled to a donor shield element.

In some specific embodiments, the compound comprises at least two acceptor dyes, and in some of those embodiments each acceptor dye is directly coupled to an acceptor shield element. More specifically, the compound can comprise at least four acceptor dyes, and in some of those embodiments each acceptor dye can be directly coupled to an acceptor shield element.

In some embodiments, the compound comprises at least two donor dyes and at least two acceptor dyes. In more specific embodiments, each donor dye can be directly coupled to a donor shield element and/or each acceptor dye can be directly coupled to an acceptor shield element. In some embodiments, the compound comprises at least four donor dyes and at least two acceptor dyes, at least six donor dyes and at least two acceptor dyes, at least eight donor dyes and at least two acceptor dyes, at least ten donor dyes and at least two acceptor dyes, or even at least twelve donor dyes and at least two acceptor dyes.

In some embodiments, the compound further comprises a shield element or a side chain element attached to one or more dye compound linker elements without also being attached to a donor or acceptor dye. In particular, the shield element or side chain element can be attached where two dye compound linker elements are coupled, thus positioning the shield element or side chain element between different dye groups attached to different dye compound linker elements.

In still other embodiments, the dye-labeled compound is a compound of structural formula (IIIF):

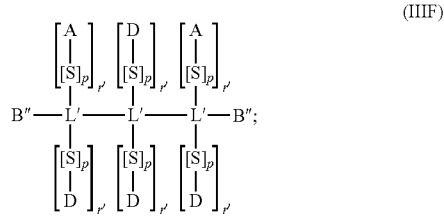

(IIIF)

wherein
 each L' is independently a dye compound linker element;
 each S is independently a shield element;
 each A is independently an acceptor dye;
 each D is independently a donor dye;
 each B" is independently a terminal coupling element;
 each p is independently 0 or 1; and
 each r' is independently an integer from 0 to 4;

wherein the compound comprises at least one shield element, at least one acceptor dye, and at least one donor dye.

In more specific embodiments of the compound of structural formula (IIIF), each r' is independently an integer from 0 to 2.

In more specific embodiments of the compound of structural formula (IIIF), each r' is independently 0 or 1.

In yet other embodiments, the dye-labeled compound is a compound of structural formula (IIIG):

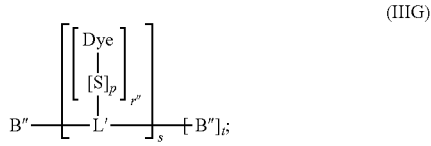

(IIIG)

wherein
each L' is independently a dye compound linker element;
each S is independently a shield element;
each Dye is independently either an acceptor dye or a donor dye;
each B" is independently a terminal coupling element;
each p is independently 0 or 1;
each r" is independently an integer from 0 to 8;
s is an integer from 1 to 6; and
t is 0 or 1;
wherein the compound comprises at least one shield element, at least one acceptor dye, and at least one donor dye.

In more specific embodiments of the compound of structural formula (IIIG), each r" is independently an integer from 0 to 4 or from 0 to 2.

In other more specific embodiments of the compound of structural formula (IIIG), each r" is independently 0 or 1.

In some embodiments of the compound of structural formula (IIIG), s is an integer from 1 to 4.

In some embodiments of the compound of structural formula (IIIG), the compound comprises at least two donor dyes, at least four donor dyes, at least six donor dyes, at least eight donor dyes, at least ten donor dyes, or at least twelve donor dyes. In other more specific embodiments of the compound of structural formula (IIIG), the compound comprises at least two acceptor dyes or at least four acceptor dyes. In still other more specific embodiments of the compound of structural formula (IIIG), the compound further comprises at least two shield elements, at least four shield elements, or even more shield elements. In some of these embodiments, the shield elements are directly coupled to a donor dye or an acceptor dye.

By "directly coupled" it should be understood that the donor or acceptor dye and the shield element are covalently attached to one another with no intervening functional components. The direct coupling can include, however, short linker groups, for example amide bonds, ether linkages, short alkyl chains, and the like, that do not significantly separate the shield element from the dye.

The donor dye and the acceptor dye of the instant dye-labeled compounds are preferably chromophores that are capable of resonance energy transfer between one another. In this regard, a pair of dyes are considered donor and acceptor dyes when the donor dye in an electronically excited state can transfer energy to the acceptor dye through a radiative or non-radiative energy transfer process. For example, processes in which a photon is emitted and those involving long-range electron transfer are included within the meaning of resonance energy transfer. Resonance energy transfer typically arises when the distance between the donor dye and the acceptor dye is small, when the emission spectrum of the donor dye and the excitation spectrum of the acceptor dye overlap sufficiently, and when the dipole moments of the donor emission and acceptor excitation are relatively aligned with one another. Examples of FRET-labeled nucleotides and donor-acceptor pairing are provided in U.S. Patent Application Publication Nos. 2010/0255488 and 2012/0058469, the full disclosures of which are hereby incorporated by reference herein in their entirety for all purposes.

The donor dye and the acceptor dye of the instant dye-labeled compounds are preferably fluorescent dyes. The dyes preferably have excitation and emission spectra in the visible region of the electromagnetic spectrum, although the dyes can in some embodiments have excitation and emission spectra in the infrared range. Any of the dyes set forth herein can be a component of a FRET pair as either the donor or acceptor. Conjugating a donor dye and an acceptor dye through reactive functional groups on the donor dye, the acceptor dye, and any necessary shield elements and/or dye compound linker elements, is well within the abilities of those of skill in the art in view of the instant disclosure.

A wide variety of fluorophores are readily available and applicable to the dye-labeled compounds of the invention and include fluorescein, or rhodamine based dyes, cyanine dyes and the like. A variety of such dyes are commercially available and include the Cy dyes available from GE Healthcare (Piscataway, N.J.), such as Cy3, Cy5, and the like, or the Alexa family of dyes available from Thermo Fisher Scientific Inc., such as Alexa 488, 500, 514, 532, 546, 555, 568, 594, 610, 633, 647, 660, 680, 700, and 750. These fluorophores can be present as individual fluorophores or they can be present in interactive pairs or groups, e.g., as fluorescent resonant energy transfer (FRET) pairs.

In preferred embodiments, the fluorescent dye is a cyanine dye, for example any of the cyanine dyes disclosed in PCT International Publication No. 2012/027618; U.S. Patent Application Publication No. 2012/0058469; U.S. Patent Application Publication No. 2012/0058482; and U.S. Patent Application Publication No. 2012/0052506; the disclosures of each of which are incorporated herein by reference in their entireties for all purposes. Additional long-wavelength heteroarylcyanine dyes usefully incorporated into the instant dye-labeled compounds are disclosed in U.S. Patent Application Publication No. 2014/0005404 A1, the full disclosure of which is hereby incorporated by reference herein for all purposes.

The term "cyanine", as used herein, thus refers to polymethine dyes such as those based upon the cyanine, merocyanine, styryl and oxonol ring. Cyanine dyes include, for example, CY3, CY3.5, CY5 and CY5.5 type dyes.

Exemplary cyanine dyes have the formula:

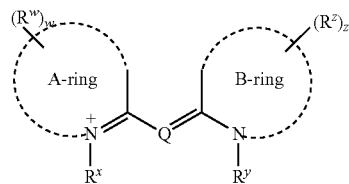

wherein the A-ring and B-ring are independently selected from monocyclic, bicyclic or polycyclic aryl or heteroaryl moieties. Q is a substituted or unsubstituted methine moiety (e.g., —(CH=C($R^u$))$_c$—CH=), in which c is an integer selected from 1, 2, 3, 4, or 5. Each $R^u$, $R^w$, $R^x$, $R^y$ and $R^z$ is independently selected from various suitable substituents, and the indices w and z are independently selected from the integers from 0 to 6.

In some embodiments, each $R^w$ and $R^z$ is independently a substituted or unsubstituted alkyl, heteroalkyl, aryl, or heteroaryl group that is coupled to the A-ring or B-ring either directly or through a carbonyl, amide, carbamide, ester, thioester, ether, thioether, or amino linkage.

In some embodiments, each $R^x$ and $R^y$, is independently an alkyl or heteroalkyl group, optionally substituted with a sulfonic acid, carboxylic acid, phosphonic acid, or phosphoric acid.

In some embodiments, each $R^u$ is independently hydrogen, alkyl, or heteroalkyl.

Specific embodiments are described more thoroughly in the above-listed patent publications. Among the dyes usefully included in the dye-labeled compounds of the instant disclosure are the dyes shown in Table 1.

TABLE 1

Exemplary fluorescent dyes.

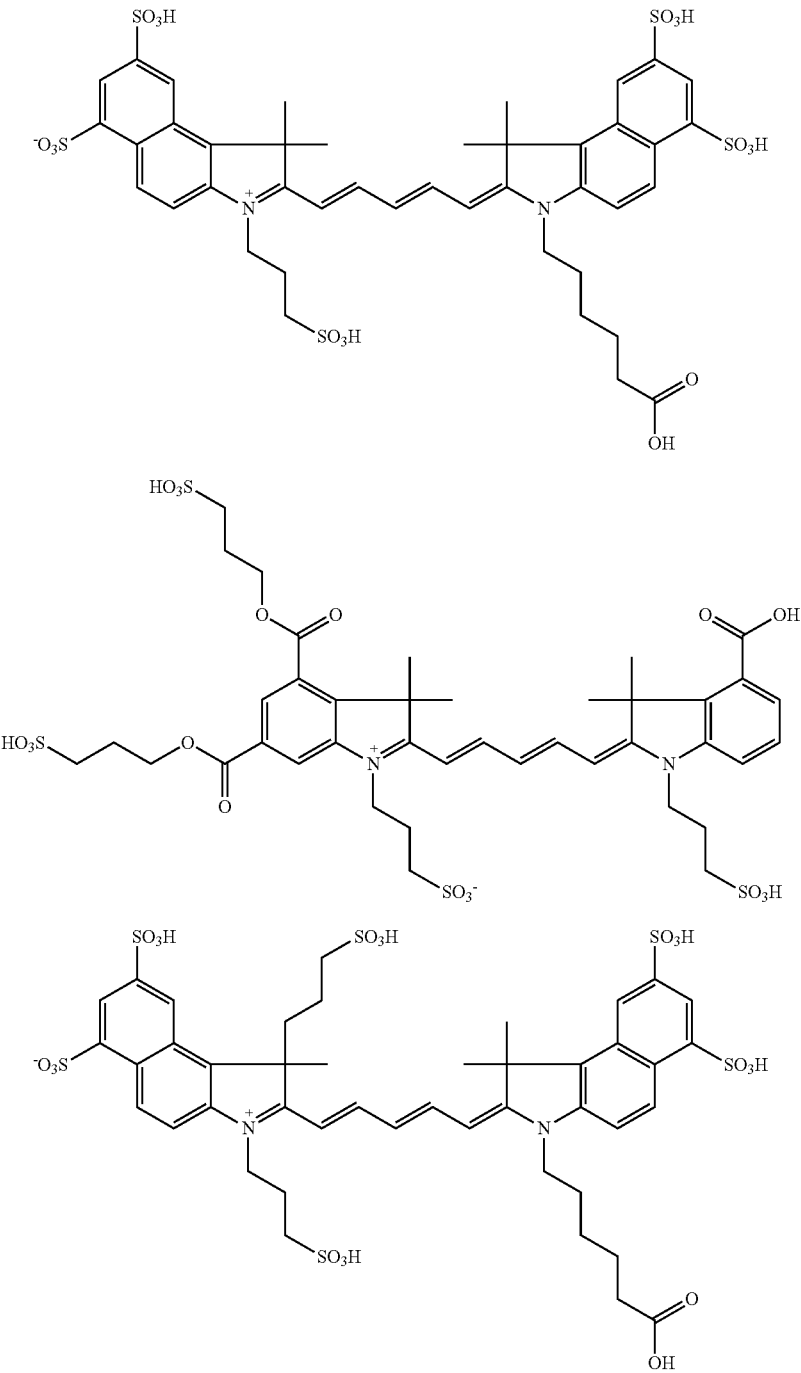

TABLE 1-continued
Exemplary fluorescent dyes.
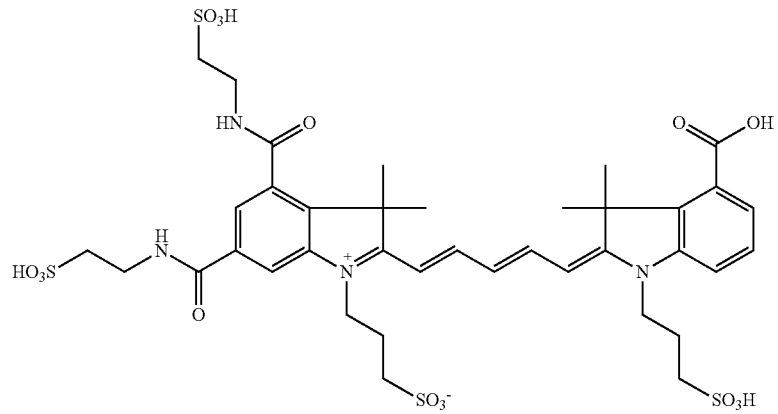
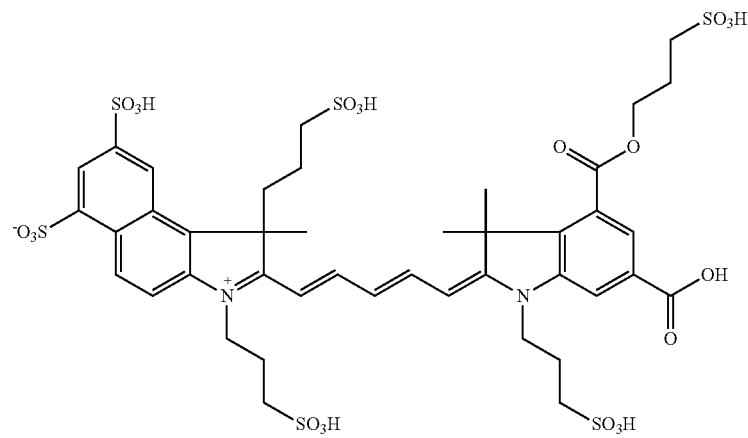
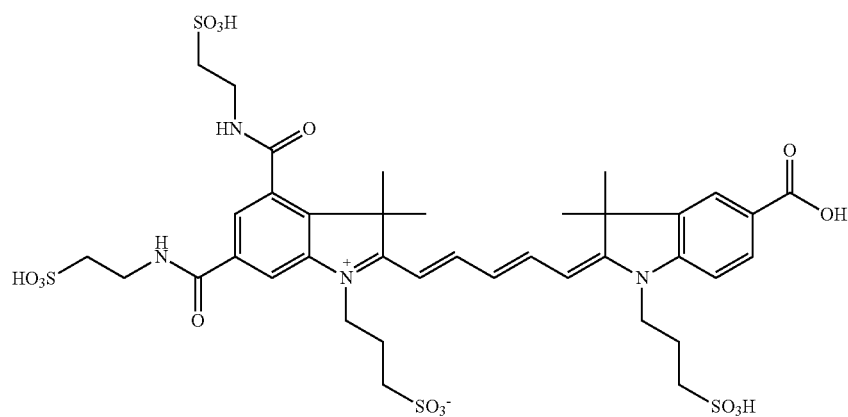

TABLE 1-continued
Exemplary fluorescent dyes.
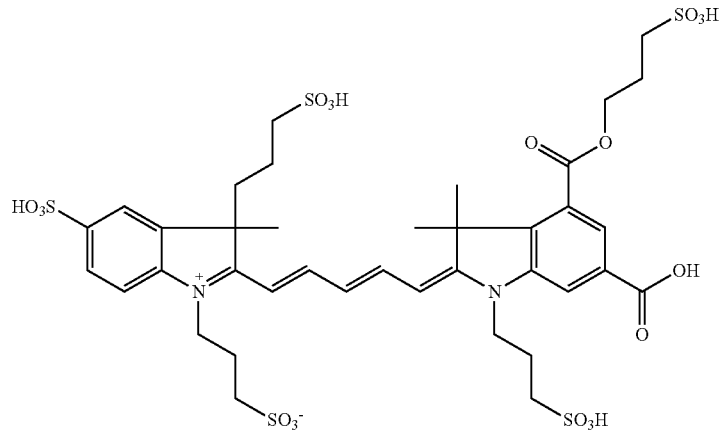
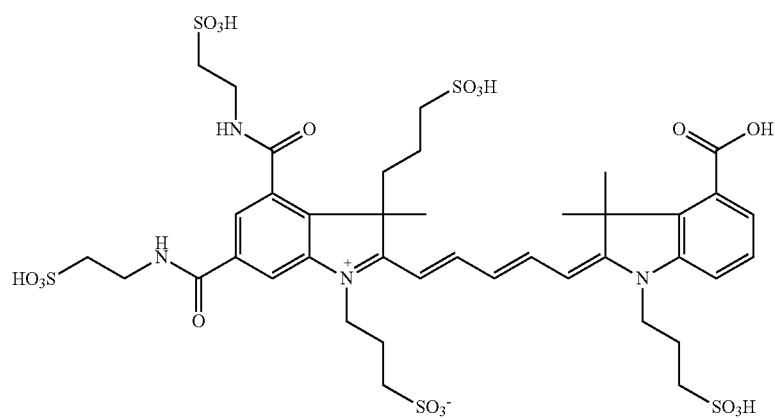
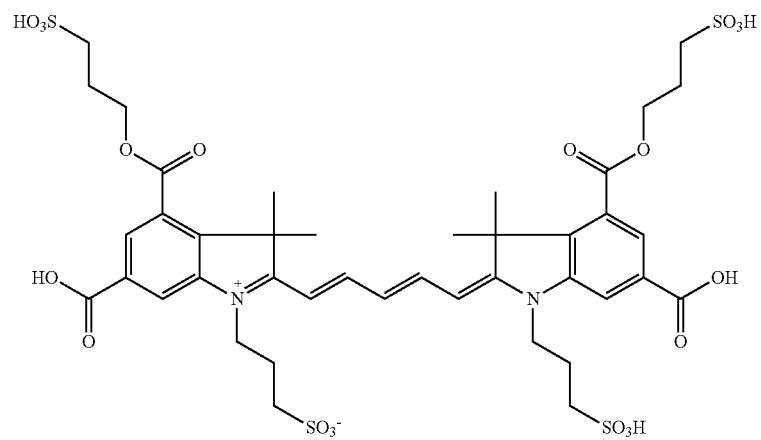

TABLE 1-continued
Exemplary fluorescent dyes.
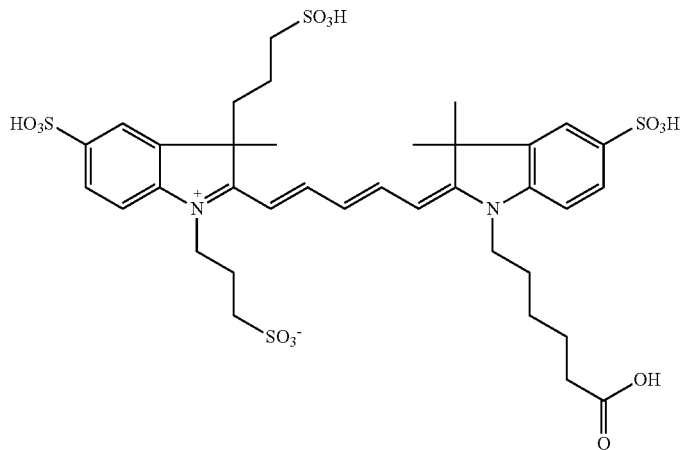
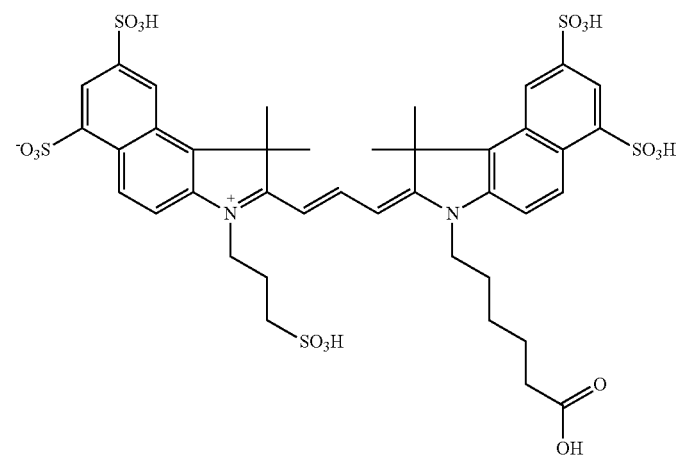
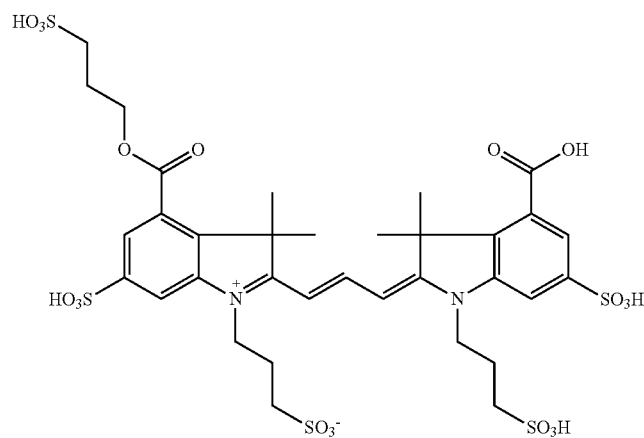

TABLE 1-continued
Exemplary fluorescent dyes.
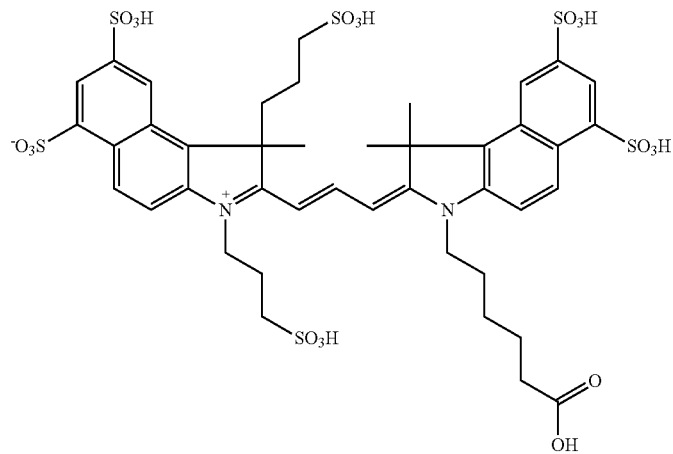
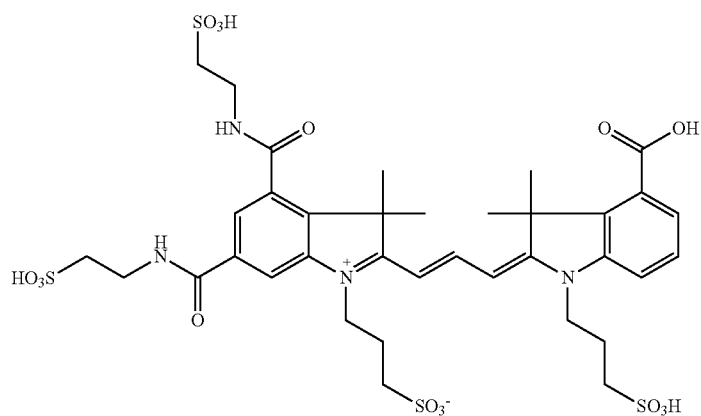
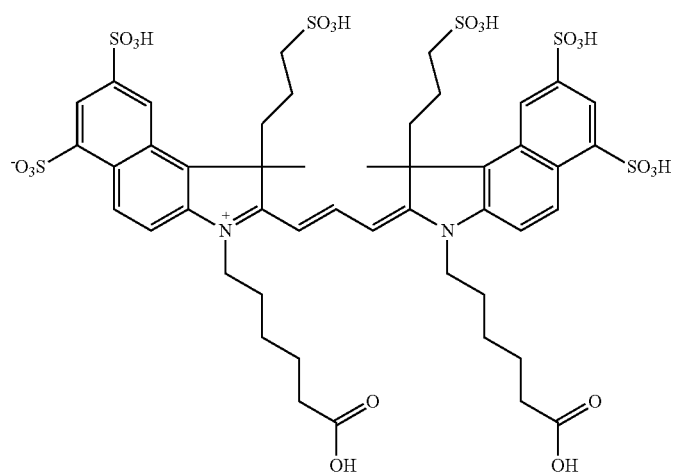

TABLE 1-continued
Exemplary fluorescent dyes.
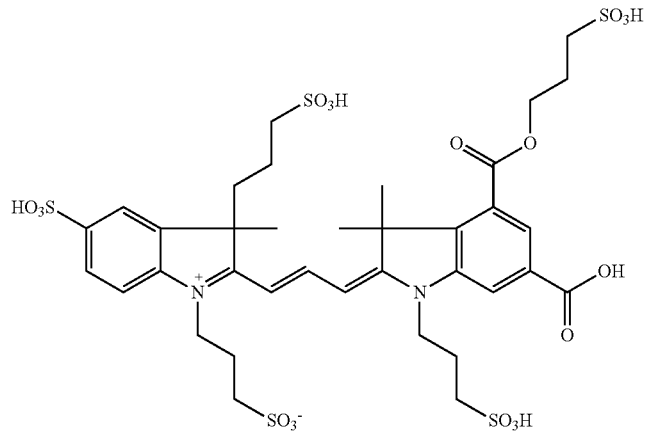
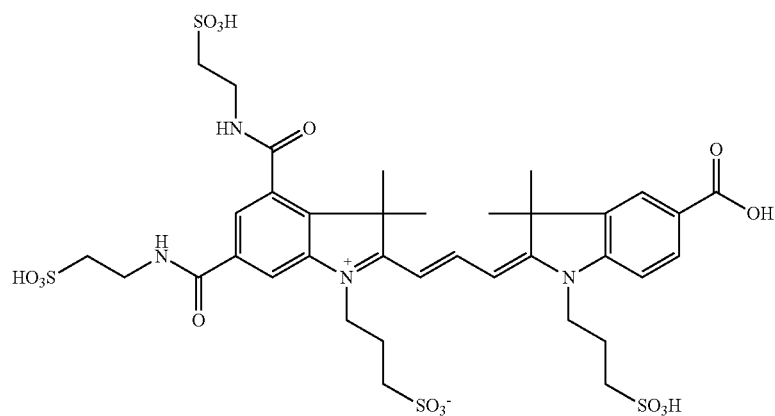
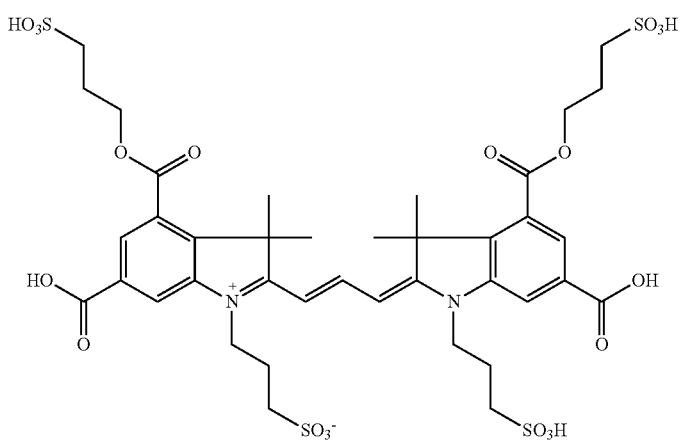

TABLE 1-continued
Exemplary fluorescent dyes.
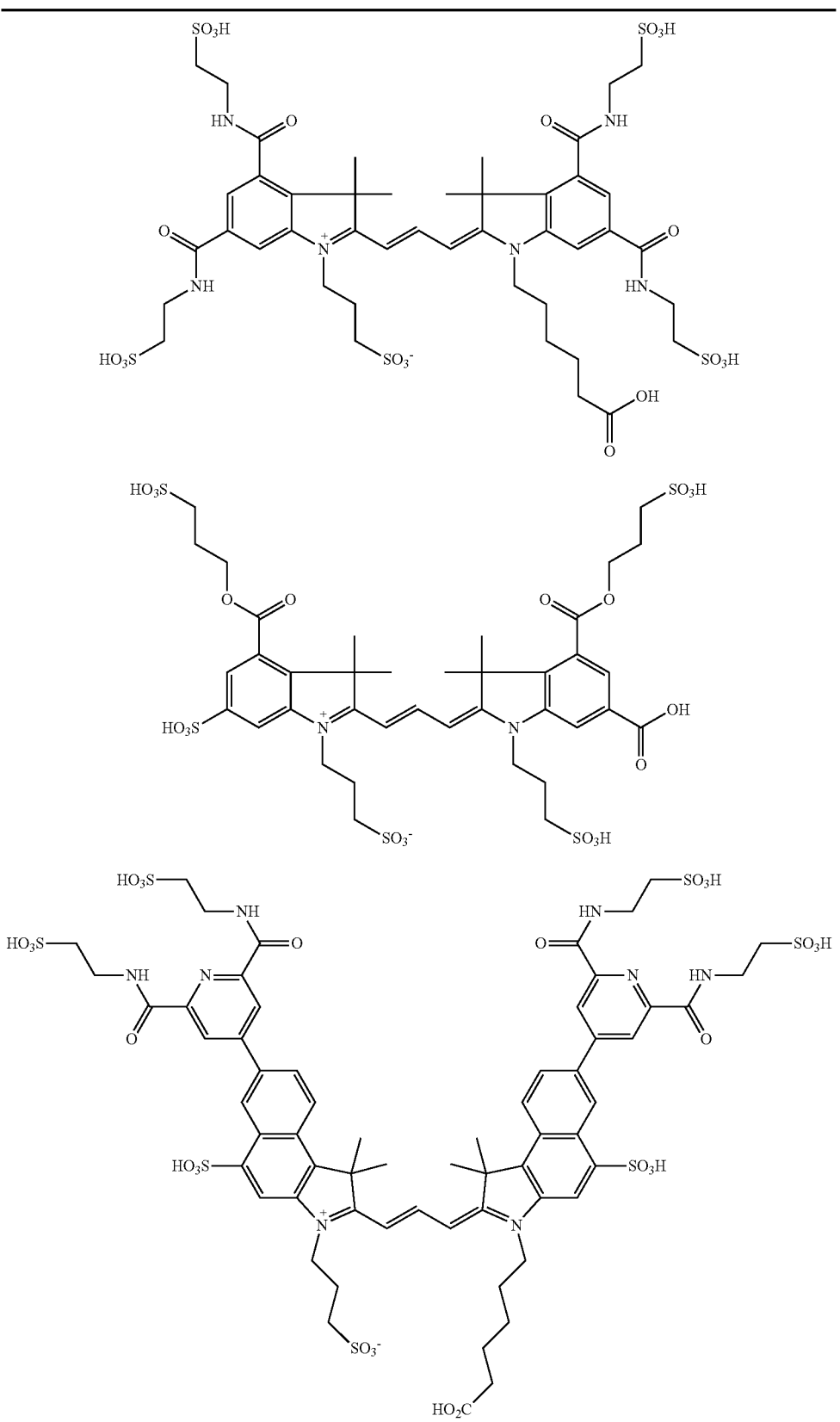

TABLE 1-continued

Exemplary fluorescent dyes.

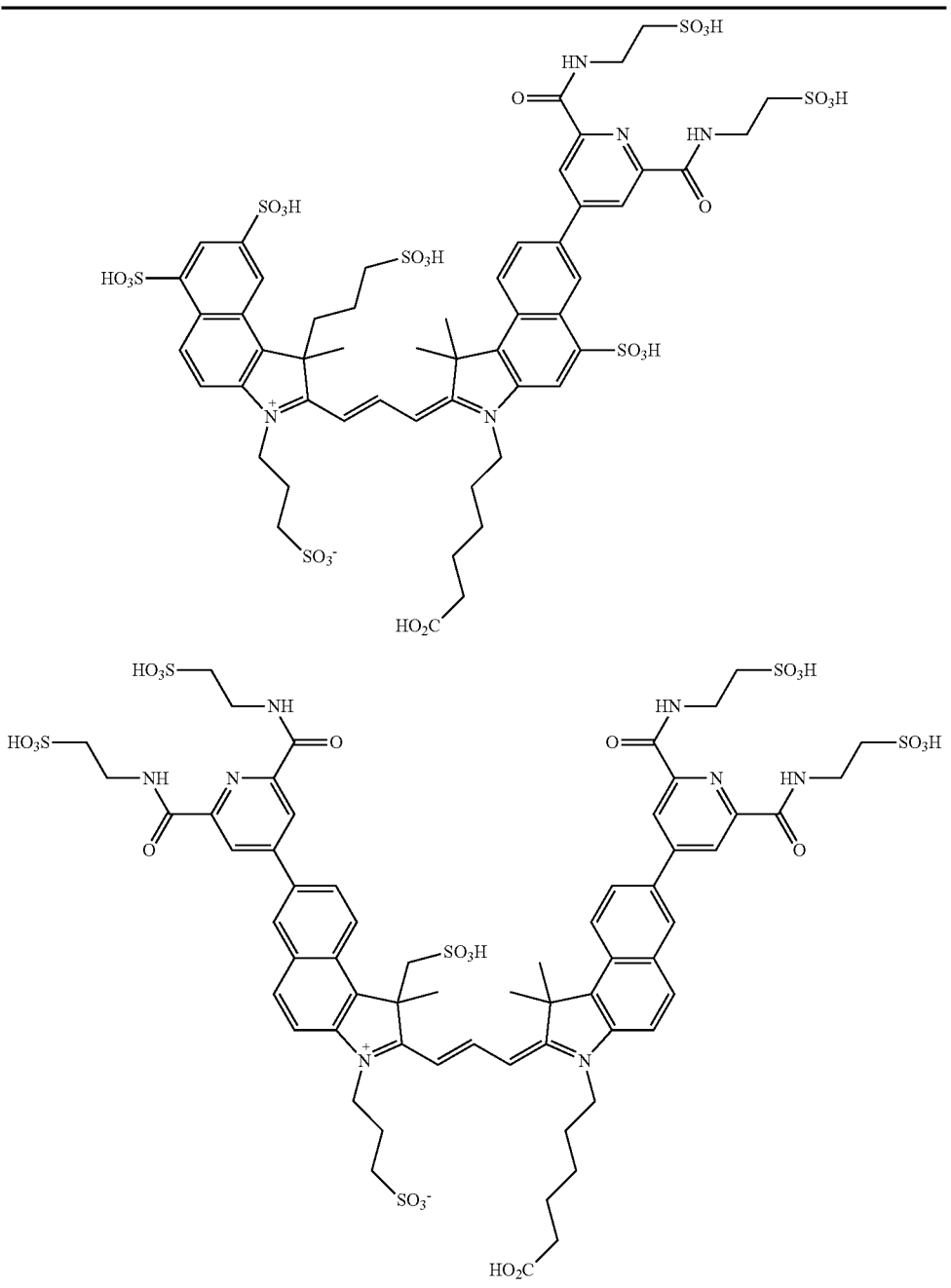

The shield element of the instant dye-labeled compounds may be any of the shield elements described above in the context of the nucleotide compounds, without limitation. Shield elements are also described in U.S. Patent Application Publication Nos. 2015/0050659 A1 and 2016/0237279 A1.

In some dye-labeled compound embodiments, the shield element decreases photodamage of the dye-labeled compound or of a biomolecule associated with the dye-labeled compound. In some compound embodiments, the shield element increases the brightness of the dye-labeled compound.

Figure 24:
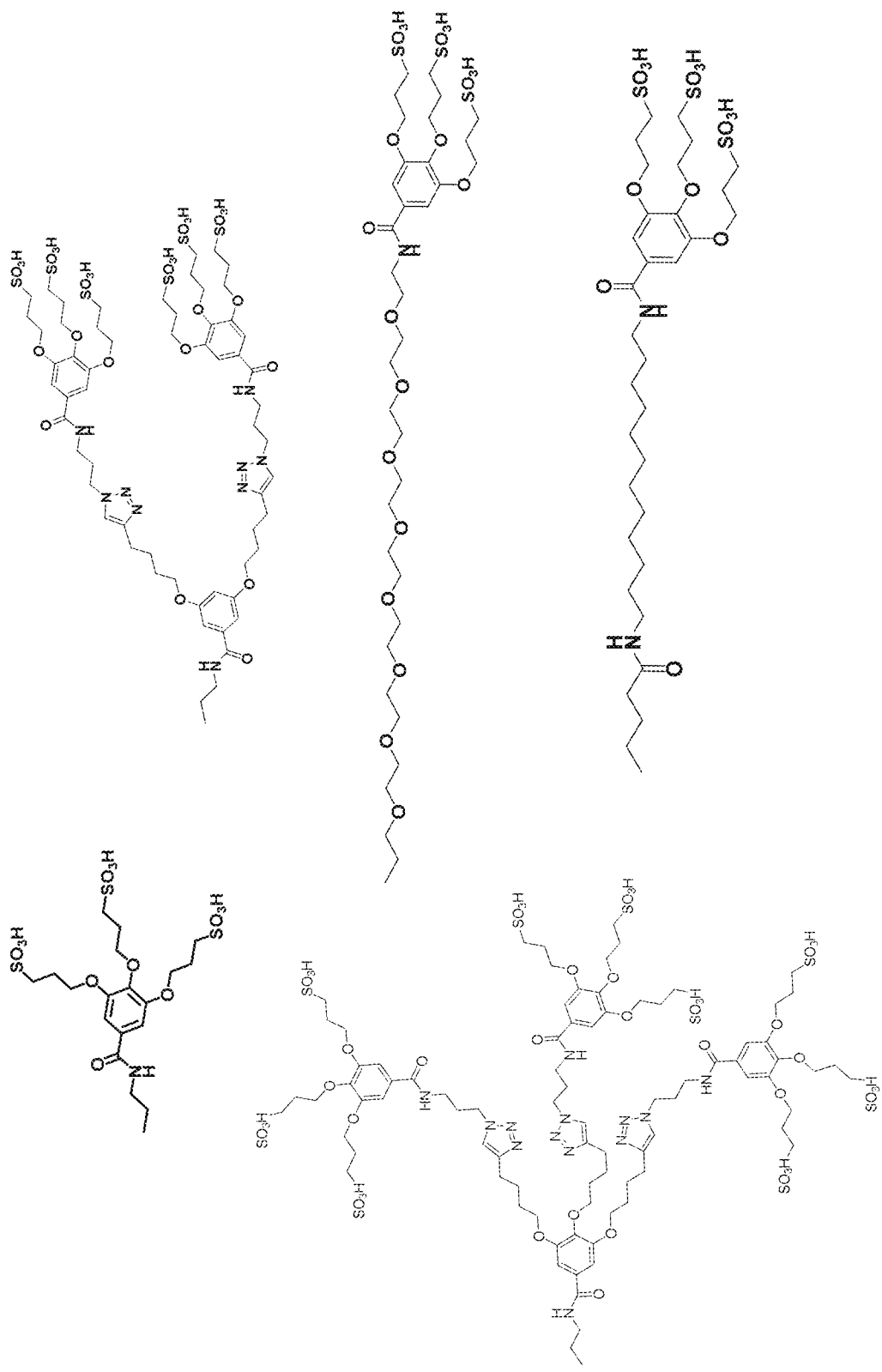
FIG. 24 illustrates further side chain embodiments of the disclosure.
Figure 24:
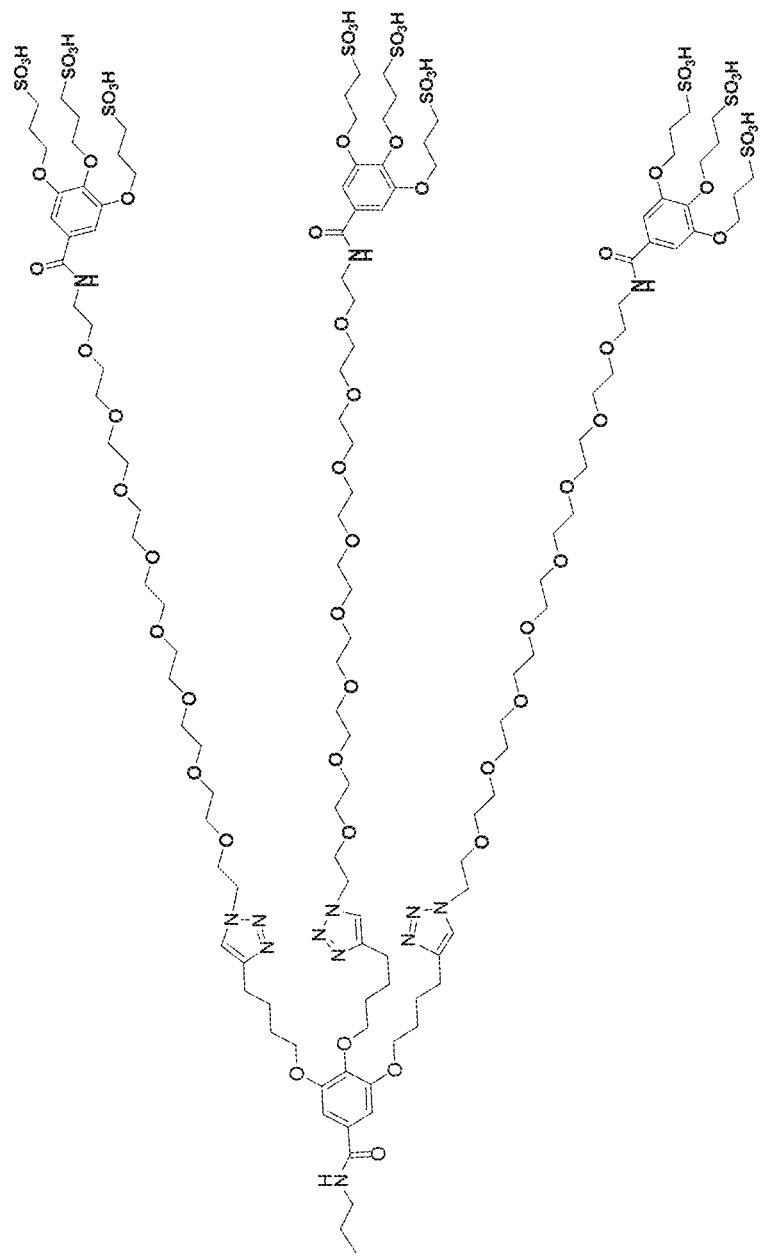

In specific compound embodiments, the shield element comprises a plurality of side chains. In some embodiments, at least one side chain has a molecular weight of at least 300. In other embodiments, all of the side chains have a molecular weight of at least 300. In some embodiments, at least one side chain comprises a polyethylene glycol. In some embodiments, at least one side chain comprises a negatively-charged component. More specifically, the negatively-charged component may comprise a sulfonic acid. In some embodiments, at least one side chain comprises a substituted phenyl group, more specifically the structure:

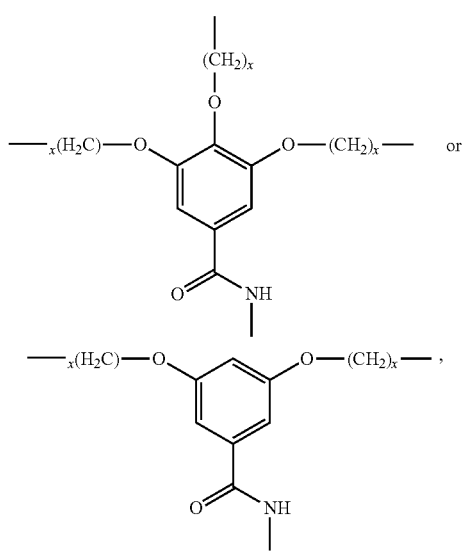

wherein each x is independently an integer from 1 to 6. Even more specifically, each x may independently be an integer from 1 to 4. In some embodiments, at least one side chain comprises a triazole, and in some embodiments at least one side chain may comprise a structure illustrated in FIG. 24.

In some dye-labeled compound embodiments, the shield element comprises the structure:

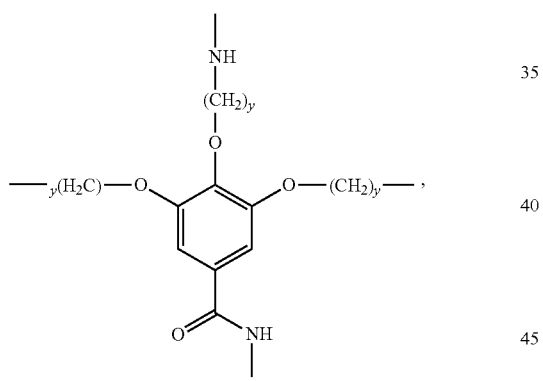

wherein each y is independently an integer from 1 to 6.

In other embodiments, the shield element comprises a structure illustrated in FIG. 20.

Figure 25:
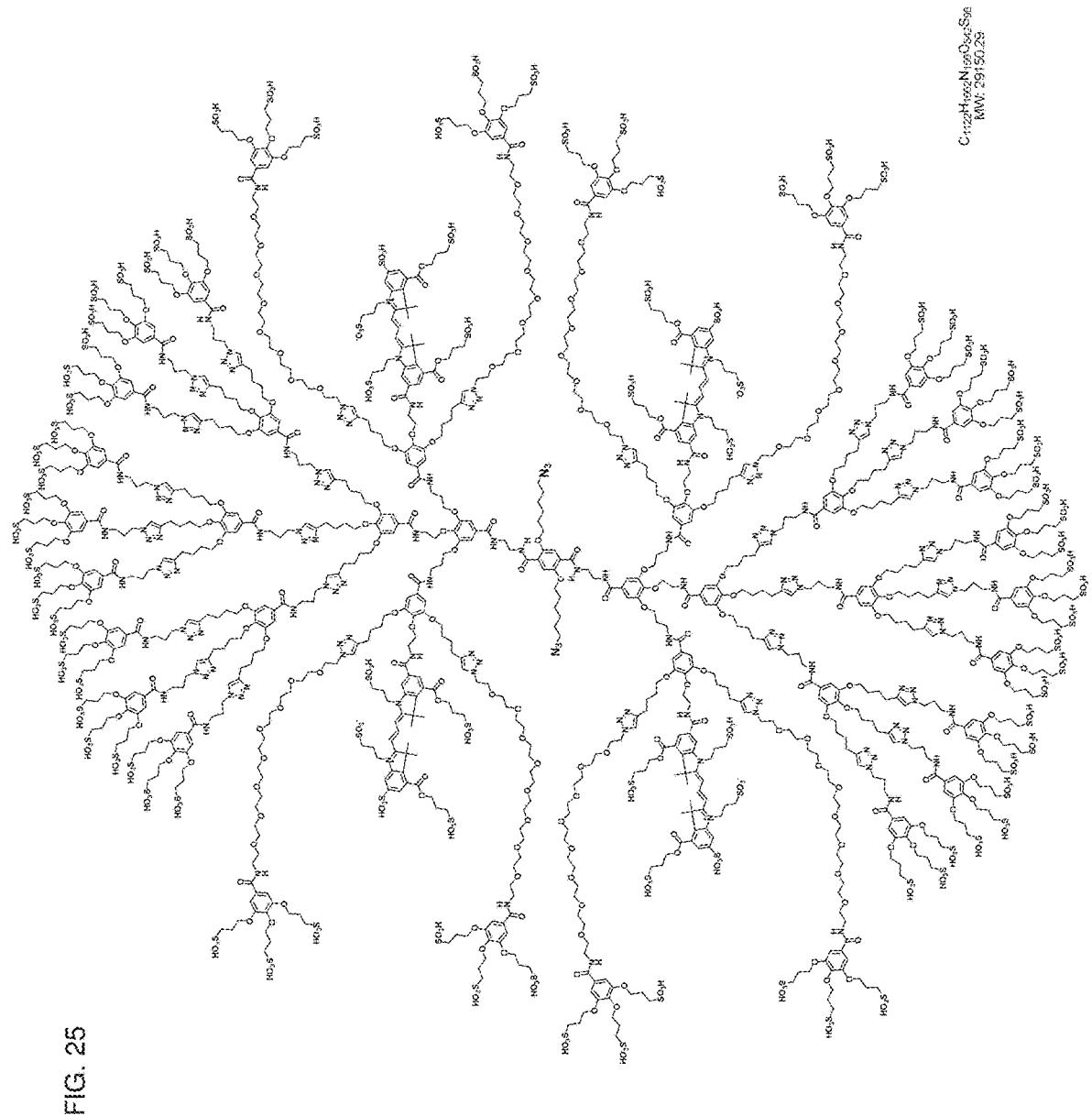
FIG. 25 illustrates an exemplary intermediate compound of the disclosure.

The shield elements of the instant dye-labeled compounds can in addition or alternatively comprise a dendrimer structure, including any of the dendrimer structures described above in the context of the nucleotide compounds. An example of an intermediate compound used to generate a dendrimer-containing dye-labeled compound of the instant disclosure is illustrated in FIG. 25.

This structure comprises two of the above-described G3 dendrimeric side chains and four donor fluorophores with their associated shield elements. It represents a higher-branched variant of the intermediate compound shown in the left panel of FIG. 7G.

The instant dye-labeled compounds still further comprise a dye compound linker element. The dye compound linker element can be any of the linkers defined above, as would be understood by those of ordinary skill in the art. The dye compound linker element serves to covalently connect the terminal coupling element or elements with the donor dye or dyes, the acceptor dye or dyes, and the shield element or elements. In some compound embodiments, more than one dye compound linker element may be necessary to connect the different components, as will be understood by the skilled artisan upon consideration of the dye labeled compounds exemplified below.

In some embodiments, the dye compound linker element comprises the structure:

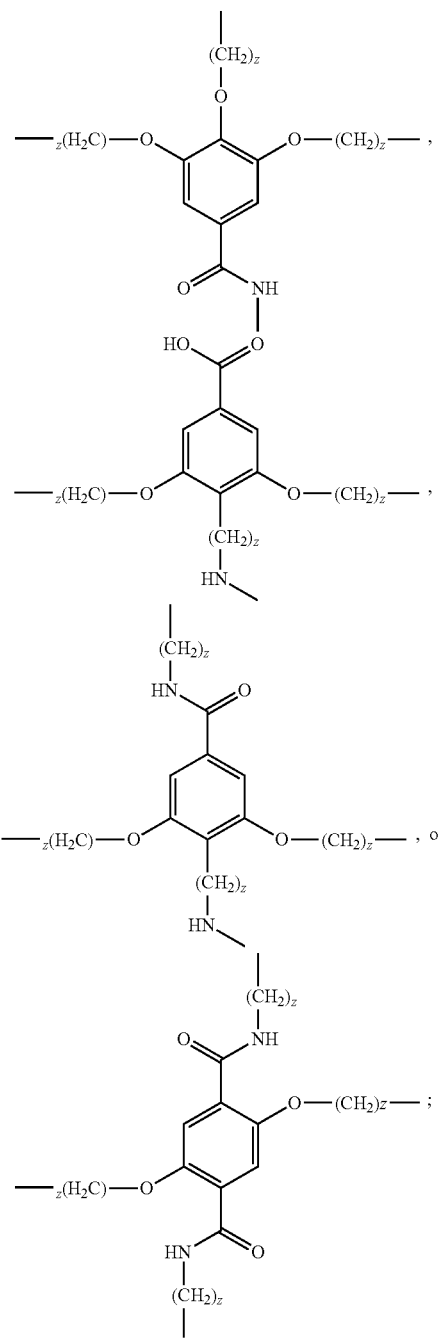

wherein each z is independently an integer from 1 to 8. In more specific embodiments, each z is independently an integer from 1 to 4. As is apparent in some of the compound examples described herein, the dye compound linker element can further comprise an aminoalkyl group or a diaminoalkyl group. The dye compound linker element can alternatively or additionally comprise other linker groups, for example, acylalkyl groups, diacylalkyl groups, or any other suitable linker group, including the branching groups described in U.S. Patent Application Publication Nos. 2015/0050659 A1 and 2016/0237279 A1, and the multivalent central core elements described above. In some compound embodiments, two or more dye compound linker elements are covalently coupled to one another.

In specific embodiments, the dye compound linker element comprises the structure:

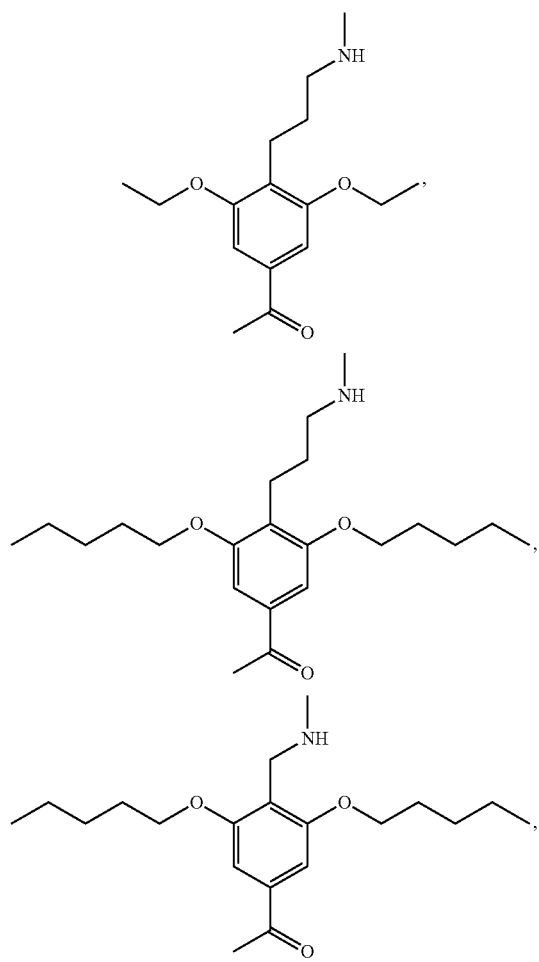

-continued

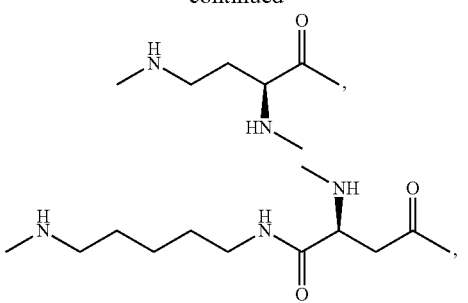

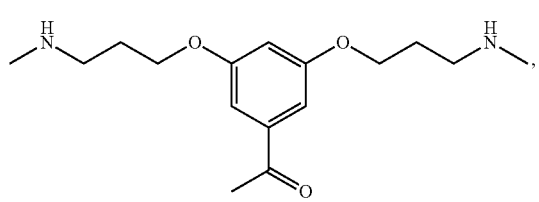

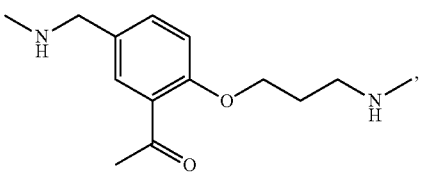

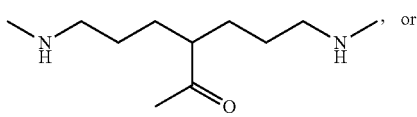

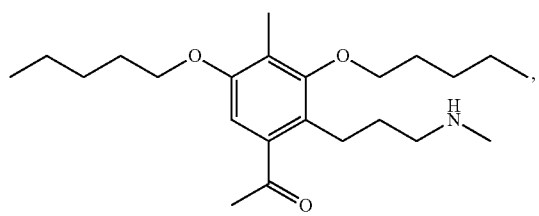

and in some embodiments comprises the structure

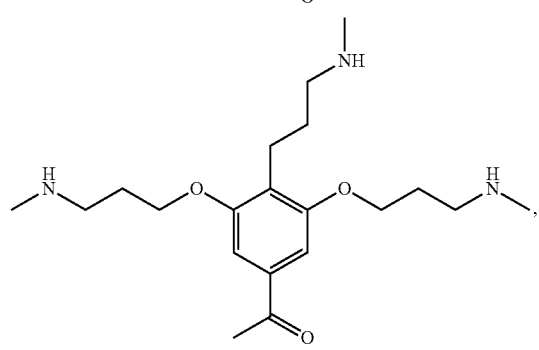

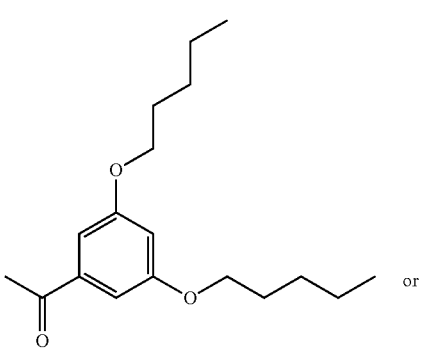

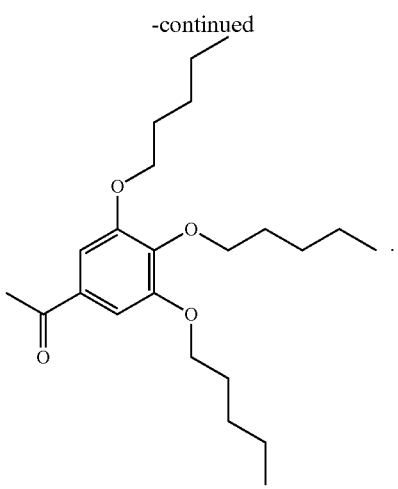

In some embodiments, the dye compound linker element comprises the structure

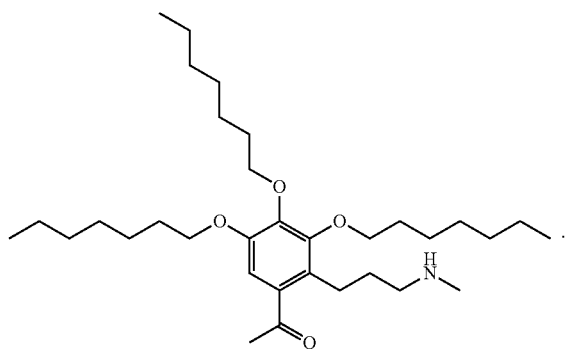 [SMILES: CCCCCCCOc1cc(C(C)=O)c(CCCNC)c(OCCCCCCC)c1OCCCCCCC]

Some dye compound linker elements can contain more than one of the above structures, and different dye compound linker element structures can be present within a single molecule of the instant compounds.

The dye-labeled compounds still further comprise a terminal coupling element. It should be understood that the terminal coupling elements can be any of the terminal coupling elements described above in the context of the nucleotide compounds, without limitation. In some embodiments, the compounds comprise two terminal coupling elements. In some embodiments, the terminal coupling element comprises a biotin. In preferred embodiments, the terminal coupling element comprises a bis-biotin, and in particular, one of the bis-biotin structures shown above.

Figure 26A:
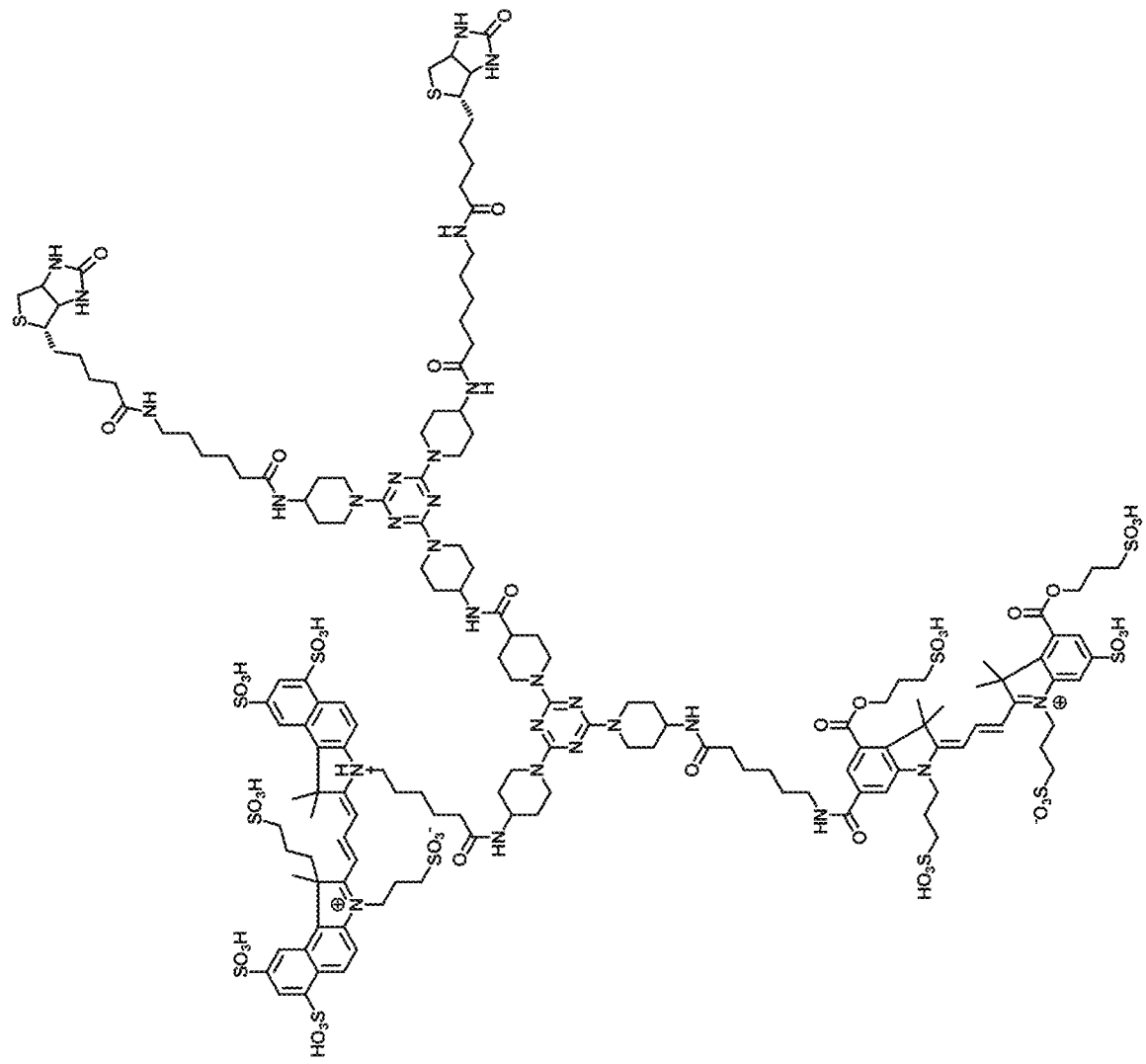
FIGS. 26A-26J illustrate exemplary dye-labeled compounds of the disclosure.
Figure 26B:
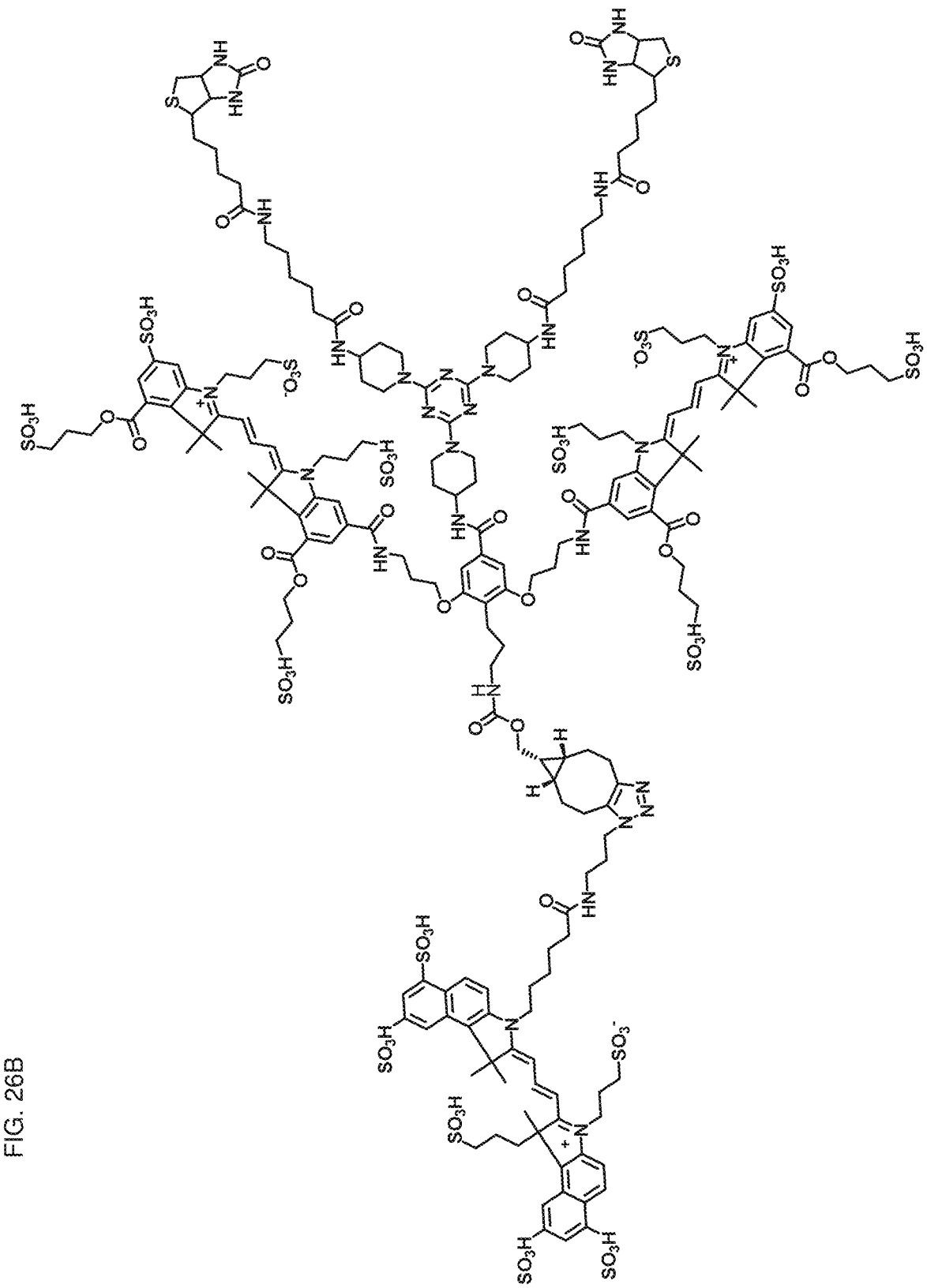
Figure 26C:
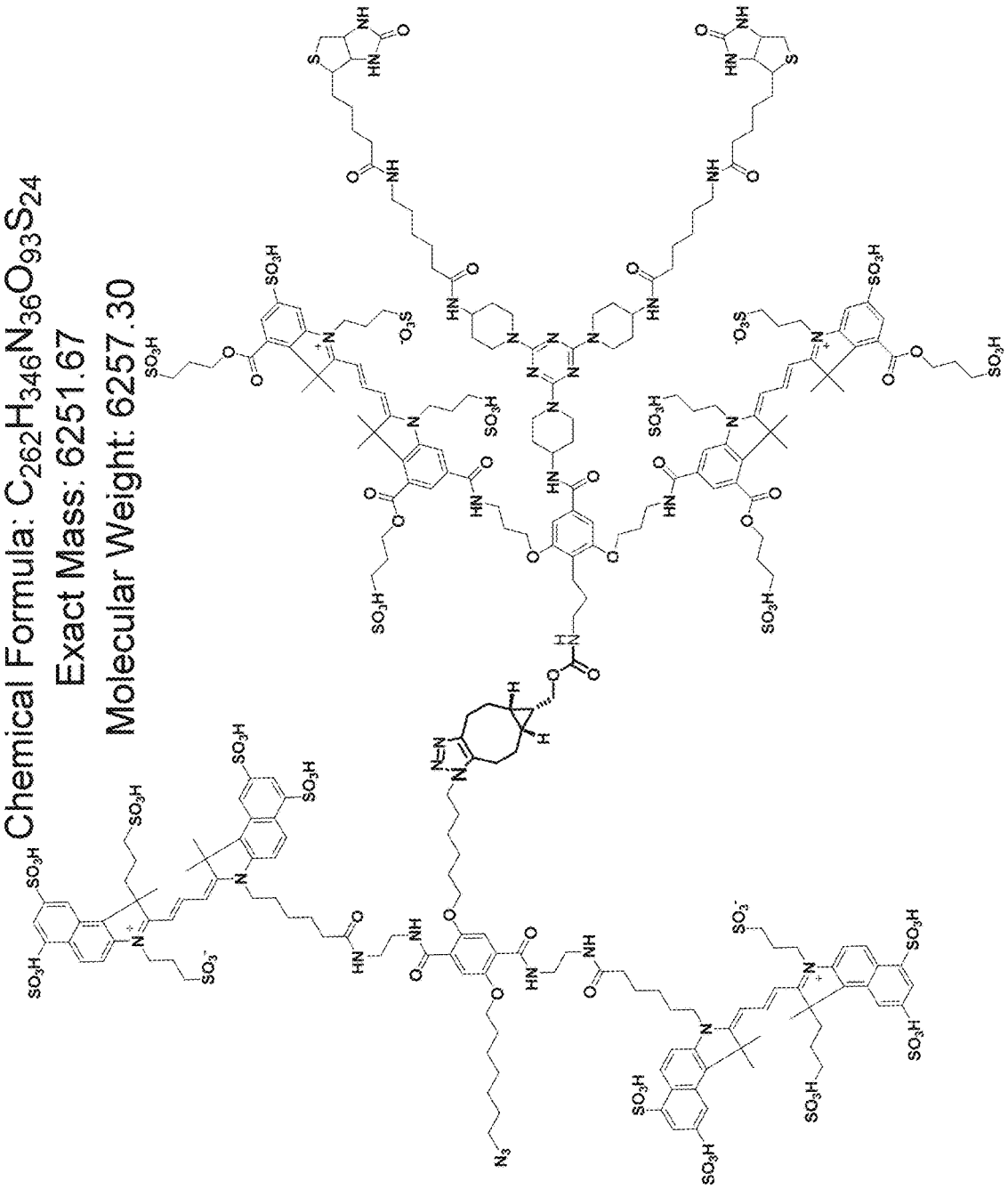
Figure 26D:
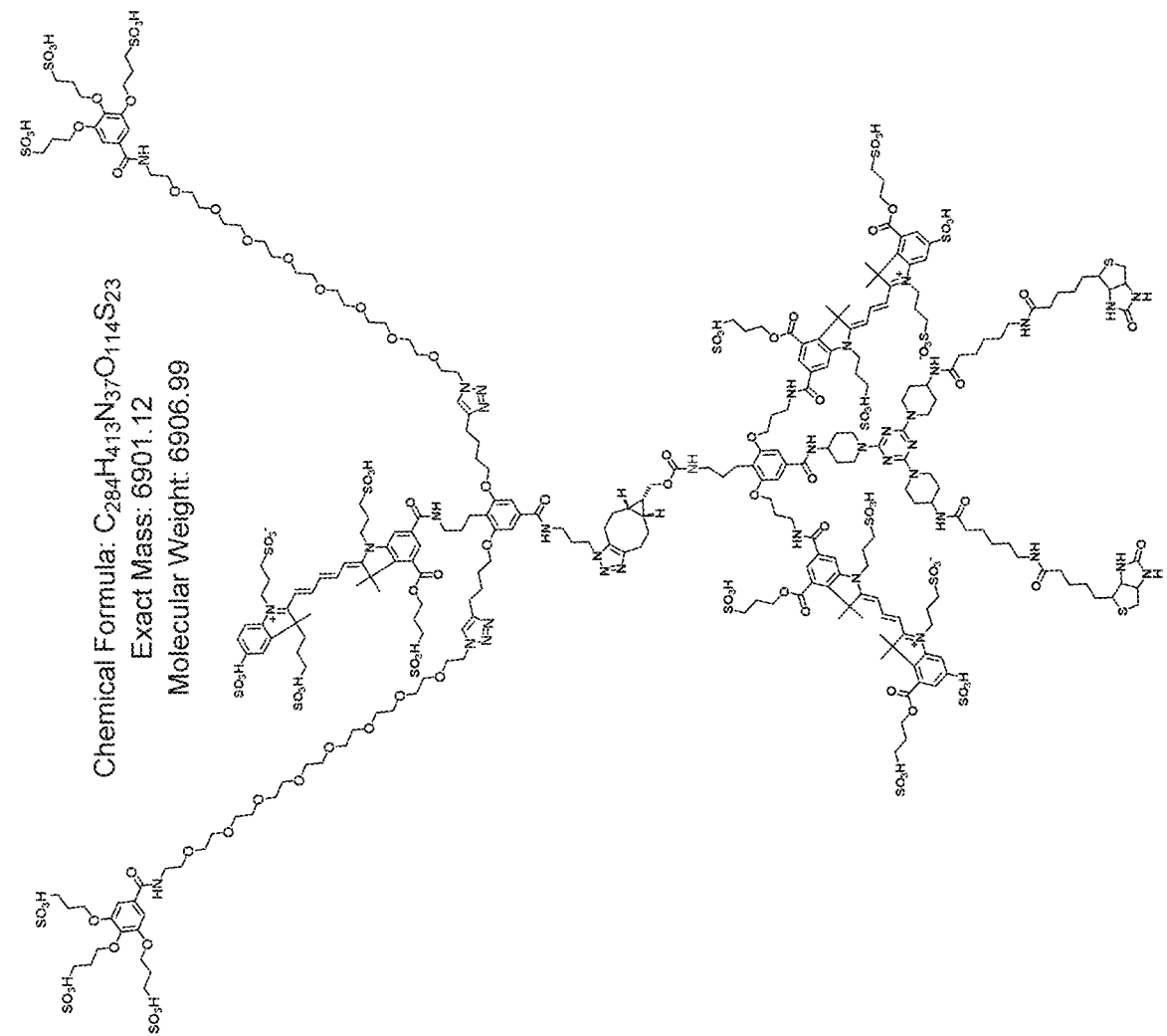
Figure 26E:
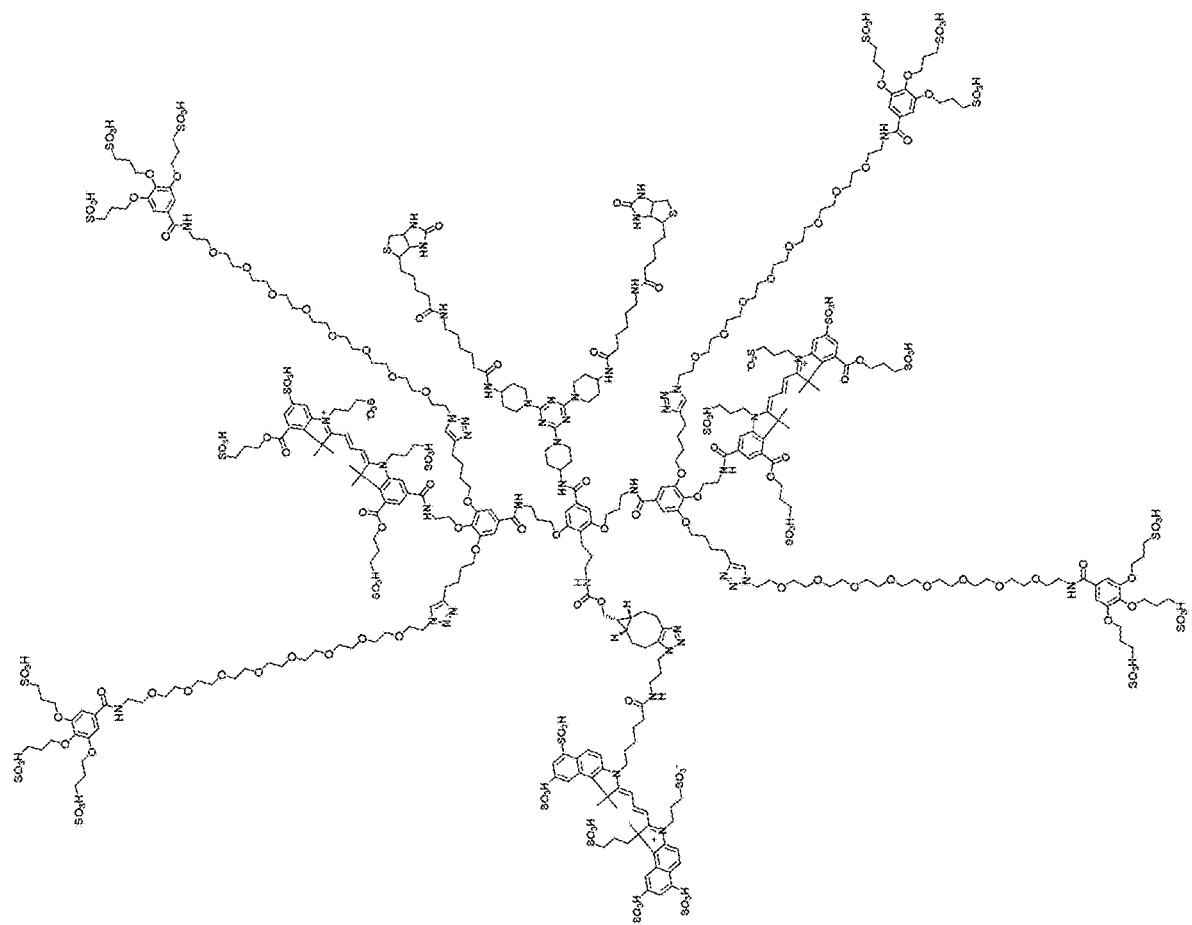
Figure 26F:
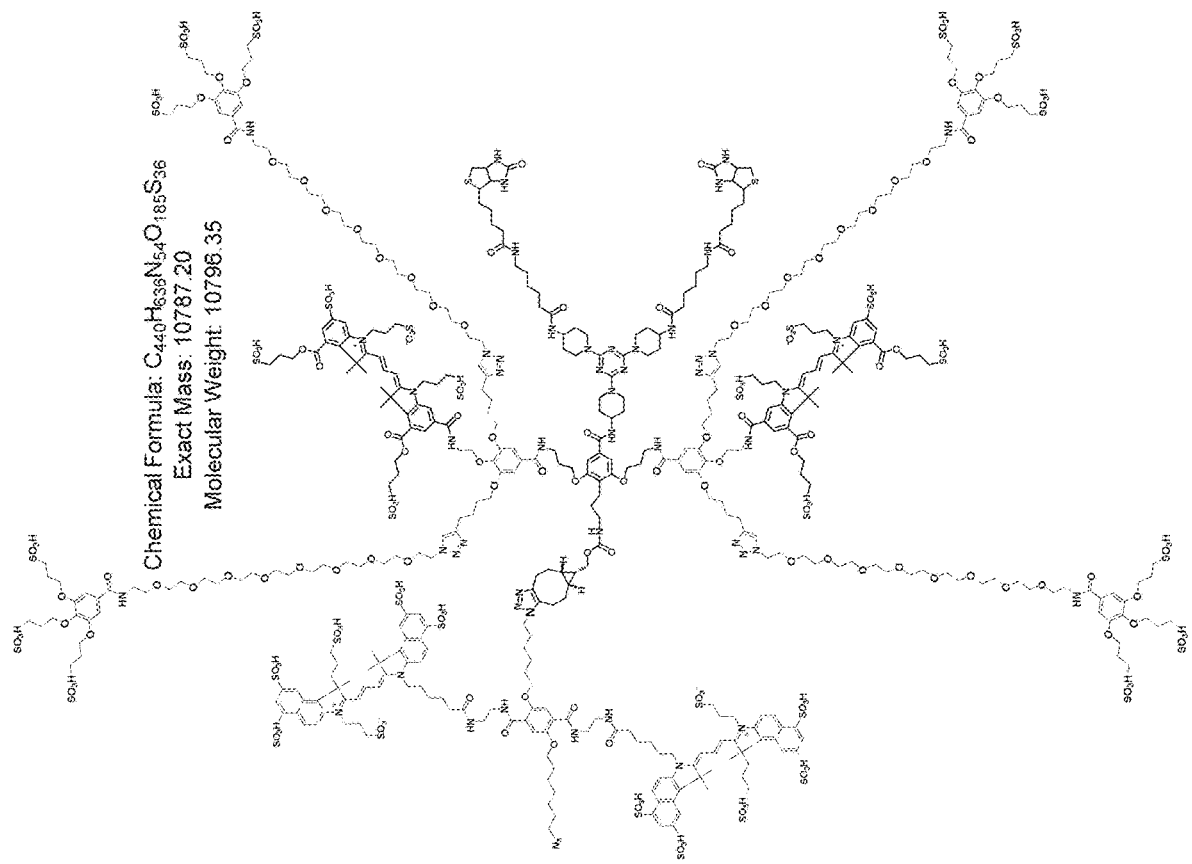
Figure 26G:
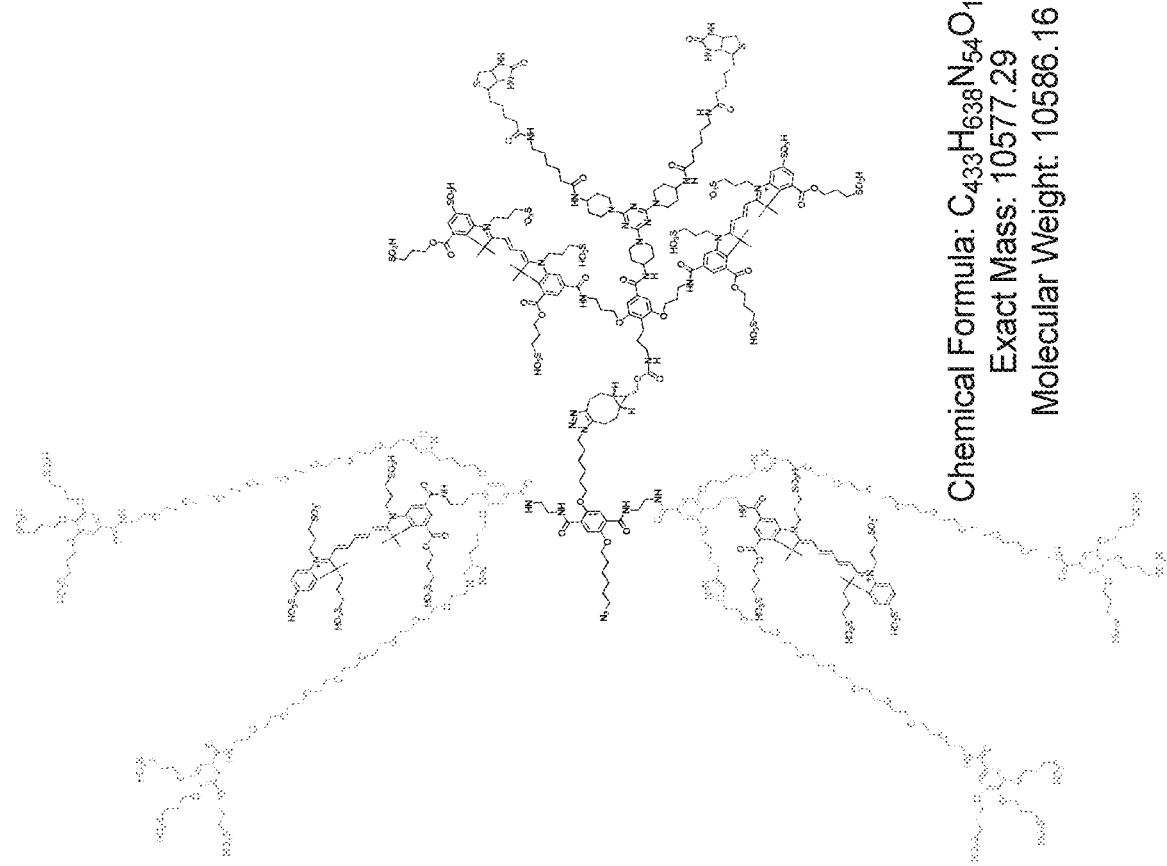
Figure 26H:
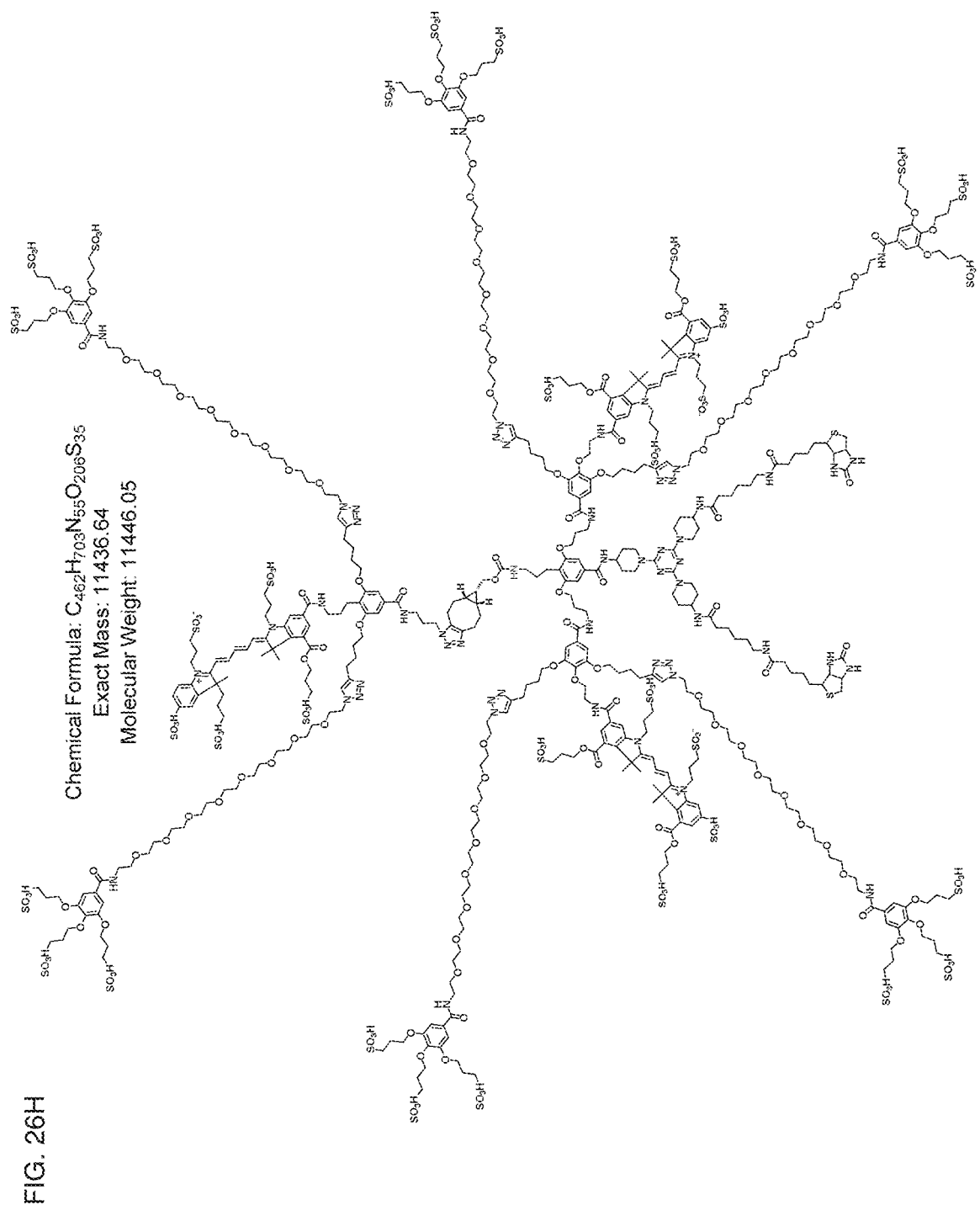
Figure 26I:
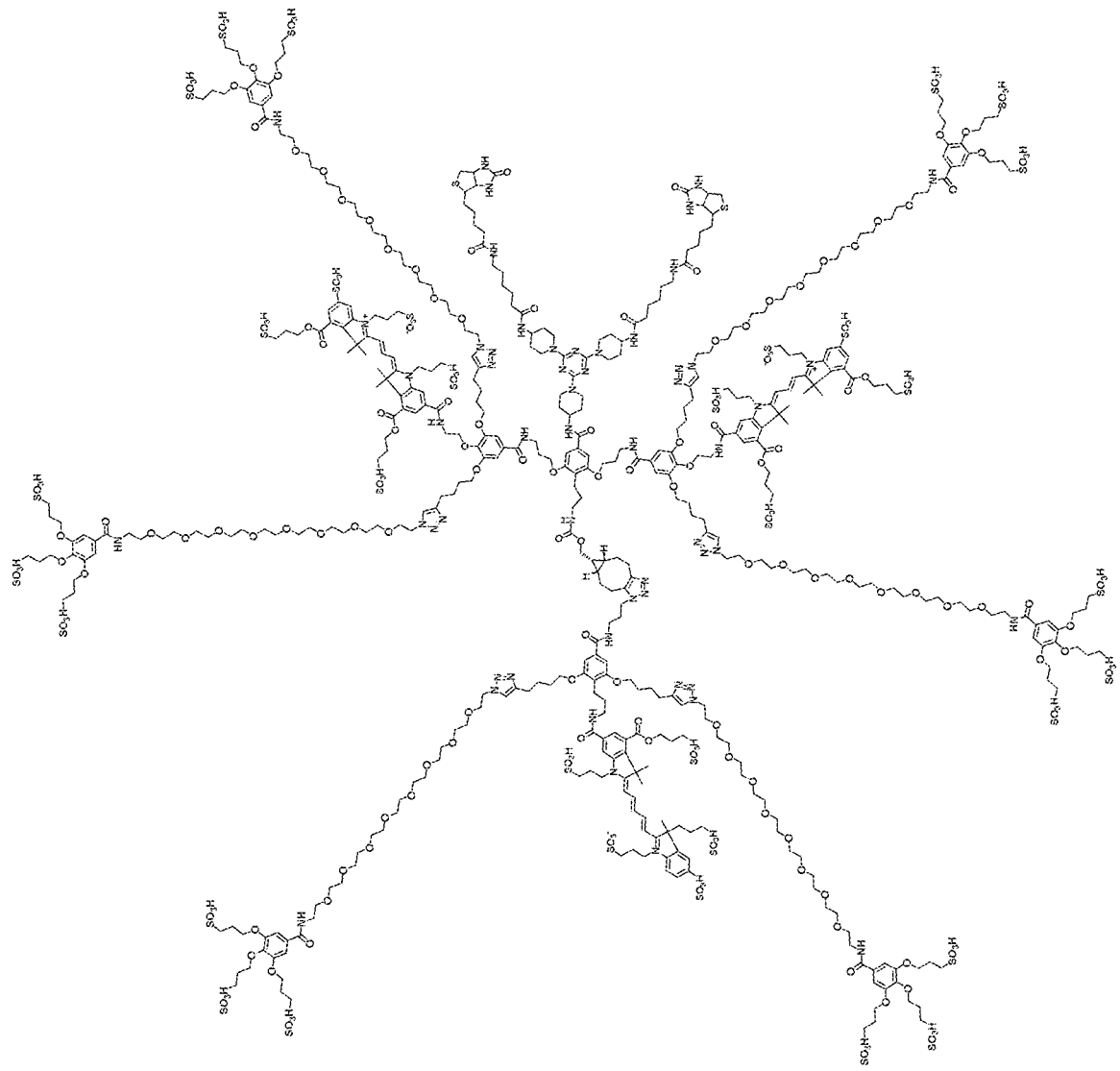
Figure 26J:
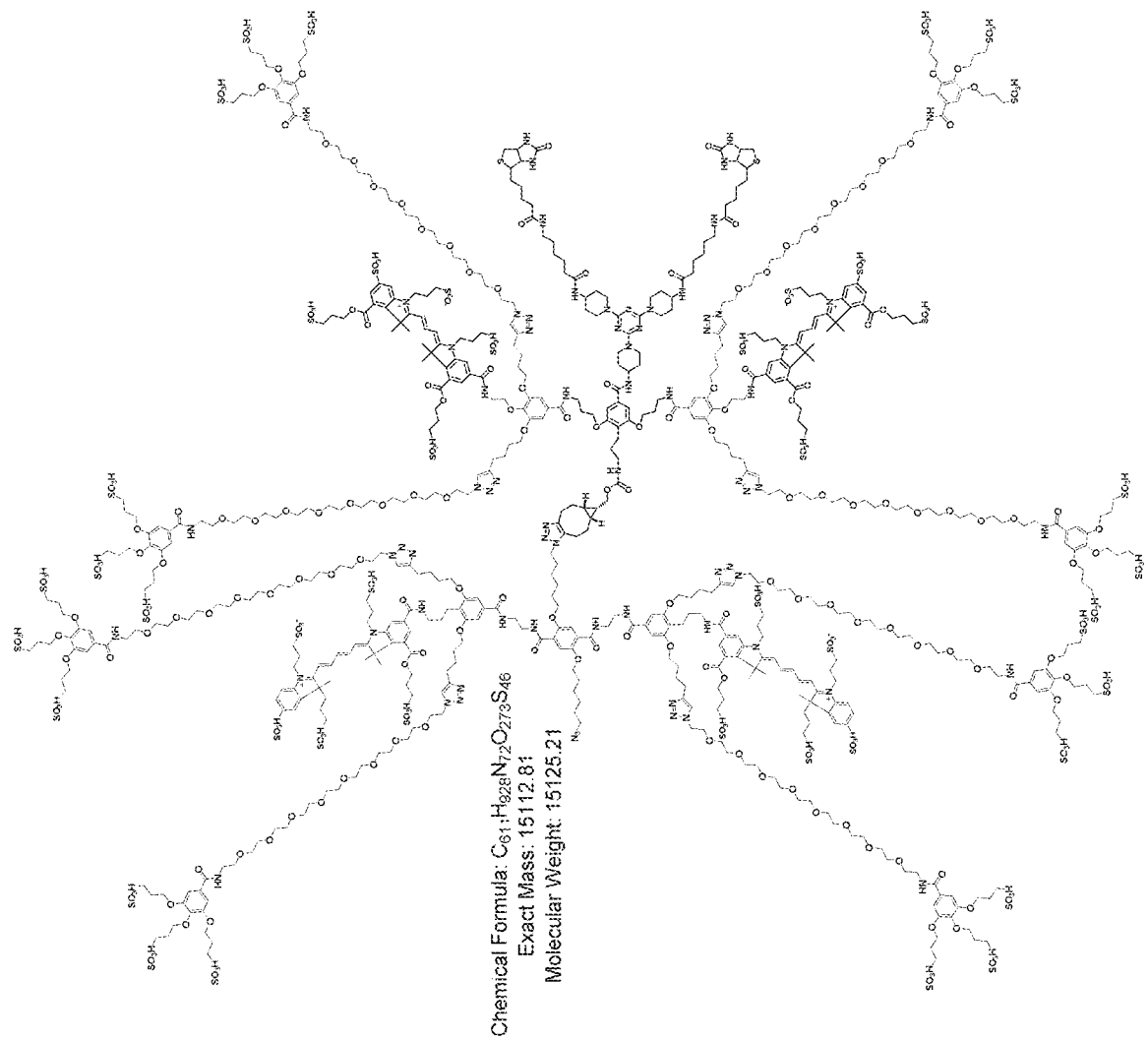

Exemplary dye-labeled compounds comprising a bis-biotin terminal coupling element, at least one acceptor dye, at least one donor dye, and at least one dye compound linker element include the compound illustrated in FIG. 26A, which includes one unshielded donor dye and one unshielded acceptor dye; the compound illustrated in FIG. 26B, which includes two unshielded donor dyes and one unshielded acceptor dye; the compound illustrated in FIG. 26C, which includes two unshielded dyes and two unshielded acceptor dyes; the compound illustrated in FIG. 26D, which includes two unshielded donor dyes and one shielded acceptor dye; the compound illustrated in FIG. 26E, which includes two shielded donor dyes and one unshielded acceptor dye; the compound illustrated in FIG. 26F, which includes two shielded donor dyes and two unshielded acceptor dyes; the compound illustrated in FIG. 26G, which includes two unshielded donor dyes and two shielded acceptor dyes; the compound illustrated in FIG. 26H, which includes two shielded donor dyes and one shielded acceptor dye; the compound illustrated in FIG. 26I, which includes two shielded donor dyes and one shielded acceptor dye; and the compound illustrated in FIG. 26J, which includes two shielded donor dyes and two shielded acceptor dyes.

Other exemplary dye-labeled compounds are illustrated as components of the labeled nucleotide analogs shown in FIGS. 3A-3O' and FIGS. 7A-7D, 7F, and 7G, and in the compounds graphically illustrated in FIGS. 4A-4C and FIGS. 5A-5M.

In preferred embodiments, the dye-labeled compounds of the instant disclosure do not contain a polyphosphate element or a nucleoside element.

As described above in the context of the instant nucleotide compounds, the terminal coupling element of the instant dye-labeled compounds typically mediates association of the dye-labeled compound with other components of the instant labeled nucleotide analogs. For example, and has been described elsewhere in the disclosure, where the terminal coupling element is a biotin or bis-biotin, the dye-labeled compound can associate non-covalently with an avidin protein with high affinity. In some aspects, the disclosure thus further provides compositions comprising a dye-labeled compound of the disclosure and an avidin protein. In these compositions, it should be understood that the terminal coupling element is not covalently modified by the association of the dye-labeled compound with the avidin protein, and the composition thus distinctly comprises the original dye-labeled compound and the avidin protein as separate molecular entities.

In another aspect of the disclosure, however, it should be contemplated that the terminal coupling element of a dye-labeled compound may comprise a reactive functional group that can be covalently bound to a complementary reactive group on a second component, for example on an appropriately modified linker element, shield element, or nucleotide compound. Unlike the just-described non-covalent compositions, such reactions generate a new molecular entity connected by a residue derived from the reactive group of each component. As described elsewhere in the specification, such residues can comprise, for example, an amide moiety derived from an amine group and an appropriately activated carboxyl group or a residue resulting from a click reaction.

In yet another aspect of the disclosure are provided methods of synthesis of the instant dye-labeled compounds and their intermediates. Such methods can comprise the step of reacting any of the intermediate compounds illustrated throughout the specification with a second intermediate compound to generate a nucleotide compound or intermediate of the invention. Exemplary synthetic pathways are illustrated in the reaction schemes below, in the Examples, and in the accompanying drawings.

Synthesis and Assembly of Nucleotide and Dye-Labeled Compounds and Analogs

In another aspect, the disclosure provides methods of synthesis and assembly of the compounds and labeled nucleotide analogs disclosed herein. These compounds and analogs are readily prepared using standard chemical techniques. Detailed examples of synthetic reactions that can be adapted to prepare the instant compounds are provided in U.S. Patent Application Publication Nos. 2015/0050659 A1 and 2016/0237279 A1. For example, the central core of exemplary shield elements can be synthesized according to the reactions illustrated in Scheme 1:

Scheme 1
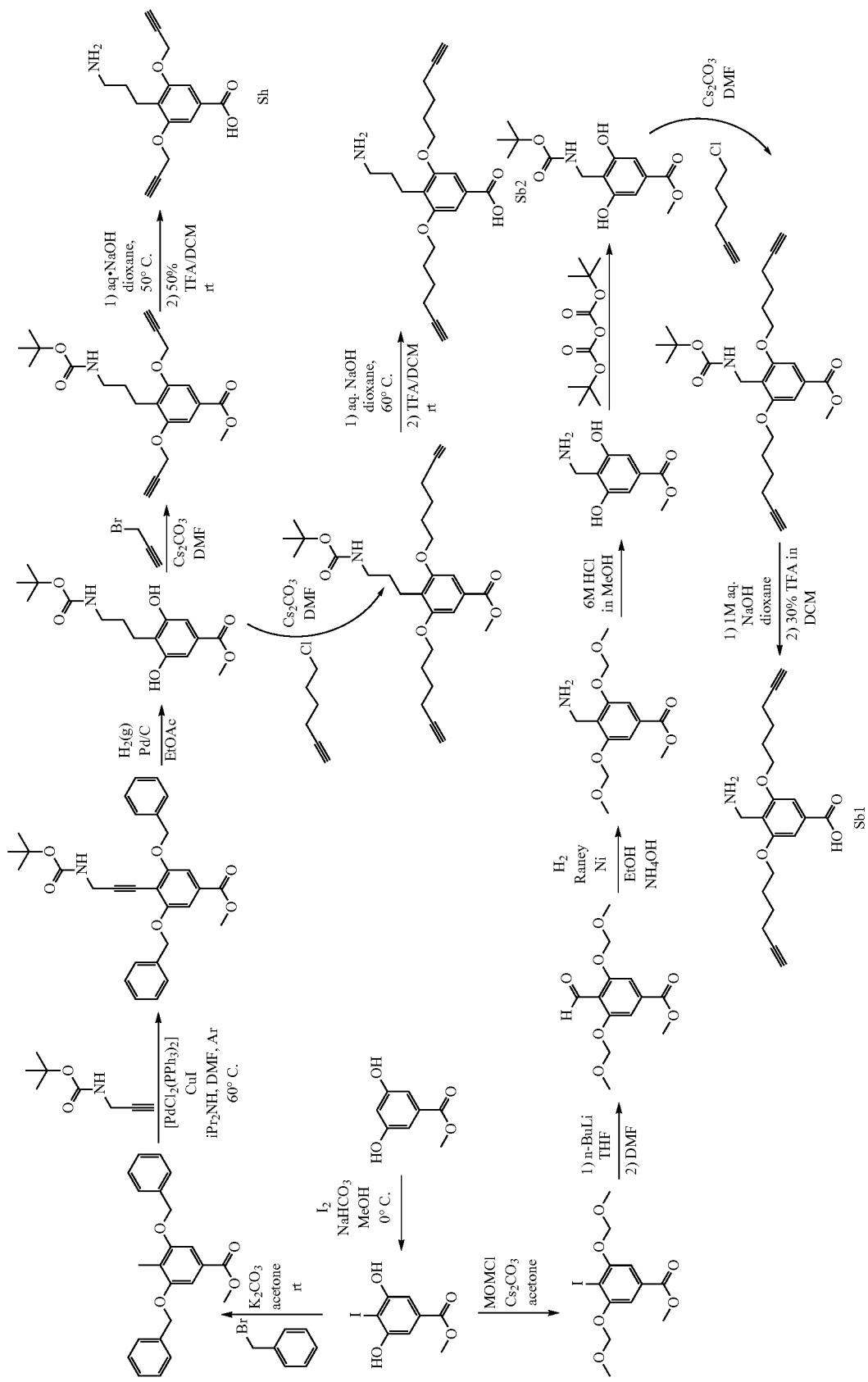

Core components of the shield element side chains can be synthesized, for example, according to the reactions illustrated in Scheme 2:
Shield elements modified with a nucleoside hexaphosphate can be synthesized, for example according to Schemes 3-1 or 3-2:
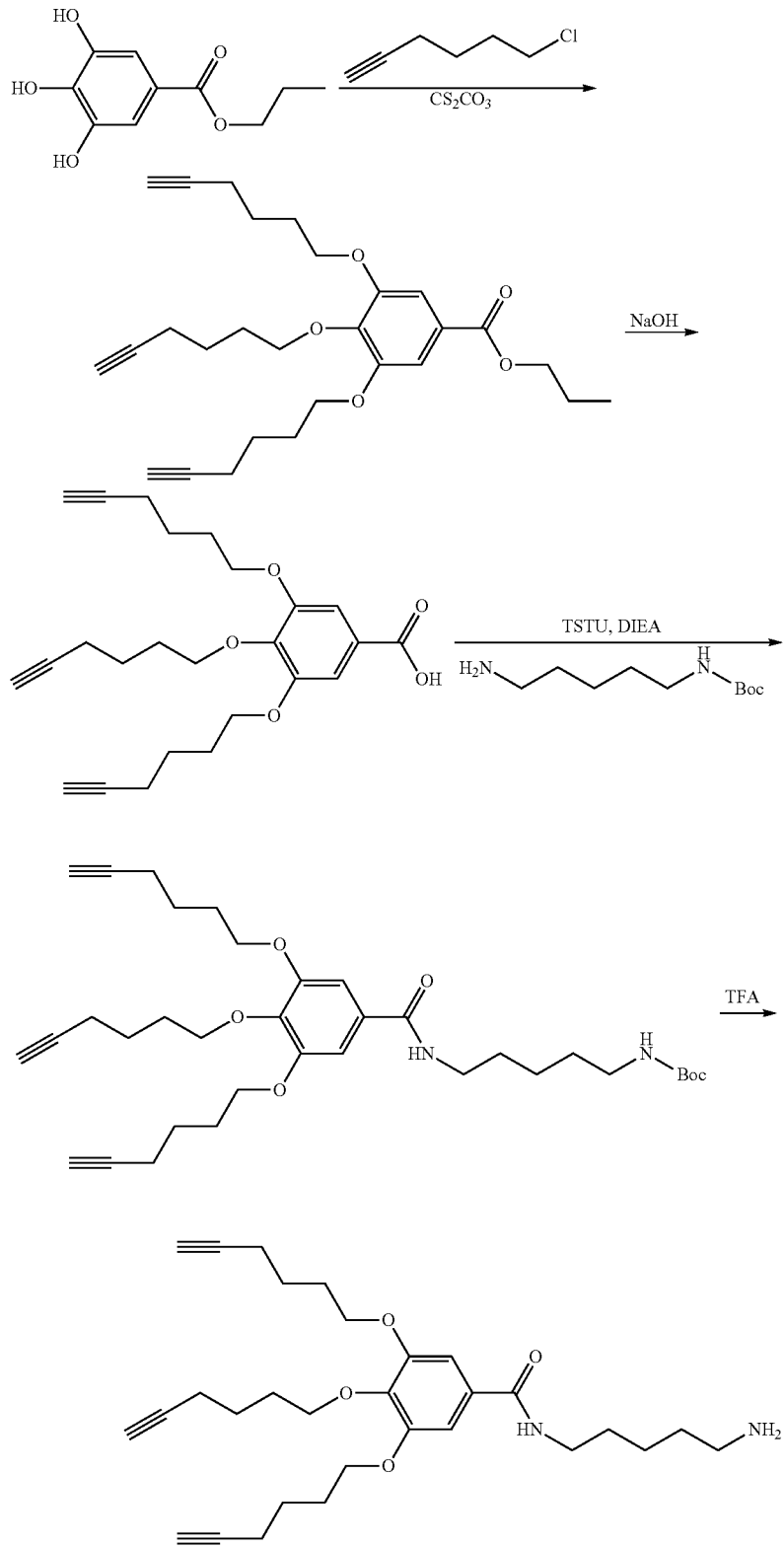

Scheme 3-1
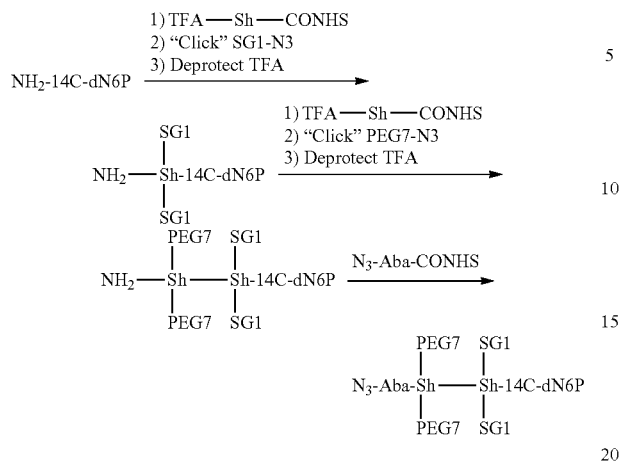

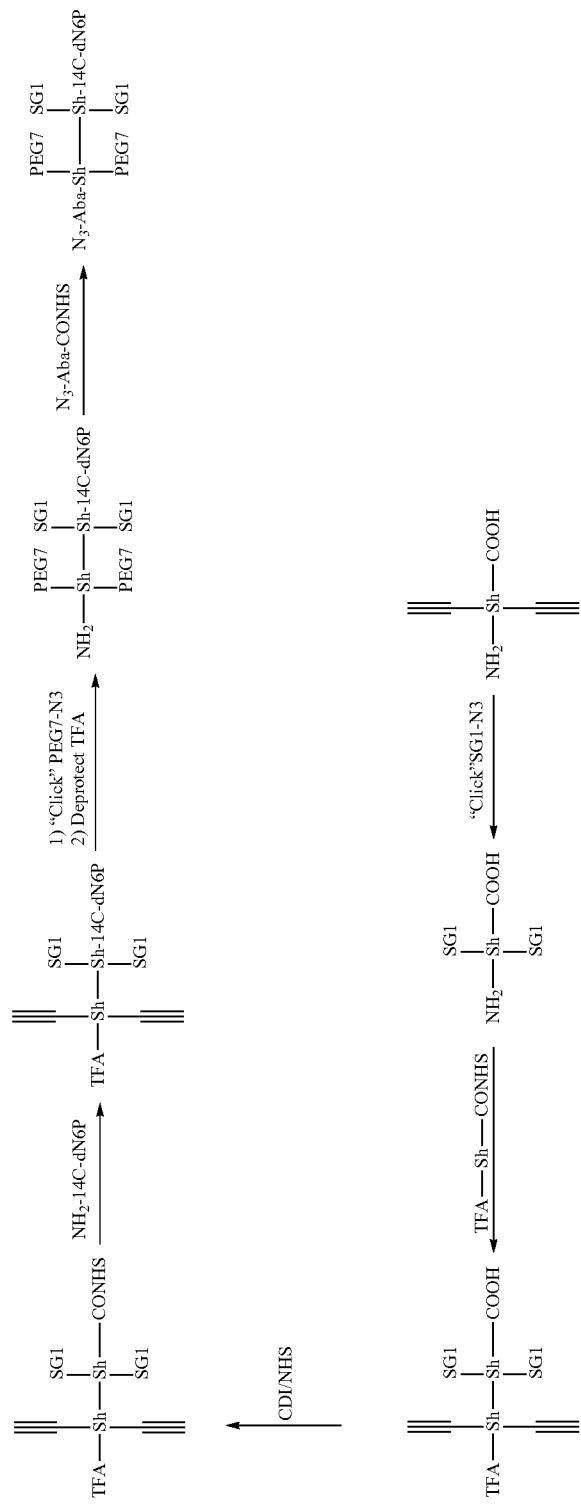
Scheme 3-2

As would be understood from the above description, the shield elements within the final structures shown in Schemes 3-1 and 3-2 represent "layered" shield elements.

The shield core element reagent, TFA-Sh-CONHS, used in the initial step of the first two reaction cycles of Scheme 3-1, can be generated by reaction of the "Sh" shield core element of Scheme 1 with TFA-NHS to form the following structure:

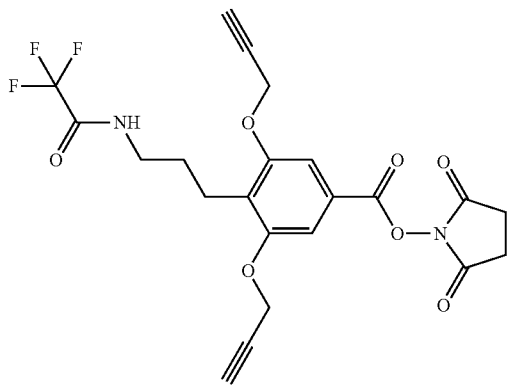 [SMILES: C#CCOc1cc(C(=O)ON2C(=O)CCC2=O)cc(OCC#C)c1CCCNC(=O)C(F)(F)F]

SG1-N$_3$ has the structure:

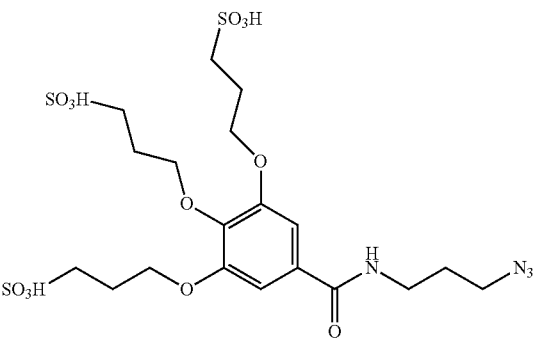 [SMILES: [N-]=[N+]=NCCCNC(=O)c1cc(OCCCS(=O)(=O)O)c(OCCCS(=O)(=O)O)c(OCCCS(=O)(=O)O)c1]

PEG7-N3 has the structure:

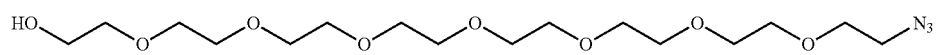 [SMILES: [N-]=[N+]=NCCOCCOCCOCCOCCOCCOCCOCCO]

N3-Aba-CONHS has the structure:

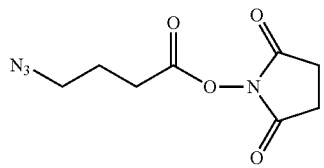 [SMILES: [N-]=[N+]=NCCCC(=O)ON1C(=O)CCC1=O]

NH$_2$-14C-dN6P represents a hexaphosphate deoxynucleotide containing a 14-carbon, or equivalent, linker chain terminating in an amino group. An exemplary species of this structure is:

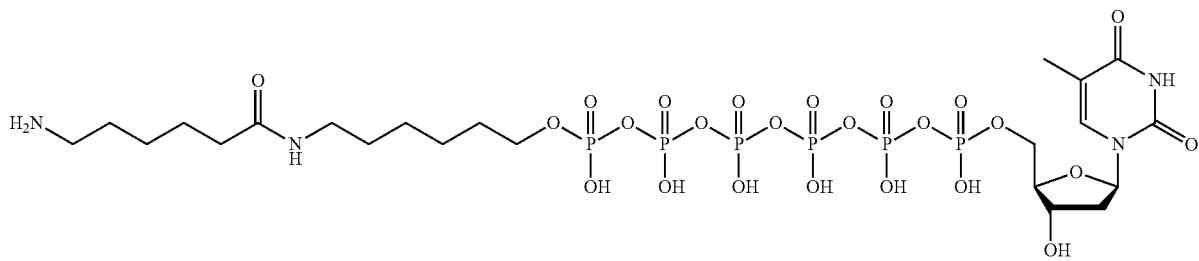

wherein the nucleobase is thymine, and the C14-linker chain includes an amide bond.

Figure 27A:
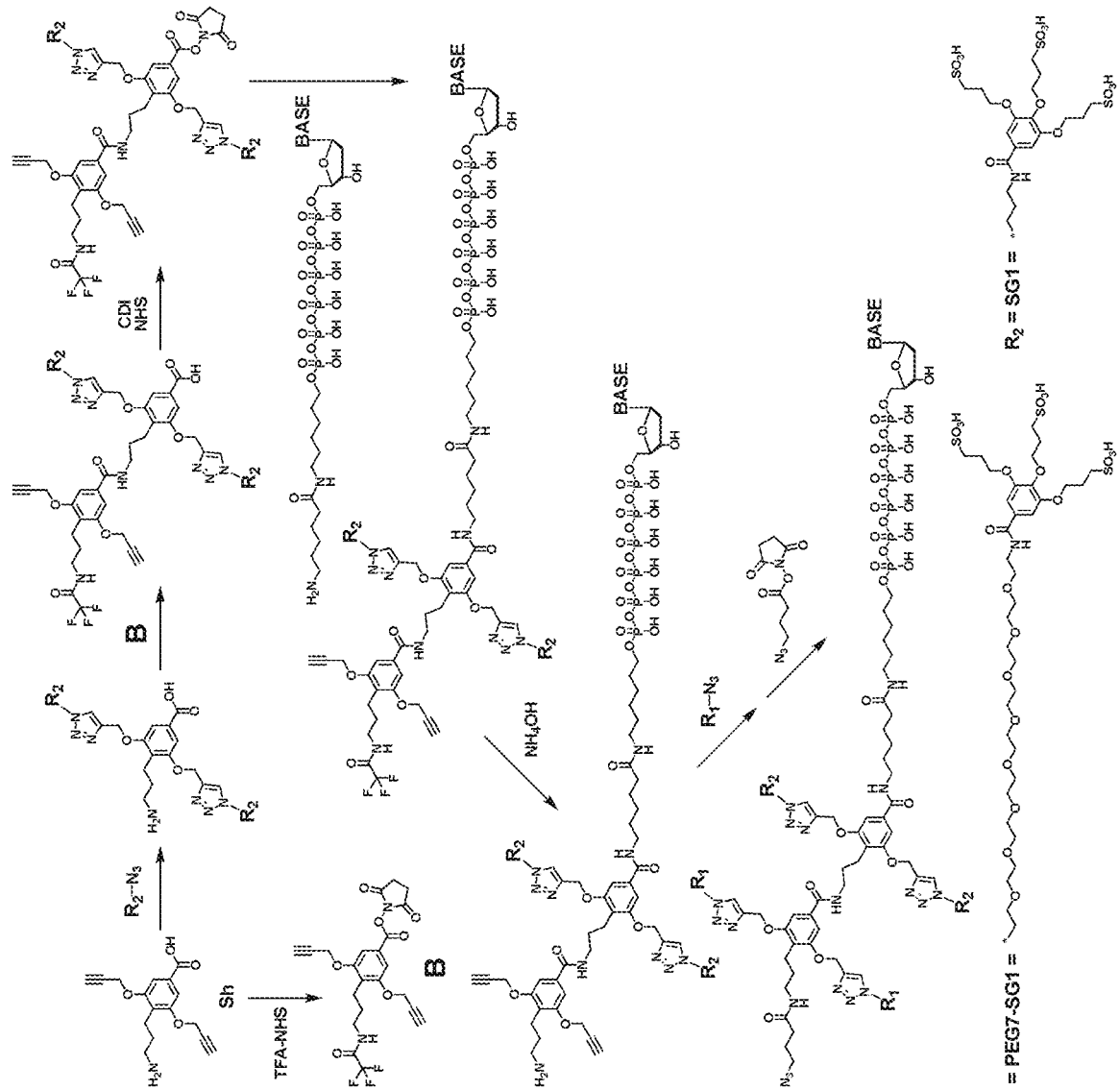
FIGS. 27A-27C illustrate pathways for generating shield element-containing reagents of the disclosure.
Figure 27B:
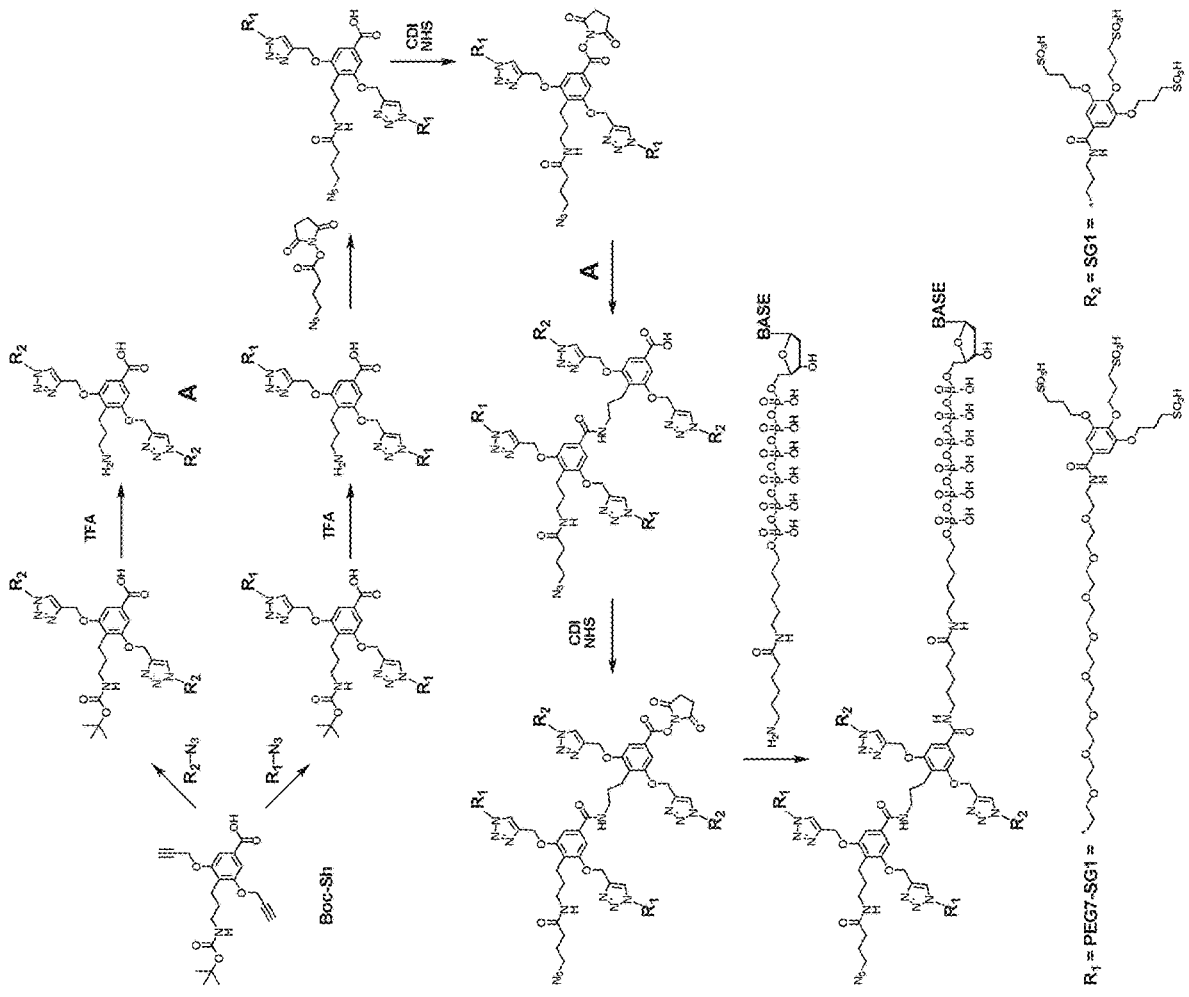
Figure 27C:
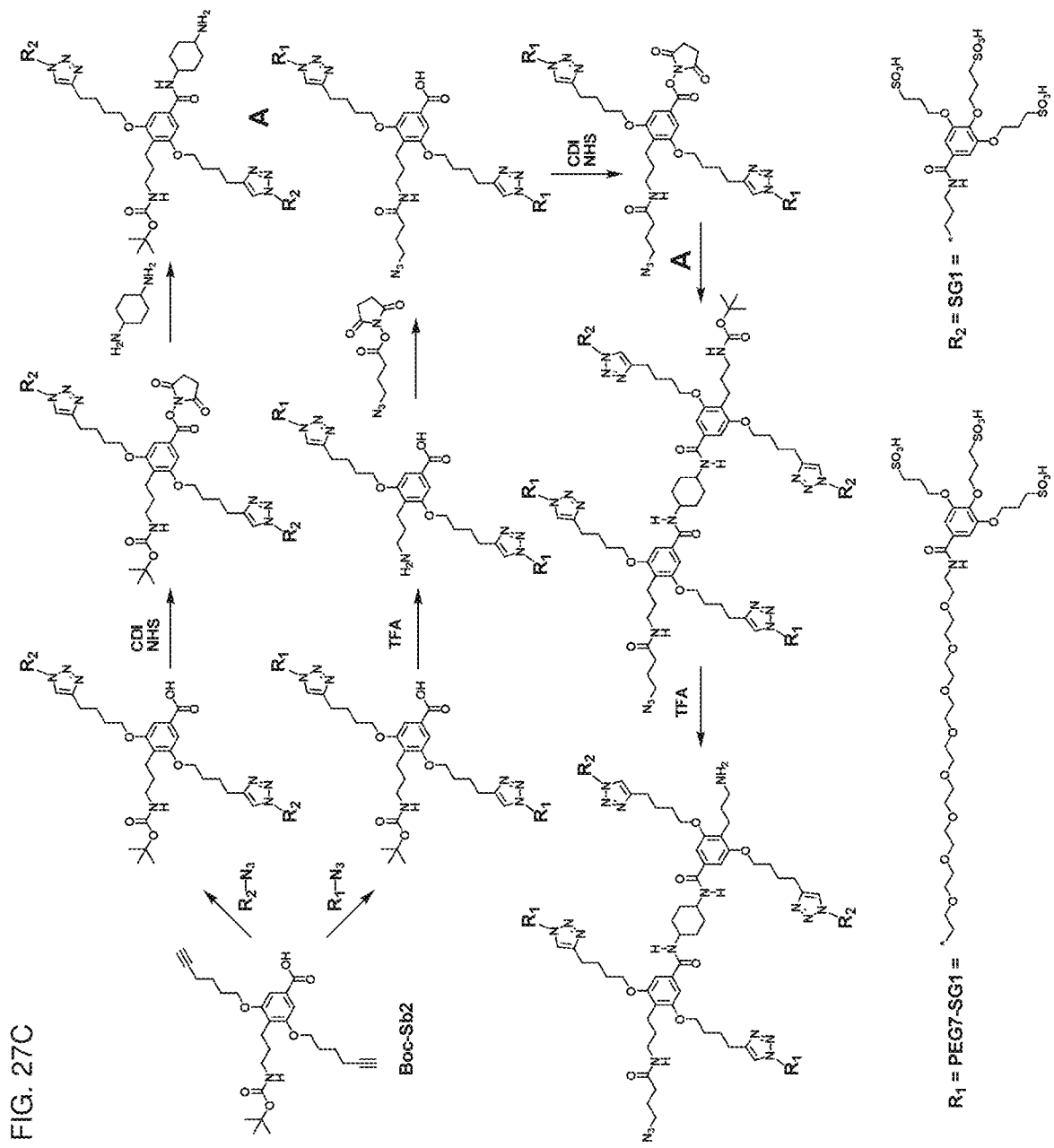

Alternative pathways for generating shield element-containing reagents useful in the synthesis of various compounds of the instant disclosure are outlined in FIGS. 27A-27C. The shield elements prepared according to the schemes of FIGS. 27A-27C correspond to "layered" shields, but the synthetic reactions can be suitably altered to generate non-layered shields if desired.

Exemplary synthetic reactions useful in the generation of the azide-containing sidechain reagents of FIGS. 27A-27C (e.g., $R_1$—$N_3$ and $R_2$—$N_3$) are outlined in Scheme 4:

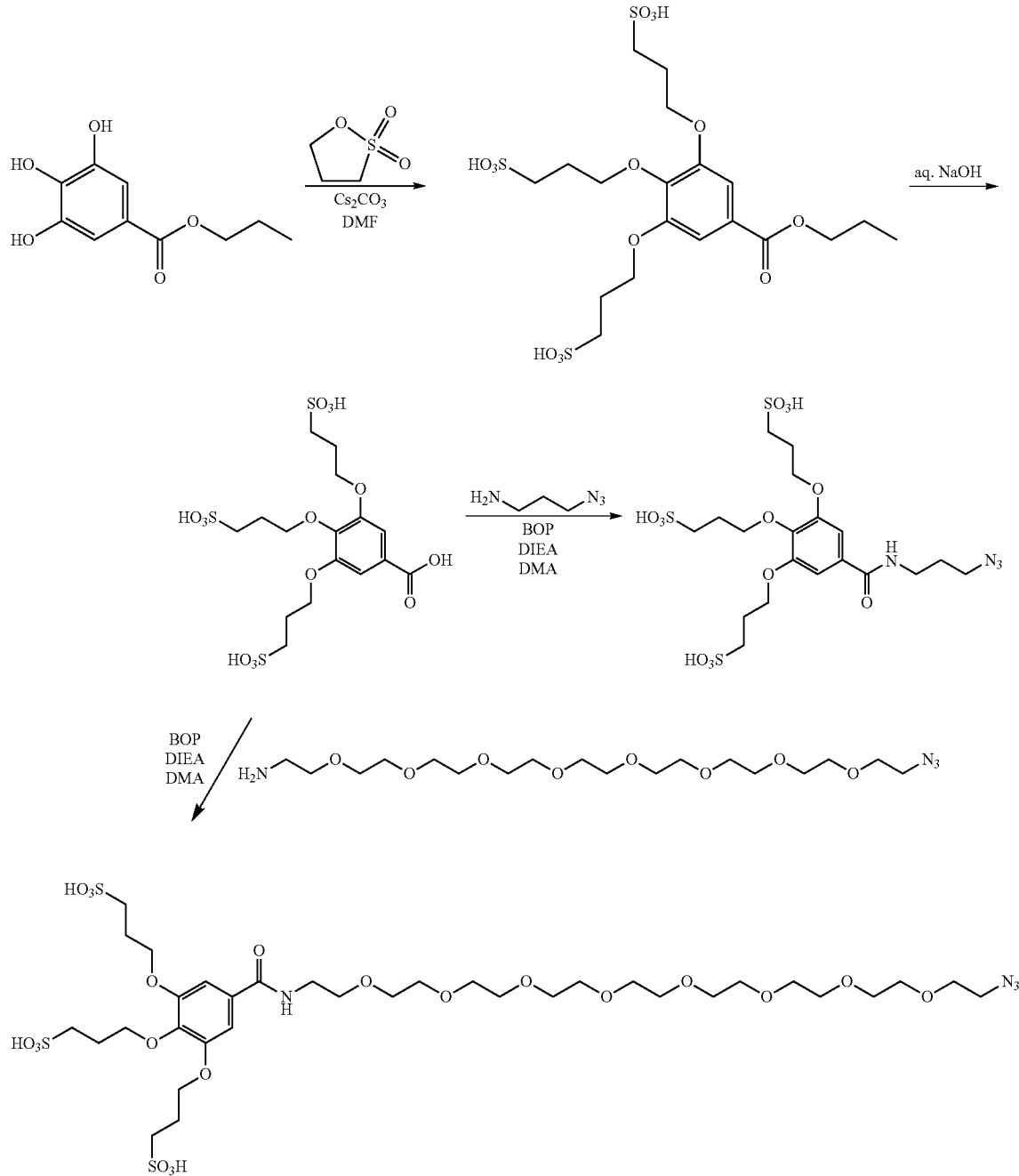

Reasonable variations in all of the above shield component intermediate structures should be considered within the scope of the disclosure.

Exemplary synthetic schemes to generate other azide intermediates are illustrated in Scheme 5:

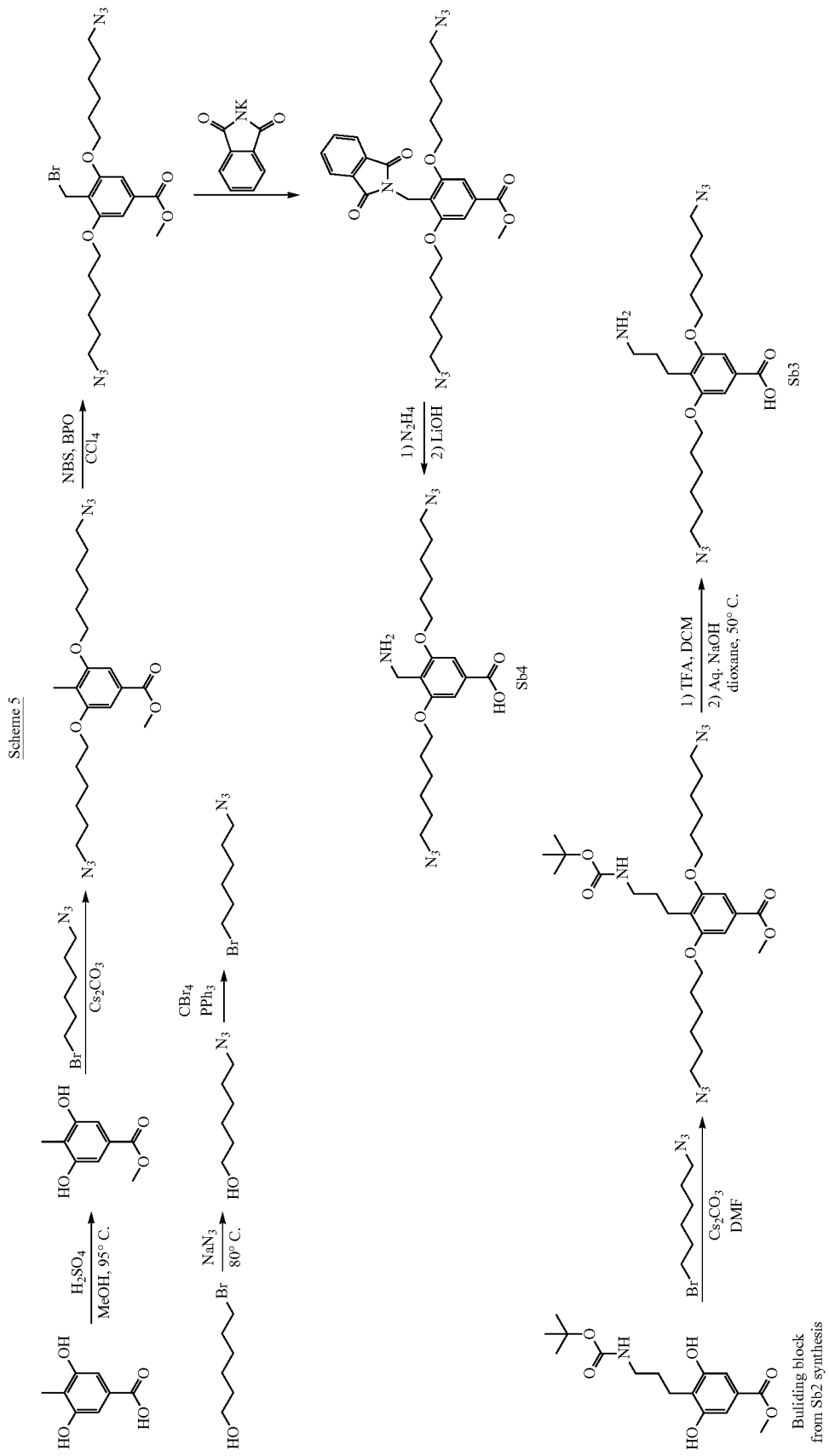

Exemplary reactions for preparing components of the just-described shield elements are illustrated in Schemes 6-1 and 6-2:
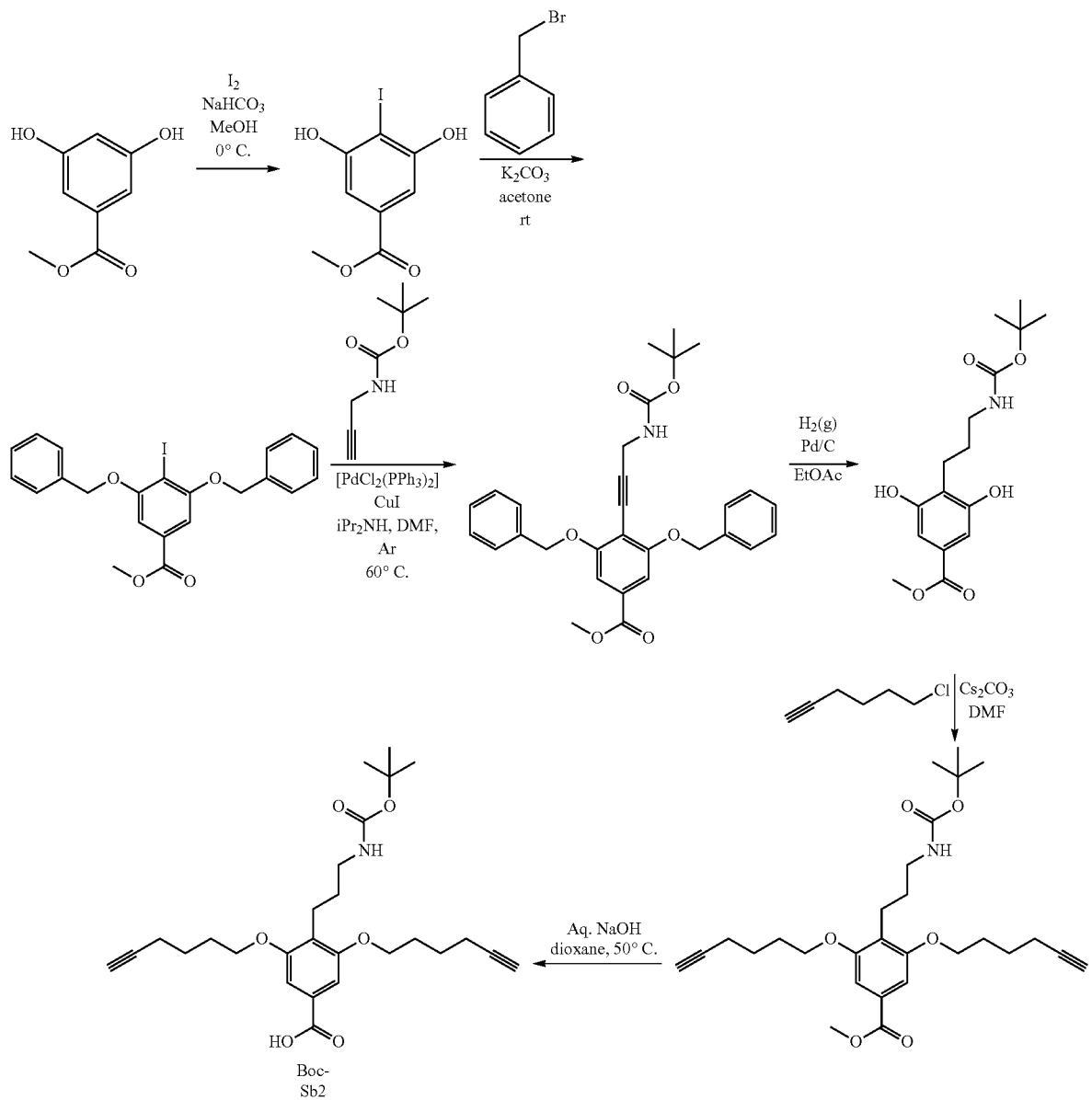
Scheme 6-1

Scheme 6-2
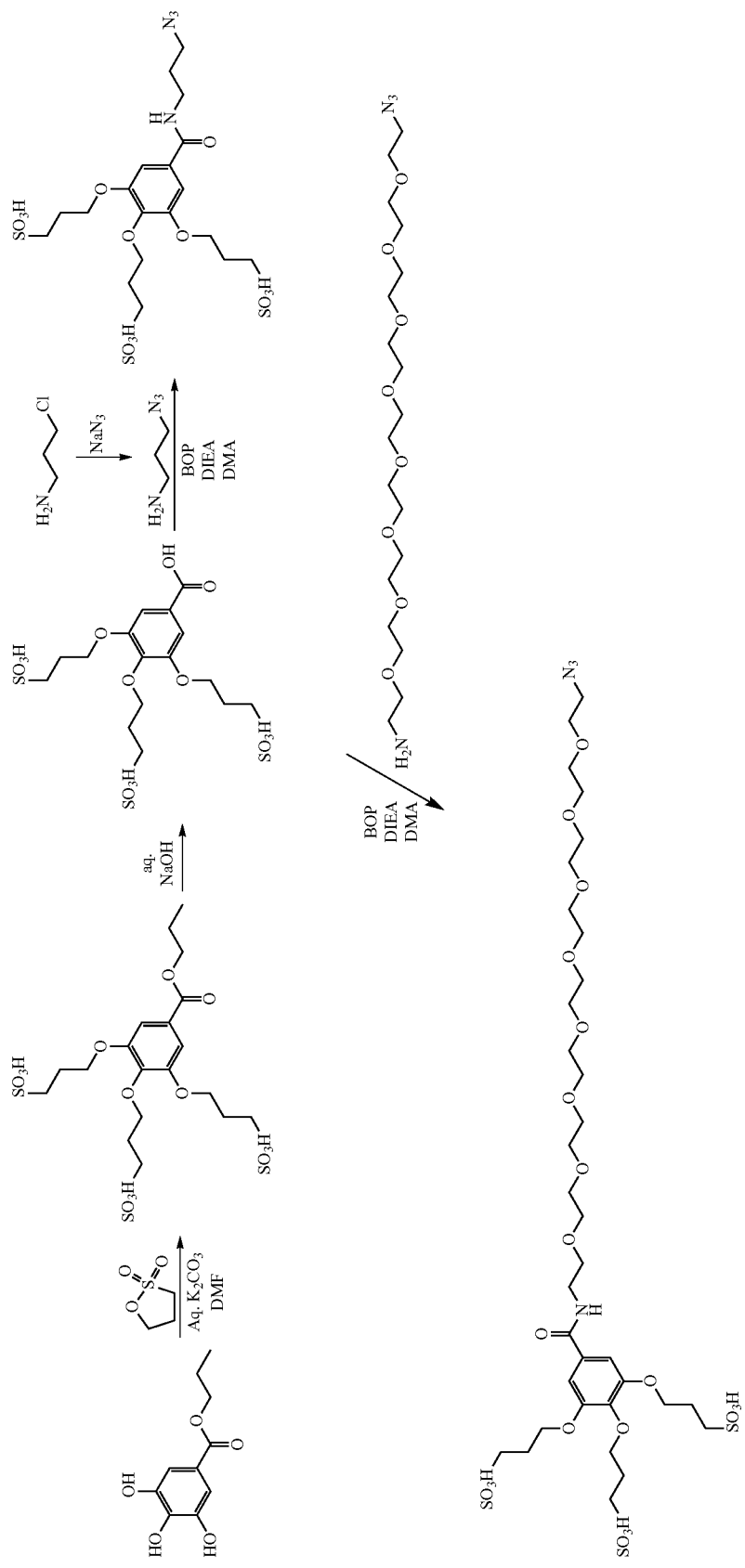

An alternative reaction sequence for preparing components of variant shield elements of the instant nucleotide and dye-labeled compounds is illustrated in Scheme 7, in which the initial step is performed with a single equivalent of the alkylating agent, thus resulting in the selective reaction at the 4-hydroxyl group. Selective alkylation reactions can be used more generally to achieve increased molecular diversity in the preparation of the instant compounds, as is known in the art.

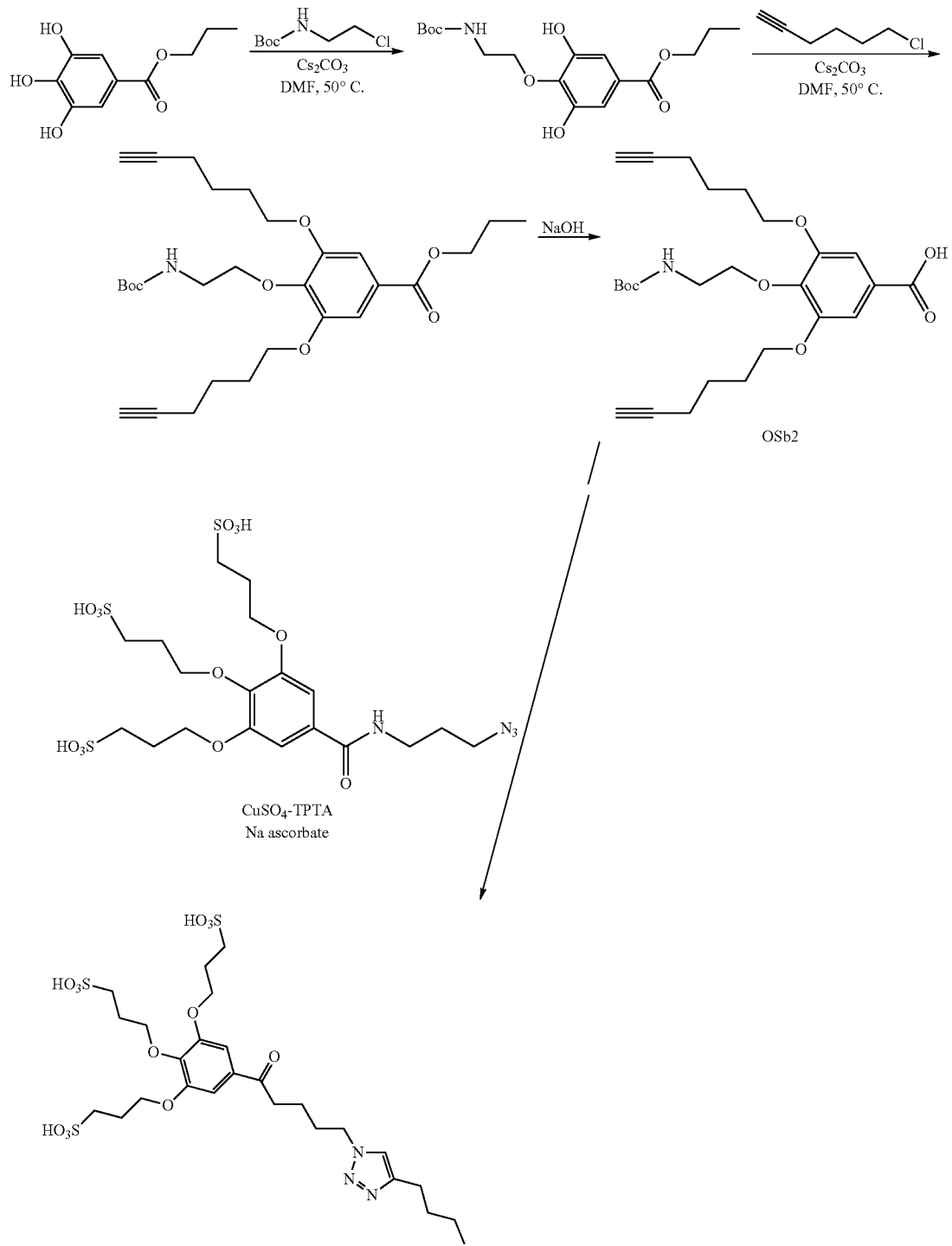

-continued

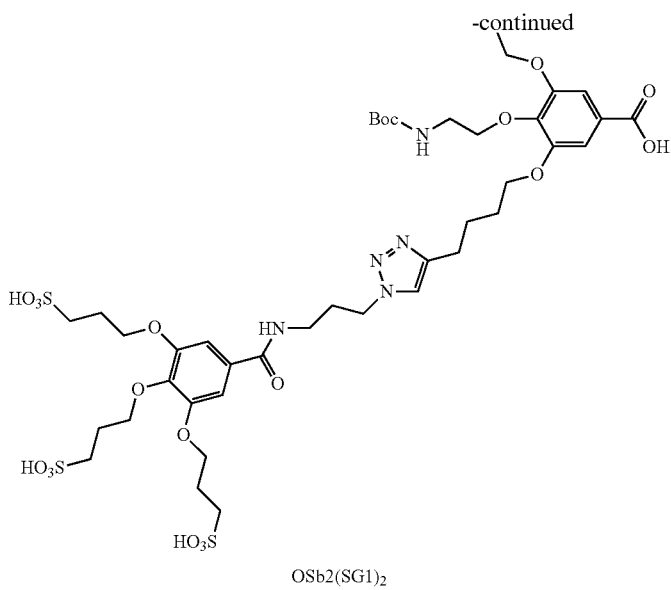

OSb2(SG1)₂

Figure 28:
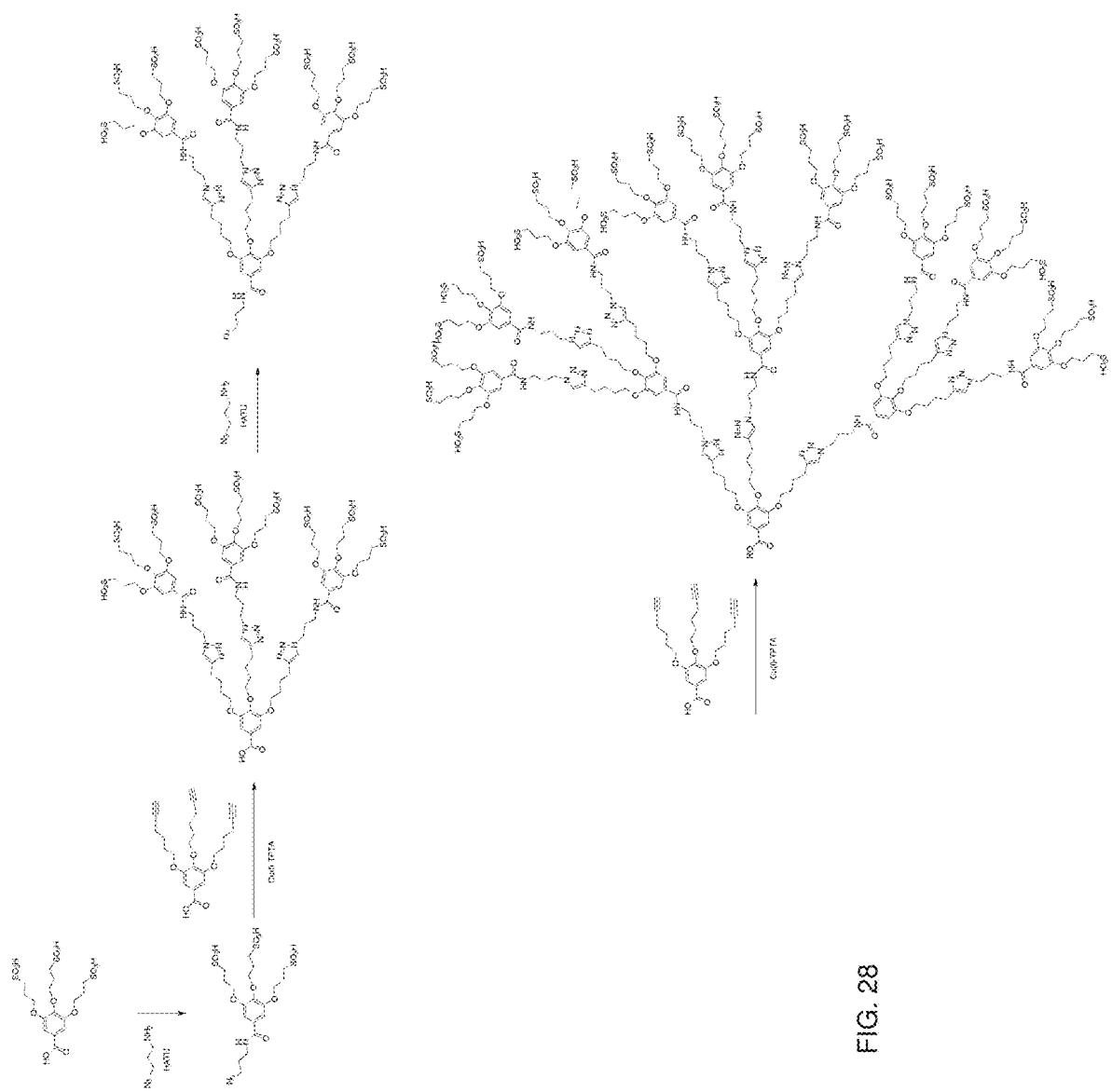
FIG. 28 illustrates an exemplary synthetic route for preparing a dendrimer side chain substituent.

An exemplary synthetic route for preparing a dendrimer side chain substituent of the instant compounds and labeled nucleotide analogs is illustrated in FIG. 28.

In the reaction scheme of FIG. 28, further variability in structure can be achieved through the use of the following exemplary alternative reagents in alternative versions of the illustrated reactions:

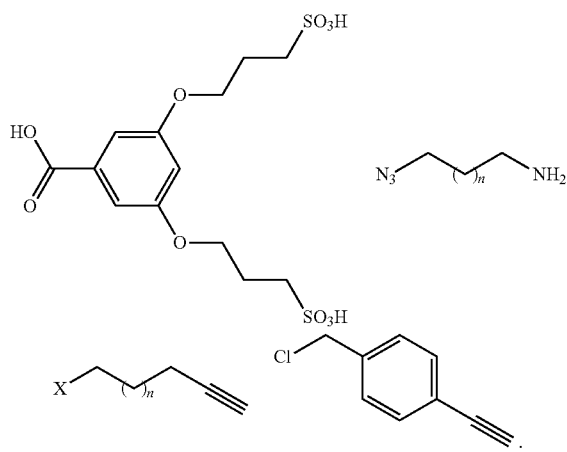

Figure 29:
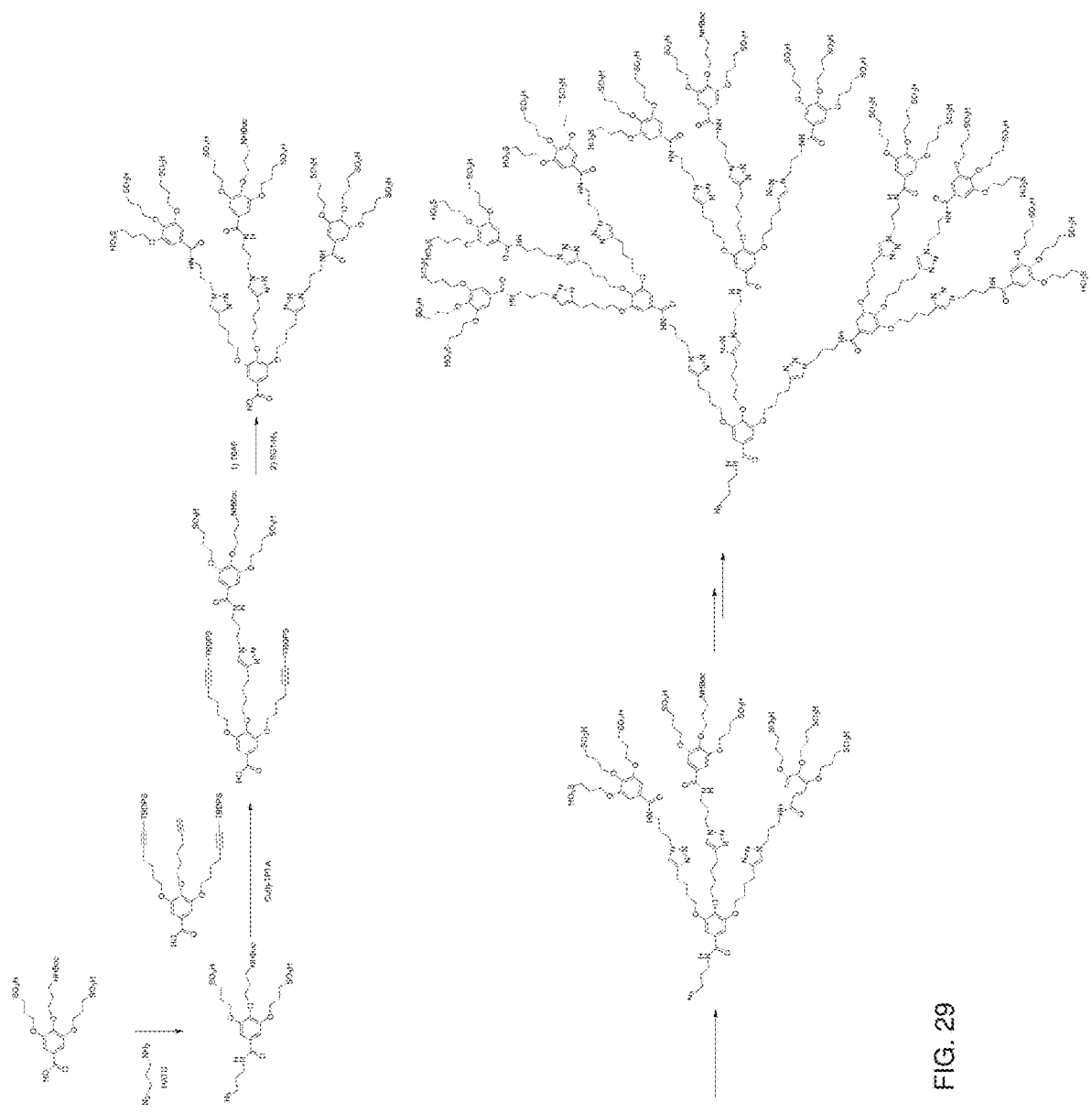
FIG. 29 illustrates an exemplary synthetic pathway for generation of a dendrimer having bifunctional reactivity as a linker.

The generation of a dendrimer having bifunctional reactivity as a linker is illustrated in the synthetic pathway of FIG. 29, where the product shown can be selectively deprotected by removal of the Boc group.

It should be generally understood that other coupling chemistry can prove suitable in synthesizing the compounds of the instant disclosure, as would be understood by those of skill in the art. Accordingly, reactions other than those exemplified in the synthetic schemes above can be utilized, without limitation.

Figure 6A:
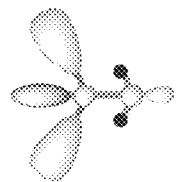
FIG. 6A graphically illustrates an exemplary intermediate structure for incorporation into a labeled nucleotide analog of the disclosure.
Figure 6B:
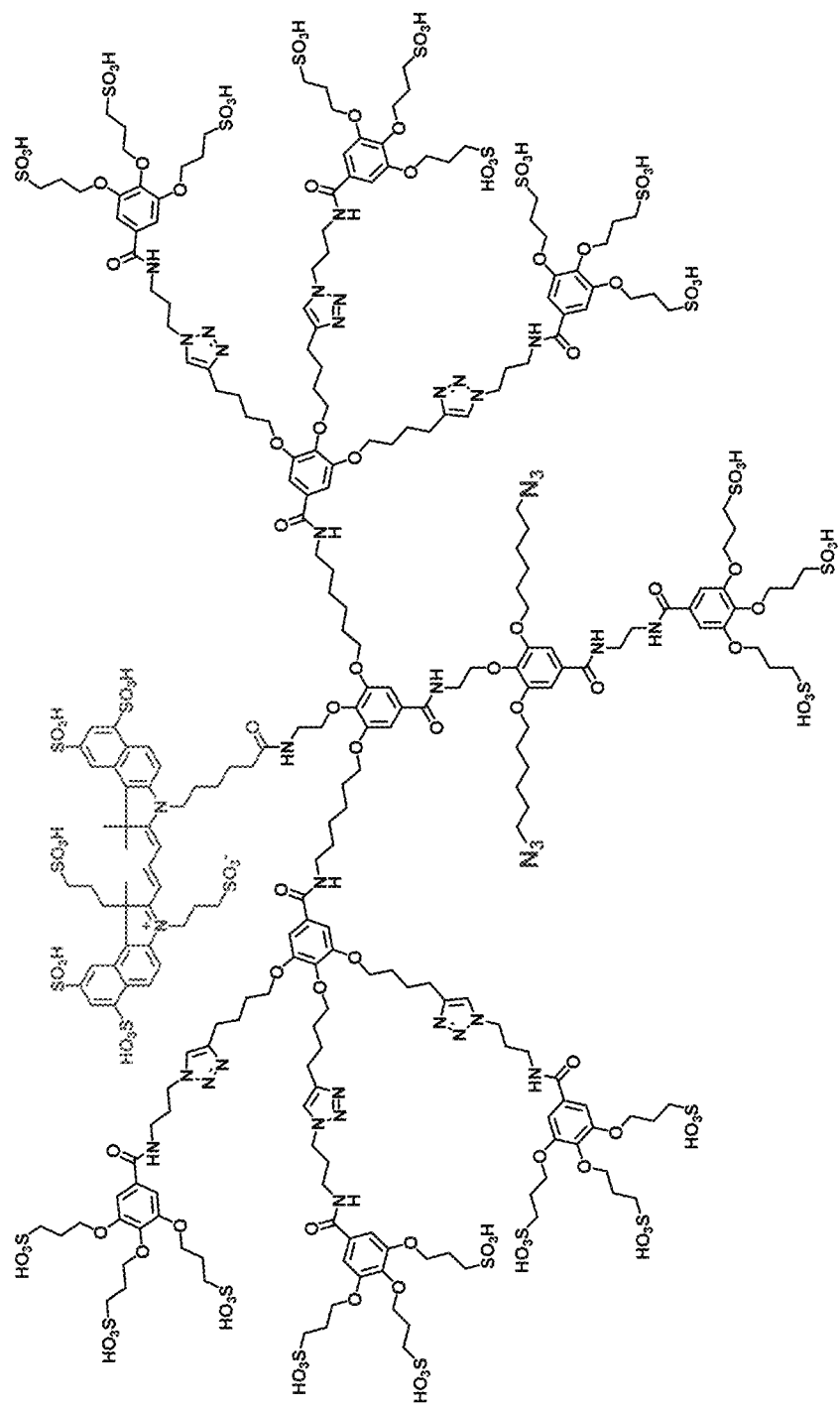
FIGS. 6B-6D illustrate exemplary chemical structures corresponding to the intermediate of FIG. 6A.
Figure 6C:
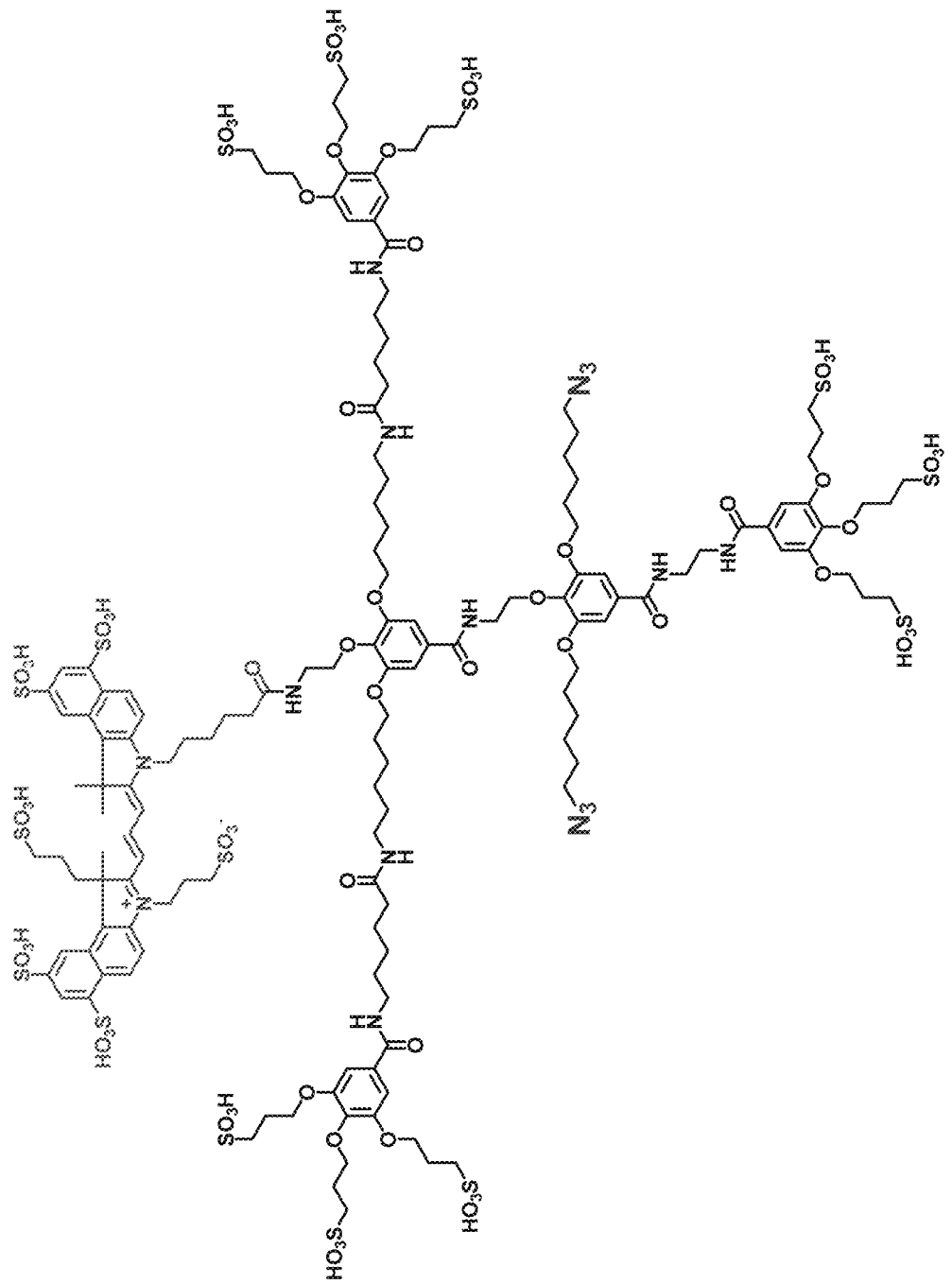
Figure 6D:
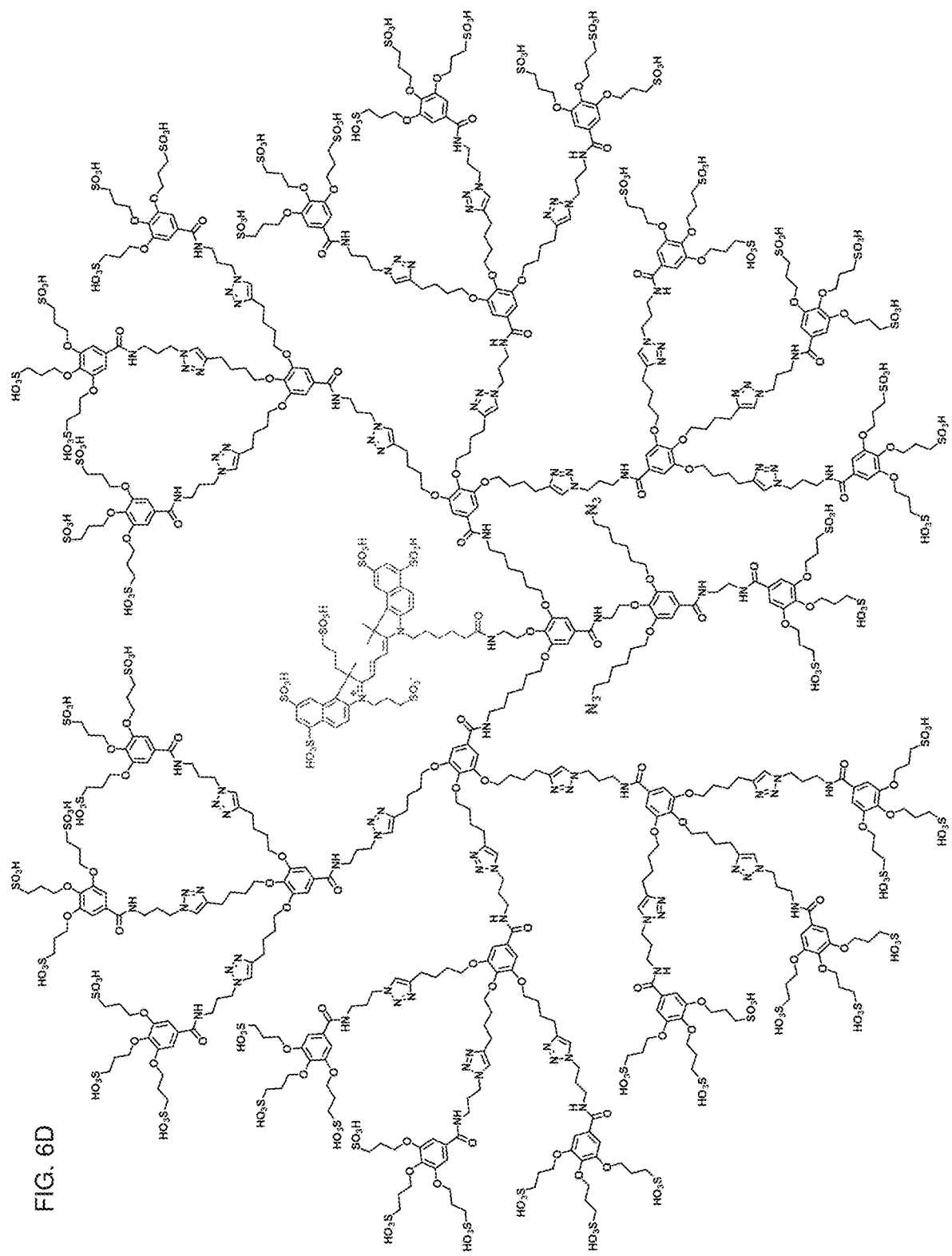

An exemplary shielded dye-labeled intermediate compound usefully incorporated into the dye-labeled compounds and analogs of the instant disclosure is illustrated graphically in FIG. 6A. This particular intermediate has been, for example, used to generate the dye-labeled compound illustrated in FIG. 5G and the labeled nucleotide analog illustrated in FIG. 3K. An exemplary chemical structure corresponding to the illustration of FIG. 6A is provided in FIG. 6B, which comprises a shield element, including a shield core element that is directly coupled to the dye, a dye compound linker element intermediate comprising two reactive azide groups, and another small side chain attached to the dye compound linker element. In this exemplary intermediate compound, the azide groups can be coupled to other dye-labeled intermediate compounds or to a terminal coupling element, such as a terminal coupling element comprising a bis-biotin, using "click" reactions, as will be illustrated below and in FIGS. 7A-7D, 7F, and 7G. The side chains of the shield element can be further varied, if desired. For example, the exemplary chemical structure of FIG. 6C has smaller side chains than the side chains in the structure of FIG. 6B, whereas the exemplary chemical structure of FIG. 6D has larger side chains than the side chains in the structure of FIG. 6B. The different sizes of the side chains in these examples arises from the inclusion of one or more side chain core structures in the larger side chains in the structures of FIGS. 6B and 6D. It should again be understood here that although the illustration of FIG. 6A shows two large side chains and one small side chain, thus corresponding to the chemical structure of FIG. 6B, the graphic illustrations provided in the disclosure should not be considered limiting in the size or exact locations of the components represented in these illustrations.

Figure 6E:
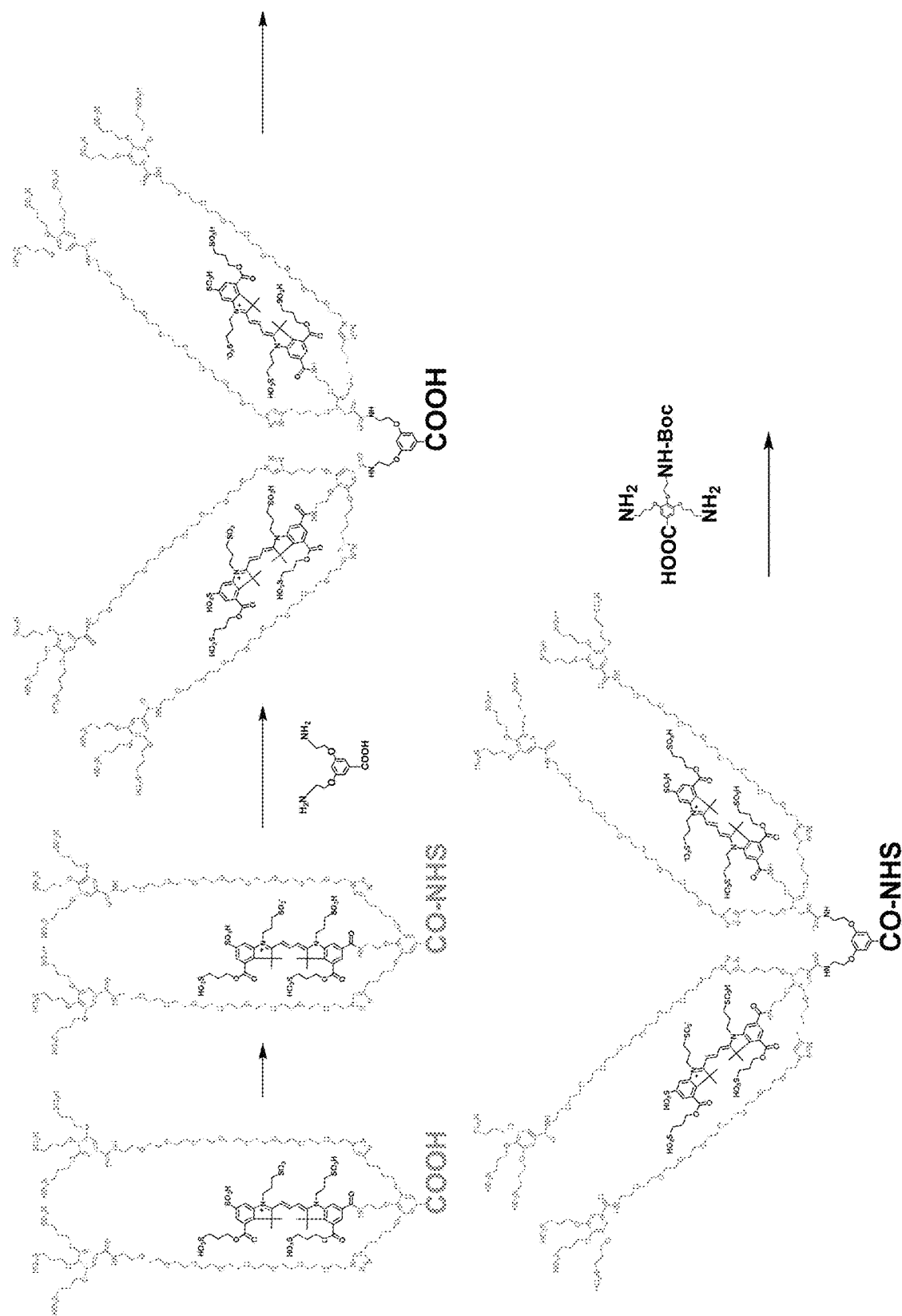
FIG. 6E illustrates the chemical synthesis of a bis-biotin-labeled, four-donor dye ("D4") shielded intermediate compound and a graphical representation of the molecule.
Figure 6E:
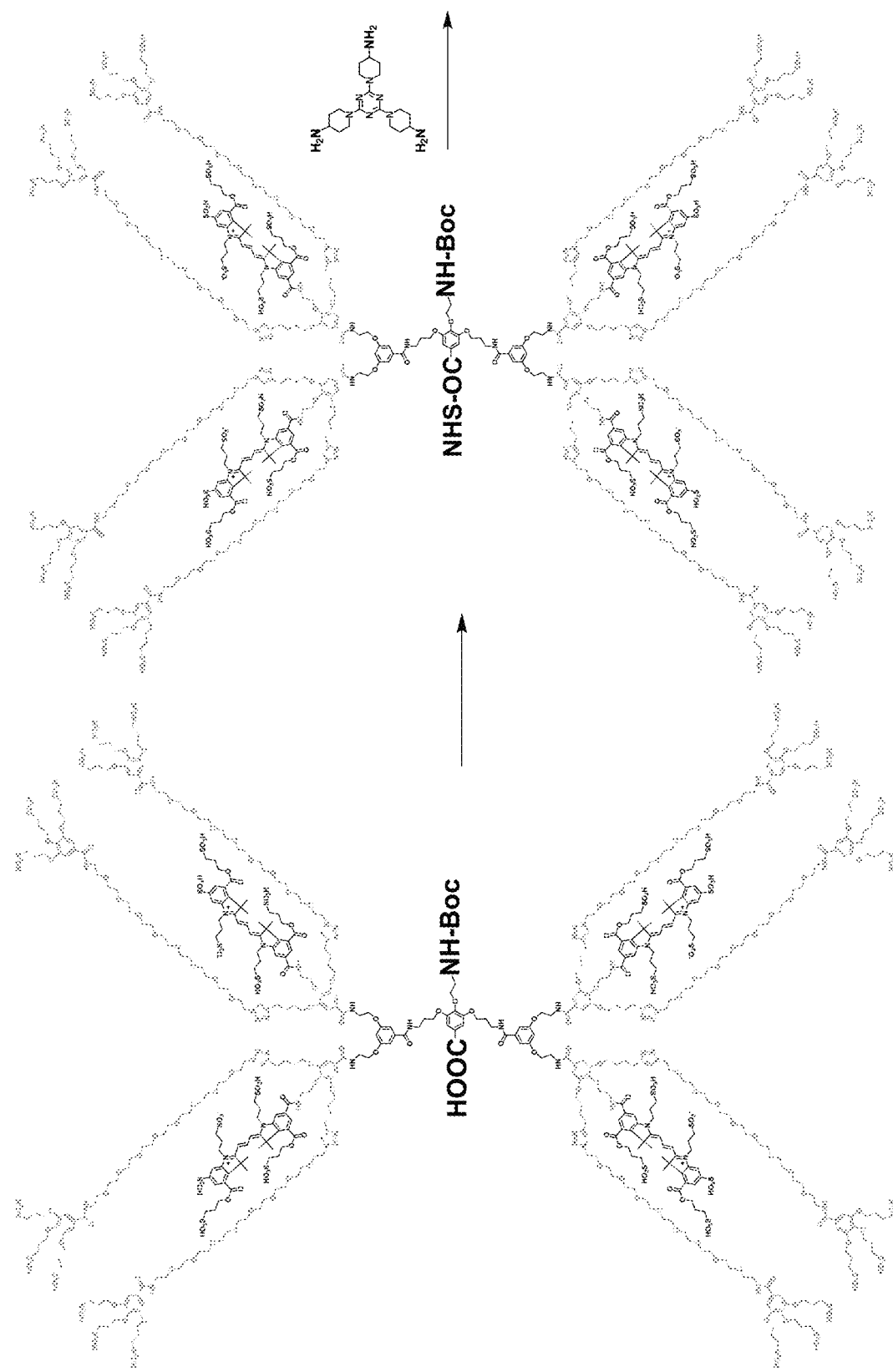
Figure 6E:
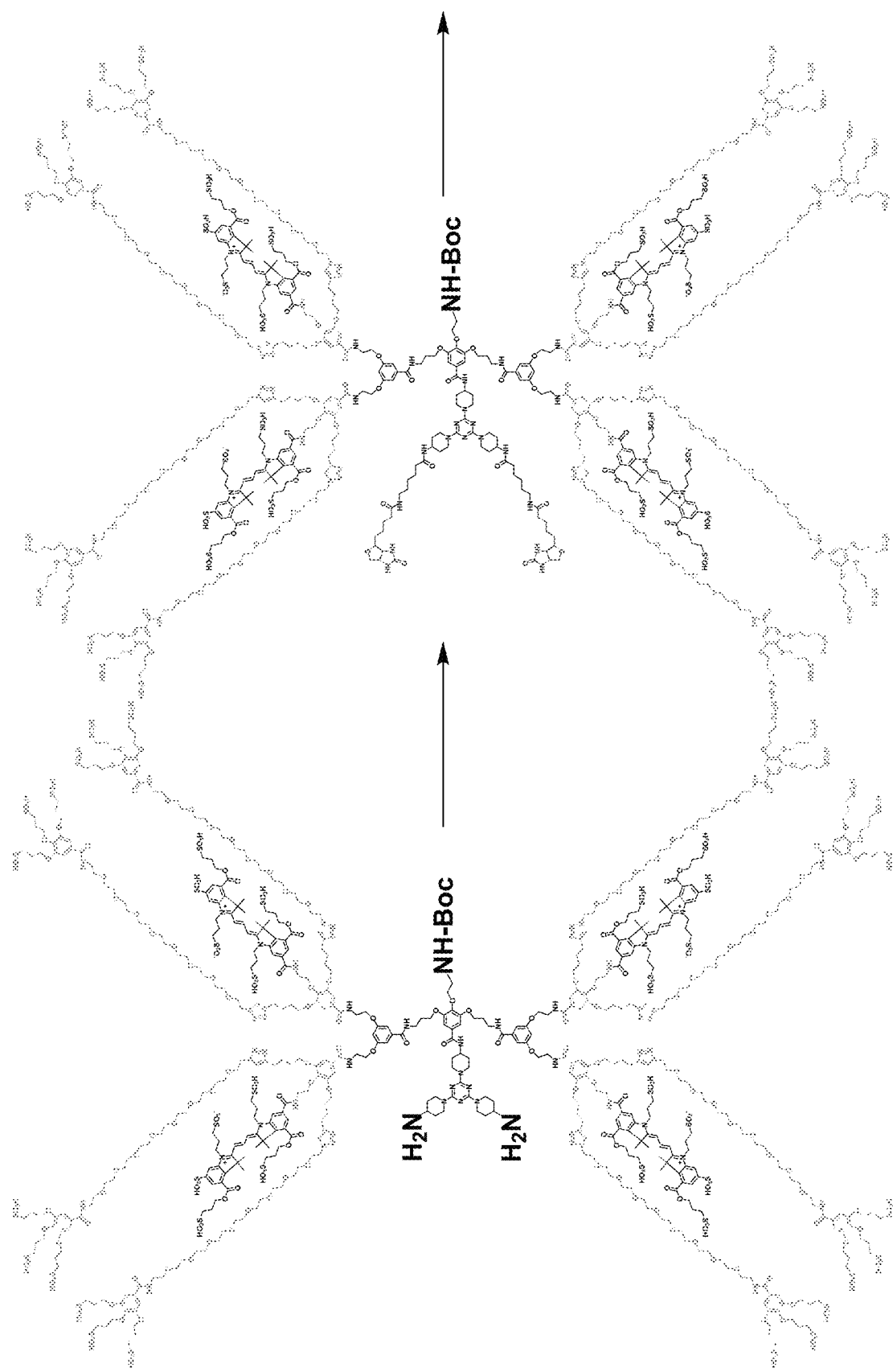
Figure 6E:
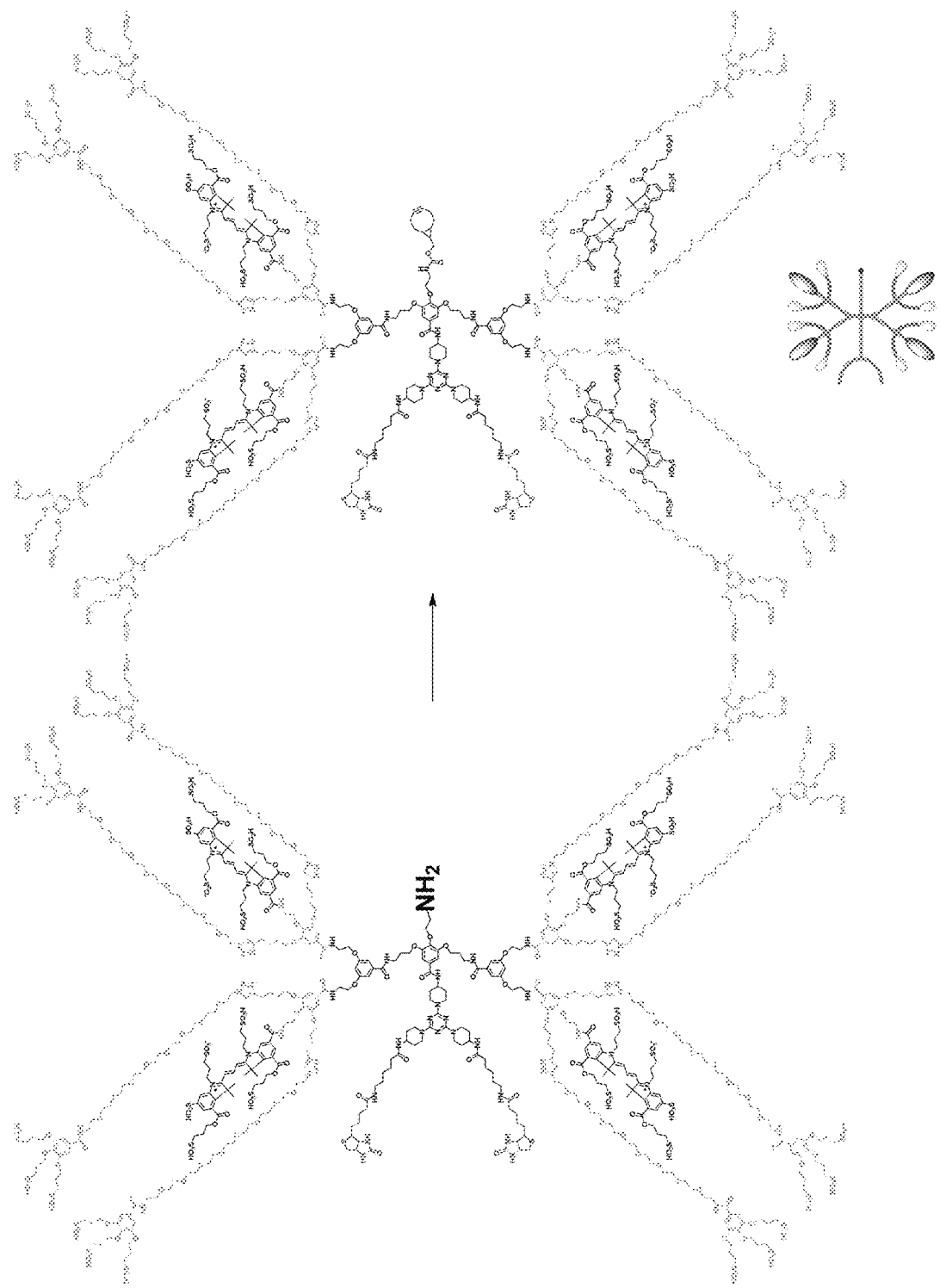
Figure 6F:
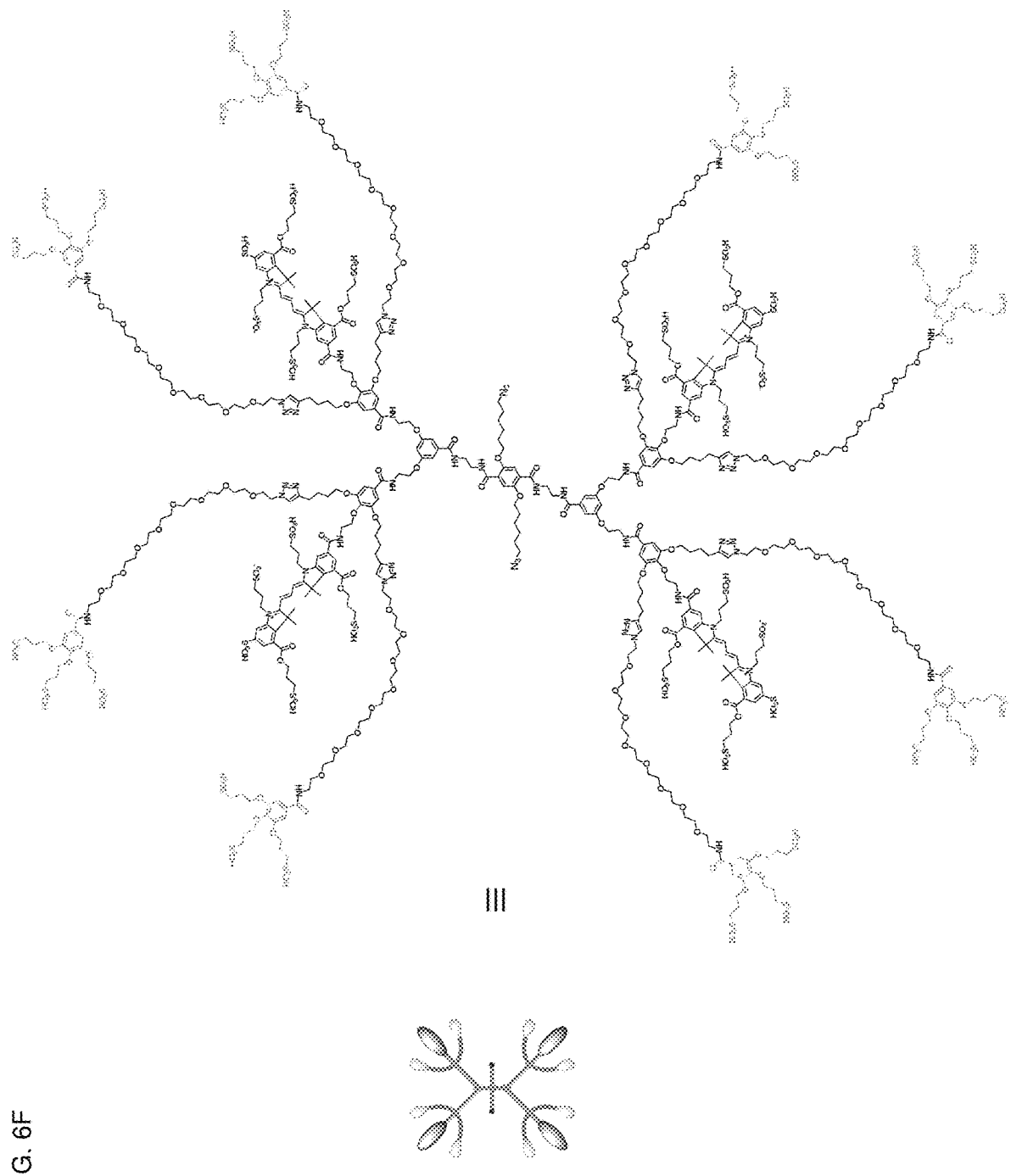
FIG. 6F illustrates another graphic illustration (left) and chemical structure (right) of an exemplary shielded four-donor dye intermediate compound used in the assembly of the instant labeled nucleotide analogs.

FIG. 6E displays a synthetic scheme for another exemplary shielded dye-labeled intermediate compound, this one containing four shielded donor dyes and a bis-biotin binding element. The final product is also displayed in a graphic representation. Note that this intermediate compound contains a cyclooctyne terminal group and is thus suitable for reaction with an azide-substituted component using a copper-free click reaction. A variant exemplary intermediate compound containing four shielded donor dyes and two azide terminal groups is illustrated in FIG. 6F.

Figure 7B:
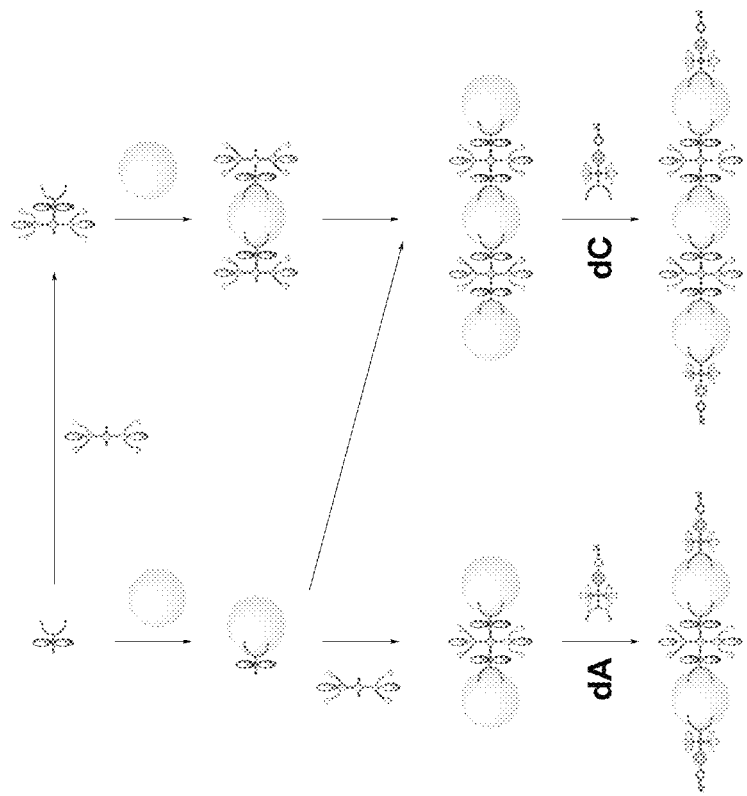
FIGS. 7A-7D outline exemplary pathways for the synthetic assembly of labeled nucleotide analogs of the disclosure.
Figure 7A:
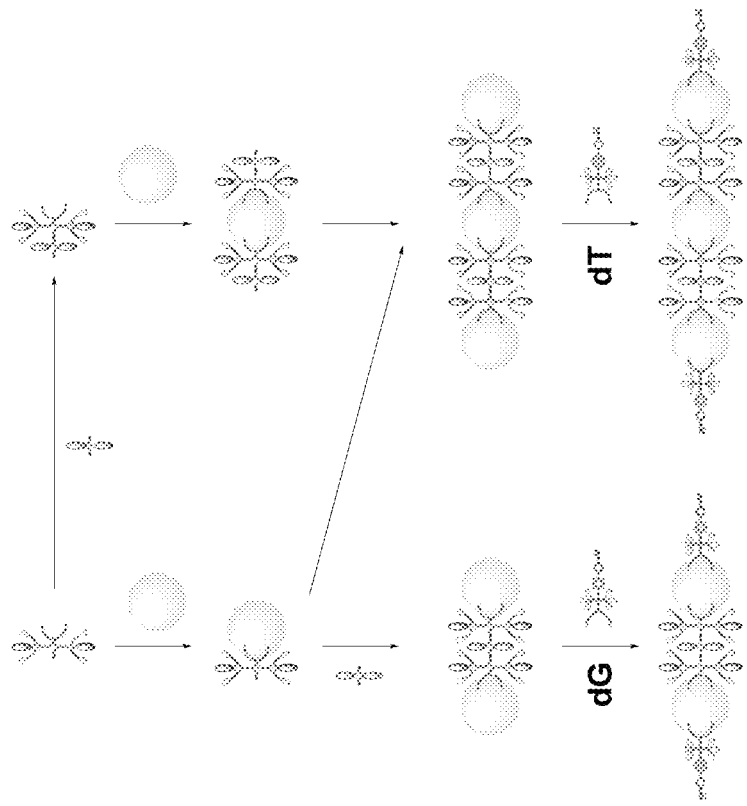

The above-described components, including nucleotide compounds, dye-labeled compounds, and the chemical intermediates used in the synthesis of those compounds, can be used to assemble the labeled nucleotide analogs of the instant disclosure, for example using the steps outlined in FIGS. 7A-7D and 7F. As shown in FIG. 7A, exemplary labeled nucleotide analogs comprising dG and dT can be prepared by starting with a first dye-labeled intermediate compound comprising two shielded donor dyes, a terminal coupling element (e.g., bis-biotin), and a dye compound linker element intermediate with a reactive terminal group. In the preparation of the exemplary dG nucleotide analog, the dye-labeled intermediate is first complexed with an avidin protein, as represented by the spherical structure. A second dye-labeled intermediate compound, this one containing two unshielded acceptor dyes connected by a dye compound linker element intermediate with two reactive terminal groups is next coupled to the partially assembled analog. This coupling reaction is carried out with an excess of the complexed first dye-labeled intermediate and avidin, such that both reactive terminal groups of the second dye-labeled intermediate compound are modified by the reactive groups of two of the first intermediate dye-labeled compounds. The coupling reaction is preferably a copper-catalyzed or copper-free click reaction, but other suitable coupling reactions could be employed to generate the intermediate complex. This complex, which comprises two avidin proteins and a dye-labeled compound comprising two unshielded acceptor dyes, four shielded donor dyes, three coupled dye compound linker elements, and two bis-biotin terminal coupling elements, is then reacted with an excess of a dG nucleotide compound to generate the final dG analog product. The nucleotide compounds used in all of the analogs shown in FIGS. 7A and 7B comprise a single nucleoside element (dG, dT, dA, or dC), a polyphosphate element, a nucleotide linker element comprising an anionic aromatic spacer element and a shield element, and a bis-biotin terminal coupling element.

An exemplary dT nucleotide analog can be prepared, for example, by the pathway shown on the right side of FIG. 7A. According to this pathway, the first dye-labeled intermediate comprising two shielded donor dyes, a terminal coupling element (e.g., bis-biotin), and a dye compound linker element intermediate with a reactive terminal group is first coupled to the second dye-labeled intermediate compound comprising two unshielded acceptor dyes connected by a dye compound linker element intermediate with two reactive terminal groups. An excess of the product of the coupling reaction is complexed with an avidin protein to generate a complex comprising one avidin protein and two of the partially coupled dye-labeled compound intermediates. This complex is next coupled to an excess of the first avidin complex from the first pathway, which comprises an avidin protein and the dye-labeled complex intermediate with two shielded donor dyes. As shown, the product of this coupling reaction comprises three avidin proteins and two of the dye-labeled compounds described above for the dG analog. The dG and dT analogs can be distinguished from one another by the difference in intensity of fluorescence signal emitted from the each complex, because the dT analog contains two dye-labeled compounds whereas the dG analog contains just one dye-labeled compound. Each of the dye-labeled compounds in the dG and dT analogs comprises four shielded donor dyes and two unshielded acceptor dyes.

The dA and dC analogs can be assembled as outlined in the exemplary pathways of FIG. 7B. The primary difference between the pathways of FIG. 7B and the pathways of FIG. 7A is the use of a first dye-labeled intermediate compound comprising two unshielded donor dyes. This first intermediate is otherwise the same as the first dye-labeled intermediate of FIG. 7A which comprises two shielded donor dyes. The other difference in the pathways is the use of a second dye-labeled intermediate compound comprising two shielded acceptor dyes compared to the second intermediate of FIG. 7A which comprises two unshielded acceptor dyes. The dA and dC analogs can be distinguished from one another by the difference in intensity of fluorescence signal emitted from the each complex, because the dC analog contains two dye-labeled compounds whereas the dA analog contains just one dye-labeled compound. Each of the dye-labeled compounds in the dA and dC analogs comprises four unshielded donor dyes and two shielded acceptor dyes. As with the dG and dT analogs, the dA and dC analogs can be distinguished from one another by the difference in intensity of fluorescence signal emitted from the each complex. The dG analog is distinguishable from the dA analog and the dT analog is distinguishable from the dC analog based on differences in spectra of the different dye-labeled compounds due to the different microenvironments of the shielded dyes.

Figure 7C:
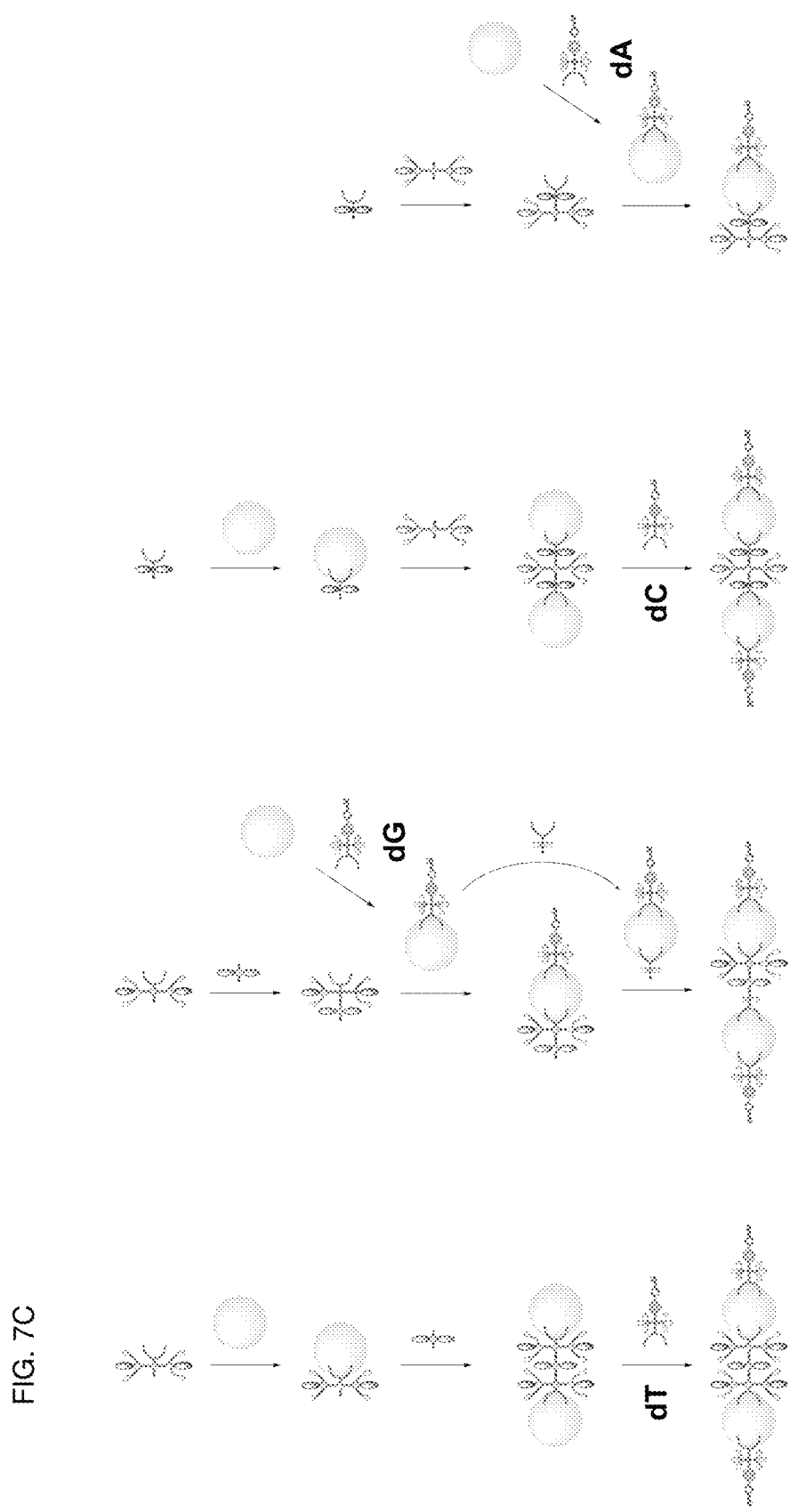
Figure 7D:
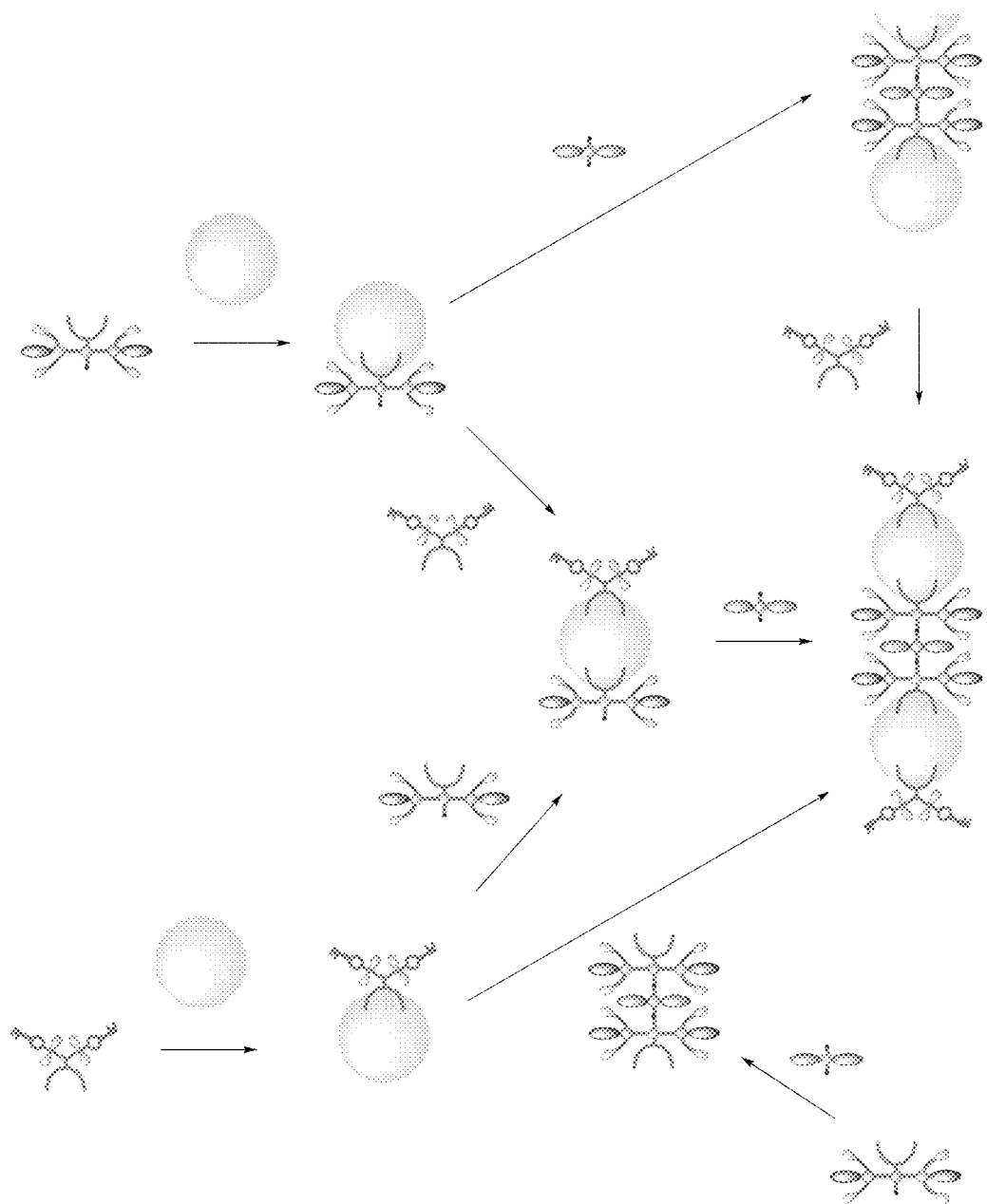
Figure 7E:
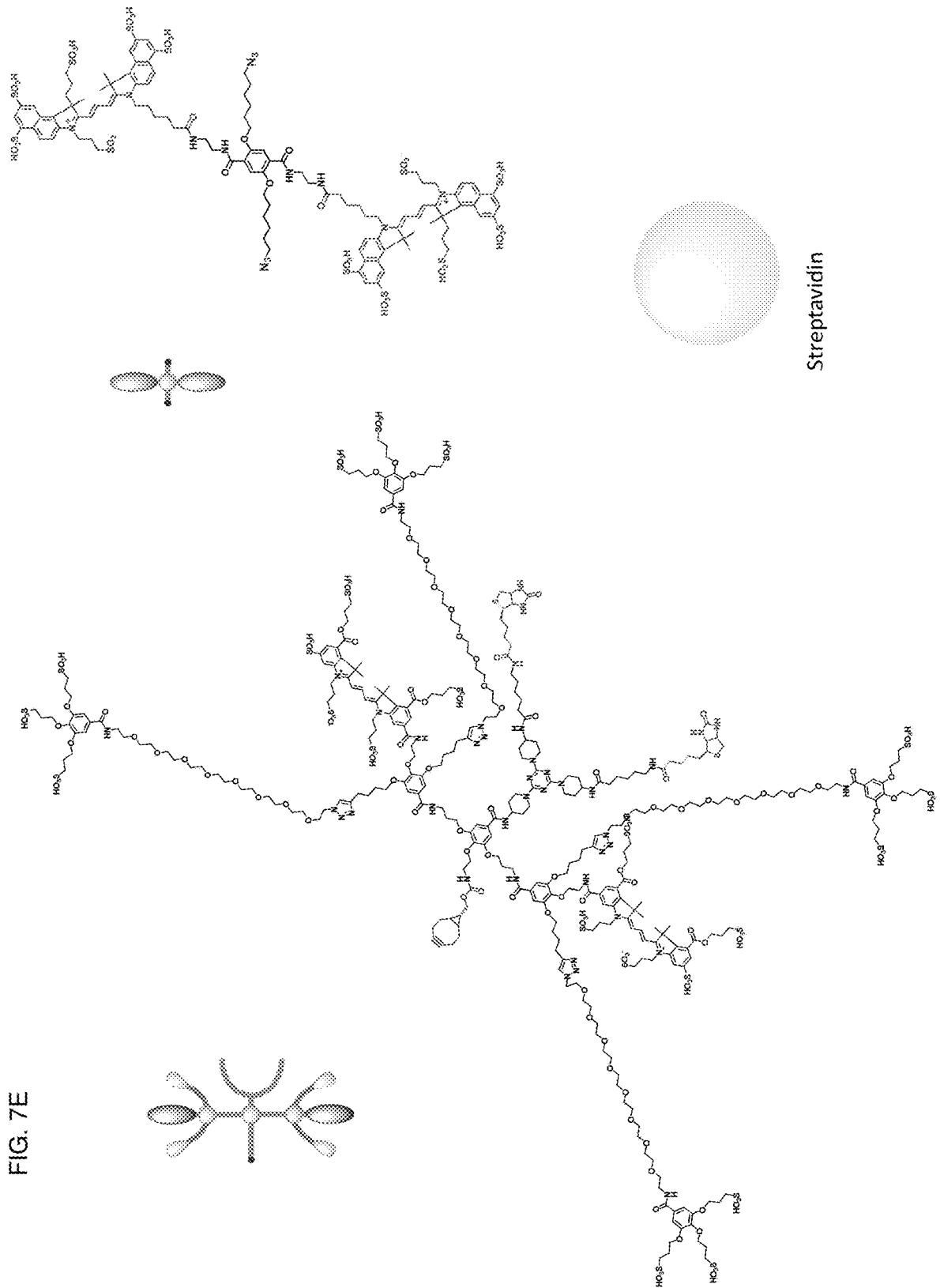
FIG. 7E illustrates the relationship between the graphic representations of some of the different intermediate components illustrated in FIGS. 7A-7D and the chemical structures of those components.
Figure 7E:
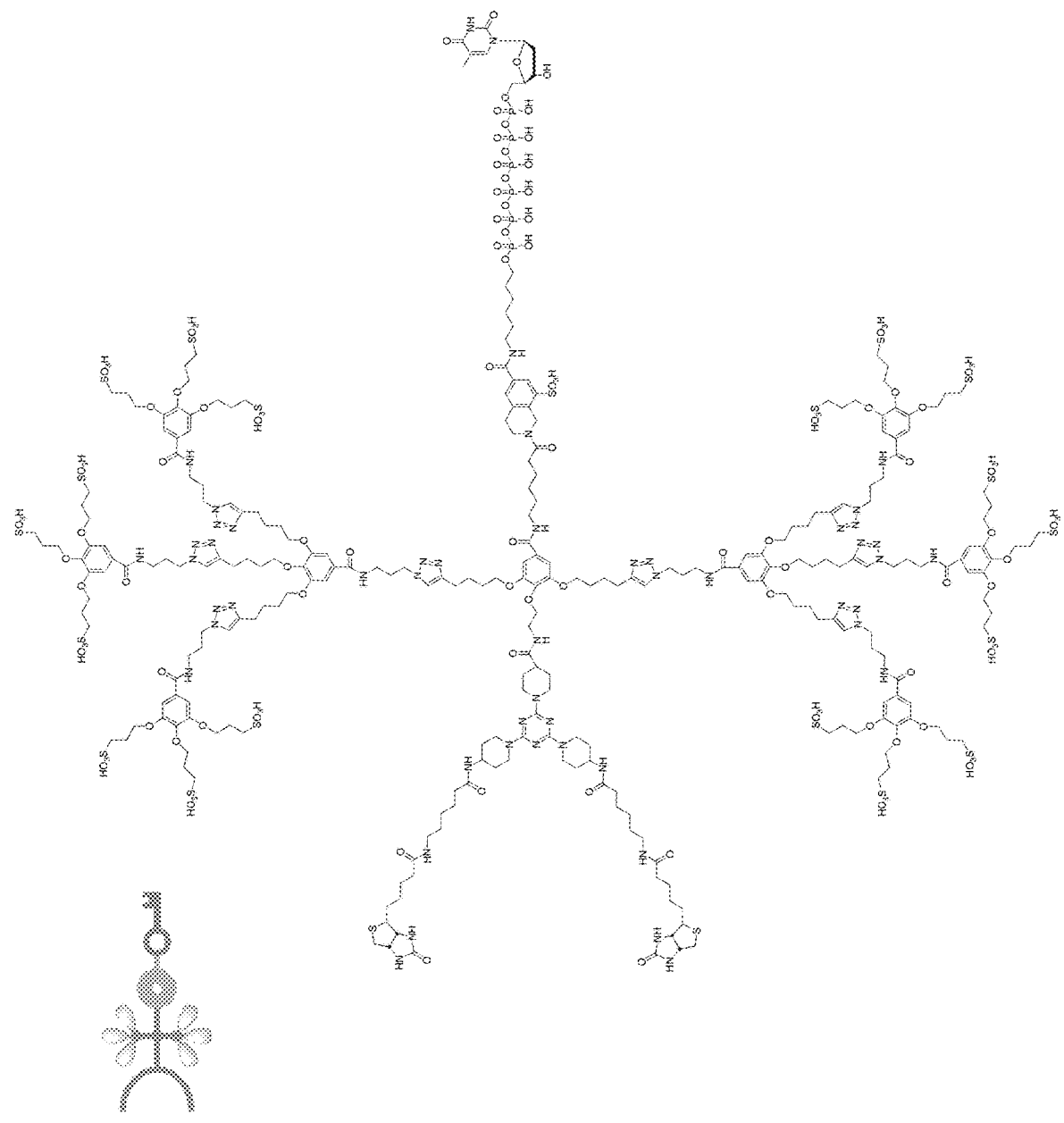
Figure 7E:
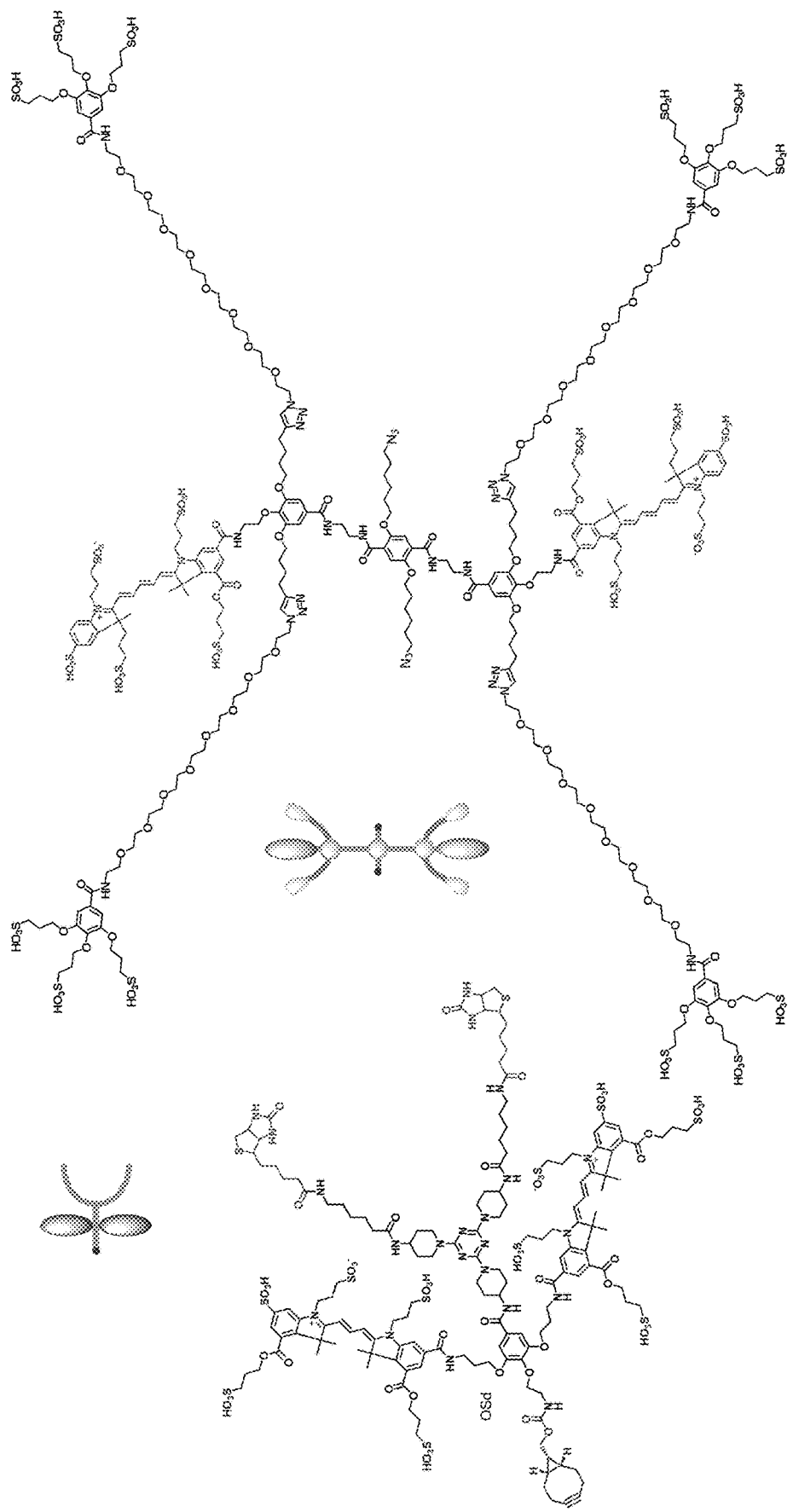
Figure 7G:
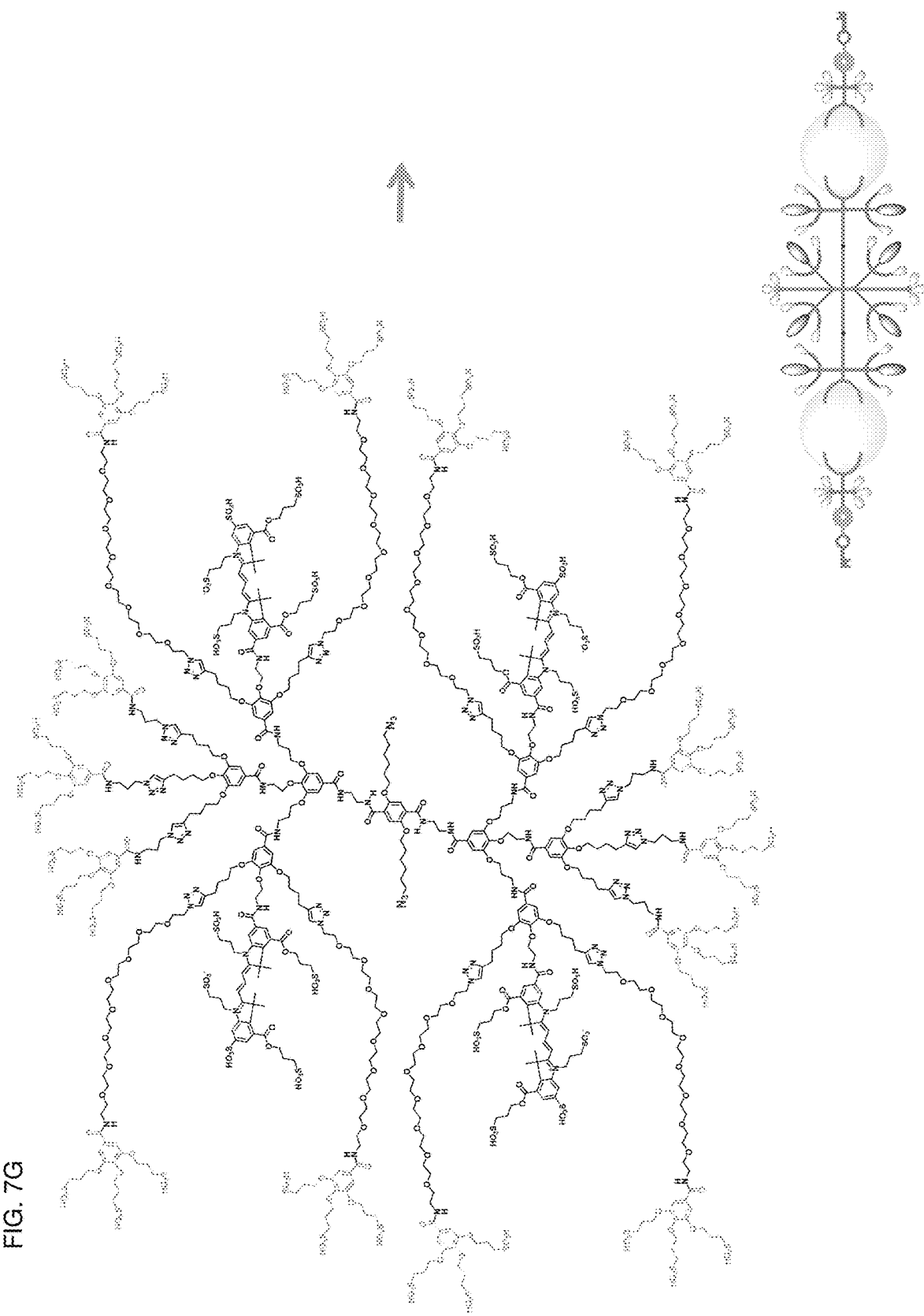
FIG. 7G shows the chemical structure of an alternatively shielded intermediate component comprising four shielded donor dyes and two azide groups (left). Also shown is a graphic representation of an exemplary labeled nucleotide analog that can be generated from the intermediate component (right).

FIGS. 7C and 7D illustrate alternative pathways useful in the assembly of analogs comprising exemplary labeled dT, dG, dC, and dA nucleotide analogs. FIG. 7E provides a legend for the relationship between some of the exemplary graphical illustrations of the figures and the chemical structures of the components represented in those illustrations. FIG. 7F displays still other exemplary components and pathways that have been used to prepare labeled nucleotide analogs of the instant disclosure.

Exemplary labeled nucleotide analogs of the instant disclosure thus include the specific analogs described in the following numbered paragraphs:

1. A labeled nucleotide analog comprising:
 a first avidin protein having four subunits, each subunit comprising one biotin binding site;
 a first nucleotide compound bound to the first avidin protein, the first nucleotide compound comprising a polyphosphate element, a nucleoside element, an optional multivalent central core element, a terminal coupling element, and a nucleotide linker element, wherein the first nucleotide compound comprises at least one affinity modulating element; and
 a first dye-labeled compound bound to the first avidin protein, the first dye-labeled compound comprising a donor dye, an acceptor dye, a terminal coupling element, and a dye compound linker element.

2. The labeled nucleotide analog of paragraph 1, wherein the first dye-labeled compound and the first nucleotide compound are each bound to the first avidin protein through a biotin moiety.

3. The labeled nucleotide analog of paragraph 1, further comprising a second avidin protein and a second nucleotide compound, wherein
 the second avidin protein is bound to the first dye-labeled compound through a biotin moiety and to the second nucleotide compound through a biotin moiety.

4. The labeled nucleotide analog of paragraph 1, wherein the first avidin protein is avidin, streptavidin, tamavidin, traptavidin, xenavidin, bradavidin, AVR2, AVR4, or a homolog thereof.

5. The labeled nucleotide analog of paragraph 1, wherein the donor dye and the acceptor dye are fluorescent dyes.

6. The labeled nucleotide analog of paragraph 1, wherein the first nucleotide compound is represented by structural formula (I):

B″─[X]ₒ─[L─P─Nu]ₙ;   (I)

wherein

L is the nucleotide linker element and comprises the affinity modulating element;

P is the polyphosphate element;

Nu is the nucleoside element;

X is the multivalent central core element;

B″ is the terminal coupling element and comprises a biotin moiety;

n is an integer from 1 to 4; and o is 0 or 1.

7. The labeled nucleotide analog of paragraph 6, wherein the affinity modulating element is an aromatic spacer element.

8. The labeled nucleotide analog of paragraph 7, wherein the aromatic spacer element is a substituted or unsubstituted monocyclic, bicyclic, tricyclic, or tetracyclic aromatic moiety.

9. The labeled nucleotide analog of paragraph 8, wherein the aromatic spacer element optionally comprises at least one anionic substituent.

10. The labeled nucleotide analog of paragraph 9, wherein the aromatic spacer element optionally comprises at least two anionic substituents.

11. The labeled nucleotide analog of paragraph 9, wherein the optional at least one anionic substituent is —SO₃H.

12. The labeled nucleotide analog of paragraph 8, wherein the aromatic spacer element is represented by one of the following structural formulae:

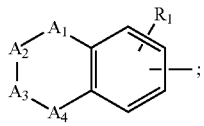
(IIA)

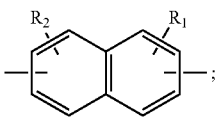
(IIB)

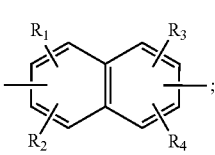
(IID)

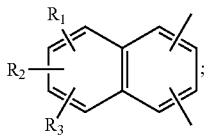
(IIE)

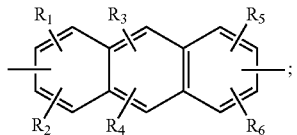
(IIF)

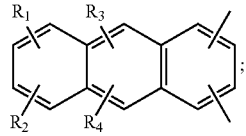
(IIG)

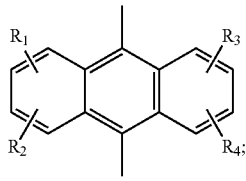
(IIH)

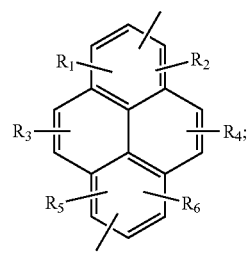
(IIJ)

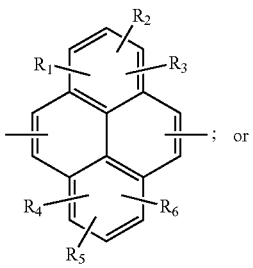
(IIK)

; or

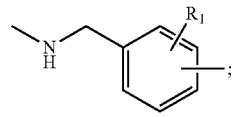
(IV)

wherein one of the A₁, A₂, A₃, and A₄ groups is

and the other groups are —CH₂— or a bond; and

R₁, R₂, R₃, R₄, R₅, and R₆ are independently H or an anionic substituent.

13. The labeled nucleotide analog of paragraph 12, wherein the aromatic spacer element is represented by one of the following structural formulae:

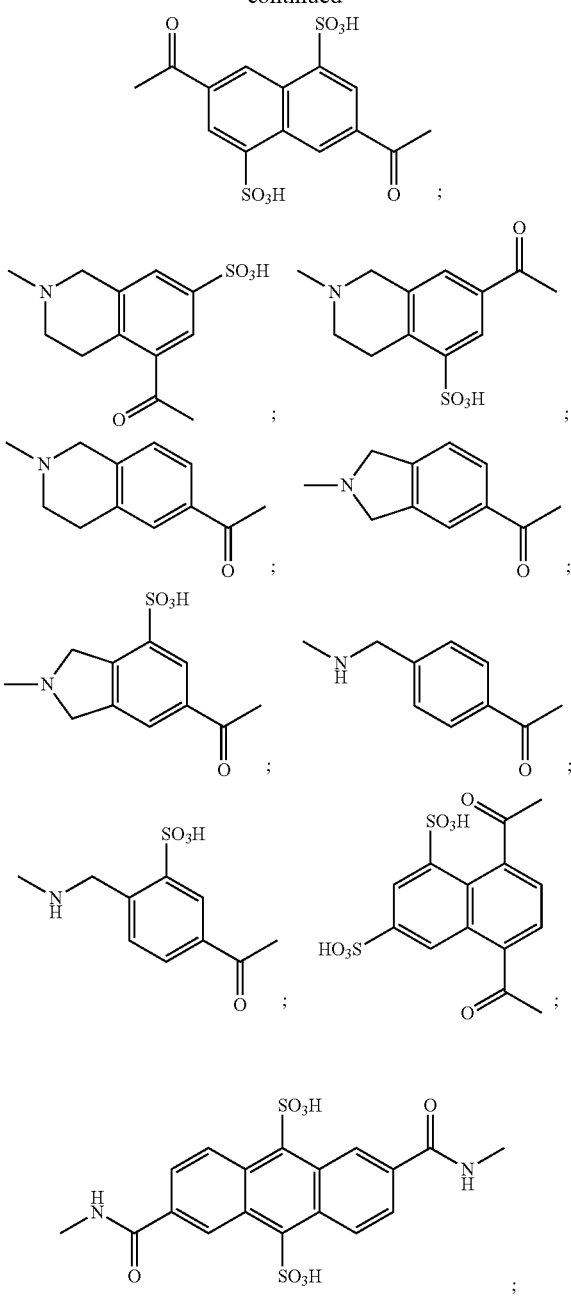

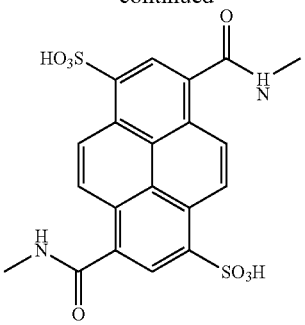

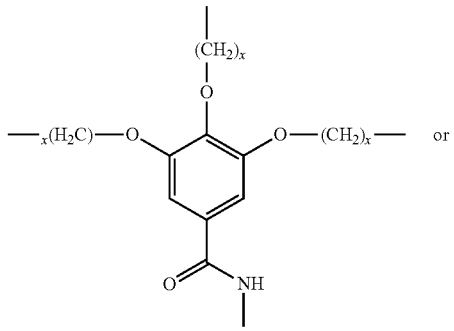

14. The labeled nucleotide analog of paragraph 6, wherein L further comprises an alkyl linker group, optionally comprising an amide bond.
15. The labeled nucleotide analog of paragraph 6, wherein L further comprises a triazole.
16. The labeled nucleotide analog of paragraph 6, wherein B" comprises a biotin moiety.
17. The labeled nucleotide analog of paragraph 16, wherein B" comprises a bis-biotin moiety.
18. The labeled nucleotide analog of paragraph 6, wherein o is 1.
19. The labeled nucleotide analog of paragraph 18, wherein n is 2.
20. The labeled nucleotide analog of paragraph 18, wherein X comprises a polyamine moiety.
21. The labeled nucleotide analog of paragraph 6, wherein o is 0 and n is 1.
22. The labeled nucleotide analog of paragraph 6, wherein the at least one nucleotide compound does not contain a dye.
23. The labeled nucleotide analog of any one of paragraphs 6-22, wherein L comprises at least one shield element.
24. The labeled nucleotide analog of paragraph 23, wherein the shield element comprises a plurality of side chains.
25. The labeled nucleotide analog of paragraph 24, wherein at least one side chain has a molecular weight of at least 300.
26. The labeled nucleotide analog of paragraph 24, wherein all of the side chains have a molecular weight of at least 300.
27. The labeled nucleotide analog of paragraph 24, wherein at least one side chain comprises a negatively-charged component.
28. The labeled nucleotide analog of paragraph 27, wherein the negatively-charged component comprises a sulfonic acid.
29. The labeled nucleotide analog of paragraph 24, wherein at least one side chain comprises a substituted phenyl group.
30. The labeled nucleotide analog of paragraph 29, wherein the at least one side chain comprises the structure:

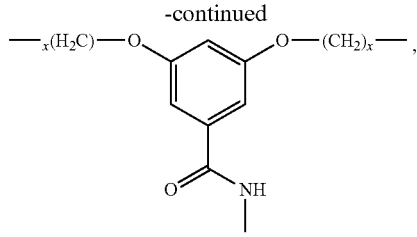
wherein each x is independently an integer from 1 to 6.
31. The labeled nucleotide analog of paragraph 30, wherein each x is independently an integer from 1 to 4.
32. The labeled nucleotide analog of paragraph 24, wherein at least one side chain comprises a triazole.
33. The labeled nucleotide analog of paragraph 24, wherein at least one side chain comprises the structure:
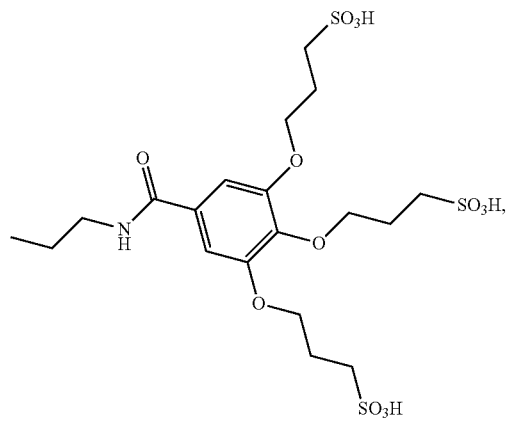
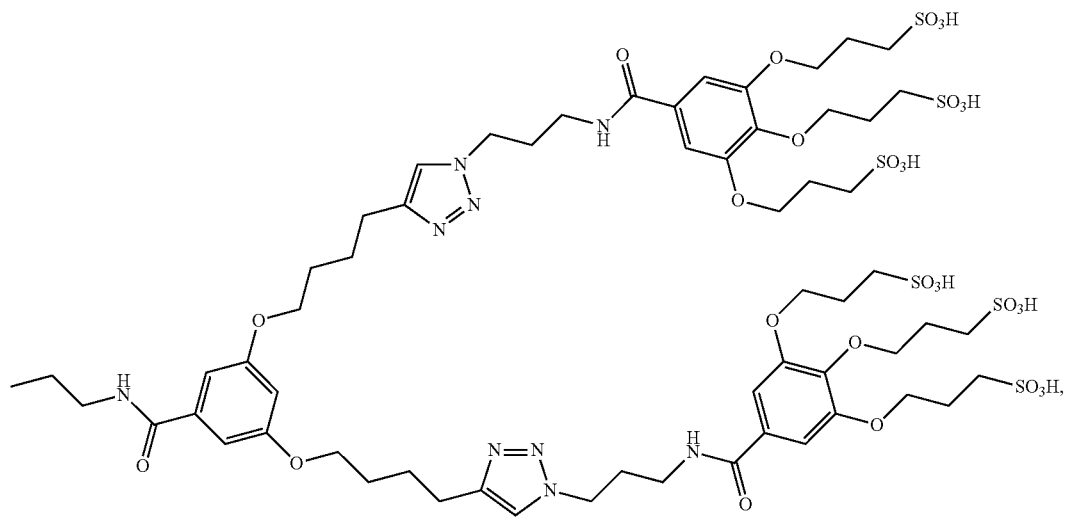

-continued
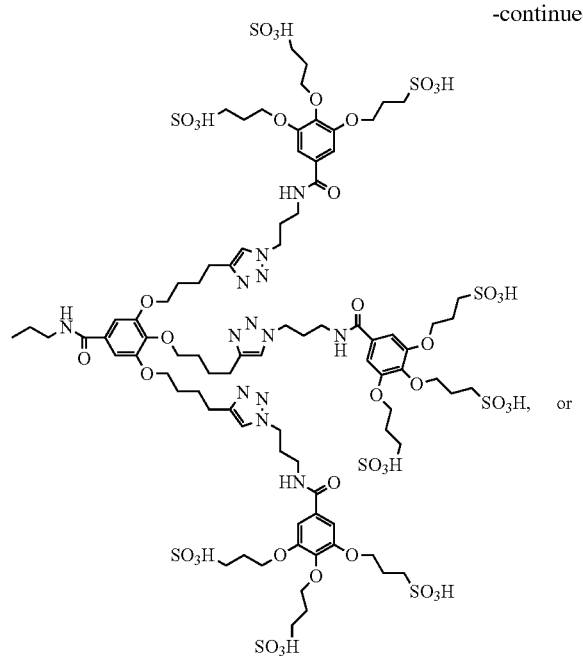
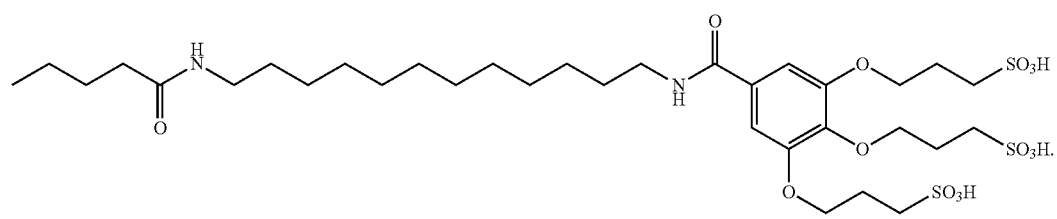 [SMILES: CCCCC(=O)NCCCCCCCCCCCCNC(=O)c1cc(OCCCS(=O)(=O)O)c(OCCCS(=O)(=O)O)c(OCCCS(=O)(=O)O)c1]
34. The labeled nucleotide analog of paragraph 23, wherein the shield element comprises the structure:
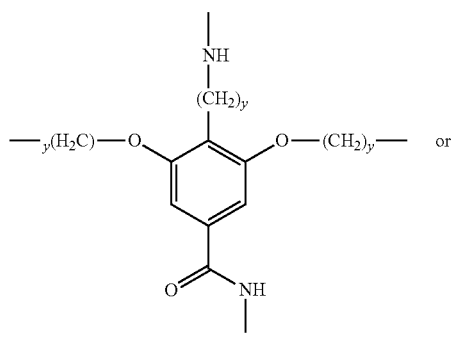
or
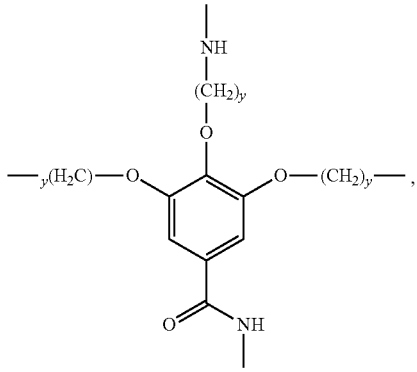
wherein each y is independently an integer from 1 to 6.
35. The labeled nucleotide analog of paragraph 23, wherein L comprises the structure:

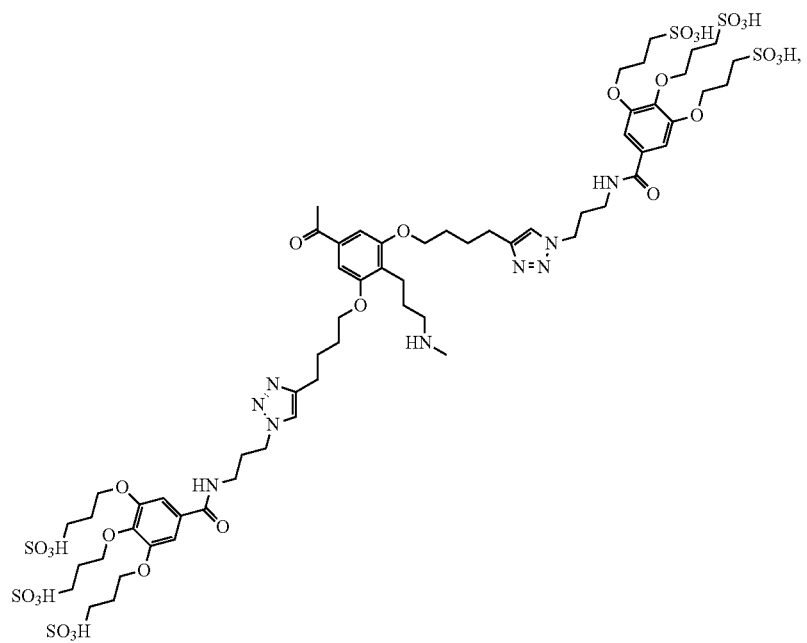
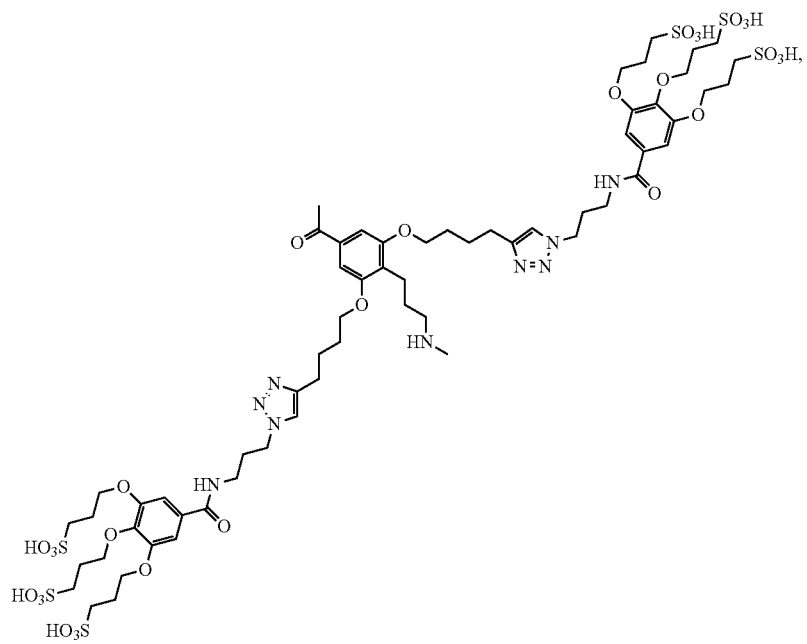

-continued
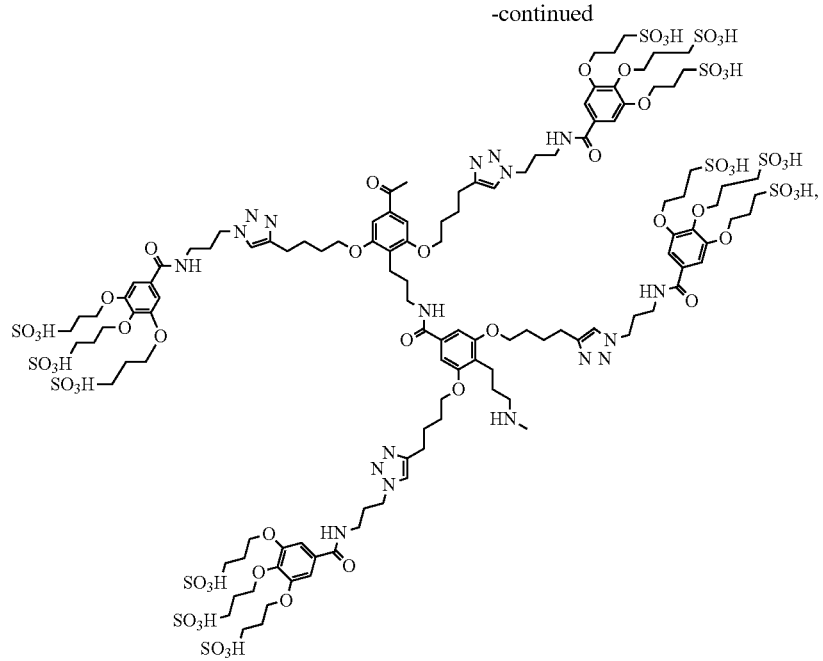
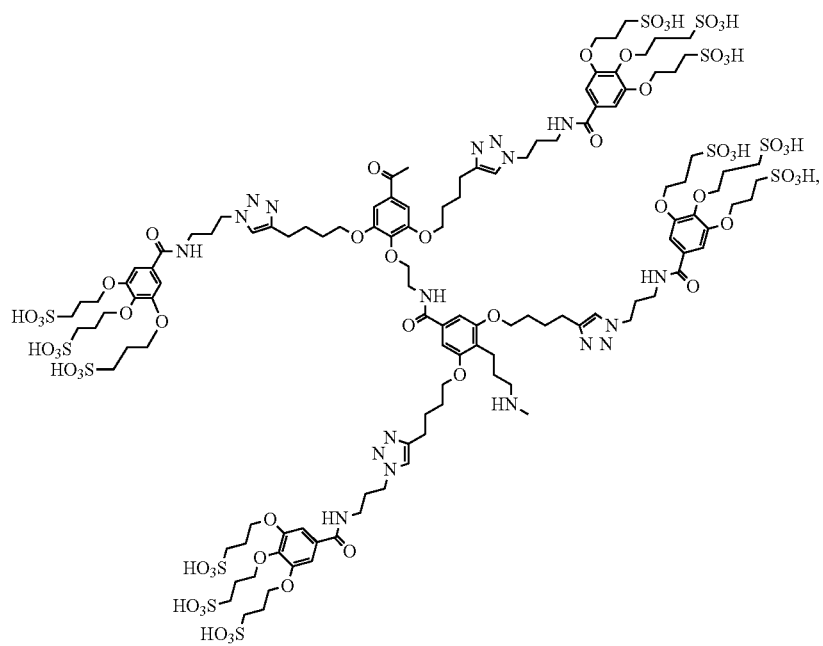

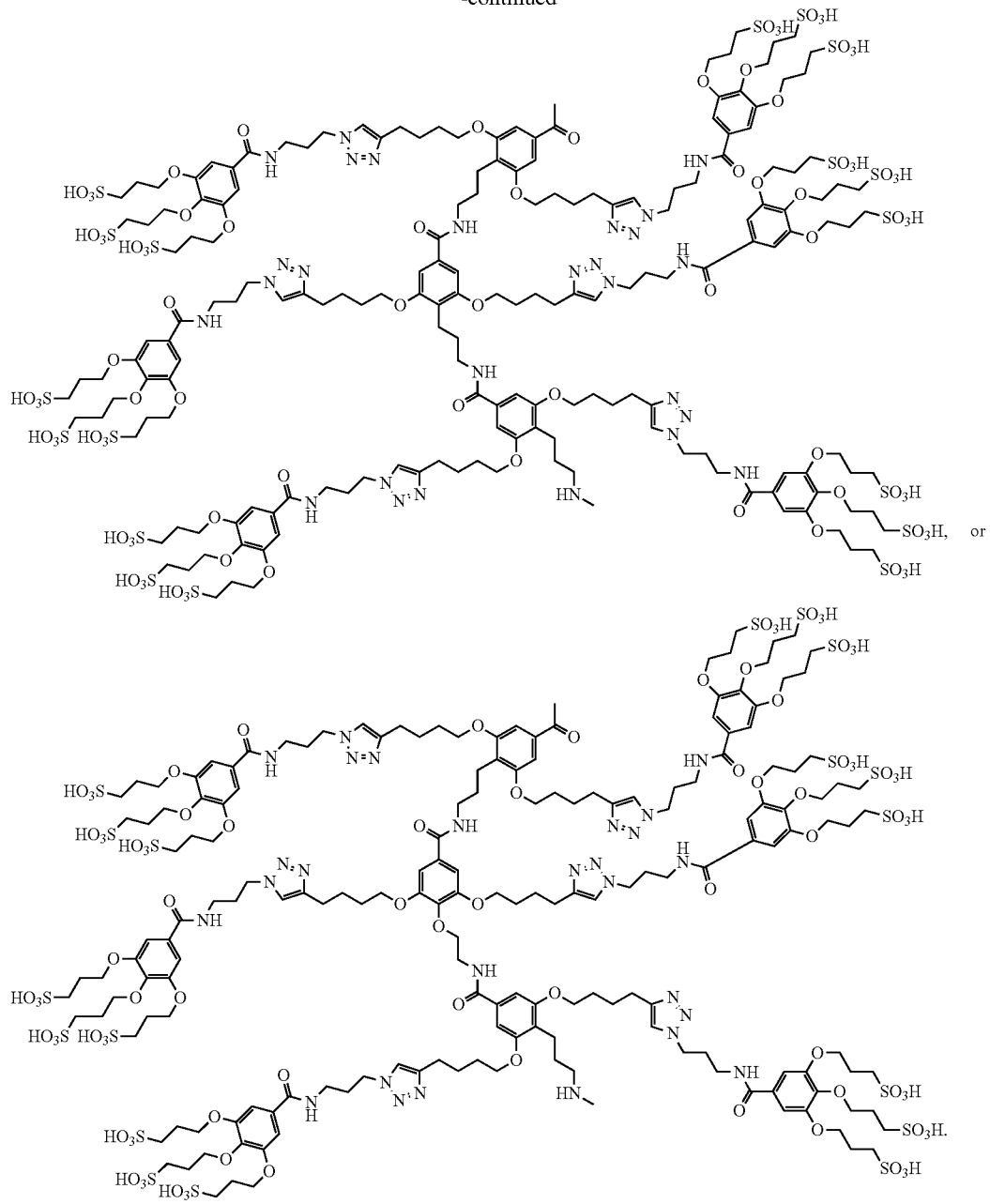

36. The labeled nucleotide analog of paragraph 23, wherein L further comprises an alkyl linker group, optionally comprising an amide bond.
37. The labeled nucleotide analog of paragraph 23, wherein L further comprises a triazole.
38. The labeled nucleotide analog of paragraph 23, wherein B" comprises a biotin moiety.
39. The labeled nucleotide analog of paragraph 38, wherein B" comprises a bis-biotin moiety.
40. The labeled nucleotide analog of paragraph 23, wherein o is 1.
41. The labeled nucleotide analog of paragraph 40, wherein n is 2.
42. The labeled nucleotide analog of paragraph 40, wherein X comprises a polyamine moiety.
43. The labeled nucleotide analog of paragraph 23, wherein o is 0 and n is 1.
44. The labeled nucleotide analog of paragraph 23, wherein the at least one nucleotide compound does not contain a dye.
45. A labeled nucleotide analog comprising:
a first avidin protein, a second avidin protein, and a third avidin protein, each avidin protein having four subunits, and each subunit comprising one biotin binding site;
a first nucleotide compound and a second nucleotide compound, each nucleotide compound comprising a polyphosphate element, a nucleoside element, an optional multivalent central core element, a terminal coupling element, and a nucleotide linker element, wherein the first nucleotide compound or the second nucleotide compound comprises at least one affinity modulating element; and a first dye-labeled compound and a second dye-labeled compound, each dye-labeled compound comprising a donor dye, an acceptor dye, a terminal coupling element, and a dye compound linker element, wherein the first avidin protein is bound to the first nucleotide compound and to the first dye-labeled compound, the second avidin protein is bound to the first dye-labeled compound and to the second dye-labeled compound, and the third avidin protein is bound to the second dye-labeled compound and to the second nucleotide compound.

46. The labeled nucleotide analog of paragraph 45, wherein the first and second dye-labeled compounds and the first and second nucleotide compounds are each bound to the first, second, and third avidin proteins through biotin moieties.

Polymerase Enzymes

The labeled nucleotide analogs disclosed herein can be optimized and adapted for use with particular polymerase enzymes, in particular through structural modulation of the nucleotide compound components of the analogs. In addition, the polymerase enzymes can themselves be adapted for use with the analogs of the instant disclosure by directed mutation. In particular, a variety of natural and modified polymerase enzymes are known in the art, and the structural and functional properties of these enzymes are well understood. DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of hundreds of polymerases are publicly available, and the crystal structures for many of these have been determined or can be inferred based upon similarity to solved crystal structures for homologous polymerases. For example, the crystal structure of Φ29, a preferred type of parental enzyme to be modified according to the invention, is available. Many polymerases are commercially available, e.g., for use in sequencing, labeling, and amplification technologies. Exemplary useful DNA polymerases include Taq and other thermostable polymerases, exonuclease deficient Taq polymerases, E. coli DNA Polymerase I, Klenow fragment, reverse transcriptases, SP6 DNA polymerase, T7 DNA polymerase, T5 DNA polymerase, T4 DNA polymerase, RB69 polymerase, etc.

Enzymes particularly suitable for use with the analogs of the invention include, but are not limited to, recombinant Φ29-type DNA polymerases. A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase (e.g., as listed in SEQ ID NO:1); examples include the B103, GA-1, PZA, Φ15, BS32, M2Y (e.g., as listed in SEQ ID NO:2; also known as M2), Nf, G1, Cp-1, PRD1, PZE, SF5, Cp-5, Cp-7, PR4, PR5, PR722, L17, Φ21, and AV-1 DNA polymerases, as well as chimeras thereof. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. For nomenclature, see also, Meijer et al. (2001) "Φ29 Family of Phages" Microbiology and Molecular Biology Reviews, 65(2):261-287. A modified recombinant Φ29-type DNA polymerase includes one or more mutations relative to naturally-occurring wild-type Φ29-type DNA polymerases, for example, one or more mutations that alter interaction with and/or incorporation of nucleotide analogs, increase stability, increase readlength, enhance accuracy, increase phototolerance, and/or alter another polymerase property, and can include additional alterations or modifications over the wild-type Φ29-type DNA polymerase, such as one or more deletions, insertions, and/or fusions of additional peptide or protein sequences (e.g., for immobilizing the polymerase on a surface or otherwise tagging the polymerase enzyme).

For example, a recombinant polymerase useful with analog(s) of the invention can be homologous to (e.g., at least 60%, at least 70%, at least 80%, at least 90%, at least 95%, at least 98%, or even at least 99% identical to) a wild type Φ29-type polymerase, e.g., to one of SEQ ID NOs:1-6. Amino acid residue identity is determined when the two sequences are compared and aligned for maximum correspondence, as measured using a sequence comparison algorithm or by visual inspection. Preferably, the identity exists over a region of the sequences that is at least about 50 residues in length, more preferably over a region of at least about 100 residues, and most preferably, over at least about 150 residues, or over the full length of the two sequences to be compared.

For reference, the amino acid sequence of a wild-type Φ29 polymerase is presented in Table 2, along with the sequences of several other wild-type Φ29-type polymerases.

TABLE 2

Amino acid sequence of exemplary wild-type Φ29-type polymerases

| | |
|---|---|
| Φ29 SEQ ID NO: 1 | MKHMPRKMYSCDFETTTKVEDCRVWAYGYMNIEDHS EYKIGNSLDEFMAWVLKVQADLYPHNLKFDGAFIINWL ERNGFKWSADGLPNTYNTIISRMGQWYMIDICLGYKGK RKIHTVIYDSLKKLPFPVKKIAKDFKLTVLKGDIDYHKE RPVGYKITPEEYAYIKNDIQIIAEALLIQFKQGLDRMTAG SDSLKGFKDIITTKKFKKVFPTLSLGLDKEVRYAYRGGF TWLNDRFKEKEIGEGMVFDVNSLYPAQMYSRLLPYGEP IVFEGKYVWDEDYPLHIQHIRCEFELKEGYIPTIQIKRSR FYKGNEYLKSSGGEIADLWLSNVDLELMKEHYDLYNV EYISGLKFKATTGLFKDFIDKWTYIKTTSEGAIKQLAKL MLNSLYGKFASNPDVTGKVPYLKENGALGFRLGEEETK DPVYTPMGVFITAWARYTTITAAQACYDRIIYCDTDSIH LTGTEIPDVIKDIVDPKKLGYWAHESTFKRAKYLRQKT |

TABLE 2-continued

Amino acid sequence of exemplary wild-type Φ29-type polymerases

```
            YIQDIYMKEVDGKLVEGSPDDYTDIKFSVKCAGMTDKI
            KKEVTFENFKVGFSRKMKPKPVQVPGGVVLVDDTFTIK

M2Y         MSRKMFSCDFETTTKLDDCRVWAYGYMEIGNLDNYKI
SEQ ID NO: 2 GNSLDEFMQWVMEIQADLYFHNLKFDGAFIVNWLEQH
            GFKWSNEGLPNTYNTIISKMGQWYMIDICFGYKGKRKL
            HTVIYDSLKKLPFPVKKIAKDFQLPLLKGDIDYHTERPV
            GHEITPEEYEYIKNDIEIIARALDIQFKQGLDRMTAGSDS
            LKGFKDILSTKKFNKVFPKLSLPMDKEIRKAYRGGFTW
            LNDKYKEKEIGEGMVFDVNSLYPSQMYSRPLPYGAPIV
            FQGKYEKDEQYPLYIQRIRFEFELKEGYIPTIQIKKNPFFK
            GNEYLKNSGVEPVELYLTNVDLELIQEHYELYNVEYID
            GFKFREKTGLFKDFIDKWTYVKTHEEGAKKQLAKLML
            NSLYGKFASNPDVTGKVPYLKDDGSLGFRVGDEEYKD
            PVYTPMGVFITAWARFTTITAAQACYDRIIYCDTDSIHL
            TGTEVPEIIKDIVDPKKLGYWAHESTFKRAKYLRQKTYI
            QDIYVKEVDGKLKECSPDEATTTKFSVKCAGMTDTIKK
            KVTFDNFAVGFSSMGKPKPVQVNGGVVLVDSVFTIK

B103        MPRKMFSCDFETTTKLDDCRVWAYGYMEIGNLDNYKI
SEQ ID NO: 3 GNSLDEFMQWVMEIQADLYFHNLKFDGAFIVNWLEHH
            GFKWSNEGLPNTYNTIISKMGQWYMIDICFGYKGKRKL
            HTVIYDSLKKLPFPVKKIAKDFQLPLLKGDIDYHAERPV
            GHEITPEEYEYIKNDIEIIARALDIQFKQGLDRMTAGSDS
            LKGFKDILSTKKFNKVFPKLSLPMDKEIRRAYRGGFTW
            LNDKYKEKEIGEGMVFDVNSLYPSQMYSRPLPYGAPIV
            FQGKYEKDEQYPLYIQRIRFEFELKEGYIPTIQIKKNPFFK
            GNEYLKNSGAEPVELYLTNVDLELIQEHYEMYNVEYID
            GFKFREKTGLFKEFIDKWTYVKTHEKGAKKQLAKLMF
            DSLYGKFASNPDVTGKVPYLKEDGSLGFRVGDEEYKDP
            VYTPMGVFITAWARFTTITAAQACYDRIIYCDTDSIHLT
            GTEVPEIIKDIVDPKKLGYWAHESTFKRAKYLRQKTYIQ
            DIYAKEVDGKLIECSPDEATTTKFSVKCAGMTDTIKKK
            VTFDNFRVGFSSTGKPKPVQVNGGVVLVDSVFTIK

GA-1        MARSVYVCDFETTTDPEDCRLWAWGWMDIYNTDKWS
SEQ ID NO: 4 YGEDIDSFMEWALNSNSDIYFHNLKFDGSFILPWWLRN
            GYVHTEEDRTNTPKEFTTTISGMGQWYAVDVCINTRGK
            NKNHVVFYDSLKKLPFKVEQIAKGFGLPVLKGDIDYKK
            YRPVGYVMDDNEIEYLKHDLLIVALALRSMFDNDFTSM
            TVGSDALNTYKEMLGVKQWEKYFPVLSLKVNSEIRKA
            YKGGFTWVNPKYQGETVYGGMVFDVNSMYPAMMKN
            KLLPYGEPVMFKGEYKKNVEYPLYIQQVRCFFELKKDK
            IPCIQIKGNARFGQNEYLSTSGDEYVDLYVTNVDWELIK
            KHYDIFEEEFIGGEMFKGEIGFFDEYIDRFMEIKNSPDSS
            AEQSLQAKLMLNSLYGKFATNPDITGKVPYLDENGVLK
            FRKGELKERDPVYTPMGCFITAYARENILSNAQKLYPRF
            IYADTDSIHVEGLGEVDAIKDVIDPKKLGYWDHEATFQ
            RARYVRQKTYFIETTWKENDKGKLVVCEPQDATKVKP
            KIACAGMSDAIKERIRFNEFKIGYSTHGSLKPKNVLGGV
            VLMDYPFAIK

AV-1        MVRQSTIASPARGGVRRSHKKVPSFCADFETTTDEDDC
SEQ ID NO: 5 RVWSWGIIQVGKLQNYVDGISLDGFMSHISERASHIYFH
            NLAFD GTFILDWLLKHGYRWTKENPGVKEFTSLISRMG
            KYYSITVVFETGFRVEFRDSFKKLPMSVSAIAKAFNLHD
            QKLEIDYEKPRPIGYIPTEQEKRYQRNDVAIVAQALEVQ
            FAEKMTKLTAGSDSLATYKKMTGKLFIRRFPILSPEIDTE
            IRKAYRGGFTYADPRYAKKLNGKGSVYDVNSLYPSVM
            RTALLPYGEPIYSEGAPRTNRPLYIASITFTAKLKPNHIPC
            IQIKKNLSFNPTQYLEEVKEPTTVVATNIDIELWKKHYD
            FKIYSWNGTFEFRGSHGFFDTYVDHFMEIKKNSTGGLR
            QIAKLHLNSLYGKFATNPDITGKHPTLKDNRVSLVMNE
            PETRDPVYTPMGVFITAYARKKTISAAQDNYETFAYAD
            TDSLHLIGPTTPPDSLWVDPVELGAWKHESSFTKSVYIR
            AKQYAEEIGGKLDVHIAGMPRNVAATLTLEDMLHGGT
            WNGKLIPVRVPGGTVLKDTTFTLKID

CP-1        MTCYYAGDFETTTNEEETEVWLSCFAKVIDYDKLDTFK
SEQ ID NO: 6 VNTSLEDFLKSLYLDLDKTYTETGEDEFIIFFHNLKFDGS
            FLLSFFLNNDIECTYFINDMGVWYSITLEFPDFTLTFRDS
            LKILNFSIATMAGLFKMPIAKGTTPLLKHKPEVIKPEWID
            YIHVDVAILARGIFAMYYEENFTKYTSASEALTEFKRIFR
            KSKRKFRDFFPILDEKVDDFCRKHIVGAGRLPTLKHRGR
            TLNQLIDIYDINSMYPATMLQNALPIGIPKRYKGKPKEIK
            EDHYYIYHIKADFDLKRGYLPTIQIKKKLDALRIGVRTS
            DYVTTSKNEVIDLYLTNFDLDLFLKHYDATIMYVETLEF
            QTESDLFDDYITTYRYKKENAQSPAEKQKAKIMLNSLY
```

TABLE 2-continued

Amino acid sequence of exemplary wild-type Φ29-type polymerases

```
GKFGAKIISVKKLAYLDDKGILRFKNDDEEEVQPVYAP
VALFVTSIARHFIISNAQENYDNFLYADTDSLHLFHSDSL
VLDIDPSEFGKWAHEGRAVKAKYLRSKLYIEELIQEDGT
THLDVKGAGMTPEIKEKITFENFVIGATFEGKRASKQIK
GGTLIYETTFKIRETDYLV
```

A recombinant polymerase useful with the analogs of the disclosure, e.g., a recombinant Φ29-type DNA polymerase, typically includes one or more mutations (e.g., amino acid substitutions, deletions, or insertions) as compared to a reference polymerase, e.g., a wild-type Φ29-type polymerase, e.g., one of SEQ ID NOs:1-6. Depending on the particular mutation or combination of mutations, the polymerase exhibits one or more properties that find use in, e.g., single molecule sequencing applications or nucleic acid amplification. Such polymerases incorporate nucleotides and/or nucleotide analogs, for example, the analogs described herein, into a growing template copy during DNA amplification. These polymerases are modified such that they have one or more desirable properties, for example, improved sequencing performance with nucleotide analogs of the invention, increased readlength, increased thermostability, increased resistance to photodamage, decreased branching fraction formation when incorporating the relevant analogs, improved DNA-polymerase complex stability or processivity, increased cosolvent resistance, reduced exonuclease activity, increased yield, altered cofactor selectivity, improved accuracy, increased or decreased speed, and/or altered kinetic properties (e.g., a reduction in the rate of one or more steps of the polymerase kinetic cycle, resulting from, e.g., enhanced interaction of the polymerase with the nucleotide analog, enhanced metal coordination, etc.) as compared to a corresponding wild-type or other parental polymerase (e.g., a polymerase from which the modified recombinant polymerase of the invention was derived, e.g., by mutation).

Exemplary polymerases include a recombinant Φ29-type DNA polymerase that comprises a mutation (e.g., an amino acid substitution) at one or more positions selected from the group consisting of S10, A68, A83, C106, A134, K135, L142, Y224, E239, V250, L253, A256, R261, R306, R308, L326, T368, T373, E375, E420, T421, T434, W436, A437, Y439, T441, C448, E466, D476, A484, S487, E508, D510, K512, E515, K539, P558, D570, and T571, where identification of positions is relative to wild-type Φ29 polymerase (SEQ ID NO:1). Optionally, the polymerase comprises mutations at two or more, three or more, five or more, 10 or more, 15 or more, 20 or more, or even 25 or more of these positions. A number of exemplary substitutions at these (and other) positions are described herein. Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences. For example, residue K221 of wild-type M2Y polymerase (SEQ ID NO:2) is identified as position Y224 relative to wild-type Φ29 polymerase (SEQ ID NO:1). Similarly, residue L138 of wild-type M2Y polymerase (SEQ ID NO:2) is identified as position V141 relative to wild-type Φ29 polymerase (SEQ ID NO:1), and an L138K substitution in the M2Y polymerase is thus identified as a V141K substitution relative to SEQ ID NO:1. Amino acid positions herein are generally identified relative to SEQ ID NO:1 unless explicitly indicated otherwise.

As a few examples, a mutation at E375 can comprise an amino acid substitution selected from the group consisting of E375Y (i.e., a tyrosine residue is present at position E375 where identification of positions is relative to SEQ ID NO:1), E375F, E375W, E375H, and E375M; a mutation at position K512 can comprise an amino acid substitution selected from the group consisting of K512Y, K512F, K512H, K512W, K512M, and K512R; a mutation at position L253 can comprise an L253A substitution; a mutation at position A484 can comprise an A484E substitution; and/or a mutation at position D510 can comprise a D510K or D510R substitution. Other exemplary substitutions include, e.g., S10M, A68S, A83E, C106S, A134S, K135Q, K135R, L142R, L142K, Y224K, E239G, V250I, A256S, R261K, R306Q, R308L, L326V, T368S, T373F, E420R, T421Y, T434A, T434S, W436Y, A437G, Y439W, T441I, C448V, E466K, D476H, S487A, E508R, E508Q, E515Q, K539E, P558A, D570S, and T571V; additional substitutions are described herein.

The polymerase mutations noted herein can be combined with each other and with essentially any other available mutations and mutational strategies to confer additional improvements in, e.g., nucleotide analog specificity, enzyme processivity, improved retention time of labeled nucleotides in polymerase-DNA-nucleotide complexes, phototolerance, and the like. For example, the mutations and mutational strategies herein can be combined with those taught in, e.g., U.S. Patent Application Publication No. 2007/0196846; U.S. Patent Application Publication No. 2008/0108082, U.S. Patent Application Publication No. 2010/0075332, U.S. Patent Application Publication No. 2010/0093555, U.S. Patent Application Publication No. 2010/0112645, U.S. Patent Application Publication No. 2011/0189659, U.S. Patent Application Publication No. 2012/0034602, U.S. Patent Application Publication 2013/0217007, U.S. Patent Application Publication No. 2014/0094374, and U.S. Patent Application Publication No. 2014/0094375. Each of these applications is incorporated herein by reference in its entirety for all purposes. This combination of mutations/mutational strategies can be used to impart several simultaneous improvements to a polymerase (e.g., enhanced utility with desired analogs, increased readlength, increased phototolerance, decreased branching fraction formation, improved specificity, improved processivity, altered rates, improved retention time, improved stability of the closed complex, tolerance for a particular metal cofactor, etc.). In addition, polymerases can be further modified for application-specific reasons, such as to improve activity of the enzyme when bound to a surface, as taught, e.g., in U.S. Patent Application Publication No. 2010/0261247 and U.S. Patent Application Publication No. 2010/0260465 (each of which is incorporated herein by reference in its entirety for all purposes) and/or to include purification or handling tags as is taught in the cited references and as is common in the art. The polymerases can include one or more exogenous or heterologous features, e.g., at the N-terminal region of the polymerase, at the C-terminal region of the polymerase, and/or internal to the polymerase. Such features find use not only for purification of the recombinant polymerase and/or immobilization of the polymerase to a substrate, but can also alter one or more properties of the polymerase. For additional information on incorporation of such features, see, e.g., U.S. Patent Application Publication Nos. 2012/0034602 and 2014/0094375 (each of which is incorporated herein by reference in its entirety for all purposes). Similarly, the modified polymerases described herein can be employed in combination with other strategies to improve polymerase performance, for example, reaction conditions for controlling polymerase rate constants such as taught in U.S. Patent Application Publication No. 2009/0286245, incorporated herein by reference in its entirety for all purposes.

As noted, the various mutations described herein can be combined in recombinant polymerases useful in the invention. Combination of mutations can be random, or more desirably, guided by the properties of the particular mutations and the characteristics desired for the resulting polymerase. Additional mutations can also be introduced into a polymerase to compensate for deleterious effects of otherwise desirable mutations. For example, a W436Y substitution can reduce branching fraction but induce pausing, Y439W can reduce pausing but also reduce yield, and R261K can increase yield; thus, a W436Y/Y439W/R261K combination can be desirable.

A number of exemplary mutations and the properties they confer are described herein, and it will be evident that these mutations can be favorably combined in many different combinations. Exemplary combinations are also provided herein, e.g., in Table 3, and an example of strategies by which additional favorable combinations are readily derived follows. For the sake of simplicity, a few exemplary combinations using only a few exemplary mutations are discussed, but it will be evident that any of the mutations described herein can be employed in such strategies to produce polymerases with desirable properties.

Figure 8:
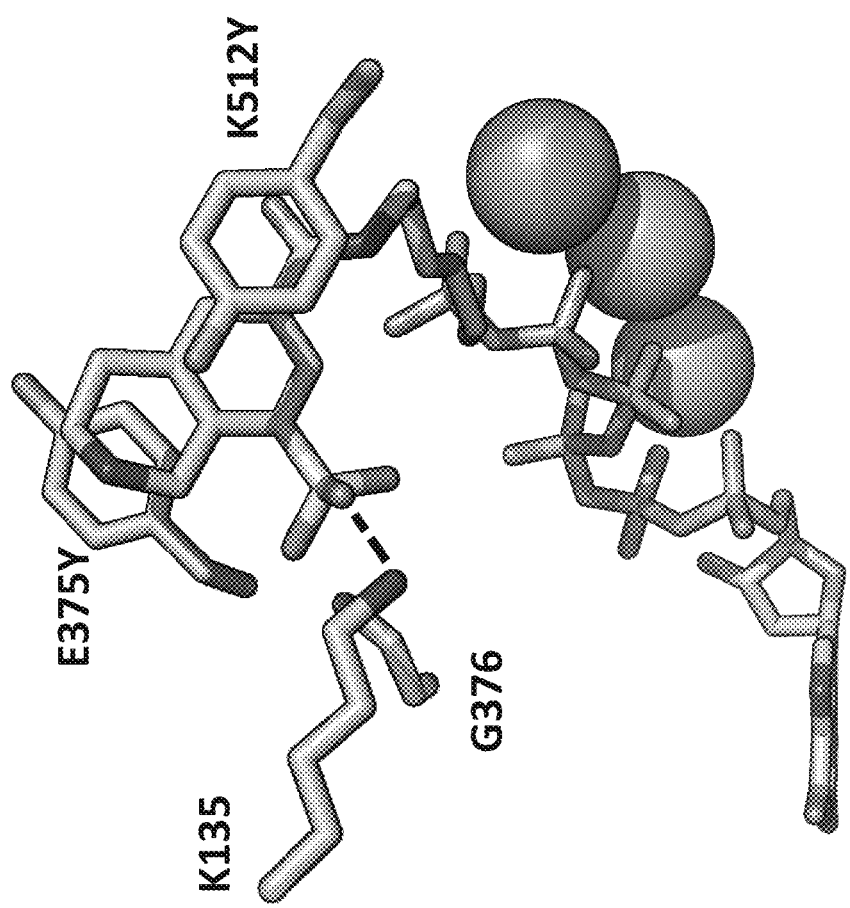
FIG. 8 depicts interactions with the 1H-2,3-dihydroisoquinoline-8-sulfo-6-carboxylic acid ("DISC") group in the crystal structure of a mutant Φ29 polymerase with a DISC-containing hexaphosphate analog. The polymerase includes E375Y and K512Y substitutions.
Figure 9:
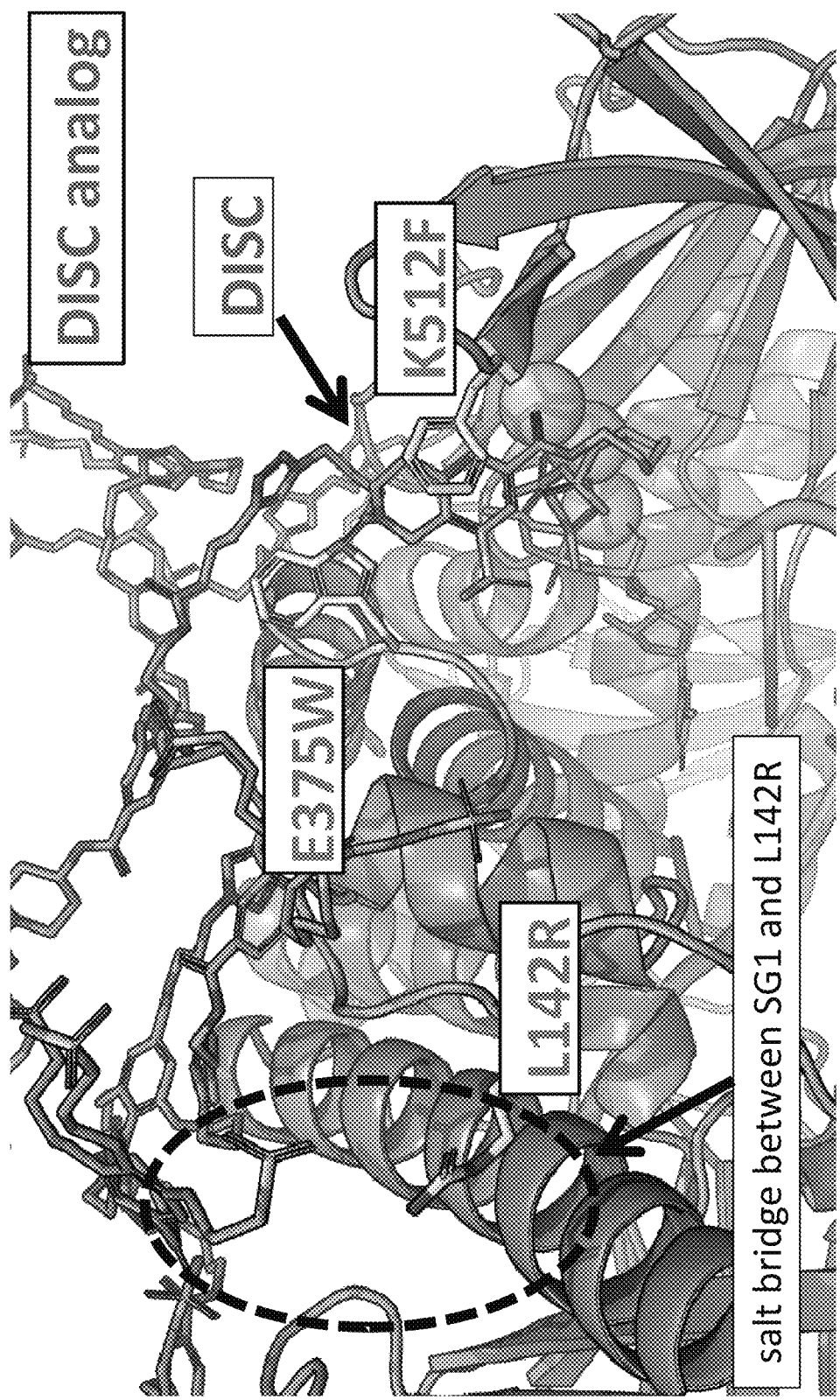
FIG. 9 depicts interactions with DISC and SG1 groups in the crystal structure of a mutant Φ29 polymerase with a hexaphosphate analog. The polymerase includes E375W, K512F, and L142R substitutions.
Figure 10:
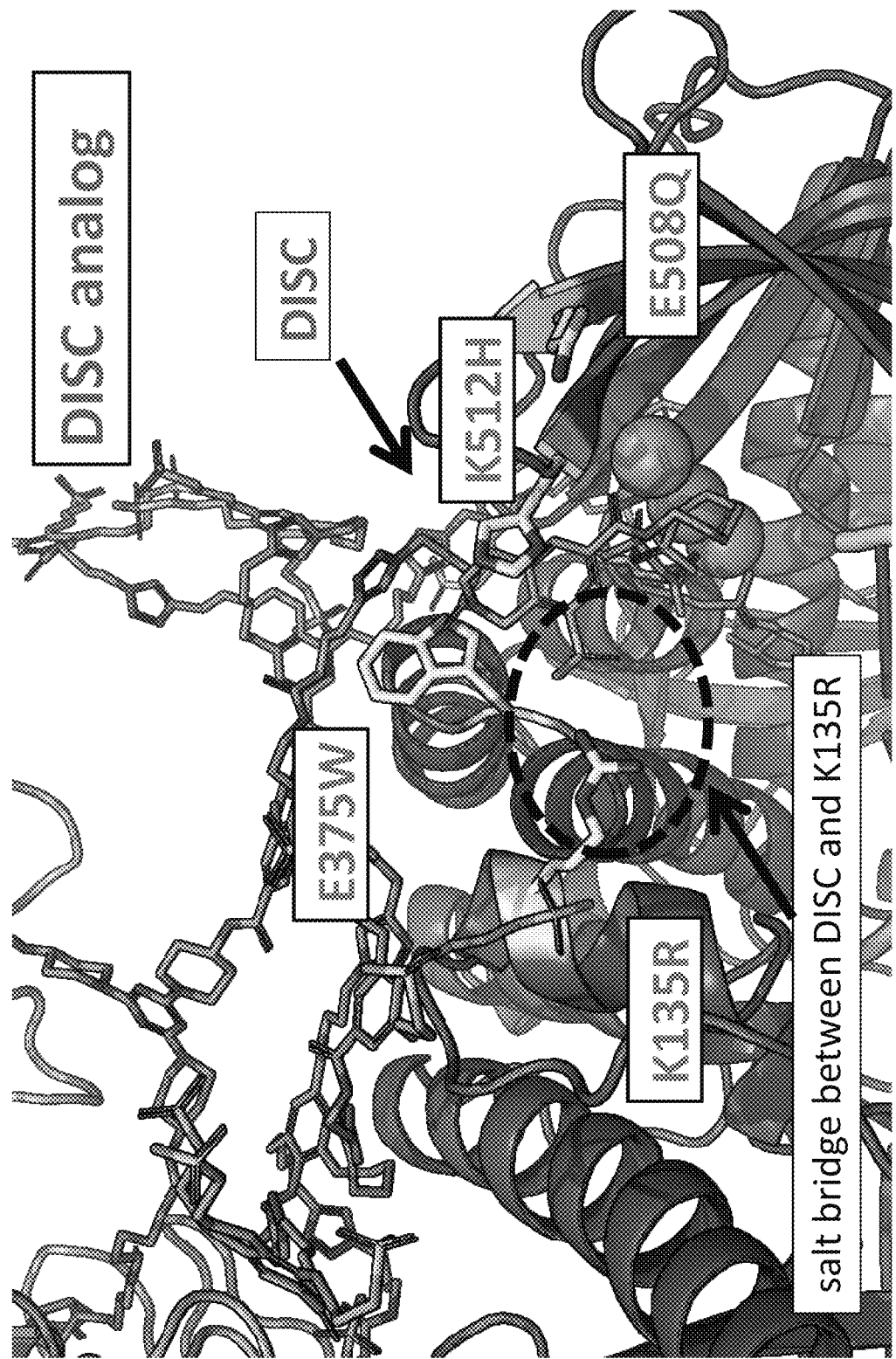
FIG. 10 depicts interactions with the DISC group in the crystal structure of a mutant Φ29 polymerase with a DISC-containing hexaphosphate analog. The polymerase includes E375W, K512H, and K135R substitutions.
Figure 11B:
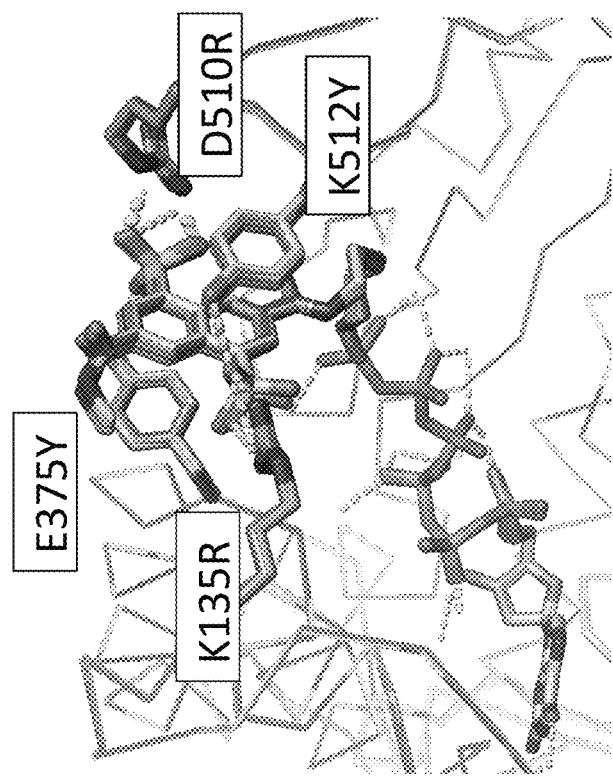
FIG. 11B depicts interactions with the DSDC group in a model of a mutant Φ29 polymerase with a DSDC-containing hexaphosphate analog. The polymerase includes K135R, E375Y, D510R, and K512Y substitutions.
Figure 11A:
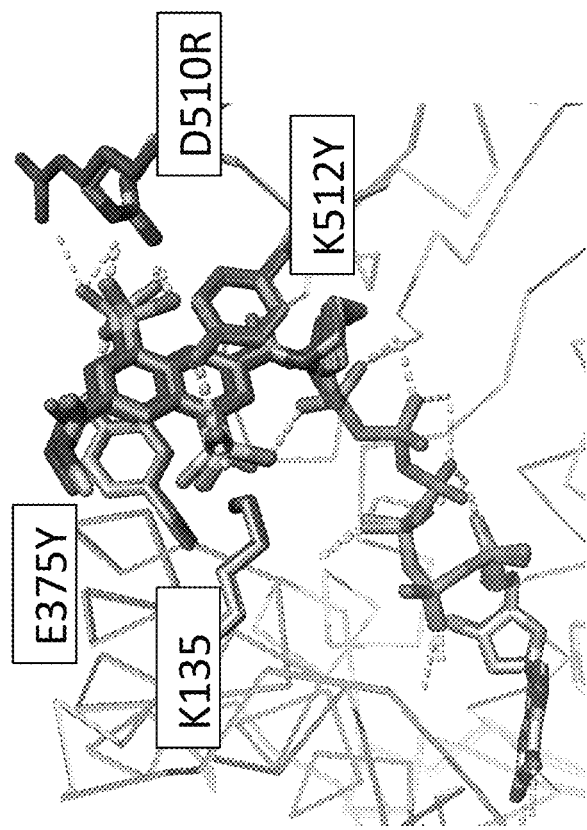
FIG. 11A depicts interactions with the DSDC group in a model of a mutant Φ29 polymerase with a DSDC-containing hexaphosphate analog. The polymerase includes E375Y, D510R, and K512Y substitutions.

For example, where a recombinant polymerase is desired to incorporate analogs of the invention, one or more substitutions that enhance analog binding through interactions with an aromatic group on the terminal phosphate, with a charged substituent on the aromatic group, and/or with a substituent elsewhere on the analog can be incorporated, e.g., an amino acid substitution at position K135, L142, T373, E375, and/or K512, e.g., K135Q, K135R, L142R, L142K, T373F, E375Y, E375F, E375W, E375H, E375M, D510R, K512Y, K512F, K512H, K512W, K512M, and/or K512R. As shown in FIG. 8, the tyrosine residues in a polymerase including E375Y and K512Y substitutions are positioned to stack with the DISC group on a DISC-containing hexaphosphate analog. In addition, the lysine at position 135 forms a salt bridge with the DISC sulfonate group. As shown in FIG. 9, in a polymerase including E375W, K512F, and L142R substitutions, the tryptophan and phenylalanine rings are positioned to stack with the DISC group, while the arginine at position 142 can form a salt bridge with an SG1 group elsewhere on the analog. As shown in FIG. 10, in a polymerase including E375W, K512H, and K135R substitutions, the tryptophan and histidine rings are again positioned to interact with the DISC rings, and the arginine at position 135 forms a salt bridge with the DISC sulfonate group. As shown in FIG. 11A, in a polymerase including E375Y, K512Y, and D510R substitutions, the tyrosine residues can stack with a 4,8-disulfonaphthalene-2,6-dicarboxylic acid ("DSDC") spacer group.

The arginine at position 510 can form a salt bridge with one of the DSDC sulfonate groups, and the tyrosine at position 375 can hydrogen bond to this sulfonate. The lysine at position 135 can form a salt bridge with the other DSDC sulfonate group, which can also form a hydrogen bond with the tyrosine at position 512. Similarly, as shown in FIG. 11B, in a polymerase including E375Y, K512Y, D510R, and K135R substitutions, the tyrosine residues can stack with the DSDC group. The arginine at position 510 can form a salt bridge with one of the DSDC sulfonate groups, which can also form a hydrogen bond with the tyrosine at position 375. The arginine at position 135 can form a bifurcated salt bridge with the other DSDC sulfonate group, which can also form a hydrogen bond with the tyrosine at position 512. Other substitutions that enhance analog binding (e.g., A484E) can also be incorporated into the polymerase.

Where the polymerase is desired to incorporate the analogs in a $Mg^{++}$-containing single molecule sequencing reaction, one or more substitutions that alter metal cofactor usage (e.g., L253A, L253H, L253C, or L253S) can be incorporated. Polymerase speed can be enhanced by inclusion of substitutions such as A437G, E508R, E508K, L142K, D510R, D510K, and/or V250I. Accuracy can be enhanced by inclusion of substitutions such as E515Q and/or A134S. Processivity can be increased by inclusion of substitutions such as D570S and/or T571V. Stability and/or yield can be increased by inclusion of substitutions such as Y224K, E239G, and/or V250I. Stability can also be increased, e.g., by employing M2Y as the parental polymerase and/or including a stability-enhancing exogenous feature (e.g., a C-terminal exogenous feature, e.g., a His10 or other polyhistidine tag). Use of large analogs, for example, analogs including protein moieties, can undesirably narrow pulse width and increase interpulse distance, so one or more substitutions that increase pulse width (e.g., P558A, A256S and/or S487A) or that decrease interpulse distance or reduce pausing (e.g., L142K, R306Q, R308L, T441I, C448V, E466K, D476H, and/or E508R) can be included in the polymerase. For discussion of pulse width and interpulse distance, see, e.g., U.S. Patent Application Publication No. 2014/0094375 (previously incorporated by reference in its entirety for all purposes).

It will be evident that different polymerase properties, and therefore different combinations of mutations, are desirable for different applications involving recombinant polymerases. As will be understood, a polymerase can display one of the aforementioned properties alone or can display two or more of the properties in combination. Moreover, it will be understood that while a particular mutation or polymerase can be described with respect to a particular property, the mutation or polymerase can possess additional modified properties not mentioned in every instance for ease of discussion. It will also be understood that particular properties are observed under certain conditions. For example, a stability-improving mutation can, e.g., confer increased stability on the polymerase-DNA substrate binary complex (as compared to such a complex containing a parental polymerase lacking the mutation) when observed in a thermal inactivation assay or it can confer increased readlength when observed in a single molecule sequencing reaction where the lifetime of the parental polymerase-DNA substrate complex (and therefore readlength) is limited by its stability. A single mutation (e.g., a single amino acid substitution, deletion, insertion, or the like) can give rise to one or more altered properties, or the one or more properties can result from two or more mutations which act in concert to confer the desired activity.

A list of exemplary mutations and combinations thereof is provided in Table 3, and additional exemplary mutations are described herein. Essentially any of these mutations, or any combination thereof, can be introduced into a polymerase to produce a modified recombinant polymerase (e.g., into wild-type Φ29 polymerase, wild-type M2 polymerase, an exonuclease deficient Φ29 polymerase, or an exonuclease deficient M2 polymerase, as just a few examples).

TABLE 3

Exemplary mutations introduced into a Φ29 DNA polymerase. Positions are identified relative to SEQ ID NO: 1.

A68S C106S K135Q L142R Y224K E239G V250I L253A R306Q R308L T368S E375W T421Y A437G E466K D476H A484E E508R D510R K512F E515Q K539E P558A D570S T571V
A68S K135R L142K Y224K E239G V250I L253A R261K R306Q R308L T368S E375W T421Y W436Y A437G Y439W T441I C448V E466K D476H A484E E508Q D510R K512H E515Q K539E P558A D570S T571V
A68S C106S A134S K135R L142K Y224K E239G V250I L253A R261K R306Q R308L L326V E375F T421Y W436Y A437G Y439W E466K

TABLE 3-continued

Exemplary mutations introduced into a Φ29 DNA polymerase. Positions are identified relative to SEQ ID NO: 1.

D476H A484E E508R D510R K512F E515Q K539E P558A D570S T571V
A68S L142K Y224K E239G V250I L253A R306Q R308L T368S E375W T421Y A437G E466K D476H A484E E508R D510K K512F E515Q K539E P558A D570S T571V
A68S C106S K135Q L142K Y224K E239G V250I L253A R261K R306Q R308L L326V E375W T421Y W436Y A437G Y439W E466K D476H A484E E508R D510R K512Y E515Q K539E P558A D570S T571V
A68S K135R L142K Y224K E239G V250I L253A R261K R306Q R308L L326V E375W T421Y W436Y A437G Y439W E466K A484E E508R D510R K512H E515Q K539E P558A D570S T571V
A68S C106S K135Q L142K Y224K E239G V250I L253A R261K R306Q R308L L326V T373F E375Y T421Y W436Y A437G Y439W E466K D476H A484E E508R D510R K512Y E515Q K539E P558A D570S T571V
A68S K135Q L142K Y224K E239G V250I L253A R261K R306Q R308L L326V E375Y T421Y W436Y A437G Y439W E466K D476H A484E E508R D510R K512Y E515Q K539E P558A D570S T571V
A68S K135Q L142K Y224K E239G V250I L253A R306Q R308L T368S E375Y T421Y A437G E466K D476H A484E E508R D510R K512Y E515Q K539E P558A D570S T571V
A68S K135Q L142K Y224K E239G V250I L253A R306Q R308L T368S E375Y T421Y A437G E466K D476H A484E E508R D510R K512Y E515Q K539E P558A D570S T571V

The amino acid sequences of exemplary recombinant Φ29 polymerases harboring the exemplary mutation combinations of Table 3 are provided in Tables 4 and 5. Table 4 includes the polymerase portion of the molecule as well as one or more exogenous features at the C-terminal region of the polymerase, while Table 5 includes the amino acid sequence of the polymerase portion only.

TABLE 4

Amino acid sequences of exemplary recombinant Φ29 polymerases including C-terminal exogenous features. Amino acid positions are identified relative to SEQ ID NO: 1.

| | Amino Acid Sequence |
|---|---|
| SEQ ID NO: 7<br>A68S_C106S_K135Q_<br>L142R_Y224K_E239G_<br>V250I_L253A_R306Q_<br>R308L_T368S_E375W_<br>T421Y_A437G_E466K_<br>D476H_A484E_E508R_<br>D510R_K512F_E515Q_<br>K539E_P558A_D5705_<br>T571V.co.GGGS.LVPRGS.<br>GGGSGGGSGGGS.<br>BtagV7co.GGGSGGGSGGGS.<br>BtagV7co.G.His10co | MKHMPRKMYSCDFETTTKVEDCRVWAY<br>GYMNIEDHSEYKIGNSLDEFMAWVLKVQ<br>ADLYFHNLKFDGSFIINWLERNGFKWSAD<br>GLPNTYNTIISRMGQWYMIDISLGYKGKRK<br>IHTVIYDSLKKLPFPVKKIAQDFKLTVRKG<br>DIDYHKERPVGYKITPEEYAYIKNDIQIIAE<br>ALLIQFKQGLDRMTAGSDSLKGFKDIITTK<br>KFKKVFPTLSLGLDKEVRKAYRGGFTWLN<br>DRFKGKEIGEGMVFDINSAYPAQMYSRLL<br>PYGEPIVFEGKYVWDEDYPLHIQHIRCEFE<br>LKEGYIPTIQIKQSLFYKGNEYLKSSGGEIA<br>DLWLSNVDLELMKEHYDLYNVEYISGLKF<br>KATTGLFKDFIDKWSYIKTTSWGAIKQLAK<br>LMLNSLYGKFASNPDVTGKVPYLKENGAL<br>GFRLGEEEYKDPVYTPMGVFITAWGRYTTI<br>TAAQACYDRIIYCDTDSIHLTGTKIPDVIKD<br>IVHPKKLGYWEHESTFKRAKYLRQKTYIQ<br>DIYMKRVRGFLVQGSPDDYTDIKFSVKCA<br>GMTDKIKEEVTFENFKVGFSRKMKPKAVQ<br>VPGGVVLVDSVFTIKGGGSLVPRGSGGGS<br>GGGSGGGSGLNDFFEAQKIEWHEGGGSGG<br>GSGGGSGLNDFFEAQKIEWHEGHHHHHH<br>HHHH |
| SEQ ID NO: 8<br>A68S_K135R_L142K_<br>Y224K_E239G_V250I_<br>L253A_R261K_R306Q_<br>R308L_L326V_T368S_<br>E375W_T421Y_W436Y_<br>A437G_Y439W_T441I_ | MKHMPRKMYSCDFETTTKVEDCRVWAY<br>GYMNIEDHSEYKIGNSLDEFMAWVLKVQ<br>ADLYFHNLKFDGSFIINWLERNGFKWSAD<br>GLPNTYNTIISRMGQWYMIDICLGYKGKR<br>KIHTVIYDSLKKLPFPVKKIARDFKLTVKK<br>GDIDYHKERPVGYKITPEEYAYIKNDIQIIA<br>EALLIQFKQGLDRMTAGSDSLKGFKDIITT |

TABLE 4-continued

Amino acid sequences of exemplary recombinant Φ29 polymerases including C-terminal exogenous features. Amino acid positions are identified relative to SEQ ID NO: 1.

| | Amino Acid Sequence |
|---|---|
| C448V_E466K_D476H_<br>A484E_E508Q_D510R_<br>K512H_E515Q_K539E_<br>P558A_D570S_T571V.<br>co.G.His10co.<br>GGGSGGGSGGGS.<br>BtagV7co.GGGSGGGSGGGS.<br>BtagV7co | KKFKKVFPTLSLGLDKEVRKAYRGGFTWL<br>NDRFKGKEIGEGMVFDINSAYPAQMYSKL<br>LPYGEPIVFEGKYVWDEDYPLHIQHIRCEF<br>ELKEGYIPTIQIKQSLFYKGNEYLKSSGGEI<br>ADVWLSNVDLELMKEHYDLYNVEYISGL<br>KFKATTGLFKDFIDKWSYIKTTSWGAIKQL<br>AKLMLNSLYGKFASNPDVTGKVPYLKENG<br>ALGFRLGEEEYKDPVYTPMGVFITAYGRW<br>TIITAAQAVYDRIIYCDTDSIHLTGTKIPDVI<br>KDIVHPKKLGYWEHESTFKRAKYLRQKTY<br>IQDIYMKQVRGHLVQGSPDDYTDIKFSVK<br>CAGMTDKIKEEVTFENFKVGFSRKMKPKA<br>VQVPGGVVLVDSVFTIKGHHHHHHHHHH<br>GGGSGGGSGGGSGLNDFFEAQKIEWHEGG<br>GSGGGSGGGSGLNDFFEAQKIEWHE |
| SEQ ID NO: 9<br>A68S_C106S_A134S_<br>K135R_L142K_Y224K_<br>E239G_V250I_L253A_<br>R261K_R306Q_R308L_<br>L326V_E375F_T421Y_<br>W436Y_A437G_Y439W_<br>E466K_D476H_A484E_<br>E508R_D510R_K512F_<br>E515Q_K539E_P558A_<br>D570S_T571V.co.<br>GGGS.LVPRGS.<br>GGGSGGGSGGGS.BtagV7co.<br>GGGSGGGSGGGS.<br>BtagV7co.G.His10co | MKHMPRKMYSCDFETTTKVEDCRVWAY<br>GYMNIEDHSEYKIGNSLDEFMAWVLKVQ<br>ADLYFHNLKFDGSFIINWLERNGFKWSAD<br>GLPNTYNTIISRMGQWYMIDISLGYKGKRK<br>IHTVIYDSLKKLPFPVKKISRDFKLTVKKGD<br>IDYHKERPVGYKITPEEYAYIKNDIQIIAEA<br>LLIQFKQGLDRMTAGSDSLKGFKDIITTKK<br>FKKVFPTLSLGLDKEVRKAYRGGFTWLND<br>RFKGKEIGEGMVFDINSAYPAQMYSKLLP<br>YGEPIVFEGKYVWDEDYPLHIQHIRCEFEL<br>KEGYIPTIQIKQSLFYKGNEYLKSSGGEIAD<br>VWLSNVDLELMKEHYDLYNVEYISGLKFK<br>ATTGLFKDFIDKWTYIKTTSFGAIKQLAKL<br>MLNSLYGKFASNPDVTGKVPYLKENGALG<br>FRLGEEEYKDPVYTPMGVFITAYGRWTTIT<br>AAQACYDRIIYCDTDSIHLTGTKIPDVIKDI<br>VHPKKLGYWEHESTFKRAKYLRQKTYIQD<br>IYMKRVRGFLVQGSPDDYTDIKFSVKCAG<br>MTDKIKEEVTFENFKVGFSRKMKPKAVQV<br>PGGVVLVDSVFTIKGGGSLVPRGSGGGSG<br>GGSGGGSGLNDFFEAQKIEWHEGGGSGGG<br>SGGGSGLNDFFEAQKIEWHEGHHHHHHH<br>HHH |
| SEQ ID NO: 10<br>A68S_L142K_Y224K_<br>E239G_V250I_L253A_<br>R306Q_R308L_T368S_<br>E375W_T421Y_A437G_<br>E466K_D476H_A484E_<br>E508R_D510K_K512R_<br>E515Q_K539E_P558A_<br>D570S_T571V.co.<br>GGGSGGGSGGGS.BtagV7co.<br>GGGSGGGSGGGS.<br>BtagV7co.G.His10co | MKHMPRKMYSCDFETTTKVEDCRVWAY<br>GYMNIEDHSEYKIGNSLDEFMAWVLKVQ<br>ADLYFHNLKFDGSFIINWLERNGFKWSAD<br>GLPNTYNTIISRMGQWYMIDICLGYKGKR<br>KIHTVIYDSLKKLPFPVKKIAKDFKLTVKK<br>GDIDYHKERPVGYKITPEEYAYIKNDIQIIA<br>EALLIQFKQGLDRMTAGSDSLKGFKDIITT<br>KKFKKVFPTLSLGLDKEVRKAYRGGFTWL<br>NDRFKGKEIGEGMVFDINSAYPAQMYSRL<br>LPYGEPIVFEGKYVWDEDYPLHIQHIRCEF<br>ELKEGYIPTIQIKQSLFYKGNEYLKSSGGEI<br>ADVWLSNVDLELMKEHYDLYNVEYISGLK<br>FKATTGLFKDFIDKWSYIKTTSWGAIKQLA<br>KLMLNSLYGKFASNPDVTGKVPYLKENGA<br>LGFRLGEEEYKDPVYTPMGVFITAWGRYT<br>TITAAQACYDRIIYCDTDSIHLTGTKIPDVIK<br>DIVHPKKLGYWEHESTFKRAKYLRQKTYI<br>QDIYMKRVKGFLVQGSPDDYTDIKFSVKC<br>AGMTDKIKEEVTFENFKVGFSRKMKPKAV<br>QVPGGVVLVDSVFTIKGGGSGGGSGGGSG<br>LNDFFEAQKIEWHEGGGSGGGSGGGSGLN<br>DFFEAQKIEWHEGHHHHHHHHHH |
| SEQ ID NO: 11<br>A68S_C106S_K135Q_<br>L142K_Y224K_E239G_<br>V250I_L253A_R261K_<br>R306Q_R308L_L326V_<br>E375W_T421Y_W436Y_<br>A437G_Y439W_E466K_<br>D476H_A484E_E508R_<br>D510R_K512Y_E515Q_<br>K539E_P558A_D570S_<br>T571V.co.GGGSGGGSGGGS. | MKHMPRKMYSCDFETTTKVEDCRVWAY<br>GYMNIEDHSEYKIGNSLDEFMAWVLKVQ<br>ADLYFHNLKFDGSFIINWLERNGFKWSAD<br>GLPNTYNTIISRMGQWYMIDISLGYKGKRK<br>IHTVIYDSLKKLPFPVKKIAQDFKLTVKKG<br>DIDYHKERPVGYKITPEEYAYIKNDIQIIAE<br>ALLIQFKQGLDRMTAGSDSLKGFKDIITTK<br>KFKKVFPTLSLGLDKEVRKAYRGGFTWLN<br>DRFKGKEIGEGMVFDINSAYPAQMYSKLL<br>PYGEPIVFEGKYVWDEDYPLHIQHIRCEFE<br>LKEGYIPTIQIKQSLFYKGNEYLKSSGGEIA |

TABLE 4-continued

Amino acid sequences of exemplary recombinant Φ29 polymerases including C-terminal exogenous features. Amino acid positions are identified relative to SEQ ID NO: 1.

| | Amino Acid Sequence |
|---|---|
| BtagV7co.GGGSGGGSGGGS. BtagV7co.G.His10co | DVWLSNVDLELMKEHYDLYNVEYISGLKF KATTGLFKDFIDKWTYIKTTSWGAIKQLA KLMLNSLYGKFASNPDVTGKVPYLKENGA LGFRLGEEEYKDPVYTPMGVFITAYGRWT TITAAQACYDRIIYCDTDSIHLTGTKIPDVIK DIVHPKKLGYWEHESTFKRAKYLRQKTYI QDIYMKRVRGYLVQGSPDDYTDIKFSVKC AGMTDKIKEEVTFENFKVGFSRKMKPKAV QVPGGVVLVDSVFTIKGGGSGGGSGGGSG LNDFFEAQKIEWHEGGGSGGGSGGGSGLN DFFEAQKIEWHEGHHHHHHHHHH |
| SEQ ID NO: 12 A68S_K135R_L142K_ Y224K_E239G_V250I_ L253A_R261K_R306Q_ R308L_L326V_E375W_ T421Y_W436Y_A437G_ Y439W_E466K_A484E_ E508R_D510R_K512H_ E515Q_K539E_P558A_ D570S_T571V.co. G.His10co.GGGSGGGSGGGS. BtagV7co.GGGSGGGSGGGS. BtagV7co (-D476H) | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIARDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSKL LPYGEPIVFEGKYVWDEDYPLHIQHIRCEF ELKEGYIPTIQIKQSLFYKGNEYLKSSGGEI ADVWLSNVDLELMKEHYDLYNVEYISGL KFKATTGLFKDFIDKWTYIKTTSWGAIKQL AKLMLNSLYGKFASNPDVTGKVPYLKENG ALGFRLGEEEYKDPVYTPMGVFITAYGRW TTITAAQACYDRIIYCDTDSIHLTGTKIPDVI KDIVDPKKLGYWEHESTFKRAKYLRQKTY IQDIYMKRVRGHLVQGSPDDYTDIKFSVKC AGMTDKIKEEVTFENFKVGFSRKMKPKAV QVPGGVVLVDSVFTIKGHHHHHHHHHHG GGSGGGSGGGSGLNDFFEAQKIEWHEGGG SGGGSGGGSGLNDFFEAQKIEWHE |
| SEQ ID NO: 13 A68S_C106S_K135Q_ L142K_Y224K_E239G_ V250I_L253A_R261K_ R306Q_R308L_L326V_ T373F_E375Y_T421Y_ W436Y_A437G_Y439W_ E466K_D476H_A484E_ E508R_D510R_K512Y_ E515Q_K539E_P558A_ D570S_T571V.co. GGGS.LVPRGS. GGGSGGGSGGGS.BtagV7co. GGGSGGGSGGGS.BtagV7co. G.His10co | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDISLGYKGKR KIHTVIYDSLKKLPFPVKKIAQDFKLTVKKG DIDYHKERPVGYKITPEEYAYIKNDIQIIAE ALLIQFKQGLDRMTAGSDSLKGFKDIITTK KFKKVFPTLSLGLDKEVRKAYRGGFTWLN DRFKGKEIGEGMVFDINSAYPAQMYSKLL PYGEPIVFEGKYVWDEDYPLHIQHIRCEFE LKEGYIPTIQIKQSLFYKGNEYLKSSGGEIA DVWLSNVDLELMKEHYDLYNVEYISGLKF KATTGLFKDFIDKWTYIKTFSYGAIKQLAK LMLNSLYGKFASNPDVTGKVPYLKENGAL GFRLGEEEYKDPVYTPMGVFITAYGRWTTI TAAQACYDRIIYCDTDSIHLTGTKIPDVIKD IVHPKKLGYWEHESTFKRAKYLRQKTYQ DIYMKRVRGYLVQGSPDDYTDIKFSVKCA GMTDKIKEEVTFENFKVGFSRKMKPKAVQ VPGGVVLVDSVFTIKGGGSLVPRGSGGGS GGGSGGGSGLNDFFEAQKIEWHEGGGSGG GSGGGSGLNDFFEAQKIEWHEGHHHHHH HHHH |
| SEQ ID NO: 14 A68S_K135Q_L142K_ Y224K_E239G_V250I_ L253A_R261K_R306Q_ R308L_L326V_E375Y_ T421Y_W436Y_A437G_ Y439W_E466K_D476H_ A484E_E508R_D510R_ K512Y_E515Q_K539E_ P558A_D570S_T571V. co.G.His10co. GGGSGGGSGGGS.BtagV7co. GGGSGGGSGGGS. BtagV7co | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIAQDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSKL LPYGEPIVFEGKYVWDEDYPLHIQHIRCEF ELKEGYIPTIQIKQSLFYKGNEYLKSSGGEI ADVWLSNVDLELMKEHYDLYNVEYISGL KFKATTGLFKDFIDKWTYIKTTSYGAIKQL AKLMLNSLYGKFASNPDVTGKVPYLKENG ALGFRLGEEEYKDPVYTPMGVFITAYGRW |

TABLE 4-continued

Amino acid sequences of exemplary recombinant Φ29 polymerases including C-terminal exogenous features. Amino acid positions are identified relative to SEQ ID NO: 1.

| | Amino Acid Sequence |
|---|---|
| | TTITAAQACYDRIIYCDTDSIHLTGTKIPDVI KDIVHPKKLGYWEHESTFKRAKYLRQKTY IQDIYMKRVRGYLVQGSPDDYTDIKFSVKC AGMTDKIKEEVTFENFKVGFSRKMKPKAV QVPGGVVLVDSVFTIKGHHHHHHHHHG GGSGGGSGGGSGLNDFFEAQKIEWHEGGG SGGGSGGGSGLNDFFEAQKIEWHE |
| SEQ ID NO: 15 A68S_K135Q_L142K_ Y224K_E239G_V250I_ L253A_R306Q_R308L_ T368S_E375Y_T421Y_ A437G_E466K_D476H_ A484E_E508R_D510R_ K512Y_E515Q_K539E_ P558A_D570S_T571V. co.GGGSGGGSGGGS. BtagV7co.GGGSGGGSGGGS. BtagV7co.G. His10co | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIAQDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSRL LPYGEPIVFEGKYVWDEDYPLHIQHIRCEF ELKEGYIPTIQIKQSLFYKGNEYLKSSGGEI ADLWLSNVDLELMKEHYDLYNVEYISGLK FKATTGLFKDFIDKWSYIKTTSYGAIKQLA KLMLNSLYGKFASNPDVTGKVPYLKENGA LGFRLGEEEYKDPVYTPMGVFITAWGRYT TITAAQACYDRIIYCDTDSIHLTGTKIPDVIK DIVHPKKLGYWEHESTFKRAKYLRQKTYI QDIYMKRVRGYLVQGSPDDYTDIKFSVKC AGMTDKIKEEVTFENFKVGFSRKMKPKAV QVPGGVVLVDSVFTIKGGGSGGGSGGGSG LNDFFEAQKIEWHEGGGSGGGSGGGSGLN DFFEAQKIEWHEGHHHHHHHHHH |
| SEQ ID NO: 16 A68S_K135Q_L142K_ Y224K_E239G_V250I_ L253A_R306Q_R308L_ T368S_E375Y_T421Y_ A437G_E466K_D476H_ A484E_E508R_D510R_ K512Y_E515Q_K539E_ P558A_D570S_T571V. co.G.His10.co. GGGSGGGSGGGS.BtagV7co. GGGSGGGSGGGS. BtagV7co | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIAQDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSRL LPYGEPIVFEGKYVWDEDYPLHIQHIRCEF ELKEGYIPTIQIKQSLFYKGNEYLKSSGGEI ADLWLSNVDLELMKEHYDLYNVEYISGLK FKATTGLFKDFIDKWSYIKTTSYGAIKQLA KLMLNSLYGKFASNPDVTGKVPYLKENGA LGFRLGEEEYKDPVYTPMGVFITAWGRYT TITAAQACYDRIIYCDTDSIHLTGTKIPDVIK DIVHPKKLGYWEHESTFKRAKYLRQKTYI QDIYMKRVRGYLVQGSPDDYTDIKFSVKC AGMTDKIKEEVTFENFKVGFSRKMKPKAV QVPGGVVLVDSVFTIKGHHHHHHHHHG GGSGGGSGGGSGLNDFFEAQKIEWHEGGG SGGGSGGGSGLNDFFEAQKIEWHE |

TABLE 5

Amino acid sequences of exemplary recombinant Φ29 polymerases. Amino acid positions are identified relative to SEQ ID NO: 1.

| | Amino Acid Sequence |
|---|---|
| SEQ ID NO: 17 A68S_C106S_K135Q_ L142R_Y224K_E239G_ V250I_L253A_R306Q_ R308L_T368S_E375W_ T421Y_A437G_E466K_ D476H_A484E_E508R_ D510R_K512F_E515Q_ K539E_P558A_D570S_ T571V | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDISLGYKGKRK IHTVIYDSLKKLPFPVKKIAQDFKLTVRKG DIDYHKERPVGYKITPEEYAYIKNDIQIIAE ALLIQFKQGLDRMTAGSDSLKGFKDIITTK KFKKVFPTLSLGLDKEVRKAYRGGFTWLN DRFKGKEIGEGMVFDINSAYPAQMYSRLL PYGEPIVFEGKYVWDEDYPLHIQHIRCEFE |

TABLE 5-continued

Amino acid sequences of exemplary recombinant Φ29 polymerases.
Amino acid positions are identified relative to SEQ ID NO: 1.

| | Amino Acid Sequence |
|---|---|
| | LKEGYIPTIQIKQSLFYKGNEYLKSSGGEIA
DLWLSNVDLELMKEHYDLYNVEYISGLKF
KATTGLFKDFIDKWSYIKTTSWGAIKQLAK
LMLNSLYGKFASNPDVTGKVPYLKENGAL
GFRLGEEEYKDPVYTPMGVFITAWGRYTTI
TAAQACYDRIIYCDTDSIHLTGTKIPDVIKD
IVHPKKLGYWEHESTFKRAKYLRQKTYIQ
DIYMKRVRGFLVQGSPDDYTDIKFSVKCA
GMTDKIKEEVTFENFKVGFSRKMKPKAVQ
VPGGVVLVDSVFTIK |
| SEQ ID NO: 18
A68S_K135R_L142K_
Y224K_E239G_V250I_
L253A_R261K_R306Q_
R308L_L326V_T368S_
E375W_T421Y_W436Y_
A437G_Y439W_T441I_
C448V_E466K_D476H_
A484E_E508Q_D510R_
K512H_E515Q_K539E_
P558A_D570S_T571V_ | MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDICLGYKGKR
KIHTVIYDSLKKLPFPVKKIARDFKLTVKK
GDIDYHKERPVGYKITPEEYAYIKNDIQIIA
EALLIQFKQGLDRMTAGSDSLKGFKDIITT
KKFKKVFPTLSLGLDKEVRKAYRGGFTWL
NDRFKGKEIGEGMVFDINSAYPAQMYSKL
LPYGEPIVFEGKYVWDEDYPLHIQHIRCEF
ELKEGYIPTIQIKQSLFYKGNEYLKSSGGEI
ADVWLSNVDLELMKEHYDLYNVEYISGL
KFKATTGLFKDFIDKWSYIKTTSWGAIKQL
AKLMLNSLYGKFASNPDVTGKVPYLKENG
ALGFRLGEEEYKDPVYTPMGVFITAYGRW
TIITAAQAVYDRITYCDTDSIHLTGTKIPDVI
KDIVHPKKLGYWEHESTFKRAKYLRQKTY
IQDIYMKQVRGHLVQGSPDDYTDIKFSVK
CAGMTDKIKEEVTFENFKVGFSRKMKPKA
VQVPGGVVLVDSVFTIK |
| SEQ ID NO: 19
A68S_C106S_A134S_
K135R_L142K_Y224K_
E239G_V250I_L253A_
R261K_R306Q_R308L_
L326V_E375F_T421Y_
W436Y_A437G_Y439W_
E466K_D476H_A484E_
E508R_D510R_K512F_
E515Q_K539E_P558A-
D570S_T571V | MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDISLGYKGKRK
IHTVIYDSLKKLPFPVKKISRDFKLTVKKGD
IDYHKERPVGYKITPEEYAYIKNDIQIIAEA
LLIQFKQGLDRMTAGSDSLKGFKDIITTKK
FKKVFPTLSLGLDKEVRKAYRGGFTWLND
RFKGKEIGEGMVFDINSAYPAQMYSKLLP
YGEPIVFEGKYVWDEDYPLHIQHIRCEFEL
KEGYIPTIQIKQSLFYKGNEYLKSSGGEIAD
VWLSNVDLELMKEHYDLYNVEYISGLKFK
ATTGLFKDFIDKWTYIKTTSFGAIKQLAKL
MLNSLYGKFASNPDVTGKVPYLKENGALG
FRLGEEEYKDPVYTPMGVFITAYGRWTTIT
AAQACYDRIIYCDTDSIHLTGTKIPDVIKDI
VHPKKLGYWEHESTFKRAKYLRQKTYIQD
IYMKRVRGFLVQGSPDDYTDIKFSVKCAG
MTDKIKEEVTFENFKVGFSRKMKPKAVQV
PGGVVLVDSVFTIK |
| SEQ ID NO: 20
A68S_L142K_Y224K_
E239G_V250I_L253A_
R306Q_R308L_T368S_
E375W_T421Y_A437G_
E466K_D476H_A484E_
E508R_D510K_K512F_
E515Q_K539E_P558A_
D570S_T571V | MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDICLGYKGKR
KIHTVIYDSLKKLPFPVKKIAKDFKLTVKK
GDIDYHKERPVGYKITPEEYAYIKNDIQIIA
EALLIQFKQGLDRMTAGSDSLKGFKDIITT
KKFKKVFPTLSLGLDKEVRKAYRGGFTWL
NDRFKGKEIGEGMVFDINSAYPAQMYSRL
LPYGEPIVFEGKYVWDEDYPLHIQHIRCEF
ELKEGYIPTIQIKQSLFYKGNEYLKSSGGEI
ADLWLSNVDLELMKEHYDLYNVEYISGLK
FKATTGLFKDFIDKWSYIKTTSWGAIKQLA
KLMLNSLYGKFASNPDVTGKVPYLKENGA
LGFRLGEEEYKDPVYTPMGVFITAWGRYT
TITAAQACYDRIIYCDTDSHILTGTKIPDVIK
DIVHPKKLGYWEHESTFKRAKYLRQKTYI
QDIYMKRVKGFLVQGSPDDYTDIKFSVKC
AGMTDKIKEEVTFENFKVGFSRKMKPKAV
QVPGGVVLVDSVFTIK |

TABLE 5-continued

Amino acid sequences of exemplary recombinant Φ29 polymerases.
Amino acid positions are identified relative to SEQ ID NO: 1.

Amino Acid Sequence

SEQ ID NO: 21
A68S_C106S_K135Q_
L142K_Y224K_E239G_
V250I_L253A_R261K_
R306Q_R308L_L326V_
E375W_T421Y_W436Y_
A437G_Y439W_E466K_
D476H_A484E_E508R_
D510R_K512Y_E515Q_
K539E_P558A_D570S_
T571V mkhmprkmyscdfetttkvedcrvwaygymniedhseykig
nsldefmawvlkvqadlyfhnlkfdgsfiinwlerngfkwsad
glpntyntiisrmgqwymidislgykgkrkihtviydslkklpfp
vkkiaqdfkltvkkgdidyhkerpvgykitpeeyayikndiqiia
ealliqfkqgldrmtagsdslkgfkdiittkkfkkvfptlslgldke
vrkayrggftwlndrfkgkeigegmvfdinsaypaqmyskllp
ygepivfegkyvwdedyplhiqhircefelkegyiptiqikqslf
ykgneylkssggeiadvwlsnvdlelmkehydlynveyisglk
fkattglfkdfidkwtyikttswgaikqlaklmlnslygkfasnpd
vtgkvpylkengalgfrlgeeeykdpvytpmgvfitaygrwttit
aaqacydriiycdtdsihltgtkipdvikdivhpkklgywehestf
krakylrqktyiqdiymkrvrgylvqgspddytdikfsvkcag
mtdkikeevtfenfkvgfsrkmkpkavqvpggvvlvdsvftik SEQ ID NO: 22
A68S_K135R_L142K_
Y224K_E239G_V250I_
L253A_R261K_R306Q_
R308L_L326V_E375W_
T421Y_W436Y_A437G_
Y439W_E466K_A484E_
E508R_D510R_K512H_
E515Q_K539E_P558A_
D570S_T571V MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDICLGYKGKR
KIHTVIYDSLKKLPFPVKKIARDFKLTVKK
GDIDYHKERPVGYKITPEEYAYIKNDIQIIA
EALLIQFKQGLDRMTAGSDSLKGFKDIITT
KKFKKVFPTLSLGLDKEVRKAYRGGFTWL
NDRFKGKEIGEGMVFDINSAYPAQMYSKL
LPYGEPIVFEGKYVWDEDYPLHIQHIRCEF
ELKEGYIPTIQIKQSLFYKGNEYLKSSGGEI
ADVWLSNVDLELMKEHYDLYNVEYISGL
KFKATTGLFKDFIDKWTYIKTTSWGAIKQL
AKLMLNSLYGKFASNPDVTGKVPYLKENG
ALGFRLGEEEYKDPVYTPMGVFITAYGRW
TTITAAQACYDRIIYCDTDSIHLTGTKIPDVI
KDIVDPKKLGYWEHESTFKRAKYLRQKTY
IQDIYMKRVRGHLVQGSPDDYTDIKFSVKC
AGMTDKIKEEVTFENFKVGFSRKMKPKAV
QVPGGVVLVDSVFTIK SEQ ID NO: 23
A68S_C106S_K135Q_
L142K_Y224K_E239G_
V250I_L253A_R261K_
R306Q_R308L_L326V_
T373F_E375Y_T421Y_
W436Y_A437G_Y439W_
E466K_D476H_A484E_
E508R_D510R_K512Y_
E515Q_K539E_P558A_
D570S_T571V MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDISLGYKGKRK
IHTVIYDSLKKLPFPVKKIAQDFKLTVKKG
DIDYHKERPVGYKITPEEYAYIKNDIQIIAE
ALLIQFKQGLDRMTAGSDSLKGFKDIITTK
KFKKVFPTLSLGLDKEVRKAYRGGFTWLN
DRFKGKEIGEGMVFDINSAYPAQMYSKLL
PYGEPIVFEGKYVWDEDYPLHIQHIRCEFE
LKEGYIPTIQIKQSLFYKGNEYLKSSGGEIA
DVWLSNVDLELMKEHYDLYNVEYISGLKF
KATTGLFKDFIDKWTYIKTFSYGAIKQLAK
LMLNSLYGKFASNPDVTGKVPYLKENGAL
GFRLGEEEYKDPVYTPMGVFITAYGRWTTI
TAAQACYDRIIYCDTDSIHLTGTKIPDVIKD
IVHPKKLGYWEHESTFKRAKYLRQKTYIQ
DIYMKRVRGYLVQGSPDDYTDIKFSVKCA
GMTDKIKEEVTFENFKVGFSRKMKPKAVQ
VPGGVVLVDSVFTIK SEQ ID NO: 24
A68S_K135Q_L142K_
Y224K_E239G_V250I_
L253A_R261K_R306Q_
R308L_L326V_E375Y_
T421Y_W436Y_A437G_
Y439W_E466K_D476H_
A484E_E508R_D510R_
K512Y_E515Q_K539E_
P558A_D570S_T571V MKHMPRKMYSCDFETTTKVEDCRVWAY
GYMNIEDHSEYKIGNSLDEFMAWVLKVQ
ADLYFHNLKFDGSFIINWLERNGFKWSAD
GLPNTYNTIISRMGQWYMIDICLGYKGKR
KIHTVIYDSLKKLPFPVKKIAQDFKLTVKK
GDIDYHKERPVGYKITPEEYAYIKNDIQIIA
EALLIQFKQGLDRMTAGSDSLKGFKDIITT
KKFKKVFPTLSLGLDKEVRKAYRGGFTWL
NDRFKGKEIGEGMVFDINSAYPAQMYSKL
LPYGEPIVFEGKYVWDEDYPLHIQHIRCEF
ELKEGYIPTIQIKQSLFYKGNEYLKSSGGEI
ADVWLSNVDLELMKEHYDLYNVEYISGL
KFKATTGLFKDFIDKWTYIKTTSYGAIKQL
AKLMLNSLYGKFASNPDVTGKVPYLKENG
ALGFRLGEEEYKDPVYTPMGVFITAYGRW
TTITAAQACYDRIIYCDTDSIHLTGTKIPDVI
KDIVHPKKLGYWEHESTFKRAKYLRQKTY
IQDIYMKRVRGYLVQGSPDDYTDIKFSVKC TABLE 5-continued Amino acid sequences of exemplary recombinant Φ29 polymerases.
Amino acid positions are identified relative to SEQ ID NO: 1.

| | Amino Acid Sequence |
|---|---|
| | AGMTDKIKEEVTFENFKVGFSRKMKPKAV QVPGGVVLVDSVFTIK |
| SEQ ID NO: 25 A68S_K135Q_L142K_ Y224K_E239G_V250I_ L253A_R306Q_R308L_ T368S_E375Y_T421Y_ A437G_E466K_D476H_ A484E_E508R_D510R_ K512Y_E515Q_K539E_ P558A_D570S_T571V_ | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIAQDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSRL LPYGEPIVFEGKYVWDEDYPLHIQHIRCEF ELKEGYIPTIQIKQSLFYKGNEYLKSSGGEI ADLWLSNVDLELMKEHYDLYNVEYISGLK FKATTGLFKDFIDKWSYIKTTSYGAIKQLA KLMLNSLYGKFASNPDVTGKVPYLKENGA LGFRLGEEEYKDPVYTPMGVFITAWGRYT TITAAQACYDRIIYCDTDSHILTGTKIPDVIK DIVHPKKLGYWEHESTFKRAKYLRQKTYI QDIYMKRVRGYLVQGSPDDYTDIKFSVKC AGMTDKIKEEVTFENFKVGFSRKMKPKAV QVPGGVVLVDSVFTIK |
| SEQ ID NO: 26 A68S_K135Q_L142K_ Y224K_E239G_V250I_ L253A_R306Q_R308L_ T368S_E375Y_T421Y_ A437G_E466K_D476H_ A484E_E508R_D510R_ K512Y_E515Q_K539E_ P558A_D570S_T571V | MKHMPRKMYSCDFETTTKVEDCRVWAY GYMNIEDHSEYKIGNSLDEFMAWVLKVQ ADLYFHNLKFDGSFIINWLERNGFKWSAD GLPNTYNTIISRMGQWYMIDICLGYKGKR KIHTVIYDSLKKLPFPVKKIAQDFKLTVKK GDIDYHKERPVGYKITPEEYAYIKNDIQIIA EALLIQFKQGLDRMTAGSDSLKGFKDIITT KKFKKVFPTLSLGLDKEVRKAYRGGFTWL NDRFKGKEIGEGMVFDINSAYPAQMYSRL LPYGEPIVFEGKYVWDEDYPLHIQHIRCEF ELKEGYIPTIQIKQSLFYKGNEYLKSSGGEI ADLWLSNVDLELMKEHYDLYNVEYISGLK FKATTGLFKDFIDKWSYIKTTSYGAIKQLA KLMLNSLYGKFASNPDVTGKVPYLKENGA LGFRLGEEEYKDPVYTPMGVFITAWGRYT TITAAQACYDRIIYCDTDSHILTGTKIPDVIK DIVHPKKLGYWEHESTFKRAKYLRQKTYI QDIYMKRVRGYLVQGSPDDYTDIKFSVKC AGMTDKIKEEVTFENFKVGFSRKMKPKAV QVPGGVVLVDSVFTIK |

Compositions, kits, and systems (e.g., sequencing systems) including such recombinant polymerases, e.g., in combination with one or more of the instant labeled nucleotide analogs, are features of the disclosure, as are methods employing the recombinant polymerases (e.g., methods of sequencing or making DNA). Many other such recombinant polymerases including these mutations and/or those described elsewhere herein will be readily apparent and are features of the disclosure.

The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), Kamtekar et al. (2006) "The phi29 DNA polymerase:protein-primer structure suggests a model for the initiation to elongation transition" EMBO J. 25(6):1335-43, and Berman et al. (2007) "Structures of phi29 DNA polymerase complexed with substrate: The mechanism of translocation in B-family polymerases" EMBO J. 26:3494-3505, respectively. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA (e.g., template and/or primer) and/or nucleotide analog, or the like, can be determined using techniques known in the art. See, e.g., U.S. Patent Application Publication No. 2014/0094375 and references therein.

Mutations can be introduced into a desired parental polymerase and the resulting recombinant polymerase can be expressed, purified, and characterized (e.g., to determine one or more properties, e.g., for an analog of the invention) using techniques known in the art. See, e.g., U.S. Patent Application Publication Nos. 2007/0196846, 2008/0108082, 2010/0075332, 2010/0093555, 2010/0112645, 2011/0189659, 2012/0034602, 2013/0217007, 2014/0094374, and 2014/0094375 (previously incorporated by reference in their entirety for all purposes), and references therein.

Reaction Mixtures, Methods, and Systems for Nucleic Acid Sequencing

The disclosure further provides, in another aspect, reaction mixtures useful in the sequencing of nucleic acids. Such mixtures preferably comprise a polymerase enzyme complex that includes a polymerase enzyme, a template nucleic acid, and optionally a primer hybridized to the template nucleic acid. Such polymerase complexes are ideally configured for immobilization on a surface, such as the surface of a ZMW. The reaction mixtures additionally comprise sequencing reagents in contact with the surface to which the polymerase complex is immobilized. The sequencing reagents include nucleotides for carrying out nucleic acid synthesis, in particular two or more of the labeled nucleotide analogs described in detail above. Further details relating to the reaction mixtures, including preferred template nucleic acids, polymerase enzymes, methods for immobilizing polymerase complexes to a surface, reaction conditions, including buffers, pH, salts, and the like, are provided, for example, in U.S. Patent Application Publication No. 2013/0316912 A1. Exemplary mutated polymerase enzymes usefully included in the instant reaction mixtures with analogs comprising the instant modified nucleotide compounds are described above.

In specific embodiments, the labeled nucleotide analog of the reaction mixture comprises at least one dye-labeled compound and at least one nucleotide compound, wherein the at least one dye-labeled compound and the at least one nucleotide compound are described above. In more specific embodiments, each dye-labeled compound and each nucleotide compound comprises a bis-biotin moiety.

Exemplary reaction mixtures of the disclosure suitable for sequencing nucleic acids thus include the mixtures described in the following numbered paragraphs:

1. A reaction mixture for sequencing a nucleic acid template comprising:

a polymerase enzyme complex comprising a polymerase enzyme, a template nucleic acid, and optionally a primer hybridized to the template nucleic acid, wherein the polymerase enzyme complex is immobilized on a surface; and sequencing reagents in contact with the surface comprising reagents for carrying out nucleic acid synthesis including two or more of any of the labeled nucleotide analogs described above.

2. The reaction mixture of paragraph 1, wherein the labeled nucleotide analog comprises one dye-labeled compound and one nucleotide compound, wherein the dye-labeled compound and the nucleotide compound each comprises a biotin moiety.

The disclosure still further provides, in yet another aspect, methods for sequencing a nucleic acid template. In these methods, a polymerase enzyme complex comprising a polymerase enzyme, a template nucleic acid, and optionally a primer hybridized to the template nucleic acid is provided. In some embodiments, the polymerase enzyme complex is immobilized on a surface. Sequencing reagents are added to the polymerase enzyme complex, wherein the reagents include nucleotides for carrying out nucleic acid synthesis, in particular two or more of the labeled nucleotide analogs described in detail above. The sequential addition of nucleotides to a nucleic acid strand complementary to a strand of the template nucleic acid is determined by observing the interaction of the labeled nucleotide analogs with the polymerase enzyme complex.

In specific method embodiments, the labeled nucleotide analog of the sequencing method comprises at least one dye-labeled compound and at least one nucleotide compound of the instant disclosure. In more specific method embodiments, the at least one dye-labeled compound and the at least one nucleotide compound each comprise a bis-biotin moiety.

For example, methods of the disclosure suitable for sequencing a nucleic acid template include any of the methods described in the following numbered paragraphs:

1. A method for sequencing a nucleic acid template comprising:

providing a polymerase enzyme complex comprising a polymerase enzyme, a template nucleic acid, and optionally a primer hybridized to the template nucleic acid, wherein the polymerase enzyme complex is immobilized on a surface;

adding sequencing reagents in contact with the surface comprising reagents for carrying out nucleic acid synthesis including two or more of any of the labeled nucleotide analogs described above; and determining the sequential addition of nucleotides to a nucleic acid strand complementary to a strand of the template nucleic acid by observing the interaction of the labeled nucleotide analogs with the polymerase enzyme complex.

2. The method of paragraph 1, wherein at least one labeled nucleotide analog comprises:

one nucleotide compound bound to the avidin protein through a biotin moiety; and one dye-labeled compound bound to the avidin protein through a biotin moiety.

3. The method of paragraph 1, wherein at least one labeled nucleotide analog comprises:

one dye-labeled compound, bound to the avidin protein through a biotin moiety; and two nucleotide compounds, each bound to the avidin protein through a biotin moiety.

4. The method of paragraph 1, wherein at least one labeled nucleotide analog comprises:

one dye-labeled compound and one nucleotide compound, each of which is bound to the avidin protein through a biotin moiety.

5. The method of paragraph 1, wherein at least one labeled nucleotide analog comprises:

two avidin proteins, two nucleotide compounds, and one dye-labeled compound; wherein the dye-labeled compound comprises two biotin moieties;

each nucleotide compound comprises one biotin moiety; and each avidin protein is bound to the dye-labeled compound through a biotin moiety and to one of the nucleotide compounds through a biotin moiety.

6. The method of any one of paragraphs 1-5, wherein the avidin protein comprises either streptavidin or tamavidin.

7. The method of any one of paragraphs 1-5, wherein the dye moieties are fluorescent dyes.

8. The method of any one of paragraphs 1-5, wherein at least one nucleotide compound is represented by structural formula (I):

$$B''\text{---}[X\text{---}]_o[L\text{---}P\text{---}Nu]_n; \qquad (I)$$

wherein

L is a nucleotide linker element comprising an affinity modulating element;

P is a polyphosphate element;

Nu is a nucleoside element;

X is a multivalent central core element;

B'' is a terminal coupling element;

n is an integer from 1 to 4; and o is 0 or 1.

9. The method of paragraph 8, wherein the affinity modulating element is an aromatic spacer element.

10. The method of paragraph 9, wherein the aromatic spacer element is a substituted or unsubstituted monocyclic, bicyclic, tricyclic, or tetracyclic aromatic moiety.

11. The method of paragraph 10, wherein the aromatic spacer element optionally comprises at least one anionic substituent.

12. The method of paragraph 11, wherein the aromatic spacer element optionally comprises at least two anionic substituents.

13. The method of paragraph 11, wherein the optional at least one anionic substituent is —SO$_3$H.

14. The method of paragraph 10, wherein the aromatic spacer element is represented by one of the following structural formulae:

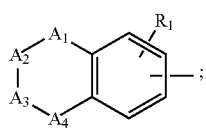
(IIA)

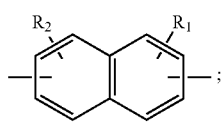
(IIB)

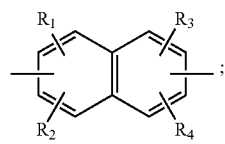
(IID)

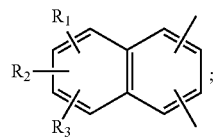
(IIE)

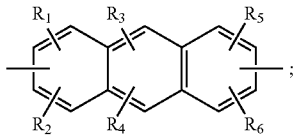
(IIF)

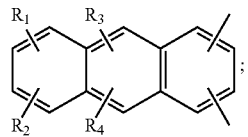
(IIG)

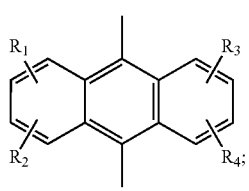
(IIH)

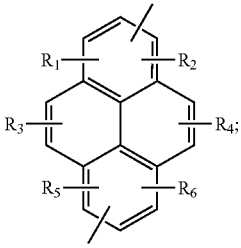
(IIJ)

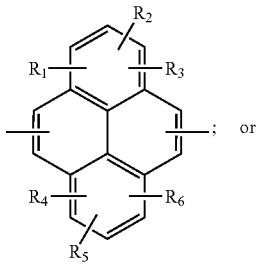
(IIK)

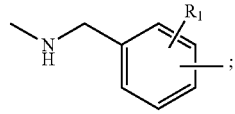
(IV)

wherein one of the A$_1$, A$_2$, A$_3$, and A$_4$ groups is

and the other groups are —CH$_2$— or a bond; and

R$_1$, R$_2$, R$_3$, R$_4$, R$_5$, and R$_6$ are independently H or an anionic substituent.

15. The method of paragraph 14, wherein the aromatic spacer element is represented by one of the following structural formulae:

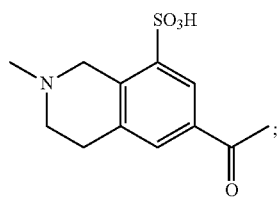

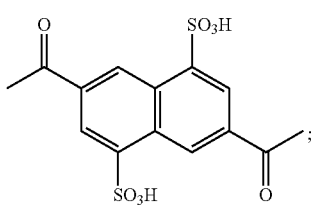

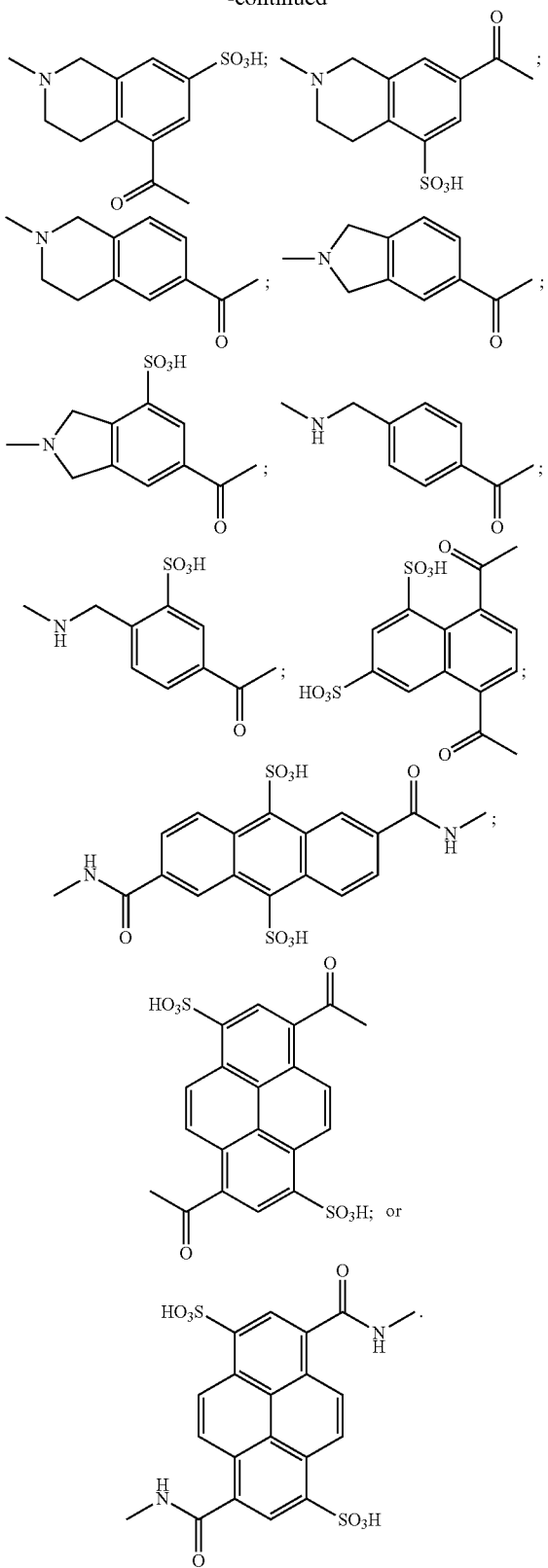

16. The method of paragraph 8, wherein L further comprises an alkyl linker group, optionally comprising an amide bond.
17. The method of paragraph 8, wherein L further comprises a triazole.
18. The method of paragraph 8, wherein B" comprises a biotin moiety.
19. The method of paragraph 18, wherein B" comprises a bis-biotin moiety.
20. The method of paragraph 8, wherein o is 1.
21. The method of paragraph 20, wherein n is 2.
22. The method of paragraph 20, wherein X comprises a polyamine moiety.
23. The method of paragraph 8, wherein o is 0 and n is 1.
24. The method of any one of paragraphs 1-5, wherein at least one dye-labeled compound comprises:
   a donor dye;
   an acceptor dye;
   a shield element;
   a terminal coupling element; and
   a dye compound linker element;
wherein the dye compound linker element covalently connects the terminal coupling element to the donor dye, the acceptor dye, or the shield element; and
wherein the acceptor dye or the donor dye is directly coupled to the shield element.
25. The method of paragraph 24, wherein the terminal coupling element comprises a biotin moiety.
26. The method of paragraph 25, wherein the terminal coupling element comprises a bis-biotin moiety.
27. The method of paragraph 8, wherein o is 1.
28. The method of paragraph 27, wherein n is 2.
29. The method of paragraph 28, wherein X comprises a polyamine moiety.
30. The method of paragraph 24, wherein o is 0 and n is 1.

In yet another aspect, the disclosure provides systems for sequencing nucleic acids. Such systems preferably comprise a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid. The system further comprises sequencing reagents in contact with the surface. The sequencing reagents comprise reagents for carrying out nucleic acid synthesis, including two or more of the labeled nucleotide analogs described in detail above. The system also comprises an illumination system for illuminating the polymerase enzyme complexes, an optical detection system for detecting fluorescence from the labeled nucleotide analogs while they are interacting with the polymerase enzyme complexes, and a computer for analyzing the signals detected by the detection system to determine the sequential addition of nucleotides to a nucleic acid strand complementary to a strand of the template nucleic acid. Such systems are further described, for example, in U.S. Patent Application Publication No. 2013/0316912 A1.

For example, the system for sequencing nucleic acids can comprise:
   a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid;
   sequencing reagents in contact with the surface comprising reagents for carrying out nucleic acid synthesis including two or more of any of the labeled nucleotide analogs described above; and
   an illumination system for illuminating the polymerase enzyme complexes;

an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid.

It will be readily apparent to one of ordinary skill in the relevant arts that other suitable modifications and adaptations to the methods and applications described herein can be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1. Synthesis of Bis-Biotin Nucleotide Compounds

A variety of nucleotide compounds containing bis-biotin linkers have been synthesized for use in single-molecule real-time sequencing reactions. These compounds have been assembled with dye-labeled compounds, or their intermediate forms, that also contain bis-biotin linkers, using avidin proteins to create dye-labeled nucleotide analog complexes, for example as described in Example 2 and as illustrated in FIGS. 7A-7D and 7F. Additional examples of labeled nucleotide analogs that have been prepared according to these methods are graphically illustrated in FIGS. 3E-3O'. Many of the analogs demonstrate improved photostability, brightness, and reaction kinetics in automated DNA sequencing reactions involving DNA polymerase. See also U.S. Patent Application Publication No. 2013/0316912 A1. Use of the assembled fluorescent nucleotide reagent complexes in real-time sequencing reactions is described in Example 3.

Figure 30:
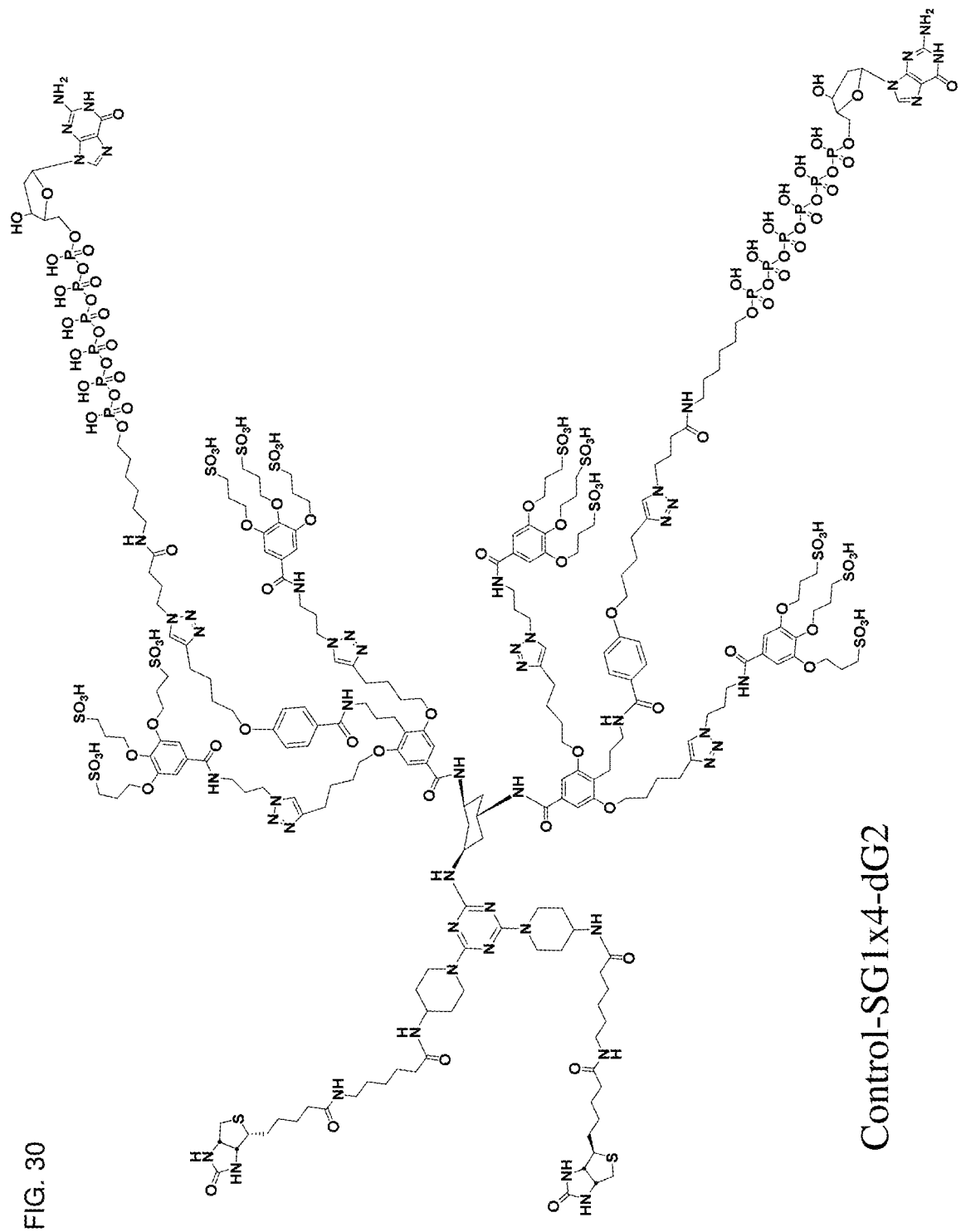

The bis-biotin-containing nucleotide reagent compounds of the instant disclosure can include two nucleotide arms, for example as shown in FIG. 30 for Control-SG1×4-dG2. As shown in this structure, each of the two nucleotide arms can contain a guanosine nucleoside, a hexaphosphate chain, a linker group, including a triazole moiety resulting from a "click" coupling reaction, and a pair of shield elements, each comprising two side chains ("SG1" side chains—see above reaction schemes) that each contains three anionic side chains. Such shield elements, when incorporated into fluorescent nucleotide reagent compounds, have been shown to prevent photodamage of the polymerase enzyme and to provide other advantages in sequencing reactions. See, e.g., U.S. Patent Application Publication Nos. 2015/0050659 A1 and 2016/0237279 A1. They have been found here to modulate the affinity of the nucleotide reagent for the polymerase enzyme and/or to provide other improvements in the kinetics of polymerase reactions using nucleotide reagents containing these groups. The exemplary Control-SG1×4-dG2 compound further contains a triamino-cyclohexyl multivalent central core element that provides a branch point for the two nucleotide arms and that also provides a binding site for the bis-biotin group, which itself comprises a triamino triazine multivalent central core element that provides a branch point for the bis-biotin terminal coupling element of the molecule.

Synthesis of the reagent compound of FIG. 30 was performed as described generally in U.S. Patent Application Publication No. 2015/0050659 A1.

Figure 31:
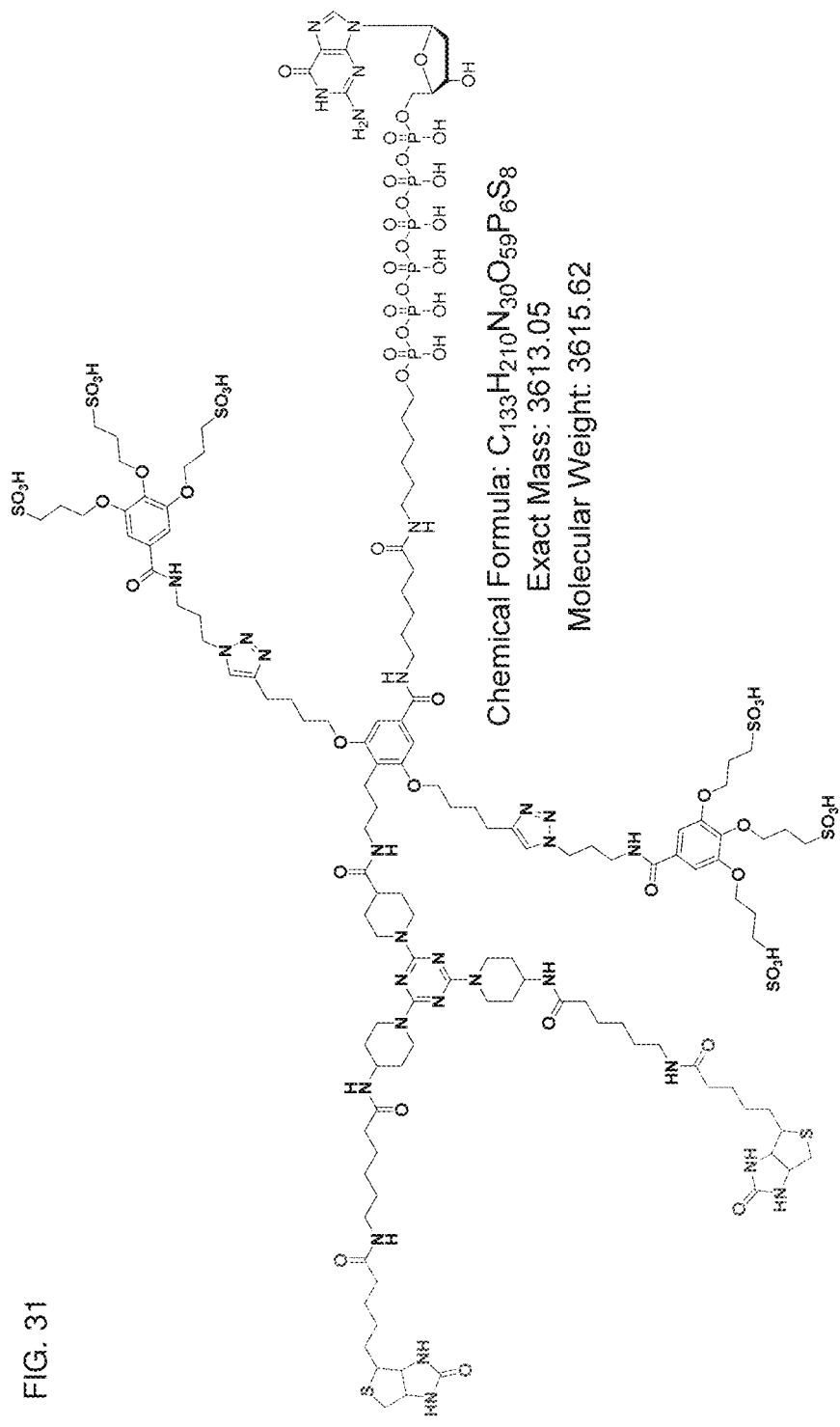

Alternative nucleotide reagent compounds can include just one nucleotide arm, for example as shown in FIG. 31 for Control-SG1×2-dG. In this compound, there is a single nucleotide arm, where the nucleoside is linked to a hexaphosphate chain, a linker group, and a pair of shield elements, much the same as in the Control-SG1×4-dG2 dinucleotide compound described above. Unlike the dinucleotide structure, however, in the mononucleotide compound, the shielded nucleotide arm is coupled directly to the triamino triazine multivalent central core element that carries the bis-biotin terminal coupling element.

The variant structures illustrated in FIG. 32 also contain a single nucleotide arm but differ from the Control-SG1×2-dG mononucleotide compound in including an extra pair, or "layer", of shield elements (for Layered-SG1×4-dG) or two extra pairs of shield elements (for Layered-SG1×6-dG). It should be understood that the compounds extend beyond the terminal triazole moiety in each case to include an extra segment of the nucleotide linker element, a linear polyphosphate element, and a nucleoside.

Figure 33:
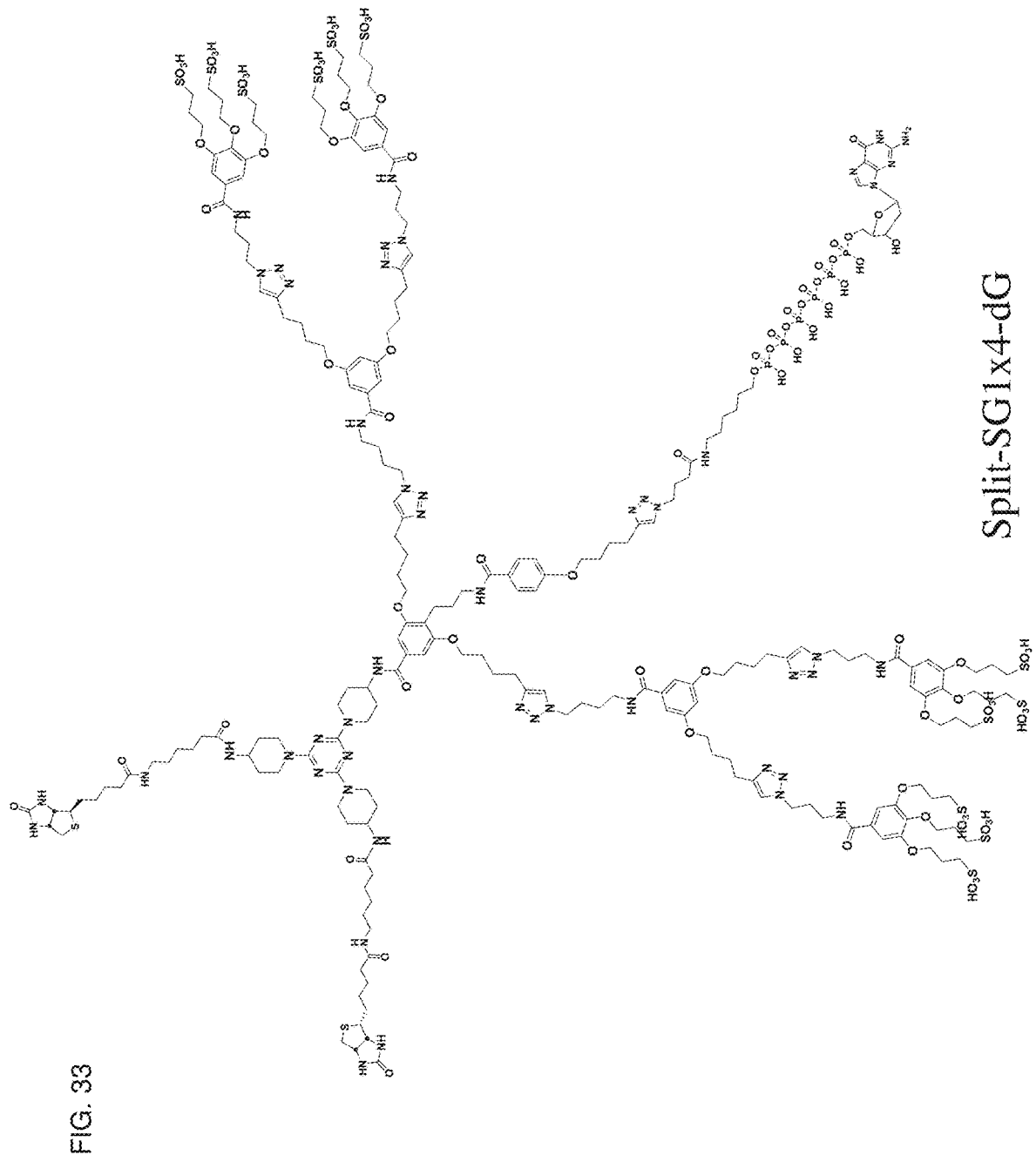

Another variant mononucleotide compound contains a branch, or "split" within each of the shield elements, such that additional anionic side chains are attached to the shield element with a branching group coupled to an aromatic group with multiple anionic side chains. The structure shown in FIG. 33, Split-SG1×4-dG, represents the complete nucleotide reagent compound, including the complete nucleotide linker, the polyphosphate element, and the nucleoside (in this case a "dG" nucleoside).

Figure 34:
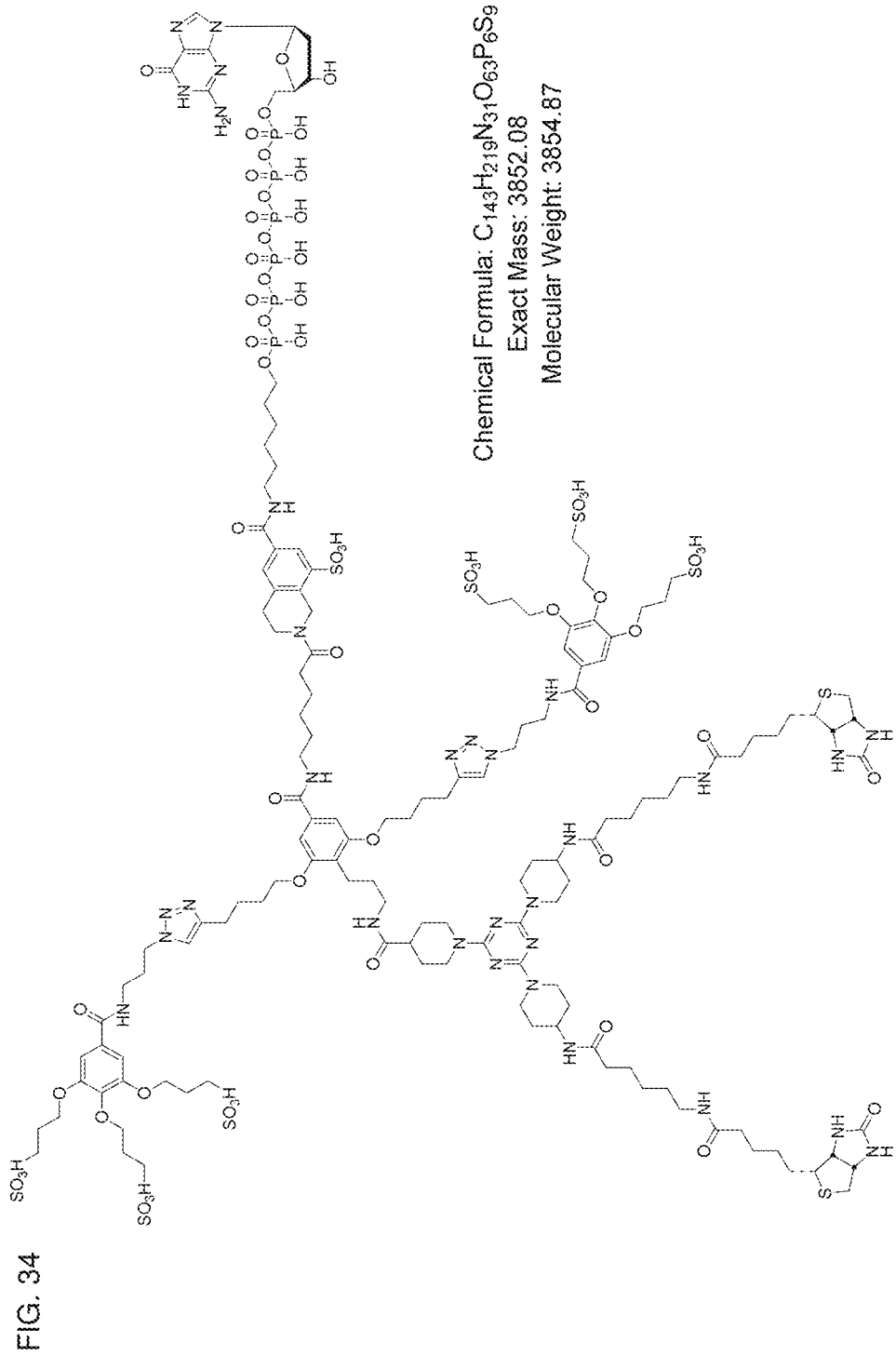

Yet another variant structure of a mononucleotide reagent includes an anionic aromatic "spacer" group within the nucleotide arm of the reagent. An exemplary structure, DISC-SG1×2-dG, is shown in FIG. 34. As shown, the structure includes a "dG" nucleoside attached to a polyphosphate element. It is otherwise identical to the Control-SG1×2-dG structure shown in FIG. 31, except that it includes a 1H-2,3-dihydroisoquinoline-8-sulfo-6-carboxylic acid ("DISC") spacer element inserted within one of the amide bonds of the nucleotide linker of the Control-SG1×2-dG structure.

Figure 35:
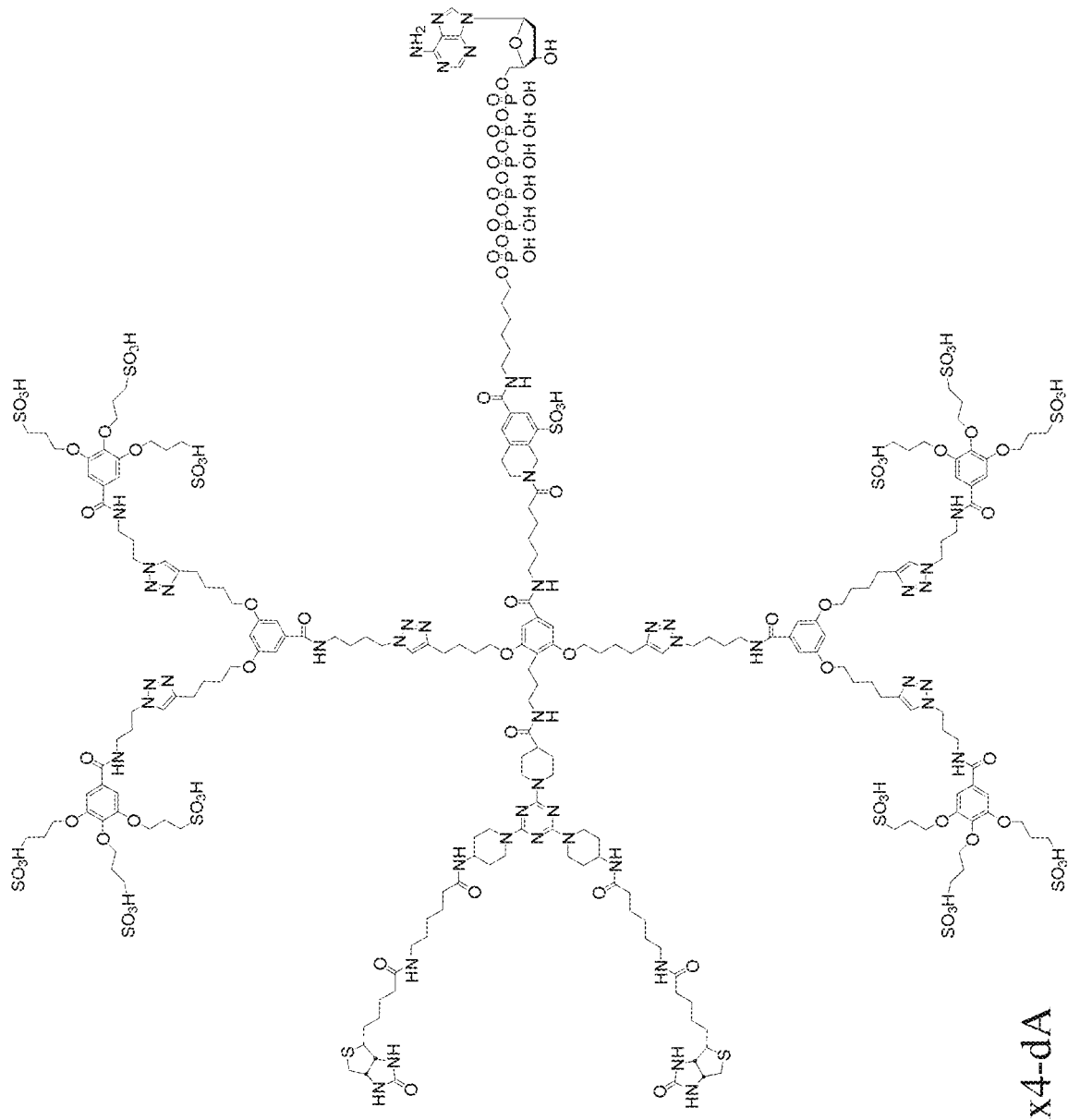

Further variant mononucleotide reagents with anionic aromatic spacer groups in their nucleotide arms include compounds comprising at least one shield element. For example, the DISC-Split-SG1×4-dA compound shown in FIG. 35 includes the DISC group of DISC-SG1×2-dG in combination with the split shield groups of Split-SG1×4-dG. In this particular example, the nucleoside is a deoxyadenosine ("dA") nucleoside. The rest of the molecule, in particular the split shield element and the bis-biotin group, is the same as Split-SG1×4-dG.

Figure 36:
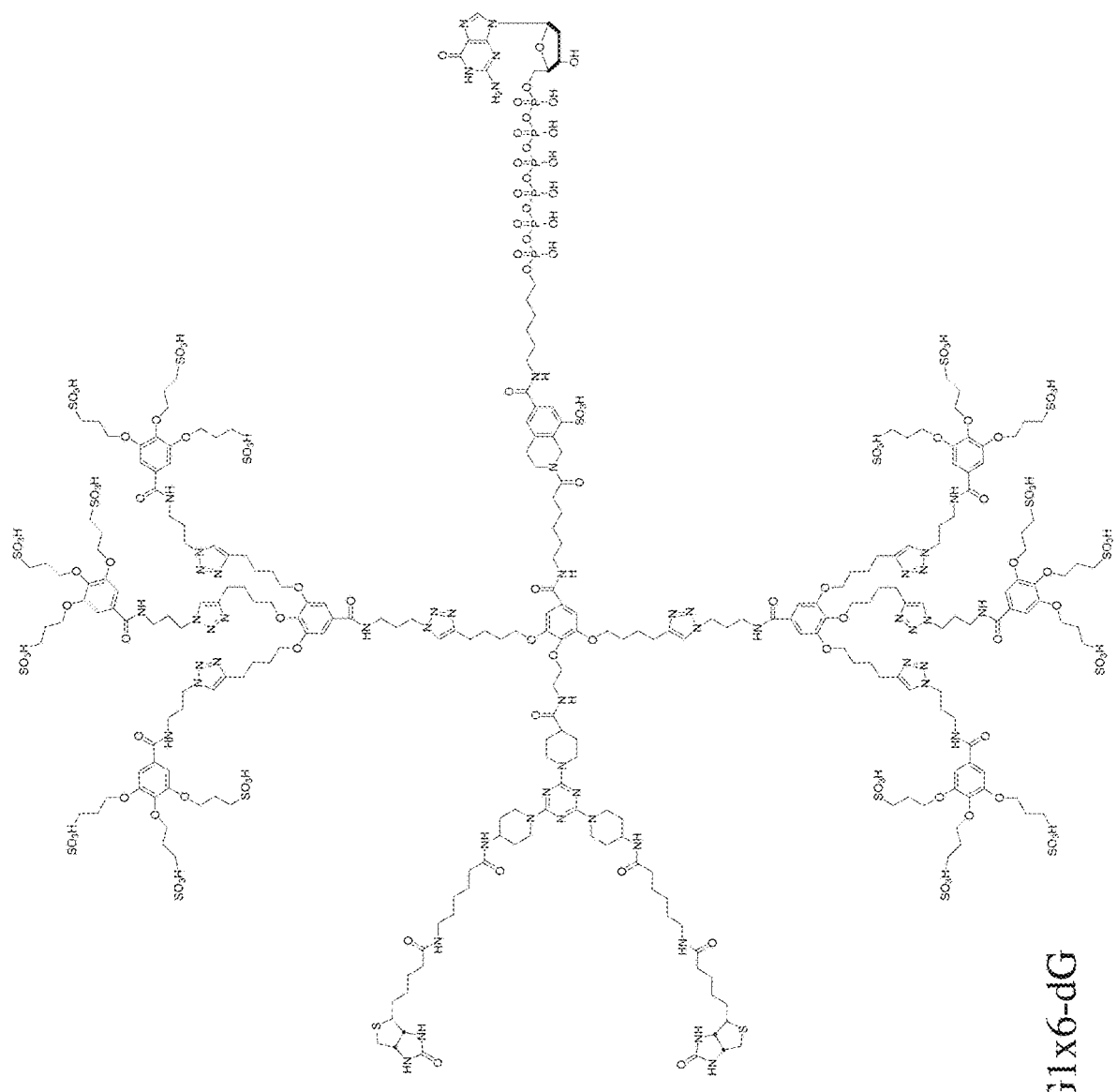

In still another variant of the shield structure in nucleotide compounds containing an anionic aromatic spacer group, the at least one shield element can include a triple-branched structure with additional anionic side chains, for example as shown in DISC-Split-SG1×6-dG of FIG. 36, thus carrying 6 of the sulfonic acid-substituted SG1 side chains.

Figure 37:
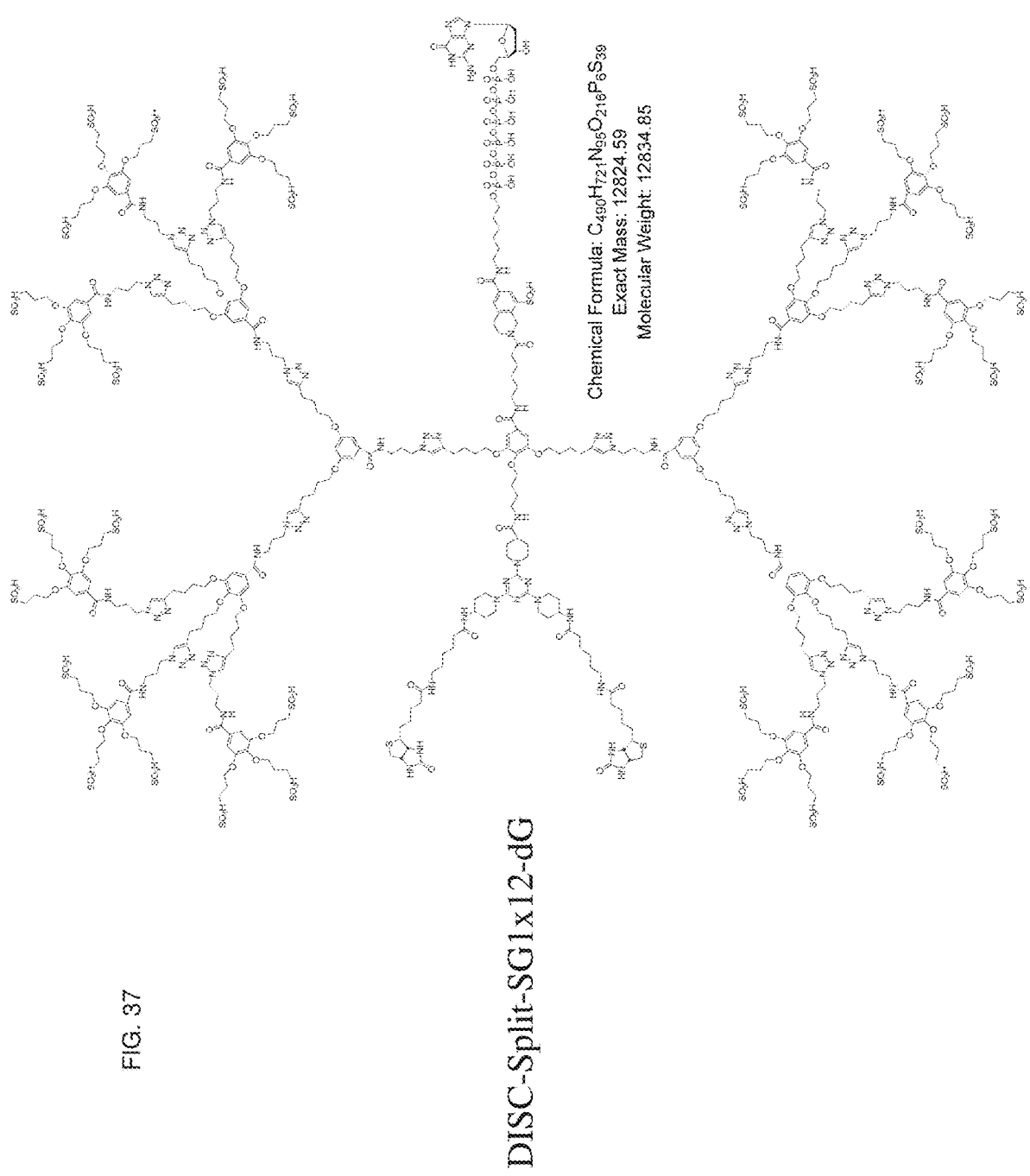

The branching of the shield groups can be extended still further, for example as shown in DISC-Split-SG1×12-dG of FIG. 37, where the side chains include an additional branching element, so that they carry 12 of the sulfonic acid-substituted SG1 groups. All of the above-described structures have been assembled using known reactions, for example using click chemistry, copper-free click chemistry, and the like, for example as described in detail in U.S. Patent Application Publication No. 2015/0050659 A1.

Figure 38:
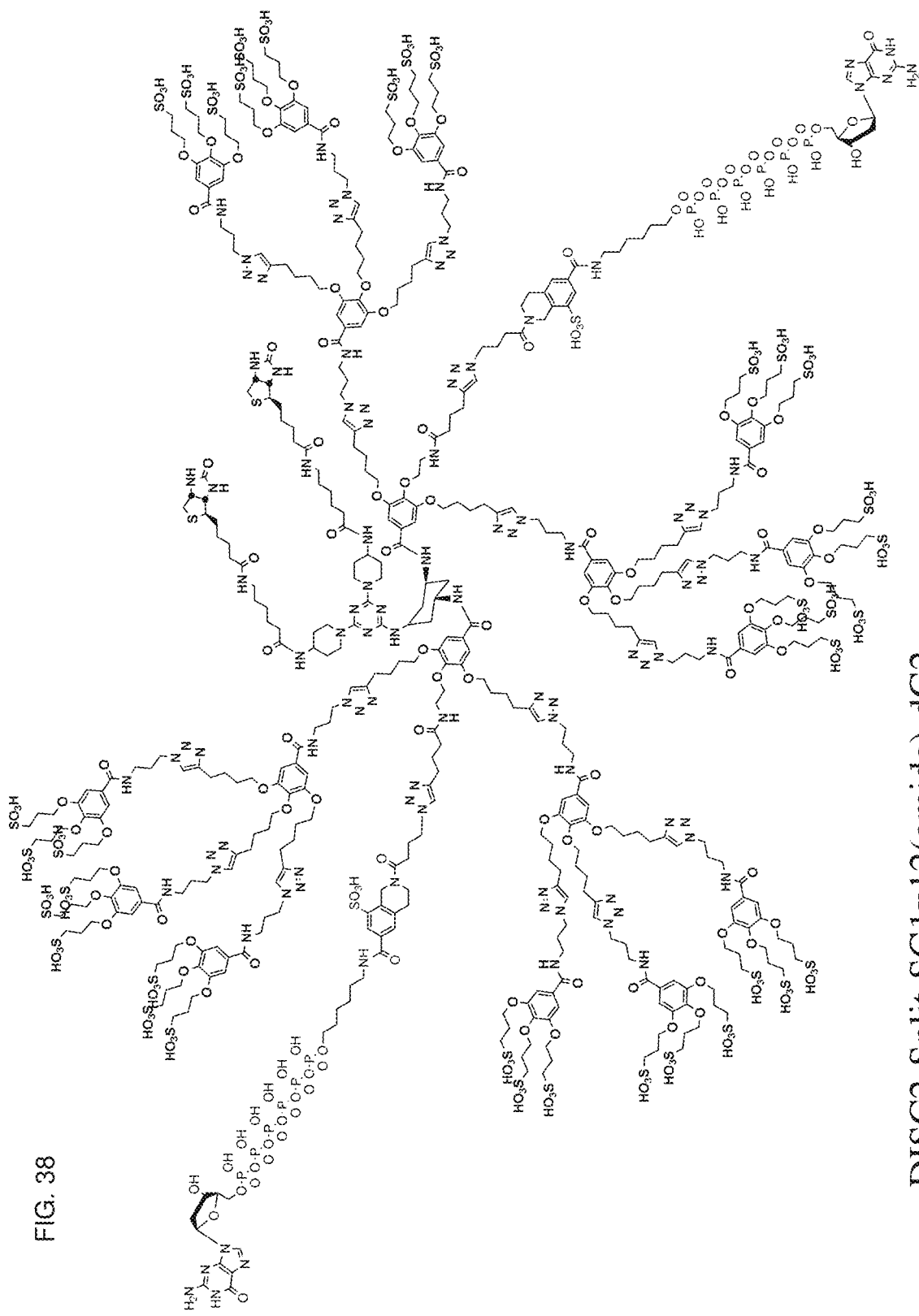

Further modifications to the instant nucleotide compounds included the incorporation of an anionic aromatic spacer group into both nucleotide linker elements of a dinucleotide compound, for example as shown in DISC2-Split-SG1×12-dG2 of FIG. 38.

Figure 39:
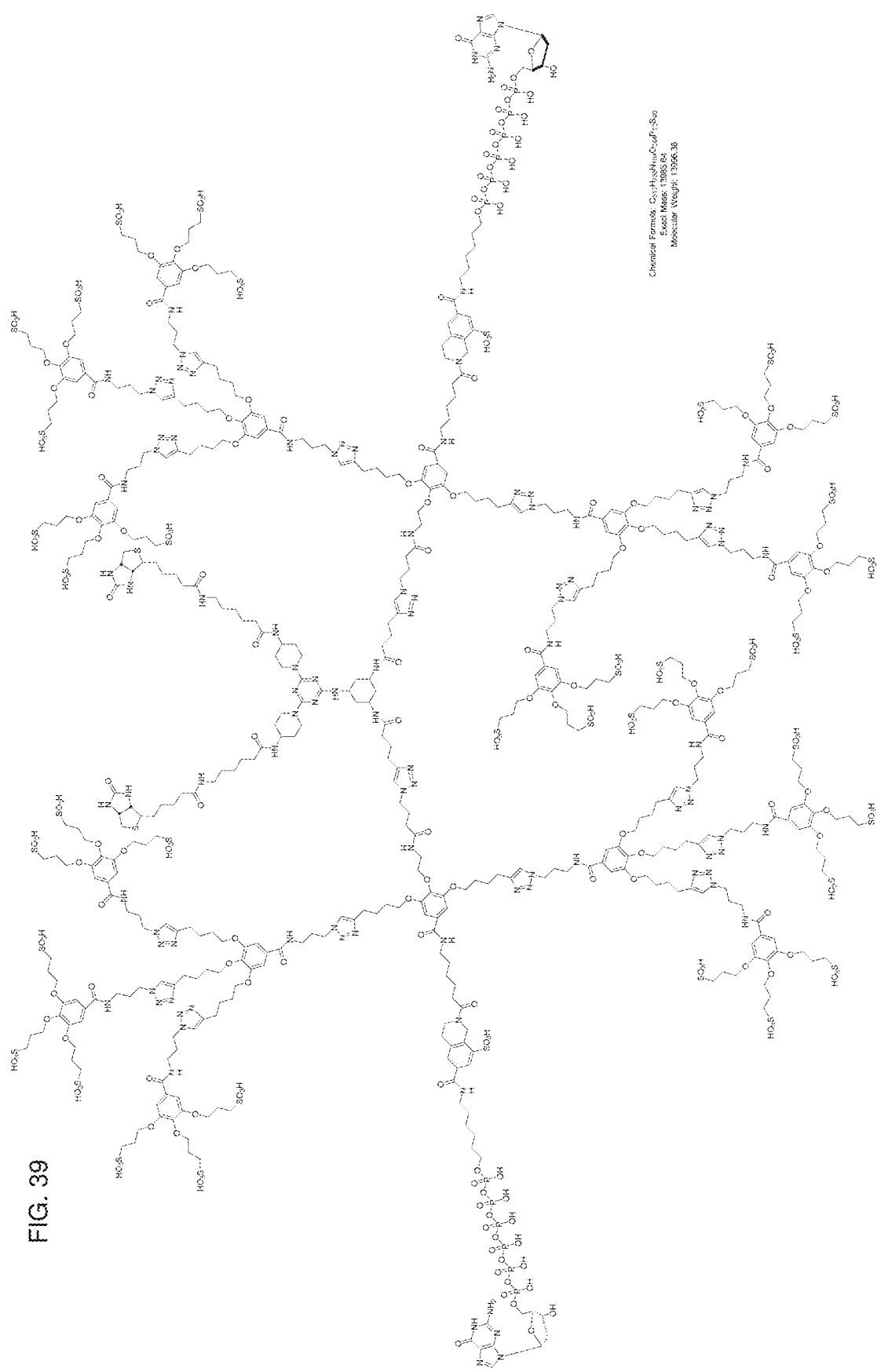

Another exemplary dinucleotide compound containing an anionic aromatic spacer group in both linker elements and 12 SG1 shield group elements is shown in FIG. 39 as DISC2-Split-SG1×12(click)-dG2. The DISC2-Split-SG1×12(click)-dG2 and DISC2-Split-SG1×12(amide)-dG2 differ in the coupling of the shield element to the nucleotide linker, and in the orientation and linkage of the central 3,4,5-trioxybenzoyl group within the linker.

Figure 40:
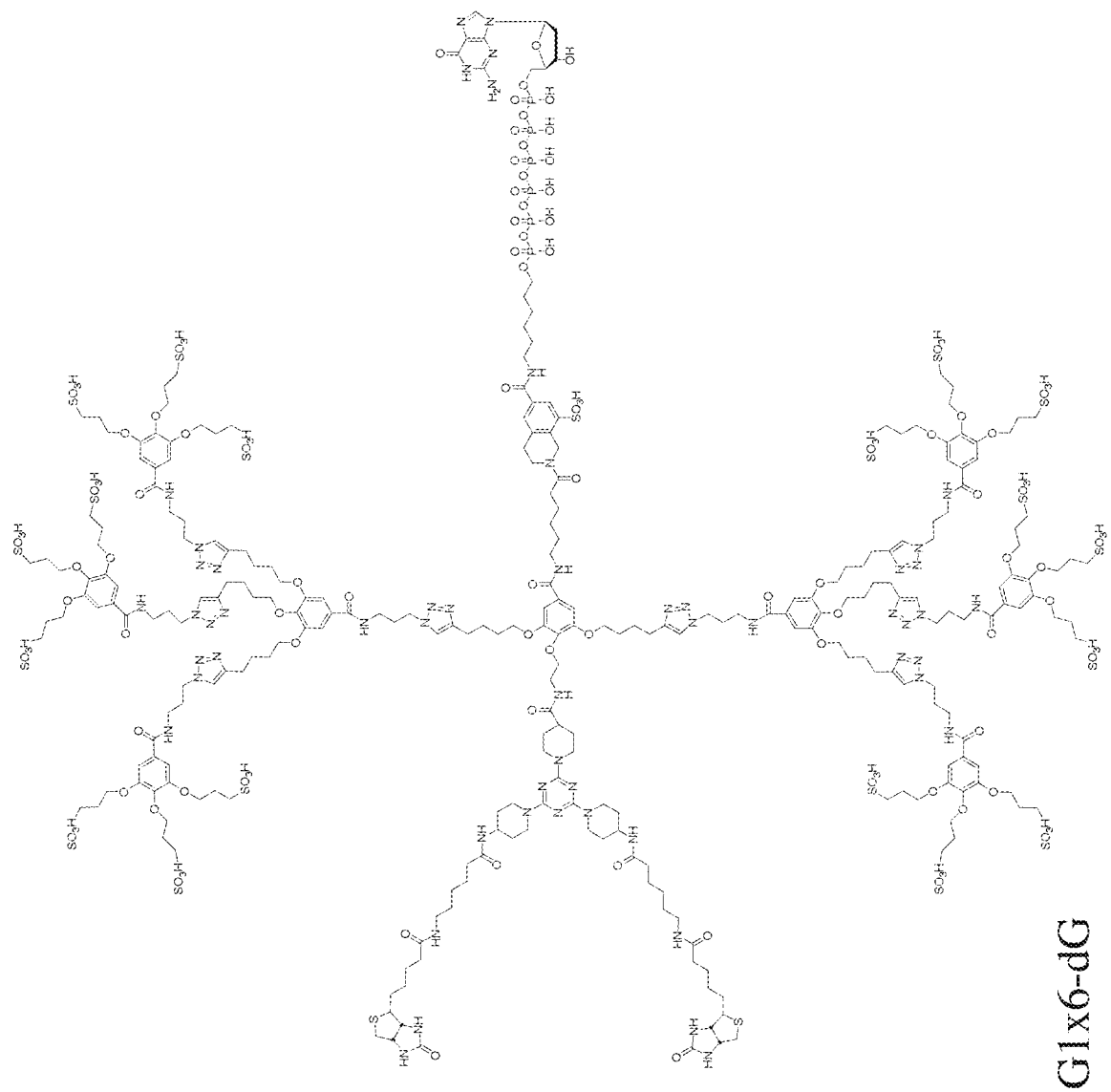
Figure 41:
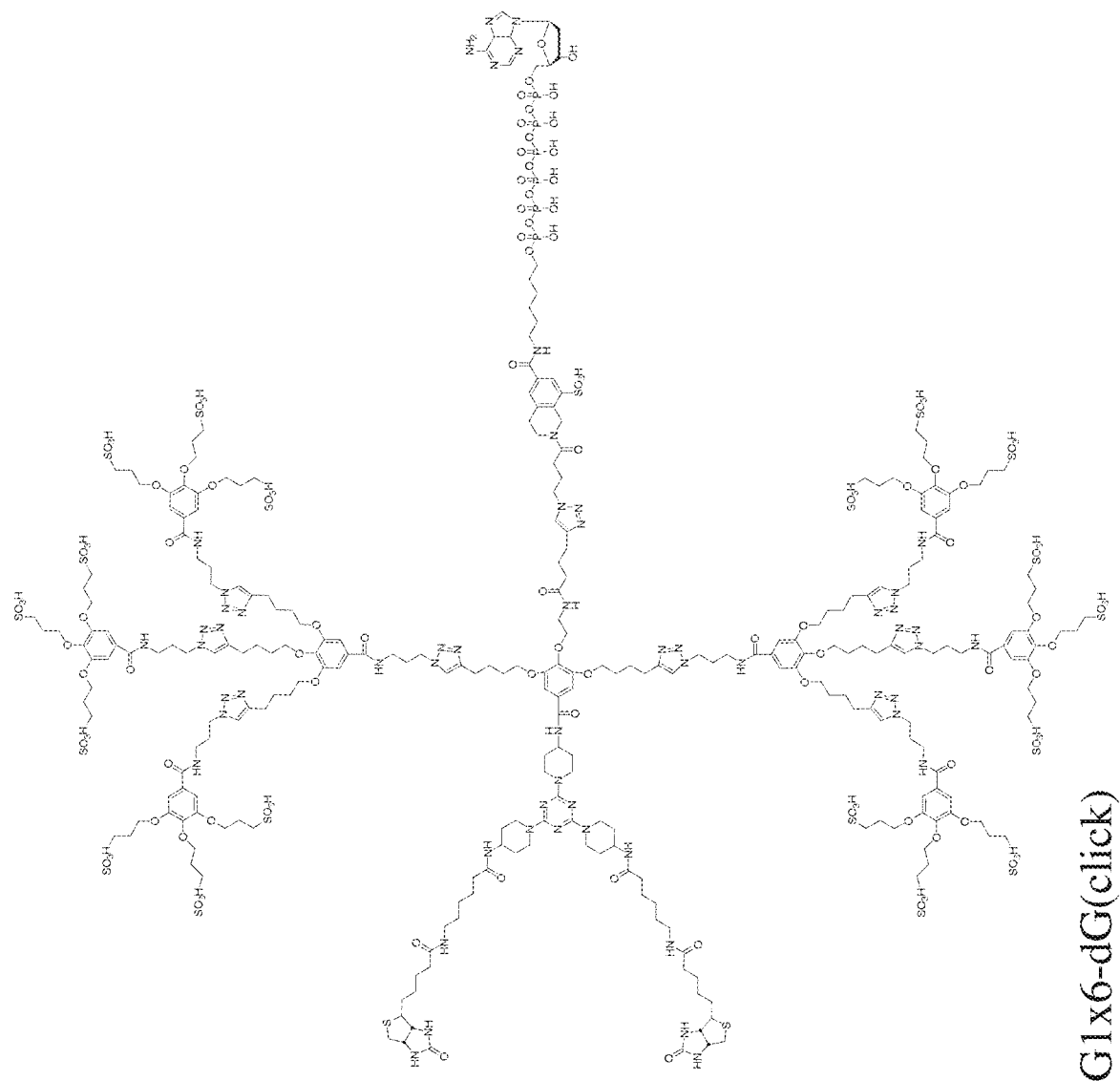

The just-described alternative coupling of the shield group elements to the nucleotide linker, and the orientation and linkage of the central 3,4,5-trioxybenzoyl group within the linker, has also been compared in mononucleotide compounds, for example as shown for DISC-Split-SG1×6-dG and DISC-Split-SG1×6-dG(click) of FIGS. 40 and 41, respectively.

The nucleotide compounds described above were assembled into labeled nucleotide analog complexes, for example as described below in Example 2. These fluorescent nucleotide analogs were then compared in DNA sequencing reactions, for example as described below in Example 3.

Example 2. Assembly of Dye-Labeled Nucleotide Analogs

The mononucleotide and dinucleotide compounds described above have been assembled into dye-labeled nucleotide analogs by combining the nucleotide compounds with one or more avidin proteins and one or more dye-labeled compounds or intermediates. For most of the kinetic experiments described in Example 3, the nucleotide compounds were assembled using a single avidin protein and a simple, unshielded dye-labeled compound such as dye-labeled compound illustrated graphically in FIG. 4A. Such assembly can be performed as described in U.S. Patent Application Publication No. 2013/0316912 A1. More complex analog structures have also been assembled, for example using the pathways shown in FIGS. 7A-7D and 7F. These analogs, such as the analogs depicted in FIG. 19A, have also been assessed in kinetic sequencing assays, as described in Example 3.

Example 3. Use of the Dye-Labeled Nucleotide Analogs in Real-Time Sequencing Reactions Single-molecule real time sequencing reactions using the fluorescent nucleotide analogs described in Example 2 were carried out in a zero-mode waveguide ("ZMW") array having 3000 discrete cores. The reactions were observed using a highly multiplexed confocal fluorescent microscope providing a targeted illumination profile, e.g., a separate spot for each core. See, e.g., U.S. Pat. No. 7,714,303, which is incorporated herein by reference in its entirety for all purposes. Fluorescent signals from the various ZMWs were detected using an EMCCD camera, and the signals were subjected to pulse recognition and base calling processes. See, e.g., U.S. Pat. No. 8,182,993, which is incorporated herein by reference in its entirety for all purposes. The sequencing was carried out generally as described in Eid, J. et al. (2009) *Science* 323:133-138, and the corresponding supplemental information included therewith.

For each of the sequencing reactions the laser power was 0.5 to 2.0 μW/μm$^2$ and a camera frame rate of 100 FPS. The template was a circular vD "SMRTbell" template of about 11000 kb as described in U.S. Pat. No. 8,236,499, filed Mar. 27, 2009. The polymerase enzyme immobilized in the zero mode waveguide was a mutant Φ29 polymerase as described in U.S. Pat. No. 8,257,954, filed Mar. 30, 2009. The reaction mixture had a Bis-Tris Propane pH 7.5 buffer, antioxidants, 40 mM DTT, 120 mM KOAc to control ionic strength; 30 mM MgOAc and 4 to 8% organic solvent additive. The mixture also contained a set of nucleotide analogs corresponding to A, G, C, and T, each present at 150-400 nM, and each having a unique dye-labeled compound complexed to the nucleotide compound through an avidin protein. Ten minute to 120 minute movies of the sequencing reactions were obtained. Data were collected on the brightness, kinetics (pulse width, the interpulse distance (IPD)), photophysical signal stability, sequencing error types, read length, and accuracy.

As shown in the sequencing reactions of FIG. 12A, a simple mononucleotide analog structure results in a roughly 1% improvement in the accuracy of the sequencing reaction (condition 1) compared to a comparable dinucleotide structure (condition 2). The data are compared directly in FIG. 12B, where the normalized accuracy is increased from 0.893 (left plot) for the dinucleotide to 0.904 (right plot) for the mononucleotide.

Figure 13A:
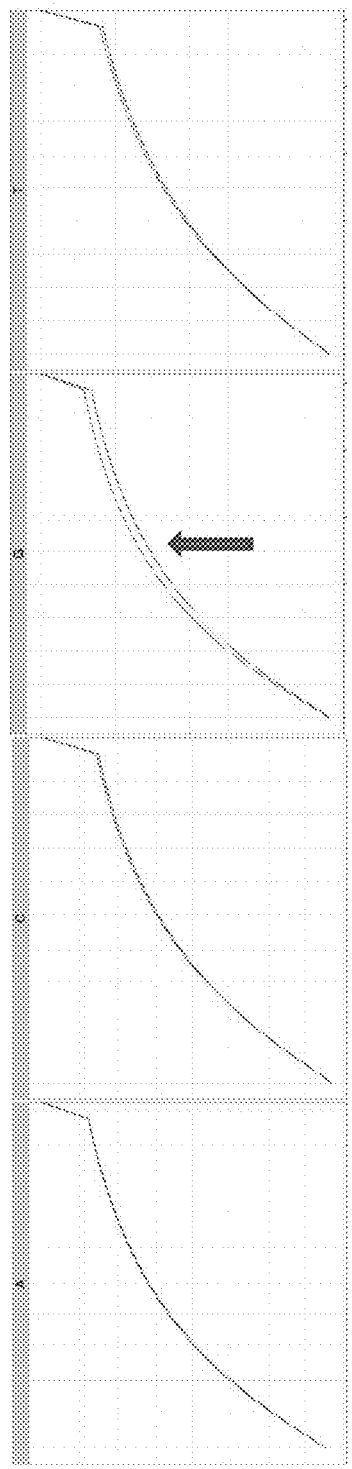
FIGS. 13A and 13B illustrate a comparison of the kinetics of sequencing with mononucleotide and dinucleotide analogs.
Figure 13B:
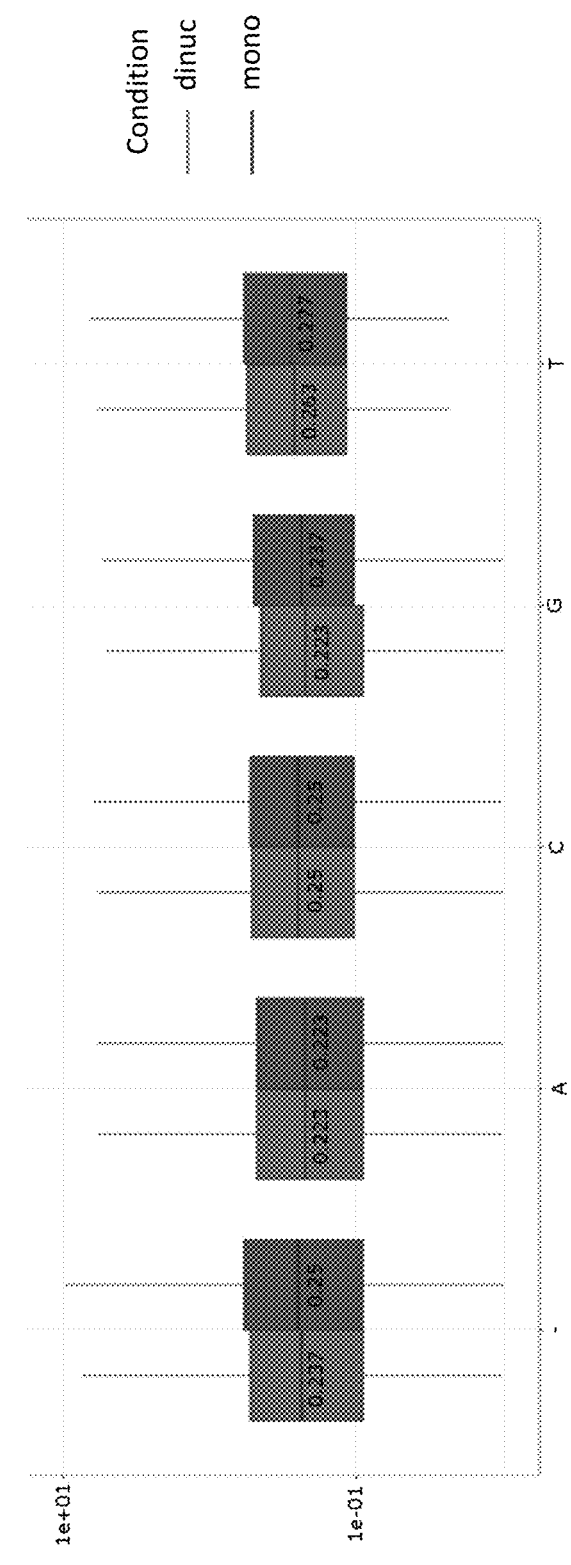

At the same time, as shown in FIGS. 13A and 13B, the kinetics of incorporation are not significantly different for the mononucleotide and dinucleotide reagents for each of the four bases. By way of background, the kinetics of a single-molecule real-time sequencing reaction are generally described as including an observable phase, which generally corresponds to the time period during which a particular phase is observable. The time period for a bright phase, for example, can be represented by the pulse width (PW) of a signal. The time period for a dark phase can be represented, for example, by the interpulse distance (IPD) of a signal. The length of each time period will not be the same for each nucleotide addition, resulting in a distribution of the length of these time periods. In some cases, the time periods with the shortest length will not be detected, thus leading to errors, for example in single-molecule sequencing. FIG. 13A shows IPD distribution curves comparing mononucleotide analogs and dinucleotide analogs for each of the four bases (A, C, G, and T), where the base is indicated at the top of each panel. In these plots, the x-axis relates to detector frames, with 1 frame equal to 10 milliseconds. The y-axis represents the empirical cumulative distribution functions (ecdf), a unitless value, ranging from 0 to 1, that describes the probability of seeing the IPD of a certain duration in frames.

Normalized IPD values for each of the conditions are provided in FIG. 13B, with the dinucleotide analog on the left and the mononucleotide analog on the right. The leftmost pair reflects the cumulative normalized IPD values for all four bases, while the following four pairs reflect the separate normalized IPD values for each indicated deoxyribonucleotide. The dinucleotides were present at 200 nM for each base, and the mononucleotides were present at 250 nM for dC and at 200 nM for dG, dT, and dA. As indicated by the large arrow in the comparison of IPD distributions for dG, the mononucleotide is slightly slower than the dinucleotide reagent.

Variants of the mononucleotide and dinucleotide structures described in Example 1 have been tested in single-molecule real-time sequencing reactions to compare the effects of various other structural features on the behavior of the dye-labeled nucleotide analogs in sequencing reactions. For example, FIGS. 14A and 14B illustrate the incorporation kinetics of the control analog (Control-SG1×4-dG2) (condition 1); a double-layered analog (Layered-SG1×4-dG) (condition 2); a split side chain analog (Split-SG1×4-dG) (condition 3); and an analog comprising the DISC anionic aromatic spacer (DISC-SG1×2-dG) (condition 4).

Figure 14A:
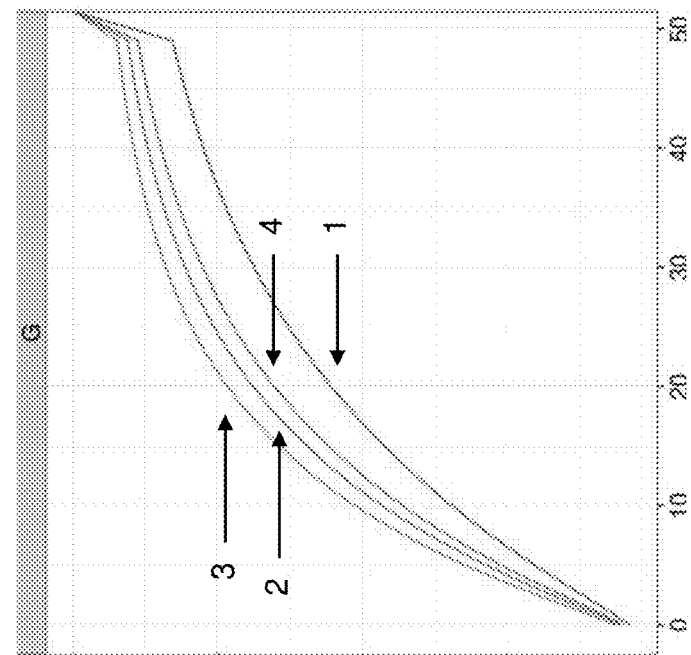
FIG. 14A compares sequencing reactions performed with a dinucleotide analog and with modified mononucleotide analogs, each labeled with dG.
Figure 14B:
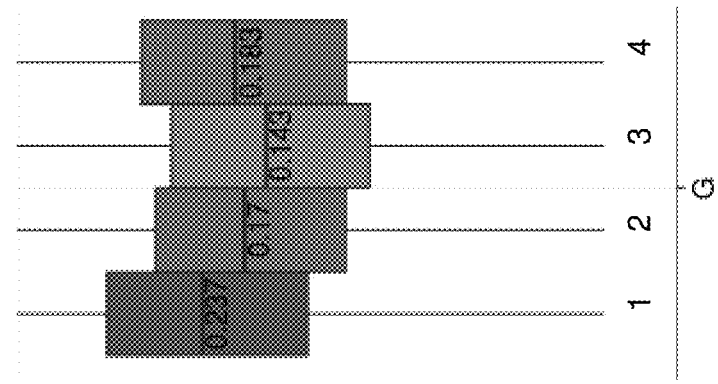
FIG. 14B displays the normalized interpulse distance values for the reactions of FIG. 14A.

As is apparent in FIG. 14A, the kinetics of incorporation of the above-described nucleotide reagents increase in the order Control-SG1×4-dG2<DISC-SG1×2-dG<Layered-SG1×4-dG<Split-SG1×4-dG for mononucleotides containing G. FIG. 14B provides a comparison of the normalized IPD values for each of these reagents. As can be calculated from these data, the acceleration factor relative to control are: Split-SG1×4-dG: 1.82×; DISC-SG1×2-dG: 1.42×; and Layered-SG1×4-dG: 1.53×.

Figure 15C:
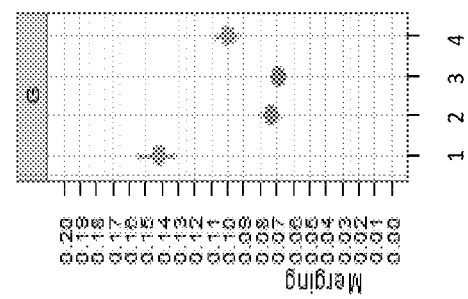
FIGS. 15A-15C illustrate normalized interpulse distances, global rates, and merging errors for a dinucleotide analog and for various modified mononucleotide analogs.
Figure 15B:
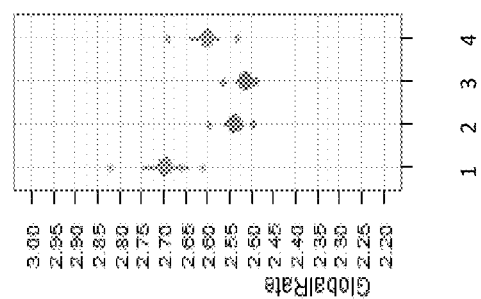
Figure 15A:
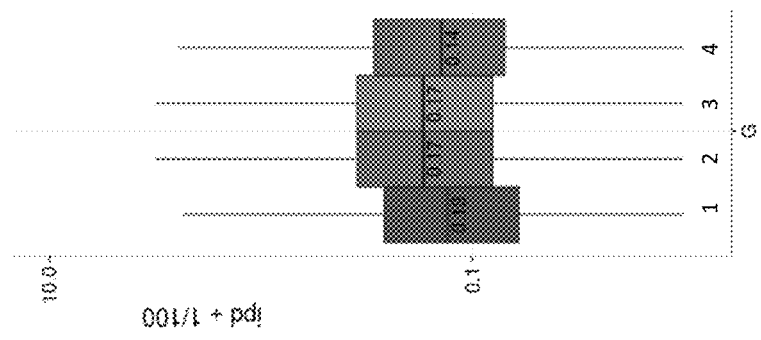

FIGS. 15A-15C illustrate the incorporation kinetics (normalized IPDs) (FIG. 15A), global rates (FIG. 15B), and merging errors (FIG. 15C) for the dinucleotide control analog (Control-SG1×4-dG2) (condition 1), for a mononucleotide analog with six shield groups but no anionic aromatic spacer (condition 2), for a mononucleotide analog with four shield groups and an anionic aromatic spacer (condition 3), and for a mononucleotide analog with six shield groups and an anionic aromatic spacer (DISC-Split-SG1×6-dG) (condition 4). In each case, the reagents are dG-nucleotide analogs.

As is apparent from the results, either including an anionic aromatic spacer group in the analogs (condition 4 vs. condition 2) or increasing the number of shield groups in the analogs from four to six (condition 4 vs. condition 3) results in improved kinetics, with the IPD value decreasing by approximately 20% in the analogs containing these modifications. Inclusion of the anionic aromatic spacer group in the analogs also improves the global rate and accuracy of sequencing.

The nature of the anionic aromatic spacer group can also impact the behavior of the modified nucleotide analogs in sequencing reactions. Specifically, as shown in FIGS. 16A-16C, substituting the DISC spacer of the DISC-Split-SG1×6-dG analog with a 4,8-disulfonaphthalene-2,6-dicarboxylic acid spacer (see below) results in approximately 10% slower kinetics (based on IPD values) but slightly wider pulse widths.

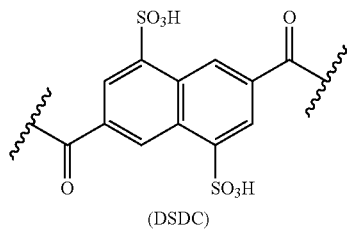

(DSDC)

Figure 16A:
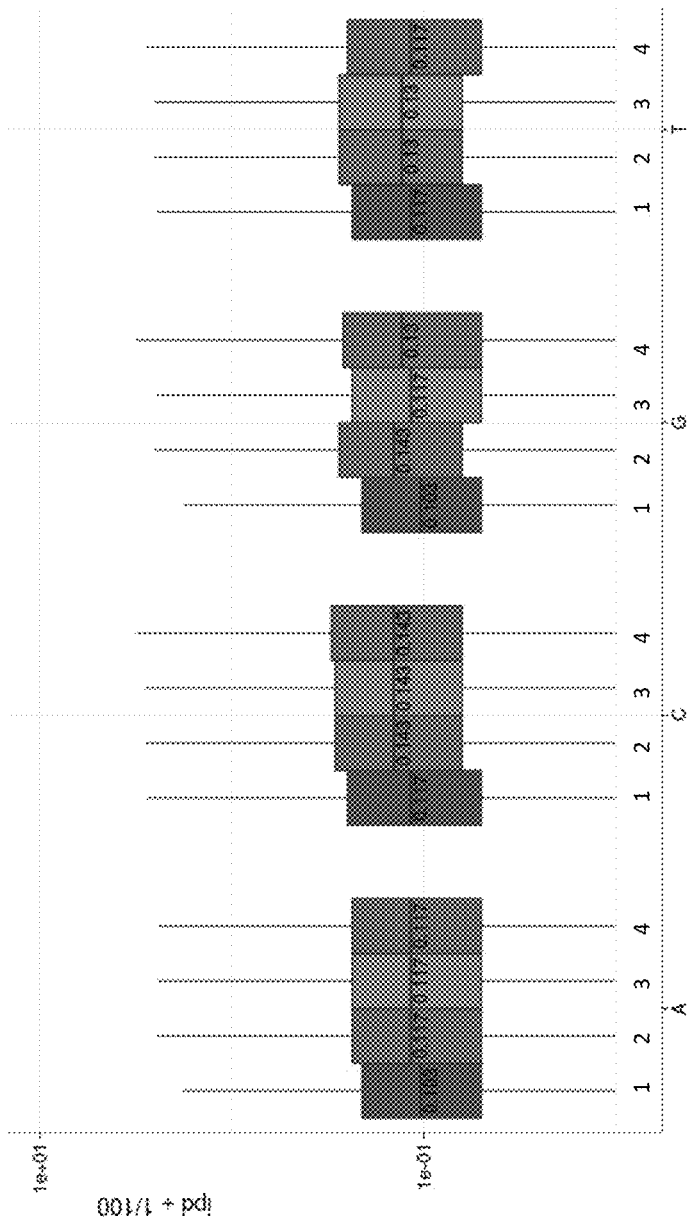
FIG. 16A shows normalized interpulse distances for nucleotide analogs with various anionic aromatic spacers.
Figure 16C:
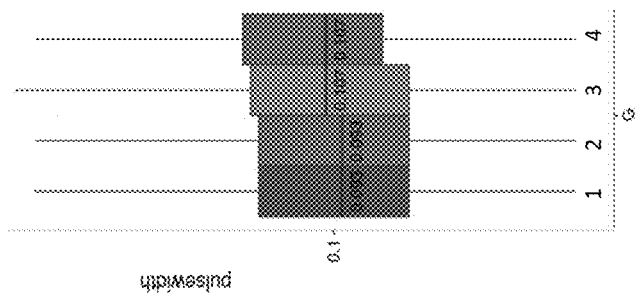
FIG. 16B shows IPD distribution curves and FIG. 16C shows normalized pulsewidths for the same analogs.
Figure 16B:
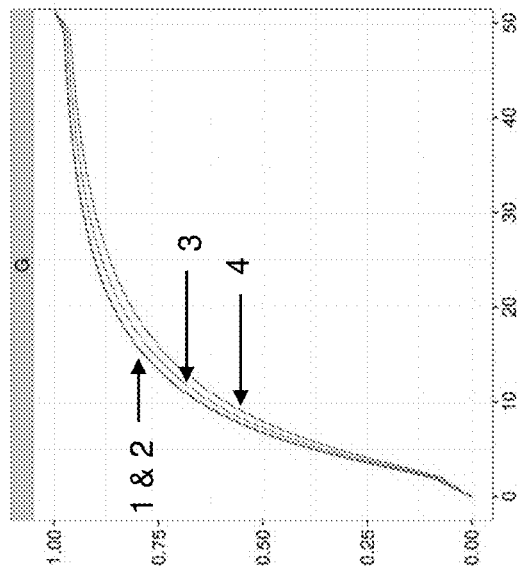

In FIG. 16A, the normalized IPD values for analogs containing each of the four bases are shown for the dinucleotide control analog (Control-SG1×4-dG2) (condition 1), for the mononucleotide analog with four shield groups and the DISC spacer group (DISC-Split-SG1×4-dG) (condition 2), for the mononucleotide analog with six shield groups and the DISC spacer group (DISC-Split-SG1×6-dG) (condition 3), and for the mononucleotide analog with six shield groups and the DSDC spacer group (condition 4). The IPD distribution curves for the G-nucleotide analogs are compared in FIG. 16B, and the normalized pulse-widths for the G-nucleotide analogs are compared in FIG. 16C.

Figure 17A:
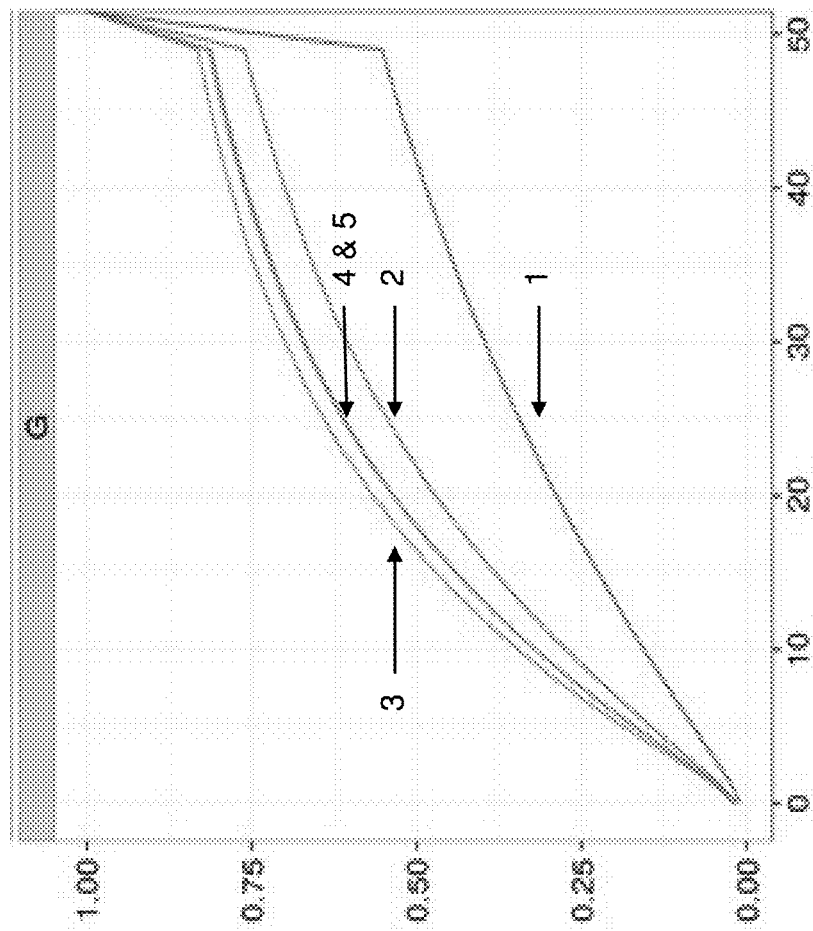
FIG. 17A shows IPD distribution curves for nucleotide analogs with increasing numbers of side chains.
Figure 17B:
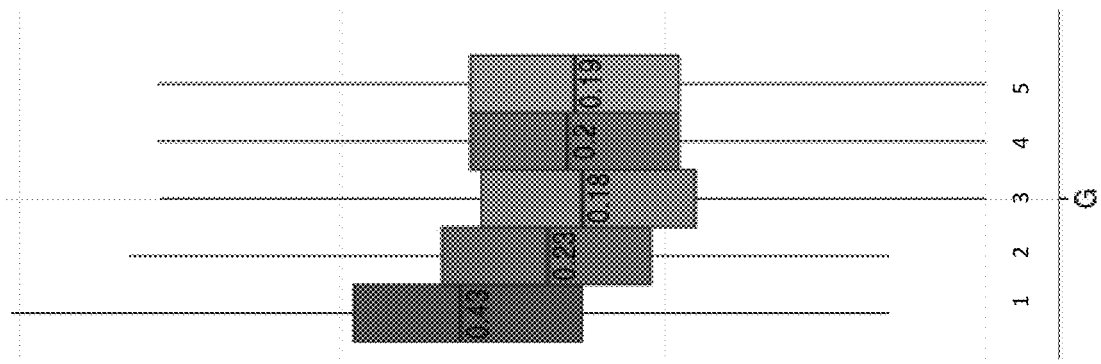
FIG. 17B shows normalized IPD values for the same analogs.

The number of side chains in the shield elements, and thus the charge adjacent to the nucleotide, can be further increased, for example as shown above in structure, DISC-Split-SG1×12-dG. The kinetics of an analog containing this structure in single-molecule real-time sequencing reactions were analyzed at various concentrations, as illustrated in FIGS. 17A and 17B. In these assays, the DISC-Split-SG1×12-dG analog was measured at 100 nM (condition 1), 150 nM (condition 2), or 200 nM (condition 3), and compared to DISC-Split-SG1×6-dG at 200 nM (condition 4) and to Control-SG1×4-dG2 at 200 nM (condition 5). The IPD distribution curves for these analogs and conditions are compared in FIG. 17A, and the normalized IPD values for the G-nucleotide analogs are compared in FIG. 17B. These data indicate that doubling the charge of the side chains does not lead to a significant acceleration in IPD.

Figure 18:
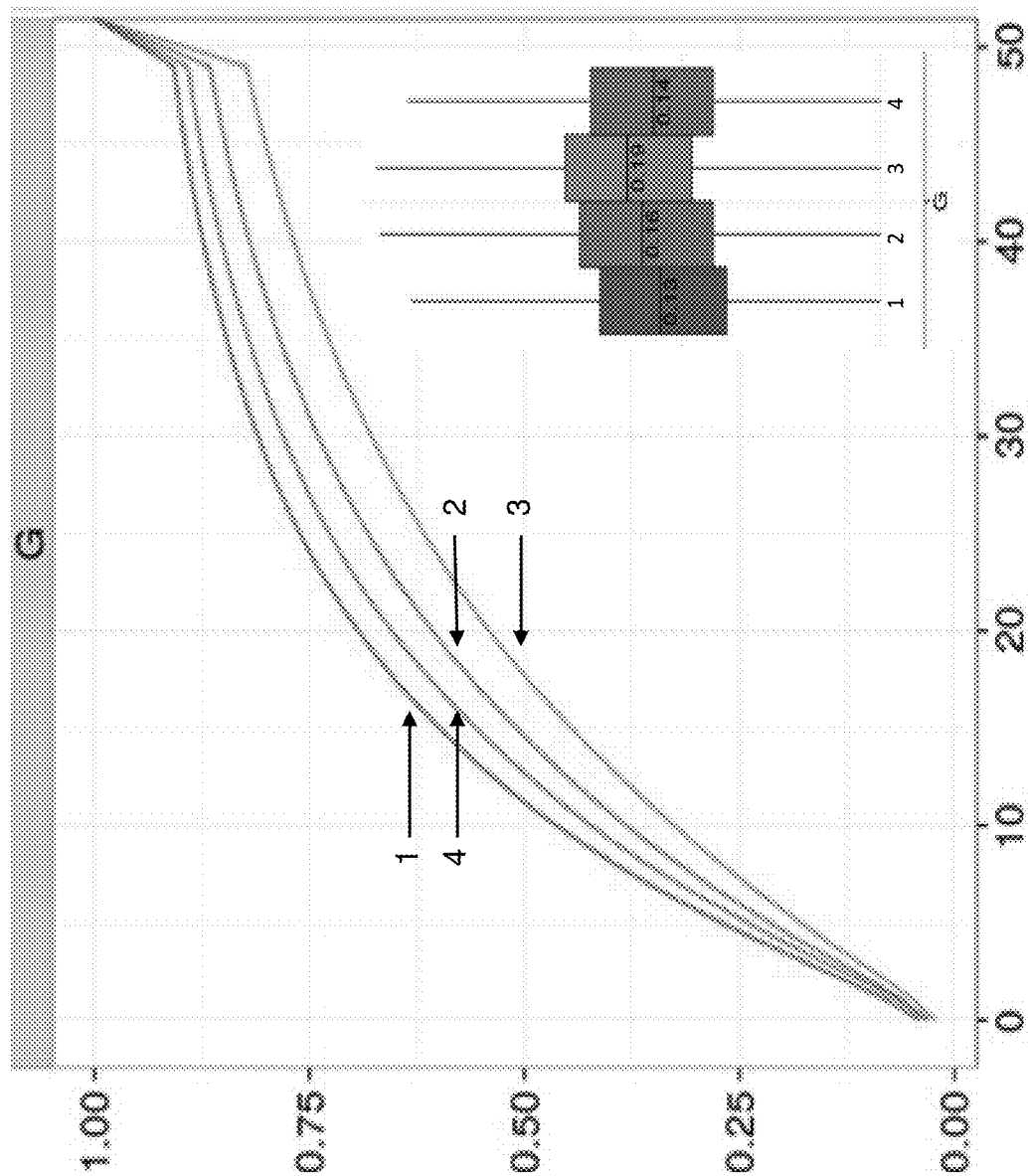
FIG. 18 shows IPD distribution curves and normalized IPD values (inset) for mononucleotide and dinucleotide analogs with an anionic aromatic spacer.

The anionic aromatic spacer group has additionally been incorporated into both linker groups of two dinucleotide analogs. Specifically, DISC2-Split-SG1×12(amide)-dG2 and DISC2-Split-SG1×12(click)-dG2, both of which are shown above, contain a DISC anionic aromatic spacer group in each of the two linker arms. Analogs containing these structures have been compared to the comparable triple-SG mononucleotide analog, DISC-Split-SG1×6-dG, that also contains the DISC anionic aromatic spacer group in the nucleotide linker. Analogs containing these structures have also been compared to the dinucleotide analog, Control-SG1×4-dG2, that lacks the anionic aromatic spacer group in the nucleotide linkers. As illustrated in FIG. 18, the two DISC-containing dinucleotide analogs, DISC2-Split-SG1×12(amide)-dG2 (condition 1) and DISC2-Split-SG1×12 (click)-dG2 (condition 2) do not display usefully different kinetics compared to the non-DISC dinucleotide analog, Control-SG1×4-dG2 (condition 4), with one showing somewhat shorter IPD values and the other showing somewhat longer IPD values. As seen previously, the DISC-containing mononucleotide analog, DISC-Split-SG1×6-dG (condition 3), displays somewhat slower kinetics than any of the dinucleotide analogs.

Figure 19A:
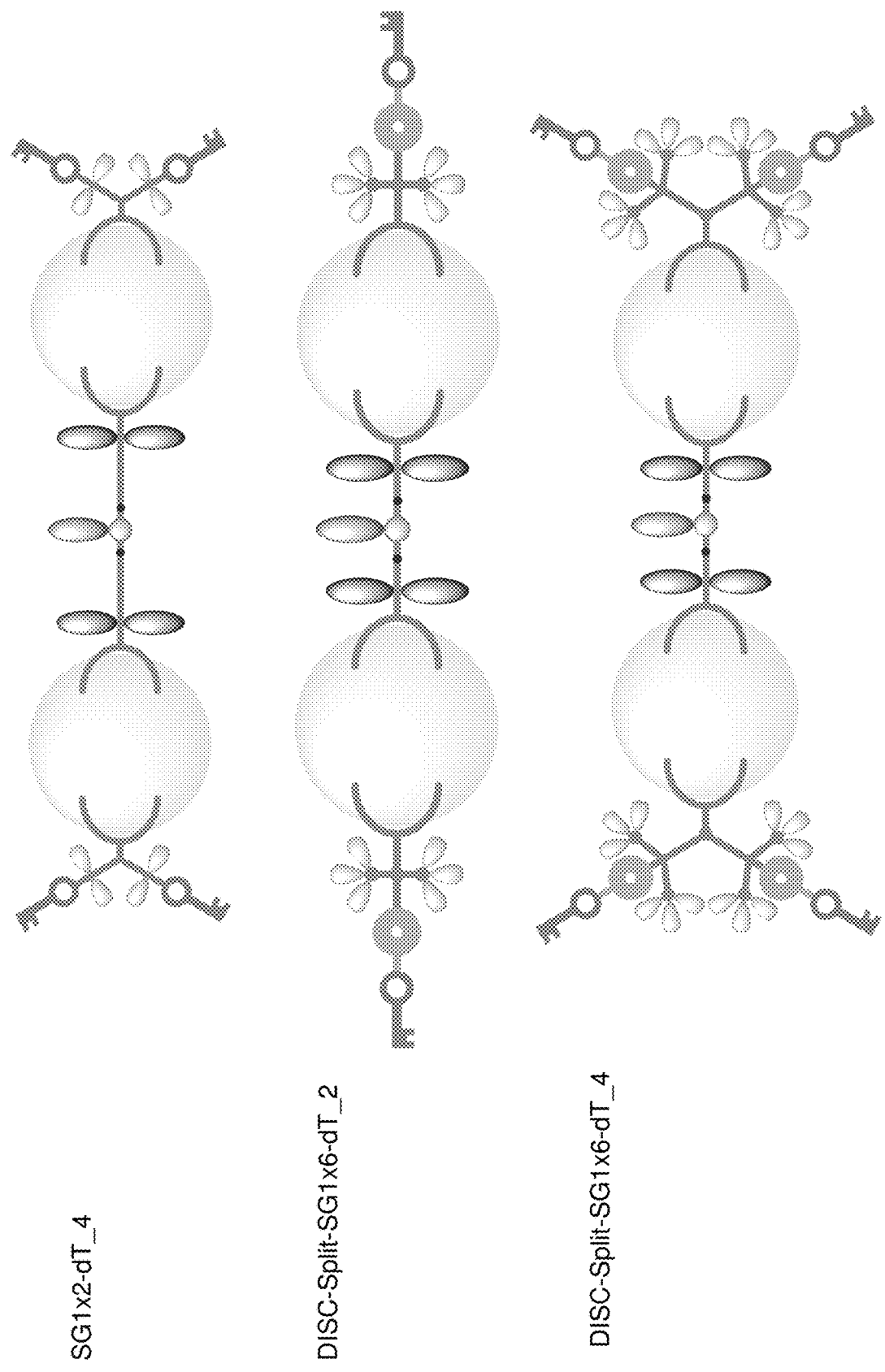
FIG. 19A graphically illustrates some exemplary analog structures of the disclosure.
Figure 19C:
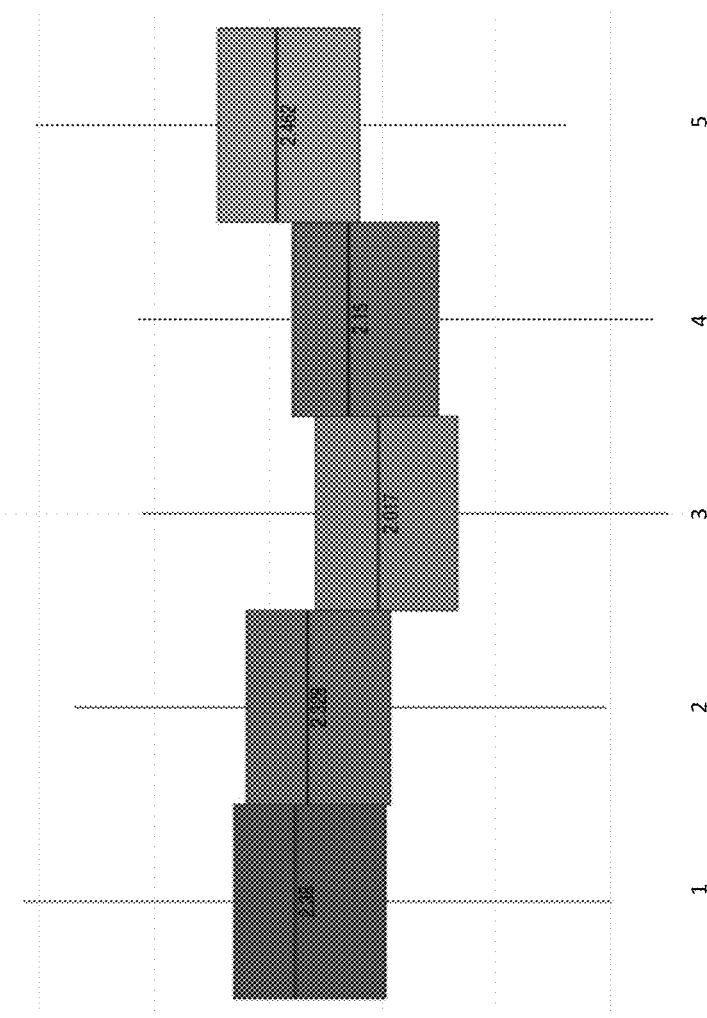
FIG. 19C illustrates polymerization rates for various nucleotide analogs of the disclosure.
Figure 19B:
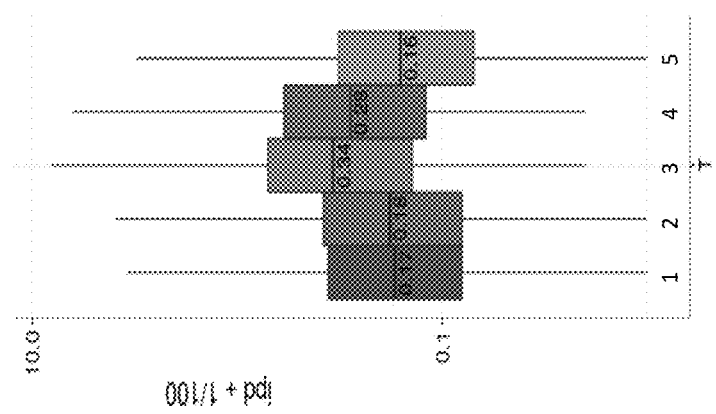
FIG. 19B illustrates normalized interpulse distances.

FIG. 19A illustrates some additional labeled nucleotide analog structures comprising two avidin proteins that have been assembled using the above-described nucleotide and dye-labeled compounds. Specifically, the SG1×2-dT_4 analog comprises a dinucleotide structure with only two side chains per shield element and no anionic aromatic spacer element. The DISC-Split-SG1×6-dT_2 analog comprises a mononucleotide structure with six side chains per shield element and a DISC anionic aromatic spacer element in the nucleotide linker. The DISC-Split-SG1×6-dT_4 is the dinucleotide variant of this structure, with six side chains per shield element and the DISC anionic aromatic spacer element. FIGS. 19B and 19C show normalized IPD values and polymerization rates for an analog comprising the DISC-Split-SG1×6-dT_4 dinucleotide variant at 100 nM (condition 3), 150 nM (condition 4), and 250 nM (condition 5) concentrations compared to an analog comprising the dinucleotide structure with two side chains and lacking an anionic aromatic spacer element, SG1×2-dT_4, at 250 nM (condition 1), and an analog comprising the mononucleotide structure with six side chains and a DISC anionic aromatic spacer element, DISC-Split-SG1×6-dT_2, at 250 nM (condition 2). It is apparent from these data that, in addition to improved accuracy, a mononucleotide compound with both a shield element and an anionic aromatic spacer element as affinity modulating elements has comparable kinetics to a dinucleotide compound that comprises these elements.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A nucleotide compound of structural formula (I):

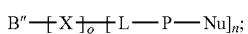
(I)

wherein
L is a nucleotide linker element comprising at least one affinity modulating element; wherein the at least one affinity modulating element is an aromatic spacer element;
P is a polyphosphate element;
Nu is a nucleoside element;
X is a multivalent central core element;
B" is a terminal coupling element;
n is an integer from 1 to 4; and
o is 0 or 1.

2. The nucleotide compound of claim 1, wherein the at least one affinity modulating element decreases the $K_m$ of a nucleotide-dependent enzyme for the nucleotide compound or increases the enzymatic rate of the nucleotide-dependent enzyme.

3. The nucleotide compound of claim 1, wherein the aromatic spacer element is a substituted or unsubstituted monocyclic, bicyclic, tricyclic, or tetracyclic aromatic moiety.

4. The nucleotide compound of claim 3, wherein the aromatic spacer element optionally comprises at least one anionic substituent.

5. The nucleotide compound of claim 4, wherein the aromatic spacer element optionally comprises at least two anionic substituents.

6. The nucleotide compound of claim 4, wherein the optional at least one anionic substituent is —SO$_3$H.

7. The nucleotide compound of claim 3, wherein the aromatic spacer element is represented by structural formula (II):

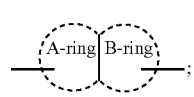
(II)

wherein
the A-ring and the B-ring is each independently a 5-7 atom cyclic structure, wherein at least one of the A-ring or the B-ring is aromatic; and
the A-ring or the B-ring optionally comprises at least one anionic substituent.

8. The nucleotide compound of claim 7, wherein the optional at least one anionic substituent is —SO$_3$H.

9. The nucleotide compound of claim 3, wherein the aromatic spacer element is represented by one of the following structural formulae:

(IIA)
(IIB)
(IID)
(IIE)
(IIF)
(IIG)
(IIH)
(IIJ)
(IIK)

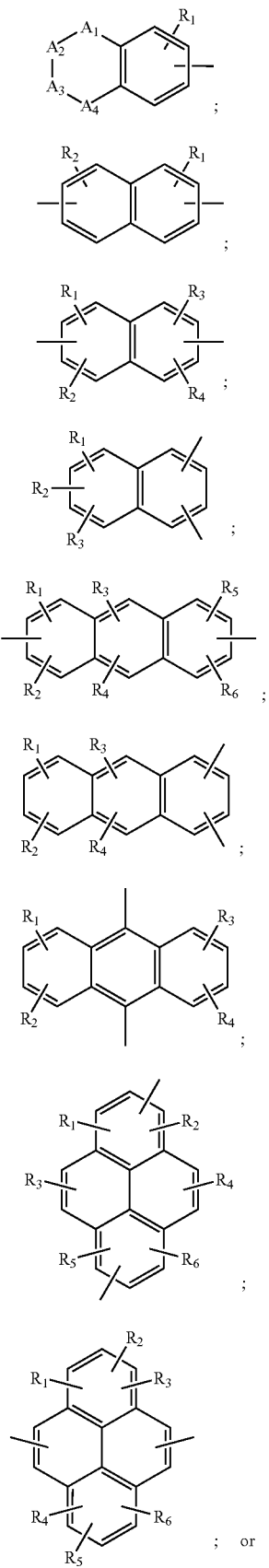

; or

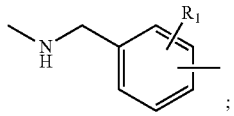

(IV)

wherein
one of the $A_1$, $A_2$, $A_3$, and $A_4$ groups is

and the other groups are —$CH_2$— or a bond; and
$R_1$, $R_2$, $R_3$, $R_4$, $R_5$, and $R_6$ are independently H or an anionic substituent.

10. The nucleotide compound of claim 9, wherein the anionic substituent is —$SO_3H$.

11. The nucleotide compound of claim 9, wherein the aromatic spacer element is represented by structural formula (IIC) or (IIC'):

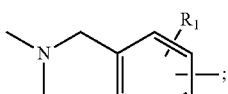

(IIC)

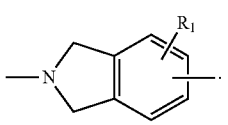

(IIC')

12. The nucleotide compound of claim 9, wherein the aromatic spacer element is represented by one of the following structural formulae:

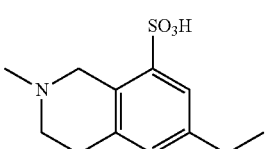

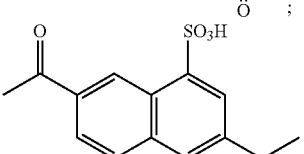

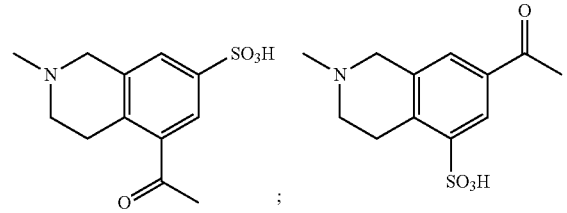

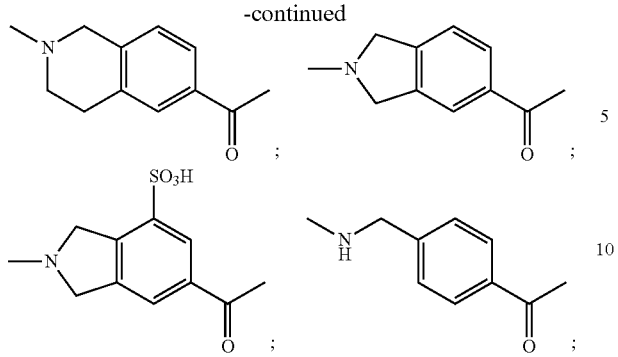
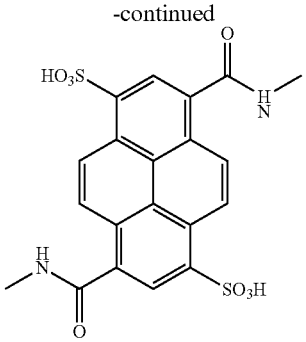
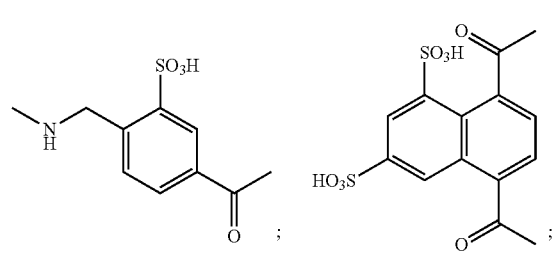
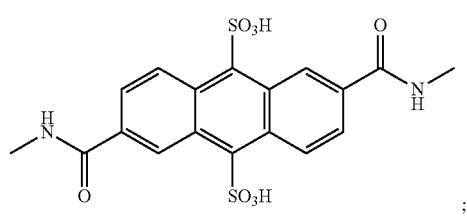
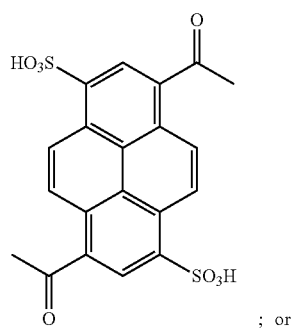

; or

13. The nucleotide compound of claim 1, wherein L further comprises an alkyl linker group, optionally comprising an amide bond.

14. The nucleotide compound of claim 1, wherein L further comprises a triazole.

15. The nucleotide compound of claim 1, wherein B" comprises a biotin moiety.

16. The nucleotide compound of claim 15, wherein B" comprises a bis-biotin moiety.

17. The nucleotide compound of claim 1, wherein o is 1.

18. The nucleotide compound of claim 17, wherein n is 2.

19. The nucleotide compound of claim 17, wherein X comprises a polyamine moiety.

20. The nucleotide compound of claim 1, wherein o is 0 and n is 1.

21. The nucleotide compound of claim 1, wherein the compound does not contain a dye.

22. The nucleotide compound of claim 1, wherein L further comprises a shield element.

23. A nucleotide reagent composition comprising an avidin protein and the nucleotide compound of claim 1.

24. The nucleotide compound of claim 1, wherein at least one B" comprises a reactive functional group.

25. The nucleotide compound of claim 24, wherein at least one B" comprises a residue derived from a reactive functional group.

26. The nucleotide compound of claim 25, wherein the residue derived from a reactive functional group is an amide moiety.

27. The nucleotide compound of claim 25, wherein the residue derived from a reactive functional group results from a click reaction.

* * * * *

SEQUENCE LISTING

```
<160> NUMBER OF SEQ ID NOS: 26

<210> SEQ ID NO 1
<211> LENGTH: 575
<212> TYPE: PRT
<213> ORGANISM: Bacteriophage phi-29

<400> SEQUENCE: 1

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
```

```
                305                 310                 315                 320
Gly Glu Ile Ala Asp Leu Trp Leu Ser Asn Val Asp Leu Glu Leu Met
                    325                 330                 335

Lys Glu His Tyr Asp Leu Tyr Asn Val Glu Tyr Ile Ser Gly Leu Lys
                    340                 345                 350

Phe Lys Ala Thr Thr Gly Leu Phe Lys Asp Phe Ile Asp Lys Trp Thr
                    355                 360                 365

Tyr Ile Lys Thr Thr Ser Glu Gly Ala Ile Lys Gln Leu Ala Lys Leu
                    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                    405                 410                 415

Gly Glu Glu Glu Thr Lys Asp Pro Val Tyr Thr Pro Met Gly Val Phe
                    420                 425                 430

Ile Thr Ala Trp Ala Arg Tyr Thr Thr Ile Thr Ala Ala Gln Ala Cys
                    435                 440                 445

Tyr Asp Arg Ile Ile Tyr Cys Asp Thr Asp Ser Ile His Leu Thr Gly
                    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                    485                 490                 495

Gln Lys Thr Tyr Ile Gln Asp Ile Tyr Met Lys Glu Val Asp Gly Lys
                    500                 505                 510

Leu Val Glu Gly Ser Pro Asp Asp Tyr Thr Asp Ile Lys Phe Ser Val
                    515                 520                 525

Lys Cys Ala Gly Met Thr Asp Lys Ile Lys Lys Glu Val Thr Phe Glu
                    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                    565                 570                 575

<210> SEQ ID NO 2
<211> LENGTH: 572
<212> TYPE: PRT
<213> ORGANISM: Bacteriophage M2Y

<400> SEQUENCE: 2

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110
```

-continued

His Thr Val Ile Tyr Asp Ser Leu Lys Lys Leu Pro Phe Pro Val Lys
115                 120                 125

Lys Ile Ala Lys Asp Phe Gln Leu Pro Leu Leu Lys Gly Asp Ile Asp
130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
    165                 170                 175

Gln Phe Lys Gln Gly Leu Asp Arg Met Thr Ala Gly Ser Asp Ser Leu
        180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
            245                 250                 255

Ser Arg Pro Leu Pro Tyr Gly Ala Pro Ile Val Phe Gln Gly Lys Tyr
        260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
            325                 330                 335

Tyr Glu Leu Tyr Asn Val Glu Tyr Ile Asp Gly Phe Lys Phe Arg Glu
        340                 345                 350

Lys Thr Gly Leu Phe Lys Asp Phe Ile Asp Lys Trp Thr Tyr Val Lys
        355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
        420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
            485                 490                 495

Tyr Ile Gln Asp Ile Tyr Val Lys Glu Val Asp Gly Lys Leu Lys Glu
        500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Ala

```
                   530                 535                 540
Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 3
<211> LENGTH: 572
<212> TYPE: PRT
<213> ORGANISM: Bacteriophage B103

<400> SEQUENCE: 3

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335
```

Tyr Glu Met Tyr Asn Val Glu Tyr Ile Asp Gly Phe Lys Phe Arg Glu
                340                 345                 350

Lys Thr Gly Leu Phe Lys Glu Phe Ile Asp Lys Trp Thr Tyr Val Lys
            355                 360                 365

Thr His Glu Lys Gly Ala Lys Lys Gln Leu Ala Lys Leu Met Phe Asp
        370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
        530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 4
<211> LENGTH: 578
<212> TYPE: PRT
<213> ORGANISM: Bacteriophage GA-1

<400> SEQUENCE: 4

Met Ala Arg Ser Val Tyr Val Cys Asp Phe Glu Thr Thr Thr Asp Pro
1               5                   10                  15

Glu Asp Cys Arg Leu Trp Ala Trp Gly Trp Met Asp Ile Tyr Asn Thr
            20                  25                  30

Asp Lys Trp Ser Tyr Gly Glu Asp Ile Asp Ser Phe Met Glu Trp Ala
        35                  40                  45

Leu Asn Ser Asn Ser Asp Ile Tyr Phe His Asn Leu Lys Phe Asp Gly
    50                  55                  60

Ser Phe Ile Leu Pro Trp Trp Leu Arg Asn Gly Tyr Val His Thr Glu
65                  70                  75                  80

Glu Asp Arg Thr Asn Thr Pro Lys Glu Phe Thr Thr Ile Ser Gly
                85                  90                  95

Met Gly Gln Trp Tyr Ala Val Asp Val Cys Ile Asn Thr Arg Gly Lys
            100                 105                 110

Asn Lys Asn His Val Val Phe Tyr Asp Ser Leu Lys Lys Leu Pro Phe
        115                 120                 125

Lys Val Glu Gln Ile Ala Lys Gly Phe Gly Leu Pro Val Leu Lys Gly
        130                 135                 140

```
Asp Ile Asp Tyr Lys Lys Tyr Arg Pro Val Gly Tyr Val Met Asp Asp
145                 150                 155                 160

Asn Glu Ile Glu Tyr Leu Lys His Asp Leu Leu Ile Val Ala Leu Ala
            165                 170                 175

Leu Arg Ser Met Phe Asp Asn Asp Phe Thr Ser Met Thr Val Gly Ser
            180                 185                 190

Asp Ala Leu Asn Thr Tyr Lys Glu Met Leu Gly Val Lys Gln Trp Glu
        195                 200                 205

Lys Tyr Phe Pro Val Leu Ser Leu Lys Val Asn Ser Glu Ile Arg Lys
        210                 215                 220

Ala Tyr Lys Gly Gly Phe Thr Trp Val Asn Pro Lys Tyr Gln Gly Glu
225                 230                 235                 240

Thr Val Tyr Gly Gly Met Val Phe Asp Val Asn Ser Met Tyr Pro Ala
                245                 250                 255

Met Met Lys Asn Lys Leu Leu Pro Tyr Gly Glu Pro Val Met Phe Lys
            260                 265                 270

Gly Glu Tyr Lys Lys Asn Val Glu Tyr Pro Leu Tyr Ile Gln Gln Val
        275                 280                 285

Arg Cys Phe Phe Glu Leu Lys Lys Asp Lys Ile Pro Cys Ile Gln Ile
290                 295                 300

Lys Gly Asn Ala Arg Phe Gly Gln Asn Glu Tyr Leu Ser Thr Ser Gly
305                 310                 315                 320

Asp Glu Tyr Val Asp Leu Tyr Val Thr Asn Val Asp Trp Glu Leu Ile
                325                 330                 335

Lys Lys His Tyr Asp Ile Phe Glu Glu Phe Ile Gly Phe Met
            340                 345                 350

Phe Lys Gly Phe Ile Gly Phe Phe Asp Glu Tyr Ile Asp Arg Phe Met
            355                 360                 365

Glu Ile Lys Asn Ser Pro Asp Ser Ser Ala Glu Gln Ser Leu Gln Ala
370                 375                 380

Lys Leu Met Leu Asn Ser Leu Tyr Gly Lys Phe Ala Thr Asn Pro Asp
385                 390                 395                 400

Ile Thr Gly Lys Val Pro Tyr Leu Asp Glu Asn Gly Val Leu Lys Phe
                405                 410                 415

Arg Lys Gly Glu Leu Lys Glu Arg Asp Pro Val Tyr Thr Pro Met Gly
            420                 425                 430

Cys Phe Ile Thr Ala Tyr Ala Arg Glu Asn Ile Leu Ser Asn Ala Gln
        435                 440                 445

Lys Leu Tyr Pro Arg Phe Ile Tyr Ala Asp Thr Asp Ser Ile His Val
        450                 455                 460

Glu Gly Leu Gly Glu Val Asp Ala Ile Lys Asp Val Ile Asp Pro Lys
465                 470                 475                 480

Lys Leu Gly Tyr Trp Asp His Glu Ala Thr Phe Gln Arg Ala Arg Tyr
                485                 490                 495

Val Arg Gln Lys Thr Tyr Phe Ile Glu Thr Thr Trp Lys Glu Asn Asp
            500                 505                 510

Lys Gly Lys Leu Val Val Cys Glu Pro Gln Asp Ala Thr Lys Val Lys
        515                 520                 525

Pro Lys Ile Ala Cys Ala Gly Met Ser Asp Ala Ile Lys Glu Arg Ile
        530                 535                 540

Arg Phe Asn Glu Phe Lys Ile Gly Tyr Ser Thr His Gly Ser Leu Lys
545                 550                 555                 560
```

```
Pro Lys Asn Val Leu Gly Gly Val Val Leu Met Asp Tyr Pro Phe Ala
                565                 570                 575
Ile Lys

<210> SEQ ID NO 5
<211> LENGTH: 566
<212> TYPE: PRT
<213> ORGANISM: Bacteriophage AV-1

<400> SEQUENCE: 5

Met Val Arg Gln Ser Thr Ile Ala Ser Pro Ala Arg Gly Gly Val Arg
  1               5                  10                  15

Arg Ser His Lys Lys Val Pro Ser Phe Cys Ala Asp Phe Glu Thr Thr
                 20                  25                  30

Thr Asp Glu Asp Asp Cys Arg Val Trp Ser Trp Gly Ile Ile Gln Val
             35                  40                  45

Gly Lys Leu Gln Asn Tyr Val Asp Gly Ile Ser Leu Asp Gly Phe Met
 50                  55                  60

Ser His Ile Ser Glu Arg Ala Ser His Ile Tyr Phe His Asn Leu Ala
 65                  70                  75                  80

Phe Asp Gly Thr Phe Ile Leu Asp Trp Leu Lys His Gly Tyr Arg
                 85                  90                  95

Trp Thr Lys Glu Asn Pro Gly Val Lys Glu Phe Thr Ser Leu Ile Ser
                100                 105                 110

Arg Met Gly Lys Tyr Tyr Ser Ile Thr Val Val Phe Glu Thr Gly Phe
                115                 120                 125

Arg Val Glu Phe Arg Asp Ser Phe Lys Lys Leu Pro Met Ser Val Ser
            130                 135                 140

Ala Ile Ala Lys Ala Phe Asn Leu His Asp Gln Lys Leu Glu Ile Asp
145                 150                 155                 160

Tyr Glu Lys Pro Arg Pro Ile Gly Tyr Ile Pro Thr Glu Gln Glu Lys
                165                 170                 175

Arg Tyr Gln Arg Asn Asp Val Ala Ile Val Ala Gln Ala Leu Glu Val
                180                 185                 190

Gln Phe Ala Glu Lys Met Thr Lys Leu Thr Ala Gly Ser Asp Ser Leu
            195                 200                 205

Ala Thr Tyr Lys Lys Met Thr Gly Lys Leu Phe Ile Arg Arg Phe Pro
210                 215                 220

Ile Leu Ser Pro Glu Ile Asp Thr Glu Ile Arg Lys Ala Tyr Arg Gly
225                 230                 235                 240

Gly Phe Thr Tyr Ala Asp Pro Arg Tyr Ala Lys Lys Leu Asn Gly Lys
                245                 250                 255

Gly Ser Val Tyr Asp Val Asn Ser Leu Tyr Pro Ser Val Met Arg Thr
            260                 265                 270

Ala Leu Leu Pro Tyr Gly Glu Pro Ile Tyr Ser Glu Gly Ala Pro Arg
            275                 280                 285

Thr Asn Arg Pro Leu Tyr Ile Ala Ser Ile Thr Phe Thr Ala Lys Leu
            290                 295                 300

Lys Pro Asn His Ile Pro Cys Ile Gln Ile Lys Lys Asn Leu Ser Phe
305                 310                 315                 320

Asn Pro Thr Gln Tyr Leu Glu Glu Val Lys Glu Pro Thr Thr Val Val
                325                 330                 335

Ala Thr Asn Ile Asp Ile Glu Leu Trp Lys Lys His Tyr Asp Phe Lys
            340                 345                 350
```

-continued

Ile Tyr Ser Trp Asn Gly Thr Phe Glu Phe Arg Gly Ser His Gly Phe
        355                 360                 365

Phe Asp Thr Tyr Val Asp His Phe Met Glu Ile Lys Lys Asn Ser Thr
370                 375                 380

Gly Gly Leu Arg Gln Ile Ala Lys Leu His Leu Asn Ser Leu Tyr Gly
385                 390                 395                 400

Lys Phe Ala Thr Asn Pro Asp Ile Thr Gly Lys His Pro Thr Leu Lys
                405                 410                 415

Asp Asn Arg Val Ser Leu Val Met Asn Glu Pro Glu Thr Arg Asp Pro
            420                 425                 430

Val Tyr Thr Pro Met Gly Val Phe Ile Thr Ala Tyr Ala Arg Lys Lys
        435                 440                 445

Thr Ile Ser Ala Ala Gln Asp Asn Tyr Glu Thr Phe Ala Tyr Ala Asp
    450                 455                 460

Thr Asp Ser Leu His Leu Ile Gly Pro Thr Thr Pro Pro Asp Ser Leu
465                 470                 475                 480

Trp Val Asp Pro Val Glu Leu Gly Ala Trp Lys His Glu Ser Ser Phe
                485                 490                 495

Thr Lys Ser Val Tyr Ile Arg Ala Lys Gln Tyr Ala Glu Glu Ile Gly
            500                 505                 510

Gly Lys Leu Asp Val His Ile Ala Gly Met Pro Arg Asn Val Ala Ala
        515                 520                 525

Thr Leu Thr Leu Glu Asp Met Leu His Gly Gly Thr Trp Asn Gly Lys
    530                 535                 540

Leu Ile Pro Val Arg Val Pro Gly Gly Thr Val Leu Lys Asp Thr Thr
545                 550                 555                 560

Phe Thr Leu Lys Ile Asp
                565

<210> SEQ ID NO 6
<211> LENGTH: 568
<212> TYPE: PRT
<213> ORGANISM: Bacteriophage CP-1

<400> SEQUENCE: 6

Met Thr Cys Tyr Tyr Ala Gly Asp Phe Glu Thr Thr Thr Asn Glu Glu
1               5                   10                  15

Glu Thr Glu Val Trp Leu Ser Cys Phe Ala Lys Val Ile Asp Tyr Asp
                20                  25                  30

Lys Leu Asp Thr Phe Lys Val Asn Thr Ser Leu Glu Asp Phe Leu Lys
            35                  40                  45

Ser Leu Tyr Leu Asp Leu Asp Lys Thr Tyr Thr Glu Thr Gly Glu Asp
    50                  55                  60

Glu Phe Ile Ile Phe Phe His Asn Leu Lys Phe Asp Gly Ser Phe Leu
65                  70                  75                  80

Leu Ser Phe Phe Leu Asn Asn Asp Ile Glu Cys Thr Tyr Phe Ile Asn
                85                  90                  95

Asp Met Gly Val Trp Tyr Ser Ile Thr Leu Glu Phe Pro Asp Phe Thr
            100                 105                 110

Leu Thr Phe Arg Asp Ser Leu Lys Ile Leu Asn Phe Ser Ile Ala Thr
        115                 120                 125

Met Ala Gly Leu Phe Lys Met Pro Ile Ala Lys Gly Thr Thr Pro Leu
    130                 135                 140

Leu Lys His Lys Pro Glu Val Ile Lys Pro Glu Trp Ile Asp Tyr Ile
145                 150                 155                 160

-continued

```
His Val Asp Val Ala Ile Leu Ala Arg Gly Ile Phe Ala Met Tyr Tyr
            165                 170                 175
Glu Glu Asn Phe Thr Lys Tyr Thr Ser Ala Ser Glu Ala Leu Thr Glu
            180                 185                 190
Phe Lys Arg Ile Phe Arg Lys Ser Lys Arg Lys Phe Arg Asp Phe Phe
            195                 200                 205
Pro Ile Leu Asp Glu Lys Val Asp Asp Phe Cys Arg Lys His Ile Val
            210                 215                 220
Gly Ala Gly Arg Leu Pro Thr Leu Lys His Arg Gly Arg Thr Leu Asn
225                 230                 235                 240
Gln Leu Ile Asp Ile Tyr Asp Ile Asn Ser Met Tyr Pro Ala Thr Met
            245                 250                 255
Leu Gln Asn Ala Leu Pro Ile Gly Ile Pro Lys Arg Tyr Lys Gly Lys
            260                 265                 270
Pro Lys Glu Ile Lys Glu Asp His Tyr Tyr Ile Tyr His Ile Lys Ala
            275                 280                 285
Asp Phe Asp Leu Lys Arg Gly Tyr Leu Pro Thr Ile Gln Ile Lys Lys
            290                 295                 300
Lys Leu Asp Ala Leu Arg Ile Gly Val Arg Thr Ser Asp Tyr Val Thr
305                 310                 315                 320
Thr Ser Lys Asn Glu Val Ile Asp Leu Tyr Leu Thr Asn Phe Asp Leu
            325                 330                 335
Asp Leu Phe Leu Lys His Tyr Asp Ala Thr Ile Met Tyr Val Glu Thr
            340                 345                 350
Leu Glu Phe Gln Thr Glu Ser Asp Leu Phe Asp Asp Tyr Ile Thr Thr
            355                 360                 365
Tyr Arg Tyr Lys Lys Glu Asn Ala Gln Ser Pro Ala Glu Lys Gln Lys
            370                 375                 380
Ala Lys Ile Met Leu Asn Ser Leu Tyr Gly Lys Phe Gly Ala Lys Ile
385                 390                 395                 400
Ile Ser Val Lys Lys Leu Ala Tyr Leu Asp Asp Lys Gly Ile Leu Arg
            405                 410                 415
Phe Lys Asn Asp Asp Glu Glu Val Gln Pro Val Tyr Ala Pro Val
            420                 425                 430
Ala Leu Phe Val Thr Ser Ile Ala Arg His Phe Ile Ile Ser Asn Ala
            435                 440                 445
Gln Glu Asn Tyr Asp Asn Phe Leu Tyr Ala Asp Thr Asp Ser Leu His
            450                 455                 460
Leu Phe His Ser Asp Ser Leu Val Leu Asp Ile Asp Pro Ser Glu Phe
465                 470                 475                 480
Gly Lys Trp Ala His Glu Gly Arg Ala Val Lys Ala Lys Tyr Leu Arg
            485                 490                 495
Ser Lys Leu Tyr Ile Glu Glu Leu Ile Gln Glu Asp Gly Thr Thr His
            500                 505                 510
Leu Asp Val Lys Gly Ala Gly Met Thr Pro Glu Ile Lys Glu Lys Ile
            515                 520                 525
Thr Phe Glu Asn Phe Val Ile Gly Ala Thr Phe Glu Gly Lys Arg Ala
            530                 535                 540
Ser Lys Gln Ile Lys Gly Gly Thr Leu Ile Tyr Glu Thr Thr Phe Lys
545                 550                 555                 560
Ile Arg Glu Thr Asp Tyr Leu Val
            565
```

```
<210> SEQ ID NO 7
<211> LENGTH: 650
<212> TYPE: PRT
<213> ORGANISM: Artificial
<220> FEATURE:
<223> OTHER INFORMATION: Mutant recombinant phi29-type DNA polymerase

<400> SEQUENCE: 7

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Ser Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Arg Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
        355                 360                 365
```

```
Tyr Ile Lys Thr Thr Ser Trp Gly Ala Ile Lys Gln Leu Ala Lys Leu
    370             375                 380

Met Leu Asn Ser Leu Tyr Gly Lys Phe Ala Ser Asn Pro Asp Val Thr
385             390                 395                 400

Gly Lys Val Pro Tyr Leu Lys Glu Asn Gly Ala Leu Gly Phe Arg Leu
            405                 410                 415

Gly Glu Glu Glu Tyr Lys Asp Pro Val Tyr Thr Pro Met Gly Val Phe
            420                 425                 430

Ile Thr Ala Trp Gly Arg Tyr Thr Ile Thr Ala Ala Gln Ala Cys
            435                 440                 445

Tyr Asp Arg Ile Ile Tyr Cys Asp Thr Asp Ser Ile His Leu Thr Gly
450             455                 460

Thr Lys Ile Pro Asp Val Ile Lys Asp Ile Val His Pro Lys Lys Leu
465             470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Arg Val Arg Gly Phe
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
530             535                 540

Asn Phe Lys Val Gly Phe Ser Arg Lys Met Lys Pro Lys Ala Val Gln
545             550                 555                 560

Val Pro Gly Gly Val Val Leu Val Asp Ser Val Phe Thr Ile Lys Gly
            565                 570                 575

Gly Gly Ser Leu Val Pro Arg Gly Ser Gly Gly Ser Gly Gly Gly
            580                 585                 590

Ser Gly Gly Ser Gly Leu Asn Asp Phe Phe Glu Ala Gln Lys Ile
            595                 600                 605

Glu Trp His Glu Gly Gly Ser Gly Gly Gly Ser Gly Gly Gly Ser
            610                 615                 620

Gly Leu Asn Asp Phe Phe Glu Ala Gln Lys Ile Glu Trp His Glu Gly
625             630                 635                 640

His His His His His His His His His
                645                 650

<210> SEQ ID NO 8
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 8

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65              70                  75                  80
```

Trp Ser Ala Asp Gly Leu Pro Asn Thr Tyr Asn Thr Ile Ile Ser Arg
            85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
            115                 120                 125

Pro Val Lys Lys Ile Ala Arg Asp Phe Lys Leu Thr Val Lys Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
            245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
            355                 360                 365

Tyr Ile Lys Thr Thr Ser Trp Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Tyr Lys Asp Pro Val Tyr Thr Pro Met Gly Val Phe
            420                 425                 430

Ile Thr Ala Tyr Gly Arg Trp Thr Ile Ile Thr Ala Ala Gln Ala Val
            435                 440                 445

Tyr Asp Arg Ile Ile Tyr Cys Asp Thr Asp Ser Ile His Leu Thr Gly
            450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
            485                 490                 495

Gln Lys Thr Tyr Ile Gln Asp Ile Tyr Met Lys Gln Val Arg Gly His

```
                    500              505              510
Leu Val Gln Gly Ser Pro Asp Asp Tyr Thr Asp Ile Lys Phe Ser Val
            515                  520              525

Lys Cys Ala Gly Met Thr Asp Lys Ile Lys Glu Val Thr Phe Glu
530                 535              540

Asn Phe Lys Val Gly Phe Ser Arg Lys Met Lys Pro Lys Ala Val Gln
545                 550              555              560

Val Pro Gly Gly Val Val Leu Val Asp Ser Val Phe Thr Ile Lys Gly
            565              570              575

His His His His His His His His Gly Gly Gly Ser Gly Gly
            580              585              590

Gly Ser Gly Gly Gly Ser Gly Leu Asn Asp Phe Phe Glu Ala Gln Lys
            595              600              605

Ile Glu Trp His Glu Gly Gly Gly Ser Gly Gly Gly Ser Gly Gly Gly
            610              615              620

Ser Gly Leu Asn Asp Phe Phe Glu Ala Gln Lys Ile Glu Trp His Glu
625                 630              635              640
```

<210> SEQ ID NO 9
<211> LENGTH: 650
<212> TYPE: PRT
<213> ORGANISM: Artificial
<220> FEATURE:
<223> OTHER INFORMATION: Mutant recombinant phi29-type DNA polymerase

<400> SEQUENCE: 9

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Ser Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ser Arg Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
```

-continued

```
        225                 230                 235                 240
Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
            290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Phe Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
                420                 425                 430

Ile Thr Ala Tyr Gly Arg Trp Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Phe
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

Gly Gly Ser Leu Val Pro Arg Gly Ser Gly Gly Gly Ser Gly Gly Gly
            580                 585                 590

Ser Gly Gly Gly Ser Gly Leu Asn Asp Phe Phe Glu Ala Gln Lys Ile
        595                 600                 605

Glu Trp His Glu Gly Gly Ser Gly Gly Gly Ser Gly Gly Gly Ser
            610                 615                 620

Gly Leu Asn Asp Phe Phe Glu Ala Gln Lys Ile Glu Trp His Glu Gly
625                 630                 635                 640

His His His His His His His His His
                645                 650
```

<210> SEQ ID NO 10
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 10

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
        355                 360                 365
```

```
Tyr Ile Lys Thr Thr Ser Trp Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Lys Gly Phe
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

Gly Gly Ser Gly Gly Ser Gly Gly Ser Gly Leu Asn Asp Phe
            580                 585                 590

Phe Glu Ala Gln Lys Ile Glu Trp His Glu Gly Gly Ser Gly Gly
            595                 600                 605

Gly Ser Gly Gly Gly Ser Gly Leu Asn Asp Phe Phe Glu Ala Gln Lys
            610                 615                 620

Ile Glu Trp His Glu Gly His His His His His His His His
625                 630                 635                 640

<210> SEQ ID NO 11
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 11

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95
```

```
Met Gly Gln Trp Tyr Met Ile Asp Ile Ser Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Gln Asp Phe Lys Leu Thr Val Lys Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Lys
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Trp Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Tyr Gly Arg Trp Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Tyr
            500                 505                 510
```

```
Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

Gly Gly Ser Gly Gly Ser Gly Gly Ser Gly Leu Asn Asp Phe
            580                 585                 590

Phe Glu Ala Gln Lys Ile Glu Trp His Glu Gly Gly Ser Gly Gly
            595                 600                 605

Gly Ser Gly Gly Gly Ser Gly Leu Asn Asp Phe Phe Glu Ala Gln Lys
            610                 615                 620

Ile Glu Trp His Glu Gly His His His His His His His His
625                 630                 635                 640

<210> SEQ ID NO 12
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 12

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Arg Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240
```

Glu Ile Gly Glu Gly Met Val Phe Asp Ile Asn Ser Ala Tyr Pro Ala
                    245                 250                 255

Gln Met Tyr Ser Lys Leu Leu Pro Tyr Gly Pro Ile Val Phe Glu
    260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Trp Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Tyr Gly Arg Trp Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Lys Ile Pro Asp Val Ile Lys Asp Ile Val Asp Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly His
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Glu Glu Val Thr Phe Glu
    530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

His His His His His His His His Gly Gly Ser Gly Gly
            580                 585                 590

Gly Ser Gly Gly Ser Gly Leu Asn Asp Phe Phe Glu Ala Gln Lys
        595                 600                 605

Ile Glu Trp His Glu Gly Gly Ser Gly Gly Ser Gly Gly Gly
    610                 615                 620

Ser Gly Leu Asn Asp Phe Phe Glu Ala Gln Lys Ile Glu Trp His Glu
625                 630                 635                 640

<210> SEQ ID NO 13
<211> LENGTH: 650
<212> TYPE: PRT

<213> ORGANISM: Artificial
<220> FEATURE:
<223> OTHER INFORMATION: Mutant recombinant phi29-type DNA polymerase

<400> SEQUENCE: 13

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Ser Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Lys Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Phe Ser Tyr Gly Ala Ile Lys Gln Leu Ala Lys Leu
370                 375                 380

Met Leu Asn Ser Leu Tyr Gly Lys Phe Ala Ser Asn Pro Asp Val Thr
```

```
                385              390              395              400
Gly Lys Val Pro Tyr Leu Lys Glu Asn Gly Ala Leu Gly Phe Arg Leu
                405              410              415

Gly Glu Glu Glu Tyr Lys Asp Pro Val Tyr Thr Pro Met Gly Val Phe
                420              425              430

Ile Thr Ala Tyr Gly Arg Trp Thr Ile Thr Ala Ala Gln Ala Cys
                435              440              445

Tyr Asp Arg Ile Ile Tyr Cys Asp Thr Asp Ser Ile His Leu Thr Gly
            450              455              460

Thr Lys Ile Pro Asp Val Ile Lys Asp Ile Val His Pro Lys Lys Leu
465              470              475              480

Gly Tyr Trp Glu His Glu Ser Thr Phe Lys Arg Ala Lys Tyr Leu Arg
                485              490              495

Gln Lys Thr Tyr Ile Gln Asp Ile Tyr Met Lys Arg Val Arg Gly Tyr
                500              505              510

Leu Val Gln Gly Ser Pro Asp Asp Tyr Thr Asp Ile Lys Phe Ser Val
                515              520              525

Lys Cys Ala Gly Met Thr Asp Lys Ile Lys Glu Val Thr Phe Glu
530              535              540

Asn Phe Lys Val Gly Phe Ser Arg Lys Met Lys Pro Lys Ala Val Gln
545              550              555              560

Val Pro Gly Gly Val Val Leu Val Asp Ser Val Phe Thr Ile Lys Gly
                565              570              575

Gly Ser Gly Leu Val Pro Arg Gly Ser Gly Gly Gly Ser Gly Gly Gly
                580              585              590

Ser Gly Gly Gly Ser Gly Leu Asn Asp Phe Phe Glu Ala Gln Lys Ile
            595              600              605

Glu Trp His Glu Gly Gly Ser Gly Gly Gly Ser Gly Gly Gly Ser
        610              615              620

Gly Leu Asn Asp Phe Phe Glu Ala Gln Lys Ile Glu Trp His Glu Gly
625              630              635              640

His His His His His His His His His
                645              650

<210> SEQ ID NO 14
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 14

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
```

```
                 100                 105                 110
Arg Lys Ile His Thr Val Ile Tyr Asp Ser Leu Lys Lys Leu Pro Phe
                115                 120                 125
Pro Val Lys Lys Ile Ala Gln Asp Phe Lys Leu Thr Val Lys Lys Gly
                130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Gly Phe Lys Asp Ile Ile Thr Thr Lys Lys Phe Lys
                195                 200                 205
Lys Val Phe Pro Thr Leu Ser Leu Gly Leu Asp Lys Glu Val Arg Lys
210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                245                 250                 255
Gln Met Tyr Ser Lys Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Gln Ser Leu Phe Tyr Lys Gly Asn Glu Tyr Leu Lys Ser Ser Gly
305                 310                 315                 320
Gly Glu Ile Ala Asp Val Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Tyr Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Tyr Lys Asp Pro Val Tyr Thr Pro Met Gly Val Phe
                420                 425                 430
Ile Thr Ala Tyr Gly Arg Trp Thr Thr Ile Thr Ala Ala Gln Ala Cys
                435                 440                 445
Tyr Asp Arg Ile Ile Tyr Cys Asp Thr Asp Ser Ile His Leu Thr Gly
                450                 455                 460
Thr Lys Ile Pro Asp Val Ile Lys Asp Ile Val His Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Arg Val Arg Gly Tyr
                500                 505                 510
Leu Val Gln Gly Ser Pro Asp Asp Tyr Thr Asp Ile Lys Phe Ser Val
                515                 520                 525
```

```
Lys Cys Ala Gly Met Thr Asp Lys Ile Lys Glu Glu Val Thr Phe Glu
            530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

His His His His His His His His Gly Gly Gly Ser Gly Gly
            580                 585                 590

Gly Ser Gly Gly Gly Ser Gly Leu Asn Asp Phe Phe Glu Ala Gln Lys
            595                 600                 605

Ile Glu Trp His Glu Gly Gly Ser Gly Gly Ser Gly Gly Gly
            610                 615                 620

Ser Gly Leu Asn Asp Phe Phe Glu Ala Gln Lys Ile Glu Trp His Glu
625                 630                 635                 640

<210> SEQ ID NO 15
<211> LENGTH: 640
<212> TYPE: PRT
<213> ORGANISM: Artificial
<220> FEATURE:
<223> OTHER INFORMATION: Mutant recombinant phi29-type DNA polymerase

<400> SEQUENCE: 15

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255
```

Gln Met Tyr Ser Arg Leu Leu Pro Tyr Gly Glu Pro Ile Val Phe Glu
    260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Tyr
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Glu Val Thr Phe Glu
    530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

Gly Gly Ser Gly Gly Ser Gly Gly Gly Ser Gly Leu Asn Asp Phe
            580                 585                 590

Phe Glu Ala Gln Lys Ile Glu Trp His Glu Gly Gly Ser Gly Gly
        595                 600                 605

Gly Ser Gly Gly Gly Ser Gly Leu Asn Asp Phe Phe Glu Ala Gln Lys
    610                 615                 620

Ile Glu Trp His Glu Gly His His His His His His His His
625                 630                 635                 640

<210> SEQ ID NO 16
<211> LENGTH: 640
<212> TYPE: PRT
<213> ORGANISM: Artificial
<220> FEATURE:

<223> OTHER INFORMATION: Mutant recombinant phi29-type DNA polymerase

<400> SEQUENCE: 16

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
        355                 360                 365

Tyr Ile Lys Thr Thr Ser Tyr Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400
```

Gly Lys Val Pro Tyr Leu Lys Glu Asn Gly Ala Leu Gly Phe Arg Leu
                405                 410                 415

Gly Glu Glu Tyr Lys Asp Pro Val Tyr Thr Pro Met Gly Val Phe
            420                 425                 430

Ile Thr Ala Trp Gly Arg Tyr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Tyr
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys Gly
                565                 570                 575

His His His His His His His His Gly Gly Ser Gly Gly
                580                 585                 590

Gly Ser Gly Gly Ser Gly Leu Asn Asp Phe Phe Glu Ala Gln Lys
            595                 600                 605

Ile Glu Trp His Glu Gly Gly Ser Gly Gly Ser Gly Gly Gly
    610                 615                 620

Ser Gly Leu Asn Asp Phe Phe Glu Ala Gln Lys Ile Glu Trp His Glu
625                 630                 635                 640

<210> SEQ ID NO 17
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 17

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Ser Leu Gly Tyr Lys Gly Lys
            100                 105                 110

Arg Lys Ile His Thr Val Ile Tyr Asp Ser Leu Lys Lys Leu Pro Phe
        115                 120                 125

```
Pro Val Lys Lys Ile Ala Gln Asp Phe Lys Leu Thr Val Arg Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Ser
        355                 360                 365

Tyr Ile Lys Thr Thr Ser Trp Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Trp Gly Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Phe
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
```

```
                545                 550                 555                 560
Val Pro Gly Gly Val Val Leu Val Asp Ser Val Phe Thr Ile Lys
                565                 570                 575

<210> SEQ ID NO 18
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 18

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Arg Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
```

```
                340                 345                 350
Phe Lys Ala Thr Thr Gly Leu Phe Lys Asp Phe Ile Asp Lys Trp Ser
            355                 360                 365

Tyr Ile Lys Thr Thr Ser Trp Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Tyr Gly Arg Trp Thr Ile Ile Thr Ala Ala Gln Ala Val
        435                 440                 445

Tyr Asp Arg Ile Ile Tyr Cys Asp Thr Asp Ser Ile His Leu Thr Gly
450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Gln Val Arg Gly His
            500                 505                 510

Leu Val Gln Gly Ser Pro Asp Asp Tyr Thr Asp Ile Lys Phe Ser Val
        515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560

Val Pro Gly Gly Val Val Leu Val Asp Ser Val Phe Thr Ile Lys
                565                 570                 575

<210> SEQ ID NO 19
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 19

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Ser Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ser Arg Asp Phe Lys Leu Thr Val Lys Lys Gly
```

```
            130                 135                 140
Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Lys Lys Phe Lys
                195                 200                 205

Lys Val Phe Pro Thr Leu Ser Leu Gly Leu Asp Lys Glu Val Arg Lys
210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
                290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Phe Gly Ala Ile Lys Gln Leu Ala Lys Leu
                370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
                420                 425                 430

Ile Thr Ala Tyr Gly Arg Trp Thr Thr Ile Thr Ala Ala Gln Ala Cys
                435                 440                 445

Tyr Asp Arg Ile Ile Tyr Cys Asp Thr Asp Ser Ile His Leu Thr Gly
                450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Phe
                500                 505                 510

Leu Val Gln Gly Ser Pro Asp Asp Tyr Thr Asp Ile Lys Phe Ser Val
                515                 520                 525

Lys Cys Ala Gly Met Thr Asp Lys Ile Lys Glu Glu Val Thr Phe Glu
530                 535                 540

Asn Phe Lys Val Gly Phe Ser Arg Lys Met Lys Pro Lys Ala Val Gln
545                 550                 555                 560
```

-continued

Val Pro Gly Gly Val Val Leu Val Asp Ser Val Phe Thr Ile Lys
                565                 570                 575

<210> SEQ ID NO 20
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 20

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

```
Phe Lys Ala Thr Thr Gly Leu Phe Lys Asp Phe Ile Asp Lys Trp Ser
            355                 360                 365
Tyr Ile Lys Thr Thr Ser Trp Gly Ala Ile Lys Gln Leu Ala Lys Leu
        370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Tyr Lys Asp Pro Val Tyr Thr Pro Met Gly Val Phe
                420                 425                 430
Ile Thr Ala Trp Gly Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
        450                 455                 460
Thr Lys Ile Pro Asp Val Ile Lys Asp Ile Val His Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Arg Val Lys Gly Phe
            500                 505                 510
Leu Val Gln Gly Ser Pro Asp Asp Tyr Thr Asp Ile Lys Phe Ser Val
        515                 520                 525
Lys Cys Ala Gly Met Thr Asp Lys Ile Lys Glu Val Thr Phe Glu
530                 535                 540
Asn Phe Lys Val Gly Phe Ser Arg Lys Met Lys Pro Lys Ala Val Gln
545                 550                 555                 560
Val Pro Gly Gly Val Val Leu Val Asp Ser Val Phe Thr Ile Lys
                565                 570                 575

<210> SEQ ID NO 21
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 21

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
    50                  55                  60
Phe Asp Gly Ser Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Ser Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Gln Asp Phe Lys Leu Thr Val Lys Lys Gly
    130                 135                 140
```

```
Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
                195                 200                 205

Lys Val Phe Pro Thr Leu Ser Leu Gly Leu Asp Lys Glu Val Arg Lys
            210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Trp Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Tyr Lys Asp Pro Val Tyr Thr Pro Met Gly Val Phe
            420                 425                 430

Ile Thr Ala Tyr Gly Arg Trp Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Lys Ile Pro Asp Val Ile Lys Asp Ile Val His Pro Lys Lys Leu
465                 470                 475                 480

Gly Tyr Trp Glu His Glu Ser Thr Phe Lys Arg Ala Lys Tyr Leu Arg
                485                 490                 495

Gln Lys Thr Tyr Ile Gln Asp Ile Tyr Met Lys Arg Val Arg Gly Tyr
            500                 505                 510

Leu Val Gln Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
530                 535                 540

Asn Phe Lys Val Gly Phe Ser Arg Lys Met Lys Pro Lys Ala Val Gln
545                 550                 555                 560
```

Val Pro Gly Gly Val Leu Val Asp Ser Val Phe Thr Ile Lys
                565                 570                 575

<210> SEQ ID NO 22
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 22

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Arg Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

```
Phe Lys Ala Thr Thr Gly Leu Phe Lys Asp Phe Ile Asp Lys Trp Thr
            355                 360                 365
Tyr Ile Lys Thr Thr Ser Trp Gly Ala Ile Lys Gln Leu Ala Lys Leu
370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Tyr Lys Asp Pro Val Tyr Thr Pro Met Gly Val Phe
                420                 425                 430
Ile Thr Ala Tyr Gly Arg Trp Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Lys Ile Pro Asp Val Ile Lys Asp Ile Val Asp Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Arg Val Arg Gly His
                500                 505                 510
Leu Val Gln Gly Ser Pro Asp Asp Tyr Thr Asp Ile Lys Phe Ser Val
            515                 520                 525
Lys Cys Ala Gly Met Thr Asp Lys Ile Lys Glu Glu Val Thr Phe Glu
            530                 535                 540
Asn Phe Lys Val Gly Phe Ser Arg Lys Met Lys Pro Lys Ala Val Gln
545                 550                 555                 560
Val Pro Gly Gly Val Val Leu Val Asp Ser Val Phe Thr Ile Lys
                565                 570                 575

<210> SEQ ID NO 23
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 23

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
    50                  55                  60
Phe Asp Gly Ser Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Ser Leu Gly Tyr Lys Gly Lys
            100                 105                 110
Arg Lys Ile His Thr Val Ile Tyr Asp Ser Leu Lys Lys Leu Pro Phe
        115                 120                 125
Pro Val Lys Lys Ile Ala Gln Asp Phe Lys Leu Thr Val Lys Lys Gly
    130                 135                 140
```

-continued

```
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ile Ala Glu Ala
                165                 170                 175
Leu Leu Ile Gln Phe Lys Gln Gly Leu Asp Arg Met Thr Ala Gly Ser
            180                 185                 190
Asp Ser Leu Lys Gly Phe Lys Asp Ile Ile Thr Thr Lys Lys Phe Lys
        195                 200                 205
Lys Val Phe Pro Thr Leu Ser Leu Gly Leu Asp Lys Glu Val Arg Lys
210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                245                 250                 255
Gln Met Tyr Ser Lys Leu Leu Pro Tyr Gly Glu Pro Ile Val Phe Glu
                260                 265                 270
Gly Lys Tyr Val Trp Asp Glu Asp Tyr Pro Leu His Ile Gln His Ile
            275                 280                 285
Arg Cys Glu Phe Glu Leu Lys Glu Gly Tyr Ile Pro Thr Ile Gln Ile
        290                 295                 300
Lys Gln Ser Leu Phe Tyr Lys Gly Asn Glu Tyr Leu Lys Ser Ser Gly
305                 310                 315                 320
Gly Glu Ile Ala Asp Val Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
            355                 360                 365
Tyr Ile Lys Thr Phe Ser Tyr Gly Ala Ile Lys Gln Leu Ala Lys Leu
        370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Tyr Lys Asp Pro Val Tyr Thr Pro Met Gly Val Phe
                420                 425                 430
Ile Thr Ala Tyr Gly Arg Trp Thr Thr Ile Thr Ala Ala Gln Ala Cys
            435                 440                 445
Tyr Asp Arg Ile Ile Tyr Cys Asp Thr Asp Ser Ile His Leu Thr Gly
        450                 455                 460
Thr Lys Ile Pro Asp Val Ile Lys Asp Ile Val His Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Arg Val Arg Gly Tyr
                500                 505                 510
Leu Val Gln Gly Ser Pro Asp Asp Tyr Thr Asp Ile Lys Phe Ser Val
            515                 520                 525
Lys Cys Ala Gly Met Thr Asp Lys Ile Lys Glu Val Thr Phe Glu
        530                 535                 540
Asn Phe Lys Val Gly Phe Ser Arg Lys Met Lys Pro Lys Ala Val Gln
545                 550                 555                 560
Val Pro Gly Gly Val Val Leu Val Asp Ser Val Phe Thr Ile Lys
```

<210> SEQ ID NO 24
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 24

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ser Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Gln Asp Phe Lys Leu Thr Val Lys Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Lys
    210                 215                 220

Ala Tyr Arg Gly Gly Phe Thr Trp Leu Asn Asp Arg Phe Lys Gly Lys
225                 230                 235                 240

Glu Ile Gly Glu Gly Met Val Phe Asp Ile Asn Ser Ala Tyr Pro Ala
                245                 250                 255

Gln Met Tyr Ser Lys Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Gln Ser Leu Phe Tyr Lys Gly Asn Glu Tyr Leu Lys Ser Ser Gly
305                 310                 315                 320

Gly Glu Ile Ala Asp Val Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
```

-continued

```
            355                 360                 365
Tyr Ile Lys Thr Thr Ser Tyr Gly Ala Ile Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Tyr Lys Asp Pro Val Tyr Thr Pro Met Gly Val Phe
            420                 425                 430
Ile Thr Ala Tyr Gly Arg Trp Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Lys Ile Pro Asp Val Ile Lys Asp Ile Val His Pro Lys Lys Leu
465                 470                 475                 480
Gly Tyr Trp Glu His Glu Ser Thr Phe Lys Arg Ala Lys Tyr Leu Arg
                485                 490                 495
Gln Lys Thr Tyr Ile Gln Asp Ile Tyr Met Lys Arg Val Arg Gly Tyr
            500                 505                 510
Leu Val Gln Gly Ser Pro Asp Asp Tyr Thr Asp Ile Lys Phe Ser Val
            515                 520                 525
Lys Cys Ala Gly Met Thr Asp Lys Ile Lys Glu Val Thr Phe Glu
530                 535                 540
Asn Phe Lys Val Gly Phe Ser Arg Lys Met Lys Pro Lys Ala Val Gln
545                 550                 555                 560
Val Pro Gly Gly Val Val Leu Val Asp Ser Val Phe Thr Ile Lys
                565                 570                 575

<210> SEQ ID NO 25
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 25

Met Lys His Met Pro Arg Lys Met Tyr Ser Cys Asp Phe Glu Thr Thr
1               5                   10                  15
Thr Lys Val Glu Asp Cys Arg Val Trp Ala Tyr Gly Tyr Met Asn Ile
            20                  25                  30
Glu Asp His Ser Glu Tyr Lys Ile Gly Asn Ser Leu Asp Glu Phe Met
        35                  40                  45
Ala Trp Val Leu Lys Val Gln Ala Asp Leu Tyr Phe His Asn Leu Lys
50                  55                  60
Phe Asp Gly Ser Phe Ile Ile Asn Trp Leu Glu Arg Asn Gly Phe Lys
65                  70                  75                  80
Trp Ser Ala Asp Gly Leu Pro Asn Thr Tyr Asn Thr Ile Ile Ser Arg
                85                  90                  95
Met Gly Gln Trp Tyr Met Ile Asp Ile Cys Leu Gly Tyr Lys Gly Lys
            100                 105                 110
Arg Lys Ile His Thr Val Ile Tyr Asp Ser Leu Lys Lys Leu Pro Phe
            115                 120                 125
Pro Val Lys Lys Ile Ala Gln Asp Phe Lys Leu Thr Val Lys Lys Gly
        130                 135                 140
Asp Ile Asp Tyr His Lys Glu Arg Pro Val Gly Tyr Lys Ile Thr Pro
```

-continued

```
            145                 150                 155                 160
Glu Glu Tyr Ala Tyr Ile Lys Asn Asp Ile Gln Ile Ile Ala Glu Ala
                    165                 170                 175
Leu Leu Ile Gln Phe Lys Gln Gly Leu Asp Arg Met Thr Ala Gly Ser
                    180                 185                 190
Asp Ser Leu Lys Gly Phe Lys Asp Ile Ile Thr Thr Lys Lys Phe Lys
                    195                 200                 205
Lys Val Phe Pro Thr Leu Ser Leu Gly Leu Asp Lys Glu Val Arg Lys
            210                 215                 220
Ala Tyr Arg Gly Gly Phe Thr Trp Leu Asn Asp Arg Phe Lys Gly Lys
225                 230                 235                 240
Glu Ile Gly Glu Gly Met Val Phe Asp Ile Asn Ser Ala Tyr Pro Ala
                    245                 250                 255
Gln Met Tyr Ser Arg Leu Leu Pro Tyr Gly Glu Pro Ile Val Phe Glu
                    260                 265                 270
Gly Lys Tyr Val Trp Asp Glu Asp Tyr Pro Leu His Ile Gln His Ile
                    275                 280                 285
Arg Cys Glu Phe Glu Leu Lys Glu Gly Tyr Ile Pro Thr Ile Gln Ile
            290                 295                 300
Lys Gln Ser Leu Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                    325                 330                 335
Lys Glu His Tyr Asp Leu Tyr Asn Val Glu Tyr Ile Ser Gly Leu Lys
                    340                 345                 350
Phe Lys Ala Thr Thr Gly Leu Phe Lys Asp Phe Ile Asp Lys Trp Ser
                    355                 360                 365
Tyr Ile Lys Thr Thr Ser Tyr Gly Ala Ile Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                    405                 410                 415
Gly Glu Glu Glu Tyr Lys Asp Pro Val Tyr Thr Pro Met Gly Val Phe
                    420                 425                 430
Ile Thr Ala Trp Gly Arg Tyr Thr Thr Ile Thr Ala Ala Gln Ala Cys
                    435                 440                 445
Tyr Asp Arg Ile Ile Tyr Cys Asp Thr Asp Ser Ile His Leu Thr Gly
            450                 455                 460
Thr Lys Ile Pro Asp Val Ile Lys Asp Ile Val His Pro Lys Lys Leu
465                 470                 475                 480
Gly Tyr Trp Glu His Glu Ser Thr Phe Lys Arg Ala Lys Tyr Leu Arg
                    485                 490                 495
Gln Lys Thr Tyr Ile Gln Asp Ile Tyr Met Lys Arg Val Arg Gly Tyr
                    500                 505                 510
Leu Val Gln Gly Ser Pro Asp Asp Tyr Thr Asp Ile Lys Phe Ser Val
            515                 520                 525
Lys Cys Ala Gly Met Thr Asp Lys Ile Lys Glu Glu Val Thr Phe Glu
            530                 535                 540
Asn Phe Lys Val Gly Phe Ser Arg Lys Met Lys Pro Lys Ala Val Gln
545                 550                 555                 560
Val Pro Gly Gly Val Val Leu Val Asp Ser Val Phe Thr Ile Lys
                    565                 570                 575
```

<210> SEQ ID NO 26
<211> LENGTH: 575
<212> TYPE: PRT
<213> ORGANISM: Artificial
<220> FEATURE:
<223> OTHER INFORMATION: Mutant recombinant phi29-type DNA polymerase

<400> SEQUENCE: 26

| Met | Lys | His | Met | Pro | Arg | Lys | Met | Tyr | Ser | Cys | Asp | Phe | Glu | Thr | Thr |
|---|---|---|---|---|---|---|---|---|---|---|---|---|---|---|---|
| 1 | | | | 5 | | | | | 10 | | | | | 15 | |

| Thr | Lys | Val | Glu | Asp | Cys | Arg | Val | Trp | Ala | Tyr | Gly | Tyr | Met | Asn | Ile |
|---|---|---|---|---|---|---|---|---|---|---|---|---|---|---|---|
| | | | 20 | | | | | 25 | | | | | 30 | | |

| Glu | Asp | His | Ser | Glu | Tyr | Lys | Ile | Gly | Asn | Ser | Leu | Asp | Glu | Phe | Met |
|---|---|---|---|---|---|---|---|---|---|---|---|---|---|---|---|
| | | | 35 | | | | | 40 | | | | | 45 | | |

| Ala | Trp | Val | Leu | Lys | Val | Gln | Ala | Asp | Leu | Tyr | Phe | His | Asn | Leu | Lys |
|---|---|---|---|---|---|---|---|---|---|---|---|---|---|---|---|
| | 50 | | | | | 55 | | | | | 60 | | | | |

| Phe | Asp | Gly | Ser | Phe | Ile | Ile | Asn | Trp | Leu | Glu | Arg | Asn | Gly | Phe | Lys |
|---|---|---|---|---|---|---|---|---|---|---|---|---|---|---|---|
| 65 | | | | | 70 | | | | | 75 | | | | | 80 |

| Trp | Ser | Ala | Asp | Gly | Leu | Pro | Asn | Thr | Tyr | Asn | Thr | Ile | Ile | Ser | Arg |
|---|---|---|---|---|---|---|---|---|---|---|---|---|---|---|---|
| | | | | 85 | | | | | 90 | | | | | 95 | |

| Met | Gly | Gln | Trp | Tyr | Met | Ile | Asp | Ile | Cys | Leu | Gly | Tyr | Lys | Gly | Lys |
|---|---|---|---|---|---|---|---|---|---|---|---|---|---|---|---|
| | | | | 100 | | | | | 105 | | | | | 110 | |

| Arg | Lys | Ile | His | Thr | Val | Ile | Tyr | Asp | Ser | Leu | Lys | Lys | Leu | Pro | Phe |
|---|---|---|---|---|---|---|---|---|---|---|---|---|---|---|---|
| | | | 115 | | | | | 120 | | | | | 125 | | |

| Pro | Val | Lys | Lys | Ile | Ala | Gln | Asp | Phe | Lys | Leu | Thr | Val | Lys | Lys | Gly |
|---|---|---|---|---|---|---|---|---|---|---|---|---|---|---|---|
| | 130 | | | | | 135 | | | | | 140 | | | | |

| Asp | Ile | Asp | Tyr | His | Lys | Glu | Arg | Pro | Val | Gly | Tyr | Lys | Ile | Thr | Pro |
|---|---|---|---|---|---|---|---|---|---|---|---|---|---|---|---|
| 145 | | | | | 150 | | | | | 155 | | | | | 160 |

| Glu | Glu | Tyr | Ala | Tyr | Ile | Lys | Asn | Asp | Ile | Gln | Ile | Ile | Ala | Glu | Ala |
|---|---|---|---|---|---|---|---|---|---|---|---|---|---|---|---|
| | | | | 165 | | | | | 170 | | | | | 175 | |

| Leu | Leu | Ile | Gln | Phe | Lys | Gln | Gly | Leu | Asp | Arg | Met | Thr | Ala | Gly | Ser |
|---|---|---|---|---|---|---|---|---|---|---|---|---|---|---|---|
| | | | 180 | | | | | 185 | | | | | 190 | | |

| Asp | Ser | Leu | Lys | Gly | Phe | Lys | Asp | Ile | Ile | Thr | Thr | Lys | Lys | Phe | Lys |
|---|---|---|---|---|---|---|---|---|---|---|---|---|---|---|---|
| | | | 195 | | | | | 200 | | | | | 205 | | |

| Lys | Val | Phe | Pro | Thr | Leu | Ser | Leu | Gly | Leu | Asp | Lys | Glu | Val | Arg | Lys |
|---|---|---|---|---|---|---|---|---|---|---|---|---|---|---|---|
| | 210 | | | | | 215 | | | | | 220 | | | | |

| Ala | Tyr | Arg | Gly | Gly | Phe | Thr | Trp | Leu | Asn | Asp | Arg | Phe | Lys | Gly | Lys |
|---|---|---|---|---|---|---|---|---|---|---|---|---|---|---|---|
| 225 | | | | | 230 | | | | | 235 | | | | | 240 |

| Glu | Ile | Gly | Glu | Gly | Met | Val | Phe | Asp | Ile | Asn | Ser | Ala | Tyr | Pro | Ala |
|---|---|---|---|---|---|---|---|---|---|---|---|---|---|---|---|
| | | | | 245 | | | | | 250 | | | | | 255 | |

| Gln | Met | Tyr | Ser | Arg | Leu | Leu | Pro | Tyr | Gly | Glu | Pro | Ile | Val | Phe | Glu |
|---|---|---|---|---|---|---|---|---|---|---|---|---|---|---|---|
| | | | 260 | | | | | 265 | | | | | 270 | | |

| Gly | Lys | Tyr | Val | Trp | Asp | Glu | Asp | Tyr | Pro | Leu | His | Ile | Gln | His | Ile |
|---|---|---|---|---|---|---|---|---|---|---|---|---|---|---|---|
| | | | 275 | | | | | 280 | | | | | 285 | | |

| Arg | Cys | Glu | Phe | Glu | Leu | Lys | Glu | Gly | Tyr | Ile | Pro | Thr | Ile | Gln | Ile |
|---|---|---|---|---|---|---|---|---|---|---|---|---|---|---|---|
| | 290 | | | | | 295 | | | | | 300 | | | | |

| Lys | Gln | Ser | Leu | Phe | Tyr | Lys | Gly | Asn | Glu | Tyr | Leu | Lys | Ser | Ser | Gly |
|---|---|---|---|---|---|---|---|---|---|---|---|---|---|---|---|
| 305 | | | | | 310 | | | | | 315 | | | | | 320 |

| Gly | Glu | Ile | Ala | Asp | Leu | Trp | Leu | Ser | Asn | Val | Asp | Leu | Glu | Leu | Met |
|---|---|---|---|---|---|---|---|---|---|---|---|---|---|---|---|
| | | | | 325 | | | | | 330 | | | | | 335 | |

| Lys | Glu | His | Tyr | Asp | Leu | Tyr | Asn | Val | Glu | Tyr | Ile | Ser | Gly | Leu | Lys |
|---|---|---|---|---|---|---|---|---|---|---|---|---|---|---|---|
| | | | 340 | | | | | 345 | | | | | 350 | | |

| Phe | Lys | Ala | Thr | Thr | Gly | Leu | Phe | Lys | Asp | Phe | Ile | Asp | Lys | Trp | Ser |
|---|---|---|---|---|---|---|---|---|---|---|---|---|---|---|---|
| | 355 | | | | | 360 | | | | | 365 | | | | |

-continued

```
Tyr Ile Lys Thr Thr Ser Tyr Gly Ala Ile Lys Gln Leu Ala Lys Leu
    370             375             380
Met Leu Asn Ser Leu Tyr Gly Lys Phe Ala Ser Asn Pro Asp Val Thr
385             390             395             400
Gly Lys Val Pro Tyr Leu Lys Glu Asn Gly Ala Leu Gly Phe Arg Leu
            405             410             415
Gly Glu Glu Glu Tyr Lys Asp Pro Val Tyr Thr Pro Met Gly Val Phe
            420             425             430
Ile Thr Ala Trp Gly Arg Tyr Thr Thr Ile Thr Ala Ala Gln Ala Cys
        435             440             445
Tyr Asp Arg Ile Ile Tyr Cys Asp Thr Asp Ser Ile His Leu Thr Gly
    450             455             460
Thr Lys Ile Pro Asp Val Ile Lys Asp Ile Val His Pro Lys Lys Leu
465             470             475             480
Gly Tyr Trp Glu His Glu Ser Thr Phe Lys Arg Ala Lys Tyr Leu Arg
            485             490             495
Gln Lys Thr Tyr Ile Gln Asp Ile Tyr Met Lys Arg Val Arg Gly Tyr
            500             505             510
Leu Val Gln Gly Ser Pro Asp Asp Tyr Thr Asp Ile Lys Phe Ser Val
        515             520             525
Lys Cys Ala Gly Met Thr Asp Lys Ile Lys Glu Glu Val Thr Phe Glu
    530             535             540
Asn Phe Lys Val Gly Phe Ser Arg Lys Met Lys Pro Lys Ala Val Gln
545             550             555             560
Val Pro Gly Gly Val Val Leu Val Asp Ser Val Phe Thr Ile Lys
            565             570             575
```